US007063972B2

(12) United States Patent
Wilson et al.

(10) Patent No.: US 7,063,972 B2
(45) Date of Patent: Jun. 20, 2006

(54) **CYTOCHROME P450 MONOOXYGENASE CYP52A2A FROM *CANDIDA TROPICALIS***

(75) Inventors: C. Ron Wilson, Loveland, OH (US); David L. Craft, Fort Thomas, KY (US); L. Dudley Eirich, Cincinnati, OH (US); Mark Eshoo, Fairfax, CA (US); Krishna M. Madduri, Westfield, IN (US); Cathy A. Cornett, Crescent Springs, KY (US); Alfred A. Brenner, Santa Rosa, CA (US); Maria Tang, Fairfield, CA (US); John C. Loper, Cincinnati, OH (US); Martin Gleeson, San Diego, CA (US)

(73) Assignee: Cognis Corporation, Ambler, PA (US)

( * ) Notice: Subject to any disclaimer, the term of this patent is extended or adjusted under 35 U.S.C. 154(b) by 128 days.

(21) Appl. No.: 10/138,838

(22) Filed: May 3, 2002

(65) Prior Publication Data

US 2003/0049821 A1 Mar. 13, 2003

Related U.S. Application Data

(60) Continuation of application No. 09/976,800, filed on Oct. 12, 2001, now abandoned, which is a division of application No. 09/302,620, filed on Apr. 30, 1999, now Pat. No. 6,331,420.

(60) Provisional application No. 60/123,555, filed on Mar. 10, 1999, provisional application No. 60/103,099, filed on Oct. 5, 1998, provisional application No. 60/083,798, filed on May 1, 1998.

(51) Int. Cl.

| | |
|---|---|
| *C12N 9/02* | (2006.01) |
| *C12N 15/00* | (2006.01) |
| *C12N 1/20* | (2006.01) |
| *C12P 21/04* | (2006.01) |
| *C07H 21/04* | (2006.01) |

(52) U.S. Cl. .................... 435/189; 435/69.1; 435/71.1; 435/252.3; 435/320.1; 536/23.2; 536/23.74

(58) Field of Classification Search ................ 435/190, 435/189, 252, 320.1, 69.1, 71.1; 530/350; 536/23.2, 23.74

See application file for complete search history.

(56) References Cited

U.S. PATENT DOCUMENTS 5,254,466 A 10/1993 Picataggio et al.

(Continued)

FOREIGN PATENT DOCUMENTS

WO WO 91/14781 10/1991

OTHER PUBLICATIONS

Bertrand et al. Partial Purification of Cytochrome P-450 of *Candida tropicalis* and Reconstitution of Hydroxylase Activity. FEBS Letters (1979) 105(1): 143-146.*

(Continued)

*Primary Examiner*—Manjunath Rao
*Assistant Examiner*—Yong Pak
(74) *Attorney, Agent, or Firm*—John F. Daniels

(57) ABSTRACT

Novel genes have been isolated which encode cytochrome P450 and NADPH reductase enzymes of the ω-hydroxylase complex of *C. tropicalis* 20336. Vectors including these genes, transfected host cells and transformed host cells are provided. Methods of producing of cytochrome P450 and NADPH reductase enzymes are also provided which involve transforming a host cell with a gene encoding these enzymes and culturing the cells. Methods of increasing the production of a dicarboxylic acid and methods of increasing production of the aforementioned enzymes are also provided which involve increasing in the host cell the number of genes encoding these enzymes. A method for discriminating members of a gene family by quantifying the expression of genes is also provided.

1 Claim, 89 Drawing Sheets

U.S. PATENT DOCUMENTS 5,620,878 A 4/1997 Picataggio et al.
5,648,247 A 7/1997 Picataggio et al.
6,331,420 B1 12/2001 Wilson et al.

OTHER PUBLICATIONS

Kappeli et al. Convenient procedure for the isolation of highly enriched, cytochrome p-450-containing microsomal fraction from *Candida tropicalis*. Analytical Biochemistry (1982) 126(1): 179-182.*

Sanglard et al. The distinction of different types of cytochromes P-450 from the yeasts *Candida tropicalis* and *Saccharomyces uvarum*. Archives of Biochemistry and Biophysics (1986) 251(1): 276-286.*

Sutter et al., NADPH-Cytochrome P450 reductase (EC 1.6.2.4) (CPR), Swissport Sequence Data Base, Oct. 1, 1994, Ac P37201.

Sutter et al.; *C. tropicalis* NADPH-cytochrome P450 reductase gene, complete cds. EMBL Sequence Database, Jul. 21, 1990, Heidelberg DE Ac M35199.

Nelson, D. R. 1996. P450 Superfamily: Update on New sequences, gene mapping, accession numbers, and nomenclature. Pharmacogenetics. 6(1):1-42.

Garfinkel, D. 1958. Studies on pig liver microsomes. I. Enzymatic and pigment composition of different microsomal fractions. Arch. Biochem. Biophys. 77:493-509.

Klaassen, C. D., M. O. Amdur, and J. Doull. 1986. Toxicology, 3rd ed. Macmillan, New York.

Omura, T., and R. Sato. 1964. The carbon-monoxide-binding pigment of liver microsomes. I. Evidence of its hemoprotein nature. J. Biol. Chem. 239:2370-2378.

Goeptar, A. R., Heleen Scheerens and Nico P.E. Vermeulen. 1995. Oxygen and Xenobiotic Reductase Activity of Cytochrome P450. Critical Reviews in Toxicology. 25(1):25-65.

Taniguchi, H., Y. Imai, and R. Sato. 1984. Role of electron transfer system in microsomal drug monooxygenase reaction catalyzed by cytochrome P450. Arch. Biochem. Biophys. 232:585-596.

Potter, D. W., and D. J. Reed. 1983. Involvement of FMN and phenobarbital cytochrome P450 in stimulating a one-electron reductive denitrosation of 1-(2-chloroethyl)-3-(cyclohexyl)-1-nitrosourea catalyzed by NADPH-cytochrome P450 reductase. J. Biol. Chem. 258:6906-6911.

Vermilion, J. L., and M. J. Coon. 1978. Identification of the high and low potential flavins of liver microsomal NADPH-cytochrome P450 reductase. J. Biol Chem. 253:8812-8819.

Guengerich, F.P., and M. V. Martin. 1980. Purification of cytochrome P-450, NADPH-cytochrome P-450 reductase and epoxide hydratase from a single preparation of rat liver microsomes. Arch. Biochem. Biophys. 205:365-379.

Ortiz de Montellano, P.R. 1986. Cytochrome P450; Structure, Mechanism and Biochemistry. Plenum Press, New York (Table of Contents).

Kuthen, H., and V. Ulrich. 1982. Oxidase and oxygenase function of the microsomal cytochrome P450 monooxygenase system. Eur. J. Biochem. 126:583-588.

Poulos, T.L., and R. Raag. 1992. Cytochrome P450 crystallography, oxygen activation and electron transfer. FASEB J. 6:674-679.

Mukhopadhyay, C. K. a. I. B. C. 1994. NADPH initiated cytochrome P450-mediated free metal ion independent oxidative damage of microsomal proteins. Journal of Biological Chemistry. 269(18):13390-13397.

Ross, A. D., Varghese, G., Oporto, B., Carmichael, F.J., and Isreal Y. 1995. Effects of propylthiouracil treatment on NADPH-cytochrome P450 reductase levels, oxygen consumption and hydroxyl radical formation in liver microsomes from rats fed ethanol or acetone chronically. Biochemical Pharmacology. 49(7):979-989.

Yamazaki, S., Nakano,N., Imai, Y., Ueng, Y.F., Guengerich, F.P., and T. Shimada. 1996. Roles of cytochrome b5 in the oxidation of testosterone and nifedipine by recombinant cytochrome P450 3A4 and by human liver microsomes. Archives of Biochemistry and Biophysics. 325(2):174-182.

Gotoh, O., Tagashira,Y., Iizuka, T., and Y. Fuji-kuriyama. 1983. Structural characteristics of Cytochrome P450. Possible location of the heme-binding cysteine in determined amino acid sequences. J. Biochem. 93(807-817).

Morohashi, K., Sogawa,K., Omura,T., and Y. Fuji-kuriyama. 1987. Gene structure of human cytochrome P450 (SCC), cholesterol desmolase. J. Biochem. 101:879-887.

Kalb, V. and. J. Loper. 1988. Proteins from eight eukaryotic cytochrome P-450 families share a segmented region of sequence similarity. PNAS. 85:7221-7225.

Kaiser, C., S. Michaelis, and A. Mitchell. 1994. Methods in Yeast Genetics. Cold Spring Harbor Laboratory Press, USA (Title page).

Sambrook, J., E. Fritsch, and T. Maniatis. 1989. Molecular Cloning: A Laboratory Manual. 2nd Ed. Cold Spring Harbor Laboratory Press, USA (Title page).

Boeke, J.D., LaCroute, F., and G.R. Fink. A positive selection for mutants lacking orotidine-5'-phosphate decarboxylase activity in yeast:5-fluro-orotic acid resistance. Mol. Gen. Genet. (1984) 197:345-346.

Picataggio, S., Deanda, K., and J. Mielenz. Dtermination of *Candida tropicalis* Acyl Coenzyme A Oxidase Isozyme Function by Sequential Gene Disruption. 1991. Mol. and Cell. Biol. 11:4333-4339.

Rohrer, T.L. and S.K. Picataggio. Targeted integrative transformation of *Candida tropicalis* by electroporation. Appl. Microbiol. Biotechnol. 1992. 36:650-654.

Picataggio, S., Rohrer, T., Deanda, K., Lanning, D., Reynolds, R., Mielenz, J. And L.D. Eirich. Metabolic engineering of *Candida tropicalis* for the production of long-chain dicarboxylic acids. 1992. Bio/Technology 10:894-898.

Sutter, T.R., Sangard, D. and J.C. Loper. 1990. Isolation and characterization of the alkane-inducible NADPH-cytochrome P-450 oxidoreductase gene from *Candida tropicalis*. J. Biol. Chem. 265:16428-16436.

Kargel, E., Menzel, R., Honeck, H., Vogel, F., Bohmer, A. and W. Schhunck. 1996. *Candida maltosa* NADPH-cytochrome P450 reductase: cloning of a full-length cDNA, heterologous expression in *Saccharomyces cerevisiae* and function of the N-terminus region of membrane anchoring and proliferation of the endiplasmic reticulum. Yeast. 12:333-348.

Ohkuma, M., Muraoka, S., Tanimoto, T., Fuji, M., Ohta, A. and Takagi, M. 1995. *CYP52* (cytochrome P450alk) multigene family in *Candida maltosa:* identification and characterization of eight members. DNA and Cell Biology. 14:163-173.

Seghezzi, W., Meili, C., Ruffiner, R., Kuenzi, R., Sanglard, D. and A. Fiechter. 1992. Identification and characterization of additional members of the cytochrome P450 multigene family *CYP52* of *Candida tropicalis*. DNA and Cell Biology. 11:767-780.

Ohkuma et al., C. Maltosa ALK2-A and ALK3-A Genes for n-alkane inducible cytochrome P-450, EMBL Sequence Database Mar. 14, 1995, Heidelberg DE Ac X55881.

Ohkuma et al., Cytochrome P450 52D1, Swissprot Sequence Data Base, Dec. 15, 1998, Ac Q12585.

Kobayashi et al., Quantitative Analysis of Human Multidrug Resistance 1 (MDR1) Gene Expression by Nonisotopic Competitive Reverse Transcriptase Polymerase Chain Reaction Assay, Journal of Clinical Laboratory Analysis, vol. 11, 1997, pp. 258-266.

Mattes et al., Quantitative reverse transcriptase/PCR assay for the measurement of induction in cultured hepatocytes, Chemico-Biological Interactions, vol. 107, Nov. 6, 1997, pp. 47-61.

Helfrich, et al., A quantitative reverse transcriptase polymerase chain reaction-based assay to detect carcinoma cells in peripheral blood, British Journal of Cancer, vol. 76, No. 1, Jul. 1997, pp. 25-35.

Seghezzi et al., *C. tropicalis* CYP52A6 gene encoding cytochrome P450alk3, EMBL Sequence Database, Jun. 27, 1992, Heidelberg DE, Ac Z13010.

Seghezzi et al., Cytochrome P450 52A6, Swissprot Sequence Data Base, Apr. 1, 1993, Heidelberg DE, Ac P30608.

Seghezzi et al., *Candida Tropicalis* cytochrome P450alk2 and cytochrome P450alk1 genes, EMBL Sequence Database, Jul. 10, 1991, Heidelberg DE, Ac M63258.

Seghezzi et al., Cytochrome P450 52A2, Swissprot Sequence Data Base, Apr. 1, 1993, Ac P30607.

Seghezzi et al., Characterization of a second alkane-inducible cytochrome P450-encoding gene, CYP52A2, from *Candida Tropicalis*, Gene, vol. 106, 1991, pp. 51-60.

Sanglard et al., *Candida tropicalis* alkane-inducible cytochrome P450 gene, EMBL Sequence Database, Nov. 23, 1989, Heidelberg DE, Ac M24894.

Sanglard et al., Cytochrome P450 52A1, SwissProt Sequence Data Base, Jul. 1, 1989, AC P10615.

Sanglard et al., Characterization of the alkane-inducible cytochrome P450 (P450alk) gene from the yeast *Candida tropicalis*: identification of new P450 gene family, Gene, vol. 76, No. 1, 1989, pp. 121-136.

Seghezzi et al., *C tropicalis* CYP52A8 gene encoding cytochrome P450alk5, EMBL Sequence Database, Jun. 27, 1992, Heildelberg DE, Ac Z13012.

Seghezzi et al., Cytochrome P450 52A8, Swissprot Sequence Data Base, Apr. 1, 1993, Ac P30610.

Seghezzi et al., *C. tropicalis* CYP52A7 gene encoding cytochrome P450alk4, EMBL Sequence Database, Jun. 27, 1992, Heidelberg DE, Ac Z13011.

Seghezzi et al., Cytochrome P450 52A7, Swissprot Sequence Database, Apr. 1, 1993, Ac P30609.

* cited by examiner

QC-RT-PCR primers for the 5′ coding sequence of
*Candida tropicalis* 20336 P450*CYP52A5A*

```
5'  ATGATTGAACAACTCCTAGAATATTGGTAT GTCGTTGTGCCAGTGTTGTACATCATCAAA CAACTCCTTGCATACACAAAGACTCGCGTC  3'  90
3'  TACTAACTTGTTGAGGATCTTATAACCATA CAGCAACACGGTCACAACATGTAGTAGTTT GTTGAGGAACGTATGTGTTTCTGAGCGCAG  5'

5'  TTGATGAAAAAGTTGGGTGCTGCTCCAGTC ACAAACAAGTTGTACGACAACGCTTTCGGT ATCGTCAATGGATGGAAGGCTCTCCAGTTC  3' 180
3'  AACTACTTTTTCAACCCACGACGAGGTCAG TGTTTGTTCAACATGCTGTTGCGAAAGCCA TAGCAGTTACCTACCTTCCGAGAGGTCAAG  5'

        Forward Primer 7581-97F
5'  AAGAAAGAGGGCAGGGCTCAAGAGTACAAC GATTACAAGTTTGACCACTCCAAGAACCCA AGCGTGGGCACCTACGTCAGTATTCTTTTC  3' 270
3'  TTCTTTCTCCCGTCCCGAGTTCTCATGTTG CTAATGTTCAAACTGGTGAGGTTCTTGGGT TCGCACCCGTGGATGCAGTCATAAGAAAAG  5'

5'  GGCACCAGGATCGTCGTGACCAAAGATCCA GAGAATATCAAAGCTATTTTGGCAACCCAG TTTGGTGATTTTTCTTTGGGCAAGAGGCAC  3' 360
3'  CCGTGGTCCTAGCAGCACTGGTTTCTAGGT CTCTTATAGTTTCGATAAAACCGTTGGGTC AAACCACTAAAAAGAAACCCGTTCTCCGTG  5'

5'  ACTCTTTTTAAGCCTTTGTTAGGTGATGGG ATCTTCACATTGGACGGCGAAGGCTGGAAG CACAGCAGAGCCATGTTGAGACCACAGTTT  3' 450
3'  TGAGAAAAATTCGGAAACAATCCACTACCC TAGAAGTGTAACCTGCCGCTTCCGACCTTC GTGTCGTCTCGGTACAACTCTGGTGTCAAA  5'
                              Reverse Primer 7581-97M

5'  GCCAGAGAACAAGTTGCTCATGTGACGTCG TTGGAACCACACTTCCAGTTGTTGAAGAAG CATATTCTTAAGCACAAGGGTGAATACTTT  3' 540
3'  CGGTCTCTTGTTCAACGAGTACACTGCAGC AACCTTGGTGTGAAGGTCAACAACTTCTTC GTATAAGAATTCGTGTTCCCACTTATGAAA  5'
```

FIG. 3

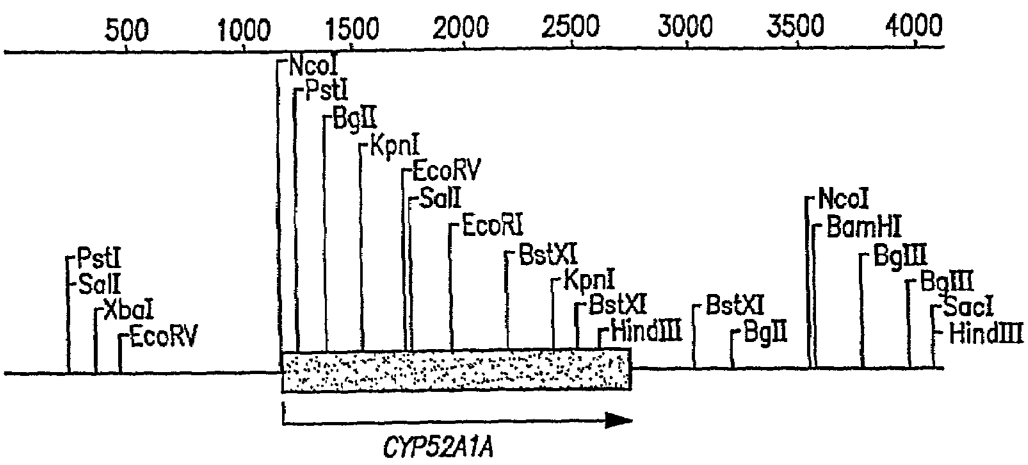
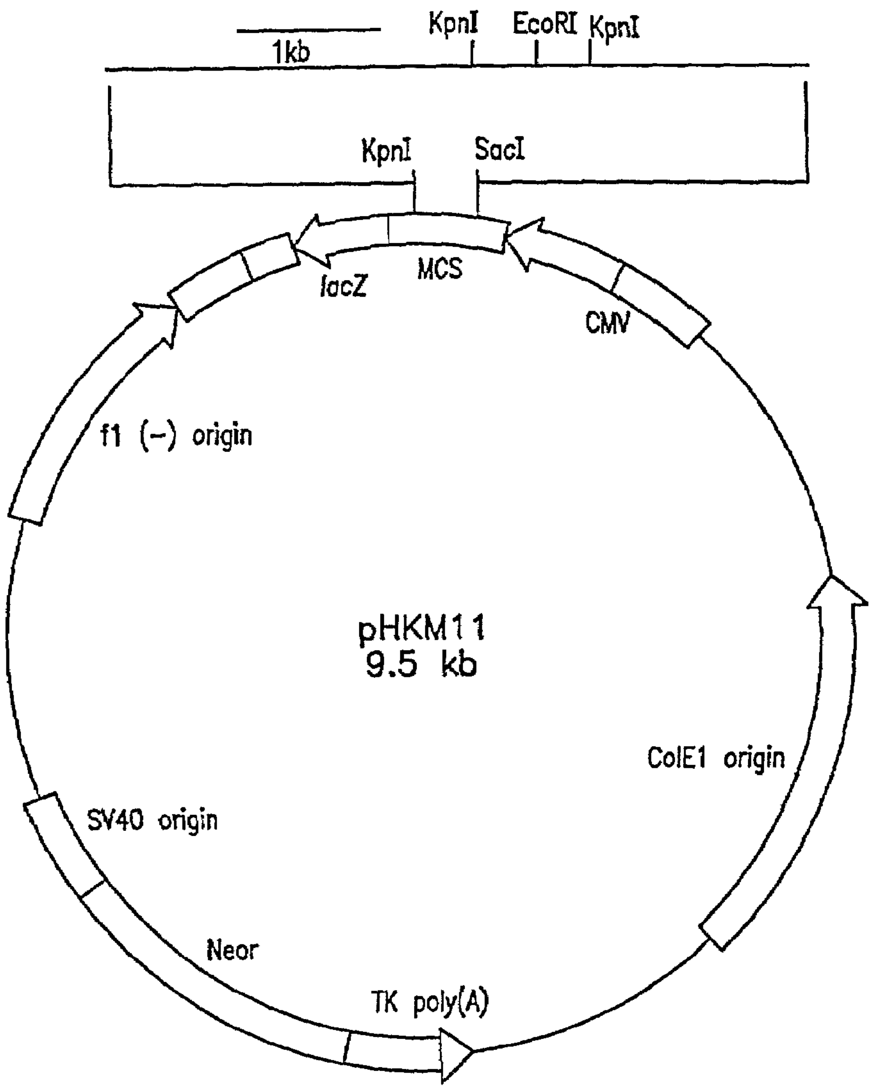
FIG. 8

*C. tropicalis* 20336 CPR Allele DNA Alignment of DS Sequence

```
CPRA     1                                                                  CATCA    5
CPRB     1  TATATGATATATGATATATCTTCCTGTGTAATTATTATTCGTATTCGTTAATACTTACTACATTTTTTTT   70
                                                                               *

CPRA     6  AGATCATCTATGGGGATAATTA-----CGACAGCAACATTGCAGAAAGAGCGTTGGTCACAATCGAAAGA   70
CPRB    71  TCTTTATTTATGAAGAAAAGGAGAGTTCGTAAGTTGAGTTGAGTAGAATAGGCTGTTGTGCATACGGGGA  140
               * ** ****  ** **  *     **  **     ***   * *   * ** *   **     **

CPRA    71  GCCTATG-GCGTTGCCGTCGTTGAGGCAAATGACAGCAC--CAACAATAACGATGGTCCCAGTGAAGAGC  137
CPRB   141  GCAGAGGAGAGTATCCGACGAGGAGGAACTGGGTGAAATTTCATCTATGCTGTTGCGTCCTGTACTGTAC  210
            **  * * * **  *** **  **** *   *     *   ** * **   * **   ** **   *  *

CPRA   138  CTTCAGAACAGTCCATTGTTGACGCT--TAAGGCACGGATAATTACGTGGGGCAAAGGAACGCGGAATTA  205
CPRB   211  TGTAAATCTTAGATTTCCTAGAGGTTGTTCTAGCAAATAAAGTGTTTCAAGATACAATTTTACAGGCAAG  280
              * *          *  * ** * *  *   ***   * * *      *  * *     * *

CPRA   206  GTTATGGGGGGATCAAA--AGCGGAAGATTTGTGTTGCTTGTGGGTTTTTTCCTTTATTTTTCATATGAT  273
CPRB   281  GGTAAAGGATCAACTGATTAGCGGAAGATTGGTGTTGCCTGTGGGGTTCTT---TTATTTTTCATATGAT  347
            * **  **   * *  *  *********** ******* ****** ** **   ****************

CPRA   274  TTCTTTGCGCAAGTAACATGTGCCAATTTAGTTTGTGATTAGCGTGCC-CCACAATTGGCATCGTGGACG  342
CPRB   348  TTCTTTGCGCGAGTAACATGTGCCAATCTAGTTTATGATTAGCGTACCTCCACAATTGGCATCTTGGACG  417
            ********** **************** ****** ********** ** ************** ******

CPRA   343  GGCGTGTTTTGTCATACCCCAAGTCTTAACTAGCTCCACAGTCTCGACGGTGTCTCGACGATGTCTTCTT  412
CPRB   418  GGCGTGTTTTGTCTTACCCCAAGCCTTATTTAGTTCCACAGTCTCGACGGTGTCTCGCCGATGTCTTCTC  487
            ************* ********* ****  *** ********************** ***********
```

FIG. 13A-1

```
CPRA  413  CCACCCCTCCCATGAATCATTCAAAGTTGTTGGGGGATCTCCACCAAGGGCACCGGAGTTAATGCTTATG  482
CPRB  488  CCACCCCTCGCAGGAATCATTCGAAGTTGTTGGGGGATCTCCTCC---------GCAGTTTATGTTCATG  548
           ********* ** ********* ****************** **         * ****  ** * ***

CPRA  483  TTTCTCCCACTTTGGTTGTGATTGGGGTAGTCTAGTGAGTTGGAGATTTTCTTTTTTTCGCAGGTGTCTC  552
CPRB  549  TCTTTCCCACTTTGGTTGTGATTGGGGTAGCGTAGTGAGTTGGTGATTTTCTTTTTT-CGCAGGTGTCTC  617
           * * ************************  *********** ************ ************

CPRA  553  CGATATCGAAATTTGATGAATATAGAGAGAAGCCAGATCAGCACAGTAGATTGCCTTTGTAGTTAGAGAT  622
CPRB  618  CGATATCGAAGTTTGATGAATATAG----GAGCCAGATCAGCATGGTATATTGCCTTTGTAGATAGAGAT  683
           ********** **************      ************* *** ************* *******

CPRA  623  GTTGAACAGCAACTAGTTGAATTACACGCCACCACTTGACAGCAAGTGCAGTGAGCTGTAAACGATGCAG  692
CPRB  684  GTTGAACAACAACTAGCTGAATTACACACCACCGCT----------------------AAACGATGCGC  730
           ******** ******* ********** ***** **                      *********

CPRA  693  CCAGAGTGTCACCACCAACTGACGTTGGGTGGAGTTGTTGTTGTTGTTGTTGGCAGGGCCATATTGCTAA  762
CPRB  731  ACAGGGTGTCACCGCCAACTGACGTTGGGTGGAGTTG---------TTGTTGGCAGGGCCATATTGCTAA  791
            *** ******** ***********************         ************************

CPRA  763  ACGAAGACAAGTAGCACAAAACCCAAGCTTAAGAACAAAAATAAAAAAAATTCATACGACAATTCCAAAG  832
CPRB  792  ACGAAGAGAAGTAGCACAAAACCCAAGGTTAAGAACAA---TTAAAAAAATTCATACGACAATTCCACAG  858
           ******* ****************** **********    * ************************ **

CPRA  833  CCATTGATTTACATAAT--CAACAG-TAAGACAGAAAAAACTTTCAACATTTCAAAGTTCCCTTTTTCCT  899
CPRB  859  CCATTTACATAATCAACAGCGACAAATGAGACAGAAAAAACTTTCAACATTTCAAAGTTCCCTTTTTCCT  928
           ***** *  **   **   * ***  * *******************************************
```

FIG. 13A-2

```
CPRA   900   ATTACTTCTTTTTTTTTCTTCTTTCCTT-------CTTTCCTTCTGTTTTTCTTACTTTATCAGTCTTTTA     962
CPRB   929   ATTACTTCTTTTTTTTCTTTCCTTCCTTTCATTTCCTTTCCTTCTGCTTTTATTACTTTACCAGTCTTTTG     998
             ***************  *** ******      *********** **** ********  *********

CPRA   963   CTTGTTTTTGCAATTCCTCATCCTCCTCCTACTCCTCCTCACCATGGCTTTAGACAAGTTAGATTTGTAT    1032
CPRB   999   CTTGTTTTTGCAATTCCTCATCCTCCTCCT---------CACCATGGCTTTAGACAAGTTAGATTTGTAT    1059
             ******************************         *******************************
```

FIG. 13A-3

```
CPRA   1033  GTCATCATAACATTGGTGGTCGCTGTAGCCGCCTATTTTGCTAAGAACCAGTTCCTTGATCAGCCCCAGG  1102
CPRB   1060  GTCATCATAACATTGGTGGTCGCTGTGGCCGCCTATTTTGCTAAGAACCAGTTCCTTGATCAGCCCCAGG  1129
             ************************** *******************************************

CPRA   1103  ACACCGGGTTCCTCAACACGGACAGCGGAAGCAACTCCAGAGACGTCTTGCTGACATTGAAGAAGAATAA  1172
CPRB   1130  ACACCGGGTTCCTCAACACGGACAGCGGAAGCAACTCCAGAGACGTCTTGCTGACATTGAAGAAGAATAA  1199
             **********************************************************************

CPRA   1173  TAAAAACACGTTGTTGTTGTTTGGGTCCCAGACGGGTACGGCAGAAGATTACGCCAACAAATTGTCCAGA  1242
CPRB   1200  TAAAAACACGTTGTTGTTGTTTGGGTCCCAGACCGGTACGGCAGAAGATTACGCCAACAAATTGTCAAGA  1269
             ********************************* * ****************************** ***

CPRA   1243  GAATTGCACTCCAGATTTGGCTTGAAAACGATGGTTGCAGATTTCGCTGATTACGATTGGGATAACTTCG  1312
CPRB   1270  GAATTGCACTCCAGATTTGGCTTGAAAACCATGGTTGCAGATTTCGCTGATTACGATTGGGATAACTTCG  1339
             ***************************** ****************************************

CPRA   1313  GAGATATCACCGAAGACATCTTGGTGTTTTTCATTGTTGCCACCTATGGTGAGGGTGAACCTACCGATAA  1382
CPRB   1340  GAGATATCACCGAAGATATCTTGGTGTTTTTCATCGTTGCCACCTACGGTGAGGGTGAACCTACCGACAA  1409
             **************** ***************** *********** ******************** **

CPRA   1383  TGCCGACGAGTTCCACACCTGGTTGACTGAAGAAGCTGACACTTTGAGTACCTTGAAATACACCGTGTTC  1452
CPRB   1410  TGCCGACGAGTTCCACACCTGGTTGACTGAAGAAGCTGACACTTTGAGTACTTTGAGATATACCGTGTTC  1479
             *************************************************** **** *** *********

CPRA   1453  GGGTTGGGTAACTCCACGTACGAGTTCTTCAATGCCATTGGTAGAAAGTTTGACAGATTGTTGAGCGAGA  1522
CPRB   1480  GGGTTGGGTAACTCCACCTACGAGTTCTTCAATGCTATTGGTAGAAAGTTTGACAGATTGTTGAGTGAGA  1549
             ***************** ***************** ***************************** ****
```

FIG. 13B-1

```
CPRA   1523  AAGGTGGTGACAGGTTTGCTGAATACGCTGAAGGTGATGACGGTACTGGCACCTTGGACGAAGATTTCAT  1592
CPRB   1550  AAGGTGGTGACAGATTTGCTGAATATGCTGAAGGTGACGACGGCACTGGCACCTTGGACGAAGATTTCAT  1619
             ************* *********** *********** ***** **************************

CPRA   1593  GGCCTGGAAGGACAATGTCTTTGACGCCTTGAAGAATGAATTGAACTTTGAAGAAAAGGAATTGAAGTAC  1662
CPRB   1620  GGCCTGGAAGGATAATGTCTTTGACGCCTTGAAGAATGACTTGAACTTTGAAGAAAAGGAATTGAAGTAC  1689
             ************ ************************** ******************************

CPRA   1663  GAACCAAACGTGAAATTGACTGAGAGAGACGACTTGTCTGCTGCTGACTCCCAAGTTTCCTTGGGTGAGC  1732
CPRB   1690  GAACCAAACGTGAAATTGACTGAGAGAGATGACTTGTCTGCTGCCGACTCCCAAGTTTCCTTGGGTGAGC  1759
             ***************************** ************** *************************

CPRA   1733  CAAACAAGAAGTACATCAACTCCGAGGGCATCGACTTGACCAAGGGTCCATTCGACCACACCCACCCATA  1802
CPRB   1760  CAAACAAGAAGTACATCAACTCCGAGGGCATCGACTTGACCAAGGGTCCATTCGACCACACCCACCCATA  1829
             **********************************************************************

CPRA   1803  CTTGGCCAGAATCACCGAGACGAGAGAGTTGTTCAGCTCCAAGGACAGACACTGTATCCACGTTGAATTT  1872
CPRB   1830  CTTGGCCAGGATCACCGAGACCAGAGAGTTGTTCAGCTCCAAGGAAAGACACTGTATTCACGTTGAATTT  1899
             ********* *********** *********************** *********** ************

CPRA   1873  GACATTTCTGAATCGAACTTGAAATACACCACCGGTGACCATCTAGCTATCTGGCCATCCAACTCCGACG  1942
CPRB   1900  GACATTTCTGAATCGAACTTGAAATACACCACCGGTGACCATCTAGCCATCTGGCCATCCAACTCCGACG  1969
             *********************************************** **********************

CPRA   1943  AAAACATTAAGCAATTTGCCAAGTGTTTCGGATTGGAAGATAAACTCGACACTGTTATTGAATTGAAGGC  2012
CPRB   1970  AAAACATCAAGCAATTTGCCAAGTGTTTCGGATTGGAAGATAAACTCGACACTGTTATTGAATTGAAGGC  2038
             ******* **************************************************************
```

FIG. 13B-2

```
CPRA   2013  GTTGGACTCCACTTACACCATCCCATTCCCAACCCCAATTACCTACGGTGCTGTCATTAGACACCATTTA  2082
CPRB   2040  ATTGGACTCCACTTACACCATTCCATTCCCAACTCCAATTACTTACGGTGCTGTCATTAGACACCATTTA  2109
              ******************** *********** ******** ***************************

CPRA   2083  GAAATCTCCGGTCCAGTCTCGAGACAATTCTTTTTGTCAATTGCTGGGTTTGCTCCTGATGAAGAAACAA  2152
CPRB   2110  GAAATCTCCGGTCCAGTCTCGAGACAATTCTTTTTGTCGATTGCTGGGTTTGCTCCTGATGAAGAAACAA  2179
             ************************************** *******************************

CPRA   2153  AGAAGGCTTTTACCAGACTTGGTGGTGACAAGCAAGAATTCGCCGCCAAGGTCACCCGCAGAAAGTTCAA  2222
CPRB   2180  AGAAGACTTTCACCAGACTTGGTGGTGACAAACAAGAATTCGCCACCAAGGTTACCCGCAGAAAGTTCAA  2249
             ***** **** ******************** *********** ******** *****************
```

FIG. 13B-3

```
CPRA  2223  CATTGCCGATGCCTTGTTATATTCCTCCAACAACGCTCCATGGTCCGATGTTCCTTTTGAATTCCTTATT  2292
CPRB  2250  CATTGCCGATGCCTTGTTATATTCCTCCAACAACACTCCATGGTCCGATGTTCCTTTTGAGTTCCTTATT  2319
            ********************************** ************************* *********

CPRA  2293  GAAAACGTTCCACACTTGACTCCACGTTACTACTCCATTTCGTCTTCGTCATTGAGTGAAAAGCAACTCA  2362
CPRB  2320  GAAAACATCCAACACTTGACTCCACGTTACTACTCCATTTCTTCTTCGTCGTTGAGTGAAAAACAACTCA  2389
            ****** * * ****************************** ******** *********** *******

CPRA  2363  TCAACGTTACTGCAGTTGTTGAAGCCGAAGAAGAAGCTGATGGCAGACCAGTCACTGGTGTTGTCACCAA  2432
CPRB  2390  TCAATGTTACTGCAGTCGTTGAGGCCGAAGAAGAAGCCGATGGCAGACCAGTCACTGGTGTTGTTACCAA  2459
            **** *********** ***** ************** ************************** *****

CPRA  2433  CTTGTTGAAGAACGTTGAAATTGTGCAAAACAAGACTGGCGAAAAGCCACTTGTCCACTACGATTTGAGC  2502
CPRB  2460  CTTGTTGAAGAACATTGAAATTGCGCAAAACAAGACTGGCGAAAAGCCACTTGTTCACTACGATTTGAGC  2529
            ************* ********* ****************************** ***************

CPRA  2503  GGCCCAAGAGGCAAGTTCAACAAGTTCAAGTTGCCAGTGCATGTGAGAAGATCCAACTTTAAGTTGCCAA  2572
CPRB  2530  GGCCCAAGAGGCAAGTTCAACAAGTTCAAGTTGCCAGTGCACGTGAGAAGATCCAACTTTAAGTTGCCAA  2599
            ***************************************** ****************************

CPRA  2573  AGAACTCCACCACCCCAGTTATCTTGATTGGTCCAGGTACTGGTGTTGCCCCATTGAGAGGTTTTGTCAG  2642
CPRB  2600  AGAACTCCACCACCCCAGTTATCTTGATTGGTCCAGGTACTGGTGTTGCCCCATTGAGAGGTTTCGTTAG  2669
            **************************************************************** ** **

CPRA  2643  AGAAAGAGTTCAACAAGTCAAGAATGGTGTCAATGTTGGCAAGACTTTGTTGTTTTATGGTTGCAGAAAC  2712
CPRB  2670  AGAAAGAGTTCAACAAGTCAAGAATGGTGTCAATGTTGGCAAGACTTTGTTGTTTTATGGTTGCAGAAAC  2739
            **********************************************************************
```

FIG. 13C-1

```
CPRA  2713  TCCAACGAGGACTTTTTGTACAAGCAAGAATGGGCCGAGTACGCTTCTGTTTTGGGTGAAAACTTTGAGA  2782
CPRB  2740  TCCAACGAGGACTTTTTGTACAAGCAAGAATGGGCCGAGTACGCTTCTGTTTTGGGTGAAAACTTTGAGA  2809
            **********************************************************************

CPRA  2783  TGTTCAATGCCTTCTCCAGACAAGACCCATCCAAGAAGGTTTACGTCCAGGATAAGATTTTAGAAAACAG  2852
CPRB  2810  TGTTCAATGCCTTCTCTAGACAAGACCCATCCAAGAAGGTTTACGTCCAGGATAAGATTTTAGAAAACAG  2879
            **************** *****************************************************

CPRA  2853  CCAACTTGTGCACGAGTTGTTGACTGAAGGTGCCATTATCTACGTCTGTGGTGATGCCAGTAGAATGGCT  2922
CPRB  2880  CCAACTTGTGCACGAATTGTTGACCGAAGGTGCCATTATCTACGTCTGTGGTGACGCCAGTAGAATGGCC  2949
            *************** ******** ***************************** **************

CPRA  2923  AGAGACGTGCAGACCACAATTTCCAAGATTGTTGCTAAAAGCAGAGAAATTAGTGAAGACAAGGCTGCTG  2992
CPRB  2950  AGAGACGTCCAGACCACGATCTCCAAGATTGTTGCCAAAAGCAGAGAAATCAGTGAAGACAAGGCCGCTG  3019
            ******** ******** ** ************** ************** ************** ****

CPRA  2993  AATTGGTCAAGTCCTGGAAGGTCCAAAATAGATACCAAGAAGATGTTTGGTAGACTCAAACGAATCTCTC  3062
CPRB  3020  AATTGGTCAAGTCCTGGAAAGTCCAAAATAGATACCAAGAAGATGTTTGGTAGACTCAAACGAATCTCTC  3089
            ******************* **************************************************

CPRA  3063  TTTCTCCCAACGCATTTATGAATCTTTATTCTCATTGAAGCTTTACATATGTTCTACACTTTATTTTTTT  3132
CPRB  3090  TTTCTCCCAACGCATTTATGAA----TATTCTCATTGAAGTTTTACATATGTTCTATATTTCATTTTTTT  3155
            **********************    ************** *************** * ** ********

CPRA  3133  TTTTTTTTTTATTATTATATTACGAAACATAGGTCAACTATATATACTTGATTAAATGTTATAGAAACAA  3202
CPRB  3156  TTT----------ATTATATTACGAAACATAGGTCAACTATATATACTTGATTAAATGTTATAGAAACAA  3215
            ***          *********************************************************
```

FIG. 13C-2

```
CPRA  3203  TAACTATTATCTACTCGTCTACTTCTTTGGCATTGACATCAACATTACCGTTCCCATTACCGTTGCCGTT  3272
CPRB  3216  TAATTATTATCTACTCGTCTACTTCTTTGGCATTGGCATTGGCATTGGCATTGGCATTGCCGTTGCCGTT  3285
            *** ******************************* ***   ****  * **  **** ***********

CPRA  3273  GGCAATGCCGGGATATTTAGTACAGTATCTCCAATCCGGATTTGAGCTATTGTAGATCAGCTGCAAGTCA  3342
CPRB  3286  GGTAATGCCGGGATATTTAGTACAGTATCTCCAATCCGGATTTGAGCTATTGTAAATCAGCTGCAAGTCA  3355
            ** *************************************************** ***************

CPRA  3343  TTCTCCACCTTCAACCAGTACTTATACTTCATCTTTGACTTCAAGTCCAAGTCATAAATATTACAAGTTA  3214
CPRB  3356  TTCTCCACCTTCAACCAGTACTTATACTTCATCTTTGACTTCAAGTCCAAGTCATAAATATTACAAGTTA  3425
            **********************************************************************
```

FIG. 13C-3

```
CPRA   3413  GCAAGAACTTCTGGCCATCCACGATATAGACGTTATTCACGTTATTATGCGACGTATGGATGTGGTTATC  3482
CPRB   3426  GCAAGAACTTCTGGCCATCCACAATATAGACGTTATTCACGTTATTATGCGACGTATGGATATGGTTATC  3495
             ********************** ************************************** ********

CPRA   3483  CTTATTGAACTTCTCAAACTTCAAAAACAACCCCACGTCCCGCAACGTCATTATCAACGACAAGTTCTGG  3552
CPRB   3496  CTTATTGAACTTCTCAAACTTCAAAAACAACCCCACGTCCCGCAACGTCATTATCAACGACAAGTTCTGA  3565
             *********************************************************************

CPRA   3553  CTCACGTCGTCGGAGCTCGTCAAGTTCTCAATTAGATCGTTCTTGTTATTGATCTTCTGGTACTTTCTCA  3622
CPRB   3566  CTCACGTCGTCGGAGCTCGTCAAGTTCTCAATTAGATCGTTCTTGTTATTGATCTTCTGGTACTTTCTCA  3635
             **********************************************************************

CPRA   3623  ATTGCTGGAACACATTGTCCTCGTTGTTCAAATAGATCTTGAACAACTTTTTCAACGGGATCAACTTCTC  3692
CPRB   3636  ACTGCTGGAACACATTGTCCTCGTTGTTCAAATAGATCTTGAACAACTTCTTCAAGGGAATCAACTTTTC  3705
             * *********************************************** ***** ** ******** **

CPRA   3693  AATCTGGGCCAAGATCTCCGCCGGGATCTTCAGAAACAAGTCCTGCAACCCCTGGTCGATGGTCTCCGGG  3762
CPRB   3706  GATCTGGGCCAAGATTTCCGCCGGGATCTTCAGAAACAAGTCCTGCAACCCCTGGTCGATGGTCTCGGGG  3775
              ************** ************************************************** ***

CPRA   3763  TACAACAAGTCCAAGGGGCAGAAGTGTCTAGGCACGTGTTTCAACTGGTTCAACGAACATGTTCGACAGT  3832
CPRB   3776  TACAACAAGTCTAAGGGGCAGAAGTGTCTAGGCACGTGTTTCAACTGGTTCAAGGAACATGTTCGACAGT  3845
             *********** ***************************************** ****************

CPRA   3833  AGTTCGAGTTATAGTTATCGTACAACCATTTTGGTTTGATTTCGAAAATGACGGAGCTGATGCCATCATT  3902
CPRB   3846  AGTTCGAGTTATAGTTATCGTACAACCACTTTGGCTTGATTTCGAAAATGACGGAGCTGATCCCATCATT  3915
             **************************** ***** ************************** ********
```

FIG. 13D-1

```
CPRA  3903  CTCCTGGTTCCTCTCATAGTACAACTGGCACTTCTTCGAGAGGCTCAATTCCTCGTAGTTCCCGTCCAAG  3972
CPRB  3916  CTCCTGGTTCCTTTCATAGTACAACTGGCATTTCTTCGAGAGACTCAACTCCTCGTAGTTCCCGTCCAAG  3985
            ************ ***************** *********** ***** *********************

CPRA  3973  ATATTCGGCAACAAGAGCCCGTACCGCTCACGGAGCATCAAGTCGTGGCCCTGGTTGTTCAACTTGTTGA  4042
CPRB  3986  ATATTCGGCAACAAGAGCCCGTAGCGCTCACGGAGCATCAAGTCGTGGCCCTGGTTGTTCAACTTGTTGA  4055
            *********************** **********************************************

CPRA  4043  TGAAGTCCGAGGTCAAGACAATCAACTGGATGTCGATGATCTGGTGCGGGAACAAGTTCTTGCATTTTAG  4112
CPRB  4056  TGAAGTCCGATGTCAAGACAATCAACTGGATGTCGATGATCTGGTGCGGAAACAAGTTCTTGCACTTTAG  4125
            ********** ************************************** ************** *****

CPRA  4113  CTCGATGAAGTCGTACAACTCACACGTCGAGATATACTCCTGTTCCTCCTTCAAGAGCCGGATCCGCAAG  4182
CPRB  4126  CTCGATGAAGTCGTACAACT                                                    4125
            ********************

CPRA  4183  AGCTTGTGCTTCAAGTAGTCGTTG  4206
CPRB  4146                            4145
```

FIG. 13D-2

```
CPRA   MALDKLDLYVIITLVVAVAAYFAKNQFLDQPQDTGFLNTDSGSNSRDVLLTLKKNNKNTL   60
CPRB   MALDKLDLYVIITLVVAVAAYFAKNQFLDQPQDTGFLNTDSGSNSRDVLLTLKKNNKNTL   60

CPRA   LLFGSQTGTAEDYANKLSRELHSRFGLKTMVADFADYDWDNFGDITEDILVFFIVATYGE  120
CPRB   LLFGSQTGTAEDYANKLSRELHSRFGLKTMVADFADYDWDNFGDITEDILVFFIVATYGE  120

CPRA   GEPTDNADEFHTWLTEEADTLSTLKYTVFGLGNSTYEFFNAIGRKFDRLLSEKGGDRFAE  180
CPRB   GEPTDNADEFHTWLTEEADTLSTLRYTVFGLGNSTYEFFNAIGRKFDRLLSEKGGDRFAE  180

CPRA   YAEGDDGTGTLDEDFMAWKDNVFDALKNDLNFEEKELKYEPNVKLTERDDLSAADSQVSL  240
CPRB   YAEGDDGTGTLDEDFMAWKDNVFDALKNDLNFEEKELKYEPNVKLTERDDLSAADSQVSL  240

CPRA   GEPNKKYINSEGIDLTKGPFDHTHPYLARITETRELFSSKDRHCIHVEFDISESNLKYTT  300
CPRB   GEPNKKYINSEGIDLTKGPFDHTHPYLARITETRELFSSKERHCIHVEFDISESNLKYTT  300

CPRA   GDHLAIWPSNSDENIKQFAKCFGLEDKLDTVIELKALDSTYTIPFPTPITYGAVIRHHLE  360
CPRB   GDHLAIWPSNSDENIKQFAKCFGLEDKLDTVIELKALDSTYTIPFPTPITYGAVIRHHLE  360

CPRA   ISGPVSRQFFLSIAGFAPDEETKKAFTRLGGDKQEFAAKVTRRKFNIADALLYSSNNAPW  420
CPRB   ISGPVSRQFFLSIAGFAPDEETKKTFTRLGGDKQEFATKVTRRKFNIADALLYSSNNTPW  420

CPRA   SDVPFEFLIENVPHLTPRYYSISSSSLSEKQLINVTAVVEAEEEADGRPVTGVVTNLLKN  480
CPRB   SDVPFEFLIENIQHLTPRYYSISSSSLSEKQLINVTAVVEAEEEADGRPVTGVVTNLLKN  480
```

FIG. 14A

```
CPRA    VEIVQNKTGEKPLVHYDLSGPRGKFNKFKLPVHVRRSNFKLPKNSTTPVILIGPGTGVAP   540
CPRB    IEIAQNKTGEKPLVHYDLSGPRGKFNKFKLPVHVRRSNFKLPKNSTTPVILIGPGTGVAP   540

CPRA    LRGFVRERVQQVKNGVNVGKTLLFYGCRNSNEDFLYKQEWAEYASVLGENFEMFNAFSRQ   600
CPRB    LRGFVRERVQQVKNGVNVGKTLLFYGCRNSNEDFLYKQEWAEYASVLGENFEMFNAFSRQ   600

CPRA    DPSKKVYVQDKILENSQLVHELLTEGAIIYVCGDASRMARDVQTTISKIVAKSREISEDK   660
CPRB    DPSKKVYVQDKILENSQLVHELLTEGAIIYVCGDASRMARDVQTTISKIVAKSREISEDK   660

CPRA    AAELVKSWKVQNRYQEDVW                                            680
CPRB    AAELVKSWKVQNRYQEDVW                                            680
```

FIG. 14B

*C. tropicalis* 20336 *CYP52* DNA Alignment of DS Sequence

```
CYP52A1A    1                                                                      0
CYP52A2A    1  GACCTGTGACGCTTCCGGTGTCTTGCCACCAGTCTCCAAGTTGACCGACGCCCAAGTCATGTACCACTTT  70
CYP52A2B    1                                                                      0
CYP52A3A    1                                                           GACATCATAAT  11
CYP52A3B    1                                                                      0
CYP52A5A    1                                                                      0
CYP52A5B    1                                                          TTACAATCATGG  12
CYP52A8A    1                                                                      0
CYP52A8B    1                                                                      0
CYP52D4A    1                                                                      0

CYP52A1A    1             CATATGCGCTAATCTTCTTTTTCTTTTTATCACAGGAGAAACTATCCCACCCCCACTTC  59
CYP52A2A   71  ATTTCCGGTTACACTTCCAAGATGGCTGGTACTGAAGAAGGTGTCACGGAACCACAAGCTACTTTCTCCG 140
CYP52A2B    1                                                                      0
CYP52A3A   12  GACCCGGTTATTTCGCCCTCAGGTTGCTTATTTGAGCCGTAAAGTGCAGTAGAAACTTTGCCTTGGGTTC  81
CYP52A3B    1                                                                      0
CYP52A5A    1                                                               TGGAGTC   7
CYP52A5B   13  AGCTCGCTAGGAACCCAGATGTCTGGGAGAAGCTCCGCGAAGAGGTCAACACGAACTTTGGCATGGAGTC  82
CYP52A8A    1                                                                      0
CYP52A8B    1                                                                      0
CYP52D4A    1                                                                      0
```

FIG. 15A-1

| | | | |
|---|---|---|---|
| CYP52A1A | 60 | GAAACACAATGACAACTCCTGCGTAACTTGCAAATTCTTGTCTGACTAATTGAAAACTCCGGACGAGTCA | 129 |
| CYP52A2A | 141 | CTTGTTTCGGTCAACCATTCTTGGTGTTGCACCCAATGAAGTACGCTCAACAATTGTCTGACAAGATCTC | 210 |
| CYP52A2B | 1 | GCTCAACAATTGTCTGACAAGATCTC | 26 |
| CYP52A3A | 82 | AAACTCTAGTATAATGGTGATAACTGGTTGCACTCTTGCCATAGGCATGAAAATAGGCCGTTATAGTACT | 151 |
| CYP52A3B | 1 | | 0 |
| CYP52A5A | 8 | GCCAGACTTGCTCACTTTTGACTCCCTTCGAAACTCAAAGTACGTTCAGGCGGTGCTCAACGAAACGCTC | 77 |
| CYP52A5B | 83 | GCCAGACTTGCTCACTTTTGACTCTCTTAGAAGCTCAAAGTACGTTCAGGCGGTGCTCAACGAAACGCTT | 152 |
| CYP52A8A | 1 | | 0 |
| CYP52A8B | 1 | AAAACCGATACAAGAAGAAGACAGTCAA | 28 |
| CYP52D4A | 1 | | 0 |
| | | | |
| CYP52A1A | 130 | GACCTCCAGTCAAACGGACAGACAGACAAACACTTGGTGCGATGTTCATACCTACAGACATGTCAACGGG | 199 |
| CYP52A2A | 211 | GCAACACAAGGCTAACGCCTGGTTGTTGAACACCGGTTGGGTTGGTTCTTCTGCTGCTAGAGGTGGTAAG | 280 |
| CYP52A2B | 27 | GCAACACAAGGCTAACGCCTGGTTGTTGAACACTGGTTGGGTTGGTTCTTCTGCTGCTAGAGGTGGTAAG | 96 |
| CYP52A3A | 152 | ATATTTAATAAGCGTAGGAGTATAGGATGCATATGACCGGTTTTTCTATATTTTTAAGATAATCTCTAGT | 221 |
| CYP52A3B | 1 | CCTGCAGA | 8 |
| CYP52A5A | 78 | CGTATCTACCCGGGGGTACCACGAAACATGAAGACAG--CTACGTGCAACACGACGTTGCCACGCGGAGG | 145 |
| CYP52A5B | 153 | CGTATCTACCCGGGGGTGCCACGAAACATGAAGACAG--CTACGTGCAACACGACGTTGCCGCGTGGAGG | 220 |
| CYP52A8A | 1 | | 0 |
| CYP52A8B | 29 | CAAGAACGTTAATGTCAACCAGGCGCCAAGAAGACGG--TTTGGCGGACTTGGAAGAATGTGGCATTTGC | 96 |
| CYP52D4A | 1 | | 0 |

FIG. 15A-2

| | | | |
|---|---|---|---|
| CYP52A1A | 200 | TGTTAGACGACGGTTTCTTGCAAAGAC-AGGTGTTGGCATCTCGTACGATGGCAACTGCAGGAGGTGTCG | 268 |
| CYP52A2A | 281 | AGATGCTCATTGAAGTACACCAGAGCCATTTTGGACGCTATCCACTCTGGTGAATTGTCCAAGGTTGAAT | 350 |
| CYP52A2B | 97 | AGATGTTCATTGAAGTACACCAGAGCCATTTTGGACGCTATCCACTCTGGTGAATTGTCCAAGGTTGAAT | 166 |
| CYP52A3A | 222 | AAATTTTGTATTCTCAGTAGGATTTCATCAAATTTCGCAACCAATTCTGGCGAAAAAATGATTCTTTTAC | 291 |
| CYP52A3B | 9 | ATTCGCGGCCGCGTCGACAGAGTAGCAGTTATGCAAGCATGTGATTGTGGTTTTTGCAACCTGTTTGCAC | 78 |
| CYP52A5A | 146 | AGGCA-AAGACGGCAAGGAACCTATCT-TGGTGCAGAAGGGACAGTCCGTTGGGTTGATTACTATTGCCA | 213 |
| CYP52A5B | 221 | AGGCA-AAGACGGTAAGGAACCTATTT-TGGTGCAGAAGGGCCAGTCCGTTGGGTTGATTACTATTGCCA | 288 |
| CYP52A8A | 1 | | 0 |
| CYP52A8B | 97 | CCATG-ATGTTTATGTTCTGGAGAGGT-TTTTCAAGGAATCGTCATCCTCCGCCACCACAAGAACCACCA | 164 |
| CYP52D4A | 1 | | 0 |

FIG. 15A-3

| | | | |
|---|---|---|---|
| CYP52A1A | 269 | ACTTCTCCTTTAGGCAATAGAAAAAGACTAAGAGAACAGCGTTTTTACAGGTTGCATTGGTTAATGTAGT | 338 |
| CYP52A2A | 351 | ACGAAACTTTCCCAGTCTTCAACTTGAATGTCCCAACCTCCTGTCCAGGTGTCCCAAGTGAAATCTTGAA | 420 |
| CYP52A2B | 167 | ACGAGACTTTCCCAGTCTTCAACTTGAATGTCCCAACCTCCTGCCCAGGTGTCCCAAGTGAAATCTTGAA | 236 |
| CYP52A3A | 292 | GTCAAAAGCTGA-ATAGTGCAGTTTAAAGCACCTAAAATCACATATACAGCCTCTAGATACGACAGAGAA | 360 |
| CYP52A3B | 79 | GACAAATGATCG-ACAGT-CGATT--ACGTAATCCATATTATTTAGAGGGGTAATAAAAAATAAATGGCA | 144 |
| CYP52A5A | 214 | CGCAGACGGACCCAGAGTATTTTGGGGCCGACGCTGGTGAGTTTAAGCCGGAGAGATGGTTTGATTCA-- | 281 |
| CYP52A5B | 289 | CGCAGACGGACCCAGAGTATTTTGGGGCAGATGCTGGTGAGTTCAAACCGGAGAGATGGTTTGATTCA-- | 356 |
| CYP52A8A | 1 | | 0 |
| CYP52A8B | 165 | GTTAACGAGATCCATATTCACAACCCACCGCAAGGTGACAATGCTCAACAACAACAGCAACAACAACA-- | 232 |
| CYP52D4A | 1 | | 0 |
| | | | |
| CYP52A1A | 339 | ATTTTTTTAGTCCCAGCATTCTGTGGGTTGCTCTGGGTTTCTAGAATAGGAAATCACAGGAGAATGCAAA | 408 |
| CYP52A2A | 421 | CCCAACCAAGGCCTGGACCGG-AAGGTGTTGACTCCTTCAACAAGGAAATCAAGTCTTTGGCTGGTAAGT | 489 |
| CYP52A2B | 237 | CCCAACCAAGGCCTGGACCG--AAGGTGTTGACTCCTTCAACAAGGAAATCAAGTCTTTGGCTGGTAAGT | 304 |
| CYP52A3A | 361 | GCTCTTTATGATCTGAAGAAGCATTAGAATAGCT---ACTATGAGCCACTATTGGTGTATATATTAGGGA | 427 |
| CYP52A3B | 145 | GCC----AGAATTTCAAACATTTTGCAAACAATGCAAAAGATGAGAAACTCCAACAGAAAAAAATAAAAAA | 210 |
| CYP52A5A | 282 | AGCATGAAGAACTTGGGGTGTAAATACTTGCCGTTCAATGCTGGGCCACGGACTTGCTTGGGGCAGCAGT | 351 |
| CYP52A5B | 357 | AGCATGAAGAACTTGGGGTGTAAGTACTTGCCGTTCAATGCTGGGCCCCGGACTTGTTTGGGGCAGCAGT | 426 |
| CYP52A8A | 1 | | 0 |
| CYP52A8B | 233 | ACCCCCACAAGAACAGTGGAATAATGCCAGTCAA-CAAAGAGTGGTGACAGACGAGGGAGAAAACGCAAG | 301 |
| CYP52D4A | 1 | | 0 |

FIG. 15B-1

```
CYP52A1A  409  TTCAGATGGAAGAACAAAGAGATAAAAAACAAAAAAAAACTGAGTTTTGCACCAATAGAATGTTTG----  474
CYP52A2A  490  TTGCTGAAAAC--TTCAAGACCTATGCTGACCAAGCTACCGCTGA--AGTGAGAGCTGCAGGTCCAGAAG  555
CYP52A2B  305  TTGCTGAAAAC--TTCAAGACCTATGCTGACCAAGCTACCGCTGA--AGTTAGAGCTGCAGGTCCAGAAG  370
CYP52A3A  428  TTGGTGCAATTAAGTACGTACTAATAAACAGAAGAAAATACTTAACCAATTTCTGGTGTATACTTAGTGG  497
CYP52A3B  211  ACTCCGCAGC--ACTCCGAACCAACAAAACAATGGGGGGCGCCAG--AATTATTGAC---TATT------  267
CYP52A5A  352  ACACTTTGATTGAAGCGAGCTACTTGCTAGTCCGGTTGGCCCAGACCTAC-CGGGCAATAGATTTG----  416
CYP52A5B  427  ACACTTTGATTGAAGCGAGCTATTTGCTAGTCAGGTTGGCGCAGACCTAC-CGGGTAATCGATTTG----  491
CYP52A8A    1                                                                          0
CYP52A8B  302  CAACAGTGGTTCTGATGCAAGATCAGCTACACCGCTTCATCAGGAAAAGC-AGGAGCTCCCACCAC----  366
CYP52D4A    1            GATGTGGTGCTTGATTTCTCGAGACACATCCTTGTGAGGTGCCATGAATCTGTACCTG----   58

CYP52A1A  475  -ATGATATCATCCACTCGCTAAACGAATCATGTGGGTGATCTTCTCTTTAGTTTTGGTCTATCATAAAAC  543
CYP52A2A  556  CTTAAAGATATTTATTCATTATTTAGTTTGCCTATTTATTTCTCATTACCCATC-ATCATTCAACACTAT  624
CYP52A2B  371  CTTAAAGATATTTATTCACTATTTAGTTTGCCTATTTATTTCTCATCACCCATC-ATCATTCAACAATAT  439
CYP52A3A  498  -TGAGGGACCTTTTCTGAACATTCGGGTCAAACTTTTTTTGGAGTGCGACATCGATTTTTCGTTTGTGT  556
CYP52A3B  268  ----GTGACTTTTTTTTATTTTTTCCGTTAA--CTTTCATTGCAGTGAAGTGT--GTTACACGGGGTGGT  329
Cyp52A5A  417  -CAGCCAGGATCGGCGTACC-CACCAAGAAAGAAGTCGTTGATCAACATGAGTGCTGCCGACGGGGTGTT  484
CYP52A5B  492  -CTGCCAGGGTCGGCGTACC-CACCAAGAAAGAAGTCGTTGATCAATATGAGTGCTGCCGATGGGGTGGT  559
CYP52A8A    1                                                                          0
CYP52A8B  367  -CATATGCCCATCACGAGCAACACCAGCAGGTTAGTGTATAGTAGTCTGTAGTTAAGTCAATGCAATGTA  435
CYP52A4A   59  -TCTGTAAGCACAGGGAACTGCTTCAACACCTTATTGCATATTCTGTCTATTGCAAGCGTGTGCTGCAAC  127
```

FIG. 15B-2

```
CYP52A1A  544  ACATGAAAGTGAAATCCAAA-TACACTACACTCCGGGTATTGTCCTTCGTTTTACAGATGTCTCATTGTC  612
CYP52A2A  625  ATATAAAGTTACTTCGGA-----------TATCATTGTAATCGTGCGTGTCGCAATTGGATGATTTGGAA  683
CYP52A2B  440  ATATAAAGTTATTTCGGAAC-TCATA---TATCATTGTAATCGTGCGTGTTGCAATTGGGTAATTTGAAA  505
CYP52A3A  567  AATAATAGTGAACCTTTGTG-TAATAAATCTTCATGCAAGACTTGCATAATTCGAGCTTGGGAGTTCACG  635
CYP52A3B  330  GATGGTGTTGGTTTCTACAA-TGCAAGGGCACAGTTGAAGGTTTCCACATAACGT-TGCACCATATCAAC  397
CYP52A5A  485  TGT--AAAGCTTTATAAGGA-TGTAACGGTAGATGGATAGTTGTGTAGGAGGAGCGGAGATAAATTAGAT  551
CYP52A5B  560  TGT--AAAGTTTCACAAGGA-TCTAGATGGATATGTA-AGGTGTGTAGGAGGAGCGGAGATAAATTAGAT  625
CYP52A8A    1                                                                           0
CYP52A8B  436  CCA--ATAAGACTATCCCTT-CTTACAACCAAGTTTTCTGCCGCGCCTGTCTGGCA-ACAGATGCTGGCC  501
CYP52D4A  128  GATATCTGCCAAGGTATATAGCAGAACGTGCTGATGGTTCCTCCGGTCATATTCTGTTGGTAGTTCTGCA  197
```

FIG. 15B-3

```
CYP52A1A   613  TTACTTTTGAGGTCATAGGAGTTGCCTGTGAGAGATCACAGAGATTATCACACTCACATTTATCGTAGTT  682
CYP52A2A   684  CTGCGCTTGAAACGGATTCATGCACGAAGCGGAGA-TAAAAGATTACGT---AATTTATCTCCTGAGACA  749
CYP52A2B   506  CTGTAGTTGGAACGGATTCATGCACGATGCGGAGA-TAACACG---------AGATTATCTCCTAAGACA  565
CYP52A3A   636  C--CAATTTGACCTCGTTCATGTGATAAAAGAAAAGCCAAAAGGTAATT---AGCAGACGC---AATGGG  697
CYP52A3B   398  T--CAATTTATCCTCATTCATGTGATAAAAGAAGAGCCAAAAGGTAATT---GGCAGACCCCCCAAGGGG  462
CYP52A5A   552  TTGATTTTG---TGTAAGGTTTTGGATGTCAACCTACTCCGCACTTCATGCA-GTGTGTGTGACACAAGG  617
CYP52A5B   626  TTGATTTTG---TGTAAGGTTTAGCACGTCAAGCTACTCCGCACTTTGT----GTGTAGGGAGCACA---  685
CYP52A8A     1                                                                           0
CYP52A8B   502  GACACACTT---TCAACTGAGTTTGGTCTAGAATTCTTGCACATGCACGACA-AGGAAACTCTTACAAAG  567
CYP52D4A   198  GGTAAATTTGGATGTCAGGTAGTGGAGGGAGGTTTGTATCGGTTGTGTT-TTCTTCTTCCTCTCTCTCTG  266

CYP52A1A   683  TCCTATCTCATGCTGTGTGTCTCTGGTTGGTTCATGAGTTTGGATT--GTTGTACATTAAAGGAATCGCT  750
CYP52A2A   750  ATTTTAGCCGTGTTCACACGCCCTTCTTTGTT-CTGAGCGAAGGAT--AAATAATTAGACTTCCACAGCT  816
CYP52A2B   566  ATTTTGGCCTCATTCACACGCCCTTCTT-----CTGAGCTAAGGAT--AAATAATTAGACTTCACAAGTT  628
CYP52A3A   698  AACATGGAGTGGAAAGCAATGGAAGCACGCCC-AGGACGGAGTAATTTAGTCCACACTACATCTGGGGGT  766
CYP52A3B   463  AACACGGAGTAGAAAGCAATGGAAACACGCCC-ATGACAGTGCCATTTAGCCCACAACACATCTAGTATT  531
CYP52A5A   618  GTGTACTACGTGTGCGTGTGCGCCAAGAGACA---GCCCAAGGGGG--TGGTAGTGT-GTGTTGGCGGAA  681
CYP52A5B   686  ---TACTCCGTCTGCGCCTGTGCCAAGAGACG---GCCCAGGGG-------TAGTGT-GTGGTGGTGGAA  741
CYP52A8A     1     GAATTCTTTGGATCTAATTCCAGCTGATC---TTGCTAATCCT--TATCAACGTAGTTGTGATCATT   62
CYP52A8B   568  --ACAACACTTGTGCTCTGATGCCACTTGATC---TTGCTAAGCCT--TATCAACGTAATTGAGATCATT  630
CYP52D4A   267  ATTCAACCTCCACGTCTCCTTCGGGTTCTGTGTCTGTGTCTGAGTC--GTACTGTTGGATTAAGTCCATC  334
```

FIG. 15C-1

```
CYP52A1A   751  GGAAAGCAAAGCTAACTAAATTTTCTTTGTCACAGGTACACTAACCTGTAAAACTTCACTGCCACGCCAG  820
CYP52A2A   817  CATTCTAATTTCCGT---CACGCGAATATTGAA-------------GGGGGGTACATGTGGCCGCTGAA-  869
CYP52A2B   629  CATTAAAATATCCGT---CACGCGAAAACTGCAACAATAAGGAAGGGGGGGTAGACGTAGCCGATGAA-  694
CYP52A3A   767  ----TTTTTTTTTGTGCGCAAGTACACACCTGGACT-TTAGTTTTTGCCCCATAAAGTTAACAATCTAA-  830
CYP52A3B   532  CTTTTTTTTTTTTGTGCGCAGGTGCACACCTGGACT-TTAGTTATTGCCCCATAAAGTTAACAATCTCA-  599
CYP52A5A   682  GTGCATGTGACACA---ACGCGTGGGTTCTGGCCAATGGTGGACTAAGTGCAGGTAAGCAGCGACCTGAA  748
CYP52A5B   742  GTGCATGTGACACA---ATACCCTGGTTCTGGCCAATTGGGGATTTAGTGTAGGTAAGCTGCGACCTGAA  808
CYP52A8A    63  GTTTGTCTGAATTAT--ACACACCAGTGGAAGAATATGGTCTAATTTGCACGTCCCACTGGCATTGTG--  128
CYP52A8B   631  GTTTGTCTGAATTAT--ACACACCAGTGGAAGAATCTGGTCTAATCTGCACGCCTCATGGGCATTGTG--  696
CYP52D4A   335  GCATGTGTGAAAAAAAGTAGCGCTTATTTAGACAACCAGTTCGTTGGGCGGGTATCAGAAATAGTCTGTT  404

CYP52A1A   821  TCTTTCCTGATTGGGCAAGTGCACAAACTACA-ACCTGCAAAACAG----CACTCCGCTTGTCACAGGTT  885
CYP52A2A   870  -TGTGGGGG--CAGTAAACGCAGTCTCTC-------------------CTCTCCCAGGAATAGTGCAACGG  918
CYP52ACB   695  -TGTGGGGTGCCAGTAAACGCAGTCTCTCTCTCCCCCCCCCCCCCCCCCCCTCAGGAATAGTACAACGG  763
CYP52A3A   831  -CCTTTGGC-TCTCCAACTCTCTCCGCCCCCAAATATTCGTTTTT-ACACCCTCAAGCTAGCGACAGCAC  897
CYP52A3B   600  -CCTTTGGC-TCTCCCAGTGTCTCCGCCTCCAGATGCTCGTTTT--ACACCCTCGAGCTAACGACAACAC  665
CYP52A5A   749  ACATTCCTCAACGCTTAAGACACTGGTGG-TAGAGATGCGGACCAGG-----CTATTCTTGTCGT-GCTA  811
CYP52A5B   809  ACACTCCTCAACGCTTGAGACACTGGTGGGTAGAGATGCGGGCCAGGA--GGCTATTCTTGTCGT-GCTA  875
CYP52A8A   129  -TGTTT-----GTGGGGGGGGGGGGTGCACACATTTTTAGTGCCA----TTCTTTGTTGATTAC-CCCT  187
CYP52A8B   697  -TGTTTT--GGGGGGGGGGGGGGGGTGCACACATTTTTAGTGCGAATGTTTGTTTGCTGGTTCC-CCCT  762
CYP52D4A   405  GTGCACGACCATGAGTATGCAACTTGACGAGACGTCGTTAGGA-----ATCCACAGAATGATAGCAGGAA  469
```

FIG. 15C-2

```
CYP52A1A   886   GTCTCCTCTCAACCAACAAAAAAATAAGATTAAACTTTCTTTGCTCATGCATCAATCGGAGTTATCTCTG   955
CYP52A2A   919   AGGAAGGATAACGGATAGAAAGCGGAATGCGAGGAAAAT--TTTGAACGCGCAAGAAAAGCAATATCCGG   986
CYP52A2B   764   GGGAAGGATAACGGATAGCAAGTGGAATGCGAGGAAAAT--TTTGAATGCGCAAGGAAAGCAATATCCGG   831
CYP52A3A   898   AACACCCATTAGAGGAATGGGGCAAAGTTAAACACTTTTGGCTTCAATGATTCCTATTCGCTACTACATT   967
CYP52A3B   666   AACACCCATGAGGGGAATGGG-CAAAGTTAAACACTTTTGGTTTCAATGATTCCTATTTGCTACT-----   729
CYP52A5A   812   CCCGGCGCATGGA-AAATCAACTGCGGGAAGAA--TAAATTTATCCGTAGAATCCACAGAGCG------G   872
CYP52A5B   876   CCCG-TGCACGGA-AAATCGATTGAGGGAAGAA--CAAATTTATCCGTGAAATCCACAGAGCG------G   935
CYP52A8A   188   CCCCCCTATCAT---TCATTCCCACAGGATTAG--TTTTTTCCTCACTGGAATTCGCTGTCC--------   244
CYP52A8B   763   CCCCCCTCCCCCCTATCATGCCCACAGGATTAG--TTTTTTCCTCACTGGAATTCGCTGTCC--------   822
CYP52D4A   470   GCTTACTACGTGAGAGATTCTGCTTAGAGGATG--TTCTCTTCTTGTTGATTCCATTAGGTGGGTATCAT   537
```

FIG. 15C-3

```
CYP52A1A   956  A--AAGAGTTGCCTTTGTGTAATGTGTCCCAAA-CTCAAACTGCAAAACTAACCACAGAATGAT------  1016
CYP52A2A   987  GCTACCAGGTTTTGAGCCAGGGAACACACTCCTATTTCTGCTCAATGACTGAACATAGAAAAAA------  1050
CYP52A2B   832  GCTATCAGGTTTTGAGCCAGGGGACACACTCCT-CTTCTGCACAAAAACTTAACGTAGACAAAAAAAAAA   900
CYP52A3A   968  CTTCTCTTGTTTTGTGCTTTGAATTGCACCATGTGAAATAAACGACAATTATATATACCTTTTCATC---  1034
CYP52A3B   730  ---CTCTTGTTTTGTGTTTTGATTTGCACCATGTGAAATAAACGACAATTATATATACCTTTTCGTC---   793
CYP52A5A   873  A--TAAATTTGCCCACCTCCATCATCAACCACG-CCGCCACTAACTACATCACTCCCCTATTTT------   933
CYP52A5B   936  A--TAAATTTGTCACATTGCTGCGTTGCCCAC------------CCACAGCATTCTC-------------   978
CYP52A8A   245  ------ACCTGTCAACCCCCCCCCCCCCCCCCCC-CCACTGCC--CTACCCTGCCCTGC-----------   293
CYP52A8B   823  ------ACCTGTCAACCCCCTCAC---------------------TGCCCTGCCCTGC------------   853
CYP52D4A   538  CTCCGGTGGTGACAACTTGACACAAGCAGTTCCGAGAACCACCCACAACAATCACCATTCCAGC------   601

CYP52A1A  1017  TTCCCTCACAATTATATAAACTCACCCACATTTCCACAGACCGTAATTTCATGTCTCAC-TTTCTCTTTT  1085
CYP52A2A  1051  -----CACCAAGACGCAATGAAACGCACATGGACATTTAGACCTCCCCACATGTGATAGTTTGTCTTAAC  1115
CYP52A2B   901  AACTCCACCAAGACACAATGAATCGCACATGGACATTTAGACCTCCCCACATGTGAAAGCTTCTCTGGCG   970
CYP52A3A  1035  CCTCCTCCTATATCTCTTTTTGCTAC-ATTTTGTTTTTTACGTTTCTTGCTTTTGCACTCTCCCACTCCC  1103
CYP52A3B   794  TGTCCTCCAATGTCTCTTTTTGCTGCCATTTTGCTTTTTGCTTTTTGCTTTTGCACTCTCTCCCACTCCC   863
CYP52A5A   934  CTCTCTCTCTCTTTGTCTTACTCCGCTCCCGTTTCCTTAGCCACAGATACACACCCACT-GCAAACAGCA  1002
CYP52A5B   979  TTTTCTCTCTCTTTGTCTTACTCCGCTCCTGTTTCCTTATCCAGAAATACACACCAACTCATATAAAGAT  1048
CYP52A8A   294  CCTGCACGTCCTGTGTTTTGTGCTGTGTCTTTCCCACGCTATAAAAGCCCTGGCGTCCGGCCAAGGTTTT   363
CYP52A8B   854  CCTGCACGCCCTGTGTTTTGTGCTGTGGCACTCCCACGCTATAAAAGCCCTGGCGTACGGCCAAGGTTTT   923
CYP52D4A   602  TATCACTTCTACATGTCAACCTACGATGTATCTCATCACCATCTAGTTTCTTGGCAATCGTTTATTTGTT   671
```

FIG. 15D-1

```
CYP52A1A 1086  GCTCTTCTTTTACTTAGTCAGGTTTGATAACTTCCTTTTTATTACCCTATCTTATTTATTTATTTATTC  1155
CYP52A2A 1116  AGA------AAAGTATAATAAGAACCCATGCCGTCCCTTTTCTTTCGCCGCTTCAACTTTTTTTTTTTTA  1179
CYP52A2B  971  AAAGCAAAAAAAGTATAATAAGGACCCATGCCTTCCCTCTTCCTGGGCCGTTTCAACTTTTTCTTTTTCT  1040
CYP52A3A 1104  ACAA---------------------------AGAAAAAAAAACTACACTATGTCGTCTTCTCCATCGTTT  1146
CYP52A3B  864  ACAATCAGTGCAGCAACACACAAAGAAGAAAAATAAAAAAACCTACACTATGTCGTCTTCTCCATCGTTT   933
CYP52A5A 1003  GCA--ACAATTATAAAGATACGCC-----AGGCCCACCTTCTTTCTTTTTCTTCACTTTTTTGACTGC-A  1064
CYP52A5B 1049  ACG--CTAGCCCAGCTGTCTTTCT-----TTTTCTTCACTTTTTTTGGTGTGTTGCTTTTTTGGCTGC-T  1110
CYP52A8A  364  TCCACCCAGCCAAAAAAACAGTCTAAAAAATTTGGTTGATCCTTTTTGGTTGCAAGGTTTT---CCAC-C   429
CYP52A8B  924  TCCTCACAGCCAAAAAAA----------AATTTGGCTGATCCTTTTGGGCTGCAAGGTTTTTCACCAC-C   982
CYP52D4A  672  ATGGGTCAACATCCAATACAACTCCACCAA--TGAAGAAGAAAAACGGAAAGCAGAATACCAGAATGACA   739

CYP52A1A 1156  ATTTATACCAACCAACC--AACCATGGCCACACAAGAAATCATCGATTCTGTACTTCCGTACTTGACCAA  1223
CYP52A2A 1180  TCTT------------ACACACATCACGACCA-TGACTGTACACGATATTATCGCCACATACTTCACCAA  1236
CYP52A2B 1041  TTGTCTATCAACACACACACACCTCACGACCA-TGACTGCACAGGATATTATCGCCACATACATCACCAA  1109
CYP52A3A 1147  GCCC-------AAGAGGTTCTCGCTACCACTAGTCCTTACATCGAGTACTTTCTTGACA-ACTACACCAG  1208
CYP52A3B  934  GCTC-------AGGAGGTTCTCGCTACCACTAGTCCTTACATCGAGTACTTTCTTGACA-ACTACACCAG   995
CYP52A5A 1065  ACTTTCTACAATCCACCACAGCCACCACCACAGCCGCTATGATTGAACAACTCCTAGAATATT-------  1127
CYP52A5B 1111  ACTTTCTACAACC-------ACCACCACCACCACCACCATGATTGAACAAATCCTAGAATATT-------  1166
CYP52A8A  430  ACCACTTCCACCA--CCTCAACTATTCGAACAA--AAGATGCTCGATCAGATCTTACATTACT-------   488
CYP52A8B  983  ACCACCACCACCA--CCTCAACTATTCAAACAA--AGGATGCTCGACCAGATCTTCCATTACT-------  1041
CYP52D4A  740  GTGTG----AGTTCCTGACCATTGCTAATCTA-TGGCTATATCTAGTTTGCTATCGTGGGATG-------   797
```

FIG. 15D-2

```
CYP52A1A 1224  ATGGTACACTGTGATTACTGCAGCAGTATTAGTCTTCCTTATCTCCACAAACATCAAGAACTACGTCAAG  1293
CYP52A2A 1237  ATGGTACGTGATAGTACCACTCGCTTTGATTGCTTATAGAGTCCTCGACTACTTCTATGGCAGATACTTG  1306
CYP52A2B 1110  ATGGTACGTGATAGTACCACTCGCTTTGATTGCTTATAGGGTCCTCGACTACTTTTACGGCAGATACTTG  1179
CYP52A3A 1209  ATGGTACTACTTCATACCTTTGGTGCTTCTTTCGTTGAACTTTATAAGTTTGCTCCACACAAGGTACTTG  1278
CYP52A3B  996  ATGGTACTACTTCATCCCTTTGGTGCTTCTTTCGTTGAACTTCATCAGCTTGCTCCACACAAAGTACTTG  1065
CYP52A5A 1128  --GGTATGTCGTTGTGCCAGTGTTGTACATCATCAAACAACTCCTTGCATACACAAAGACTCGCGTCTTG  1195
CYP52A5B 1167  --GGTATATTGTTGTGCCTGTGTTGTACATCATCAAACAACTCATTGCCTACAGCAAGACTCGCGTCTTG  1234
CYP52A8A  489  --GGTACATTGTCTTGCCATTGTTGGCCATTATCAACCAGATCGTGGCTCATGTCAGGACCAATTATTTG   556
CYP52A8B 1042  --GGTACATTGTCTTGCCATTGTTGGTCATTATCAAGCAGATCGTGGCTCATGCCAGGACCAATTATTTG  1109
CYP52D4A  798  -TGATCTGTGTCGTCTTCATTTGCGTTTGTGTTTATTTCGGGTAT-GAATATTGTTATACTAAATACTTG   865
```

FIG. 15D-3

```
CYP52A1A 1294  GCAAAGAAATTGAAATGTGTCGATCCACCATACTTGAAGGATGCCCGTCTCACTGGTATTCTGTCTTTGA  1363
CYP52A2A 1307  ATGTACAAGCTTGGTGCTAAACCATTTTTCCAGAAACAGACAGACGGCTGTTTCGGATTCAAAGCTCCGC  1376
CYP52A2B 1180  ATGTACAAGCTTGGTGCTAAACCGTTTTTCCAGAAACAAACAGACGGTTATTTCGGATTCAAAGCTCCAC  1249
CYP52A3A 1279  GAACGCAGGTTCCACGCCAAGCCACTCGGTAACTTTGTCAGGGACCCTACGTTTGGTATCGCTACTCCGT  1348
CYP52A3B 1066  GAACGCAGGTTCCACGCCAAGCCGCTCGGTAACGTCGTGTTGGATCCTACGTTTGGTATCGCTACTCCGT  1135
CYP52A5A 1196  ATGAAAAAGTTGGGTGCTGCTCCAGTCACAAACAAGTTGTACGACAACGCTTTCGGTATCGTCAATGGAT  1265
CYP52A5B 1235  ATGAAACAGTTGGGTGCTGCTCCAATCACAAACCAGTTGTACGACAACGTTTTCGGTATCGTCAACGGAT  1304
CYP52A8A  557  ATGAAGAAATTGGGTGCTAAGCCATTCACACACGTCCAACGTGACGGGTGGTTGGCTTCAAATTCGGCC   626
CYP52A8B 1110  ATGAAGAAGTTGGGCGCTAAGCCATTCACACATGTCCAACTAGACGGGTGGTTTGGCTTCAAATTTGGCC  1179
CYP52D4A  866  ATGCACAAACATGGCGCTCGAGAAATCGAGAATGTGATCAACGATGGGTTCTTTGGGTTCCGCTTACCTT   935

CYP52A1A 1364  TCGCCGCCATCAAGGCCAAGAACGACGGTAG-ATTGGCTAACTTTGCC------GATGAAGTTTT-----  1421
CYP52A2A 1377  TTGAATTGTTGAAGAAGAAGAGCGACGGTAC-CCTCATAGACTTCACA------CTCCAGCGTATC---C  1436
CYP52A2B 1250  TTGAATTGTTAAAAAAGAAGAGTGACGGTAC-CCTCATAGACTTCACT------CTCGAGCGTATC---C  1309
CYP52A3A 1349  TGCTTTTGATCTACTTGAAGTCGAAAGGTAC-GGTCATGAAGTTTGCTTGGGGCCTCTGGAACAACAAGT  1417
CYP52A3B 1136  TGATCTTGATCTACTTAAAGTCGAAAGGTAC-AGTCATGAAGTTTGCCTGGAGCTTCTGGAACAACAAGT  1204
CYP52A5A 1266  GGAAGGCTCTCCAGTTCAAGAAAGAGGGCAGGGCTCAAGAGTACAACG------ATTACAAGTTTG----  1325
CYP52A5B 1305  GGAAGGCTCTCCAGTTCAAGAAAGAGGGCAGAGCTCAAGAGTACAACG------ATCACAAGTTTG----  1364
CYP52A8A  627  GTGAATTCCTCAAAGCAAAAAGTGCTGGGAG-ACTGGTTGATTTAATC------ATCTCCCGTTT-----   684
CYP52A8B 1180  GTGAATTCCTCAAAGCTAAAAGTGCTGGGAG-GCAGGTTGATTTAATC------ATCTCCCGTTT-----  1237
CYP52D4A  936  TGCTACTCATGCGAGCCAGCAATGAGGGCCG-ACTTATCGAGTTCAGT------GTCAAGAGATTCGAGT   998
```

FIG. 15E-1

```
CYP52A1A 1422  ----CGACGAGTACCCAAACCACACCTTCTACTTGTCTGTTGCCGGTGCTTTGAAGATTGTCATGACTGT  1487
CYP52A2A 1437  ACGATCTCGATCGTCCCGATATCCCAACTTTCACATTCCCGGTCTTTTCCATCAACCTTGTCAATACCCT  1506
CYP52A2B 1310  AAGCGCTCAATCGTCCAGATATCCCAACTTTTACATTCCCAATCTTTTCCATCAACCTTATCAGCACCCT  1379
CYP52A3A 1418  ACATCGTCAGAGACCCAAAGTACAAGACAACTGGGCTCAGGATTGTTGGCCTCCCATTGATTGAAACCAT  1487
CYP52A3B 1205  ACATTGTCAAAGACCCAAAGTACAAGACCACTGGCCTTAGAATTGTCGGCCTCCCATTGATTGAAACCAT  1274
CYP52A5A 1326  ACCACTCCAAGAACCCAAGCGTGGGCACCTACGTCAGTATTCTTTTCGGCACCAGGATCGTCGTGACCAA  1395
CYP52A5B 1365  ACAGCTCCAAGAACCCAAGCGTCGGCACCTATGTCAGTATTCTTTTTGGCACCAAGATTGTCGTGACCAA  1434
CYP52A8A  685  ------CCACGA----TAATGAGGACACTTTCTCCAGCTATGCTTTTGGCAACCATGTGGTGTTCACCAG   744
CYP52A8B 1238  ------CCACGA----TAATGAGGACACTTTCTCCAGCTATGCTTTTGGCAACCATGTGGTGTTCACCAG  1297
CYP52D4A  999  -CGGCGCCACAT--CCACAGAACAAGACATTGGTCAACCGGGCATTGAGCGTTCCTGTGATACTCACCAA  1065

CYP52A1A 1488  TGACCCAGAAAACATCAAGGCTGTCTTGGCCACCCAATTCACTGACTTCTCCTTGGGTACCAGACACGCC  1557
CYP52A2A 1507  TGAGCCGGAGAACATCAAGGCCATCTTGGCCACTCAGTTCAACGATTTCTCCTTGGGTACCAGACACTCG  1576
CYP52A2B 1380  TGAGCCGGAGAACATCAAGGCTATCTTGGCCACCCAGTTCAACGATTTCTCCTTGGGCACCAGACACTCG  1449
CYP52A3A 1488  GGACCCAGAGAACATCAAGGCTGTTTTGGCTACTCAGTTCAATGATTTCTCTTTGGGAACCAGACACGAT  1557
CYP52A3B 1275  AGACCCAGAGAACATCAAAGCTGTGTTGGCTACTCAGTTCAACGATTTCTCCTTGGGAACTAGACACGAT  1344
CYP52A5A 1396  AGATCCAGAGAATATCAAAGCTATTTTGGCAACCCAGTTTGGTGATTTTTCTTTGGGCAAGAGGCACACT  1465
CYP52A5B 1435  GGATCCAGAGAATATCAAAGCTATTTTGGCAACCCAGTTTGGCGATTTTTCTTTGGGCAAGAGACACGCT  1504
CYP52A8A  745  GGACCCCGAGAATATCAAGGCGCTTTTGGCAACCCAGTTTGGTGATTTTTCATTGGGCAGCAGGGTCAAG   814
CYP52A8B 1298  GGACCCCGAGAATATCAAGGCGCTTTTGGCAACCCAGTTTGGTGATTTTTCATTGGGAAGCAGGGTCAAA  1367
CYP52D4A 1066  GGACCCAGTGAATATCAAAGCGATGCTATCGACCCAGTTTGATGACTTTTCCCTTGGGTTGAGACTACAC  1135
```

FIG. 15E-2

| | | | |
|---|---|---|---|
| CYP52A1A | 1558 | CACTTTGCTCCTTTGTTGGGTGACGGTATCTTCACCTTGGACGGAGAAGGTTGGAAGCACTCCAGAGCTA | 1627 |
| CYP52A2A | 1577 | CACTTTGCTCCTTTGTTGGGTGATGGTATCTTTACGTTGGATGGCGCCGGCTGGAAGCACAGCAGATCTA | 1646 |
| CYP52A2B | 1450 | CACTTTGCTCCTTTGTTGGGCGATGGTATCTTTACCTTGGACGGTGCCGGCTGGAAGCACAGCAGATCTA | 1519 |
| CYP52A3A | 1558 | TTCTTGTACTCCTTGTTGGGTGACGGTATTTTCACCTTGGACGGTGCTGGCTGGAAACATAGTAGAACTA | 1627 |
| CYP52A3B | 1345 | TTCTTGTACTCCTTGTTGGGCGATGGTATTTTTACCTTGGACGGTGCTGGCTGGAAACACAGTAGAACTA | 1414 |
| CYP52A5A | 1466 | CTTTTTAAGCCTTTGTTAGGTGATGGGATCTTCACATTGGACGGCGAAGGCTGGAAGCACAGCAGAGCCA | 1535 |
| CYP52A5B | 1505 | CTTTTTAAACCTTTGTTAGGTGATGGGATCTTCACCTTGGACGGCGAAGGCTGGAAGCATAGCAGATCCA | 1574 |
| CYP52A8A | 815 | TTCTTCAAACCATTATTGGGGTACGGTATCTTCACATTGGACGCCGAAGGCTGGAAGCACAGCAGAGCCA | 884 |
| CYP52A8B | 1368 | TTCTTCAAACCATTGTTGGGGTACGGTATCTTCACCTTGGACGGCGAAGGCTGGAAGCACAGCAGAGCCA | 1437 |
| CYP52D4A | 1136 | CAGTTTGCGCCGTTGTTGGGGAAAGGCATCTTTACTTTGGACGGCCCAGAGTGGAAGCAGAGCCGATCTA | 1205 |

FIG. 15E-3

| | | | |
|---|---|---|---|
| CYP52A1A | 1628 | TGTTGAGACCACAGTTTGCTAGAGACCAGATTGGACACGTTAAAGCCTTGGAACCACACATCCAAATCAT | 1697 |
| CYP52A2A | 1647 | TGTTGAGACCACAGTTTGCCAGAGAACAGATTTCCCACGTCAAGTTGTTGGAGCCACACGTTCAGGTGTT | 1716 |
| CYP52A2B | 1520 | TGTTGAGACCACAGTTTGCCAGAGAACAGATTTCCCACGTCAAGTTGTTGGAGCCACACATGCAGGTGTT | 1589 |
| CYP52A3A | 1628 | TGTTGAGACCACAGTTTGCTAGAGAACAGGTTTCTCACGTCAAGTTGTTGGAGCCACACGTTCAGGTGTT | 1697 |
| CYP52A3B | 1415 | TGTTGAGACCACAGTTTGCTAGAGAACAGGTTTCCCACGTCAAGTTGTTGGAACCACACGTTCAGGTGTT | 1484 |
| CYP52A5A | 1536 | TGTTGAGACCACAGTTTGCCAGAGAACAAGTTGCTCATGTGACGTCGTTGGAACCACACTTCCAGTTGTT | 1605 |
| CYP52A5B | 1575 | TGTTAAGACCACAGTTTGCCAGAGAACAAGTTGCTCATGTGACGTCGTTGGAACCACACTTCCAGTTGTT | 1644 |
| CYP52A8A | 885 | TGTTGAGACCACAGTTTGCCAGAGAACAAGTTGCTCATGTGACGTCGTTGGAACCACACTTCCAGTTGTT | 954 |
| CYP52A8B | 1438 | TGTTGAGACCACAGTTTGCCAGAGAGCAAGTTGCTCATGTGACGTCGTTGGAACCACATTTCCAGTTGTT | 1507 |
| CYP52D4A | 1206 | TGTTGCGTCCGCAATTTGCCAAAGATCGGGTTTCTCATATCCTGGATCTAGAACCGCATTTTGTGTTGCT | 1275 |
| | | | |
| CYP52A1A | 1698 | GGCTAAGCAGATCAAGTTGAACCAGGGAAAGACTTTCGATATCCAAGAATTGTTCTTTAGATTTACCGTC | 1767 |
| CYP52A2A | 1717 | CTTCAAACACGTCAGAAAGGCACAGGGCAAGACTTTTGACATCCAGGAATTGTTTTTCAGATTGACCGTC | 1786 |
| CYP52A2B | 1590 | CTTCAAGCACGTCAGAAAGGCACAGGGCAAGACTTTTGACATCCAAGAATTGTTTTTCAGATTGACCGTC | 1659 |
| CYP52A3A | 1698 | CTTCAAGCACGTTAGAAAGCACCGCGGTCAAACGTTCGACATCCAAGAATTGTTCTTCAGGTTGACCGTC | 1767 |
| CYP52A3B | 1485 | CTTCAAGCACGTTAGAAAACACCGCGGTCAGACTTTTGACATCCAAGAATTGTTCTTCAGATTGACCGTC | 1554 |
| CYP52A5A | 1606 | GAAGAAGCATATTCTTAAGCACAAGGGTGAATACTTTGATATCCAGGAATTGTTCTTTAGATTTACCGTT | 1675 |
| CYP52A5B | 1645 | GAAGAAGCATATCCTTAAACACAAGGGTGAGTACTTTGATATCCAGGAATTGTTCTTTAGATTTACTGTC | 1714 |
| CYP52A8A | 955 | GAAGAAGCATATCCTTAAACACAAGGGTGAGTACTTTGATATCCAGGAATTGTTCTTTAGATTTACTGTC | 1024 |
| CYP52A8B | 1508 | GAAGAAGCATATTCTTAAGCACAAGGGTGAATACTTTGATATCCAGGAATTGTTCTTTAGATTTACCGTT | 1577 |
| CYP52D4A | 1276 | TCGGAAGCACATTGATGGCCACAATGGAGACTACTTCGACATCCAGGAGCTCTACTTCCGGTTCTCGATG | 1345 |

FIG. 15F-1

```
CYP52A1A 1768  GACACCGCTACTGAGTTCTTGTTTGGTGAATCCGTTCACTCCTTGTACGATGAAAAATTGGGCATCCCAA  1837
CYP52A2A 1787  GACTCCGCCACCGAGTTTTTGTTTGGTGAATCCGTTGAGTCCTTGAGAGATGAATCTATCGGCATGTCCA  1856
CYP52A2B 1660  GACTCCGCCACTGAGTTTTTGTTTGGTGAATCCGTTGAGTCCTTGAGAGATGAATCTATTGGATGTCCA  1729
CYP52A3A 1768  GACTCCGCCACCGAGTTCTTGTTTGGTGAGTCTGCTGAATCCTTGAGGGACGAATCTATTGGATTGACCC  1837
CYP52A3B 1555  GACTCCGCCACCGAGTTCTTGTTTGGTGAGTCTGCTGAATCCTTGAGAGACGACTCTGTTGGTTTGACCC  1624
CYP52A5A 1676  GATTCGGCCACGGAGTTCTTATTTGGTGAGTCCGTGCACTCCTTAAAGGACGAATCTATTGGTATCAACC  1745
CYP52A5B 1715  GACTCGGCCACGGAGTTCTTATTTGGTGAGTCCGTGCACTCCTTAAAGGACGAAACTATCGGTATCAACC  1784
CYP52A8A 1025  GACTCGGCCACGGAGTTCTTATTTGGTGAGTCCGTGCACTCCTTAAAGGACGAGGAAATTGGCTACGACA  1094
CYP52A8B 1578  GATTCAGCGACGGAGTTCTTATTTGGTGAGTCCGTGCACTCCTTAAGGGACGAGGAAATTGGCTACGATA  1647
CYP52D4A 1346  GATGTGGCGACGGGGTTTTTGTTTGGCGAGTCTGTGGGGTCGTTGAAAGACGAAGATGCGAGG-------  1408

CYP52A1A 1838  CTCCAAACGAAA---TCCCAGGAAGAGAAAACTTTGCCGCTGCTTTCAACGTTTCCCAACACTACTTGGC  1904
CYP52A2A 1857  TCAATGCGCTTGACTTTGACGGCAAGGCTGGCTTTGCTGATGCTTTTAACTATTCGCAGAATTATTTGGC  1926
CYP52A2B 1730  TCAATGCACTTGACTTTGACGGCAAGGCTGGCTTTGCTGATGCTTTTAACTACTCGCAGAACTATTTGGC  1799
CYP52A3A 1838  CAACCACCAAGGATTTCGATGGCAGAAGAGATTTCGCTGACGCTTTCAACTATTCGCAGACTTACCAGGC  1907
CYP52A3B 1625  CAACCACCAAGGATTTCGAAGGCAGAGGAGATTTCGCTGACGCTTTCAACTACTCGCAGACTTACCAGGC  1694
CYP52A5A 1746  AAGACGATATAGATTTTGCTGGTAGAAAGGACTTTGCTGAGTCGTTCAACAAAGCCCAGGAATACTTGGC  1315
CYP52A5B 1785  AAGACGATATAGATTTTGCTGGTAGAAAGGACTTTGCTGAGTCGTTCAACAAAGCCCAGGAGTATTTGTC  1854
CYP52A8A 1095  CGAAAGACATGT---CTGAAGAAAGACGCAGATTTGCCGACGCGTTCAACAAGTCGCAAGTCTACGTGGC  1161
CYP52A8B 1648  CGAAGGACATGG---CTGAAGAAAGACGCAAATTTGCCGACGCGTTCAACAAGTCGCAAGTCTATTTGTC  1714
CYP52D4A 1409  -----------------------------------TTCCTGGAAGCATTCAATGAGTCGCAGAAGTATTTGGC  1445
```

FIG. 15F-2

```
CYP52A1A 1905  CACCAGAAGTTACTCCCAGACTTTTTACTTTTTGACCAACCCTAAGGAATTCAGAGACTGTAACGCCAAG  1974
CYP52A2A 1927  TTCGAGAGCGGTTATGCAACAATTGTACTGGGTGTTGAACGGGAAAAAGTTTAAGGAGTGCAACGCTAAA  1996
CYP52A2B 1800  TTCGAGAGCGGTTATGCAACAATTGTACTGGGTGTTGAACGGGAAAAAGTTTAAGGAGTGCAACGCTAAA  1869
CYP52A3A 1908  CTACAGATTTTTGTTGCAACAAATGTACTGGATCTTGAATGGCTCGGAATTCAGAAAGTCGATTGCTGTC  1977
CYP52A3B 1695  CTACAGATTTTTGTTGCAACAAATGTACTGGATTTTGAATGGCGCGGAATTCAGAAAGTCGATTGCCATC  1964
CYP52A5A 1816  TATTAGAACCTTGGTGCAGACGTTCTACTGGTTGGTCAACAACAAGGAGTTTAGAGACTGTACCAAGCTG  1885
CYP52A5B 1855  TATTAGAATTTTGGTGCAGACCTTCTACTGGTTGATCAACAACAAGGAGTTTAGAGACTGTACCAAGCTG  1924
CYP52A8A 1162  CACCAGAGTTGCTTTACAGAACTTGTACTGGTTGGTCAACAACAAAGAGTTCAAGGAGTGCAATGACATT  1231
CYP52A8B 1715  CACCAGAGTTGCTTTACAGACATTGTACTGGTTGGTCAACAACAAAGAGTTCAAGGAGTGCAACGACATT  1784
CYP52D4A 1447  AACTAGGGCAACGTTGCACGAGTTGTACTTTCTTTGTGACGGGTTTAGGTTTCGCCAGTACAACAAGGTT  1516
```

FIG. 15F-3

```
CYP52A1A 1975  GTCCACCACTTGGCCAAGTACTTTGTCAACAAGGCCTTGAACTTTACTCCTGAAGAACTCGAAGAGAAAT  2044
CYP52A2A 1997  GTGCACAAGTTTGCTGACTACTACGTCAACAAGGCTTTGGACTTGACGCCTGAACAATTGGAAAAGGAGG  2066
CYP52A2B 1870  GTGCACAAGTTTGCTGACTATTACGTCAGCAAGGCTTTGGACTTGACACCTGAACAATTGGAAAAGCAGG  1939
CYP52A3A 1978  GTGCACAAGTTTGCTGACCACTATGTGCAAAAGGCTTTGGAGTTGACCGACGATGACTTGCAGAAACAAG  2047
CYP52A3B 1765  GTGCACAAGTTTGCTGACCACTATGTGCAAAAGGCTTTGGAGTTGACCGACGATGACTTGCAGAAACAAG  1834
CYP52A5A 1886  GTGCACAAGTTCACCAACTACTATGTTCAGAAAGCTTTGGATGCTAGCCCAGAAGAGCTTGAAAAGCAAA  1955
CYP52A5B 1925  GTGCACAAGTTTACCAACTACTATGTTCAGAAAGCTTTGGATGCTACCCCAGAGGAACTTGAAAAGCAAG  1994
CYP52A8A 1232  GTCCACAAGTTTACCAACTACTATGTTCAGAAAGCCTTGGATGCTACCCCAGAGGAACTTGAAAAGCAAG  1301
CYP52A8B 1785  GTCCACAAGTTCACCAACTACTATGTTCAGAAAGCCTTGGATGCTACCCCAGAGGAACTTGAAAAACAAG  1854
CYP52D4A 1517  GTGCGAAAGTTCTGCAGCCAGTGTGTCCACAAGGCGTTAGATGTTGCACCGGAAGACACC---------A  1577

CYP52A1A 2045  CCAAGTCCGGTTACGTTTTCTTGTACGAATTGGTTAAGCAAACCAGAGATCCAAAGGTCTTGCAAGATCA  2114
CYP52A2A 2067  ATGGTT------ATGTGTTTTTGTACGAATTGGTCAAGCAAACCAGAGACAAGCAAGTGTTGAGAGACCA  2130
CYP52A2B 1940  ATGGTT------ATGTGTTCTTGTACGAGTTGGTCAAGCAAACCAGAGACAGGCAAGTGTTGAGAGACCA  2003
CYP52A3A 2048  ACGGCT------ATGTGTTCTTGTACGAGTTGGCTAAGCAAACCAGAGACCCAAAGGTCTTGAGAGACCA  2111
CYP52A3B 1835  ACGGCT------ATGTGTTCTTGTACGAGTTGGCTAAGCAAACTAGAGACCCAAAGGTCTTGAGAGACCA  1898
CYP52A5A 1956  GTGGGT------ATGTGTTCTTGTACGAGCTTGTCAAGCAGACAAGAGACCCCAATGTGTTGCGTGACCA  2019
CYP52A5B 1995  GCGGGT------ATGTGTTCTTGTATGAGCTTGTCAAGCAGACGAGAGACCCCAAGGTGTTGCGTGACCA  2058
CYP52A8A 1302  GCGGGT------ATGTGTTCTTGTATGAGCTTGTCAAGCAGACGAGAGACCCCAAGGTGTTGCGTGACCA  1365
CYP52A8B 1855  GCGGGT------ATGTGTTCTTGTACGAGCTTGCCAAGCAGACGAAAGACCCCAATGTGTTGCGTGACCA  1918
CYP52D4A 1578  GCGAGT------ACGTGTTTCTCCGCGAGTTGGTCAAACACACTCGAGATCCCGTTGTTTTACAAGACCA  1641
```

FIG. 15G-1

| | | | |
|---|---|---|---|
| CYP52A1A | 2115 | ATTGTTGAACATTATGGTTGCCGGAAGAGACACCACTGCCGGTTTGTTGTCCTTTGCTTTGTTTGAATTG | 2184 |
| CYP52A2A | 2131 | ATTGTTGAACATCATGGTTGCTGGTAGAGACACCACCGCCGGTTTGTTGTCGTTTGTTTTCTTTGAATTG | 2200 |
| CYP52A2B | 2004 | GTTGTTGAACATCATGGTTGCCGGTAGAGACACCACCGCCGGTTTGTTGTCGTTTGTTTTCTTTGAATTG | 2073 |
| CYP52A3A | 2112 | GTTATTGAACATTTTGGTTGCCGGTAGAGACACGACCGCCGGTTTGTTGTCATTTGTTTTCTACGAGTTG | 2181 |
| CYP52A3B | 1899 | GTTGTTGAACATTTTGGTTGCCGGTAGAGACACGACCGCCGGTTTGTTGTCGTTTGTGTTCTACGAGTTG | 1968 |
| CYP52A5A | 2020 | GTCTTTGAACATCTTGTTGGCCGGAAGAGACACCACTGCTGGGTTGTTGTCGTTTGCTGTCTTTGAGTTG | 2089 |
| CYP52A2B | 2059 | GTCTTTGAACATCTTGTTGGCAGGAAGAGACACCACTGCTGGGTTGTTGTCCTTTGCTGTGTTTGAGTTG | 2128 |
| CYP52A8A | 1366 | GTCTTTGAACATCTTGTTGGCAGGAAGAGACACCACTGCTGGGTTGTTGTCCTTTGCTGTGTTTGAGTTG | 1435 |
| CYP52A8B | 1919 | GTCTTTGAACATCTTGTTGGCTGGAAGGGACACCACTGCTGGGTTGTTGTCCTTTGCTGTGTTTGAGTTG | 1998 |
| CYP52D4A | 1642 | AGCGTTGAACGTCTTGCTTGCTGGACGCGACACCACCGCGTCGTTATTATCGTTTGCAACATTTGAGCTA | 1711 |

| | | | |
|---|---|---|---|
| CYP52A1A | 2185 | GCTAGACACCCAGAGATGTGGTCCAAGTTGAGAGAAGAAATCGAAGTTAACTTTGGTGTTGGTGAAGACT | 2254 |
| CYP52A2A | 2201 | GCCAGAAACCCAGAAGTTACCAACAAGTTGAGAGAAGAAATTGAGGACAAGTTTGGACTCGGTGAGAATG | 2270 |
| CYP52A2B | 2074 | GCCAGAAACCCAGAGGTGACCAACAAGTTGAGAGAAGAAATCGAGGACAAGTTTGGTCTTGGTGAGAATG | 2143 |
| CYP52A3A | 2182 | TCAAGAAACCCTGAGGTGTTTGCTAAGTTGAGAGAGGAGGTGGAAAACAGATTTGGACTCGGTGAAGAAG | 2251 |
| CYP52A3B | 1969 | TCGAGAAACCCTGAAGTGTTTGCCAAGTTGAGAGAGGAGGTGGAAAACAGATTTGGACTCGGCGAAGAGG | 2038 |
| CYP52A5A | 2090 | GCCAGACACCCAGAGATCTGGGCCAAGTTGAGAGAGGAAATTGAACAACAGTTTGGTCTTGGAGAAGACT | 2159 |
| CYP52A5B | 2129 | GCCAGAAACCCACACATCTGGGCCAAGTTGAGAGAGGAAATTGAACAGCAGTTTGGTCTTGGAGAAGACT | 2198 |
| CYP52A8A | 1436 | GCCAGAAACCCACACATCTGGGCCAAGTTGAGAGAGGAAATTGAACAGCAGTTTGGTCTTGGAGAAGACT | 1505 |
| CYP52A8B | 1989 | GCCAGGAACCCACACATCTGGGCCAAGTTGAGAGAGGAAATTGAATCACACTTTGGGCTGGGTGAGGACT | 2058 |
| CYP52D4A | 1712 | GCCCGGAATGACCACATGTGGAGGAAGCTACGAGAGGAGGTT-------ATCCTGA---CGATGGGACCG | 1771 |

FIG. 15G-2

```
CYP52A1A 2255  CCCGCGTTGAAGAAATTACCTTCGAAGCCTTGAAGAGATGTGAATACTTGAAGGCTATCCTTAACGAAAC  2324
CYP52A2A 2271  CTAGTGTTGAAGACATTTCCTTTGAGTCGTTGAAGTCCTGTGAATACTTGAAGGCTGTTCTCAACGAAAC  2340
CYP52A2B 2144  CTCGTGTTGAAGACATTTCCTTTGAGTCGTTGAAGTCATGTGAATACTTGAAGGCTGTTCTCAACGAAAC  2213
CYP52A3A 2252  CTCGTGTTGAAGAGATCTCGTTTGAGTCCTTGAAGTCTTGTGAGTACTTGAAGGCTGTCATCAATGAAAC  2321
CYP52A3B 2039  CTCGTGTTGAAGAGATCTCTTTTGAGTCCTTGAAGTCCTGTGAGTACTTGAAGGCTGTCATCAATGAAGC  2108
CYP52A5A 2160  CTCGTGTTGAAGAGATTACCTTTGAGAGCTTGAAGAGATGTGAGTACTTGAAAGCGTTCCTTAATGAAAC  2229
CYP52A5B 2199  CTCGTGTTGAAGAGATTACCTTTGAGAGCTTGAAGAGATGTGAGTACTTGAAAGCGTTCCTTAACGAAAC  2268
CYP52A8A 1506  CTCGTGTTGAAGAGATTACCTTTGAGAGCTTGAAGAGATGTGAGTACTTGAAGGCCGTGTTGAACGAAAC  1575
CYP52A8B 2059  CTCGTGTTGAAGAGATTACCTTTGAGAGCTTGAAGAGATGTGAGTACTTGAAAGCCGTGTTGAACGAAAC  2128
CYP52D4A 1772  TCCAG--TGATGAAATAACCGTGGCCGGGTTGAAGAGTTGCCGTTACCTCAAAGCAATCCTAAACGAAAC  1839
```

FIG. 15G-3

```
CYP52A1A 2325   CTTGCGTATGTACCCATCTGTTCCTGTCAACTTTAGAACCGCCACCAGAGACACCACTTTGCCAAGAGGT   2394
CYP52A2A 2341   CTTGAGATTGTACCCATCCGTGCCACAGAATTTCAGAGTTGCCACCAAGAACACTACCCTCCCAAGAGGT   2410
CYP52A2B 2214   TTTGAGATTGTACCCATCCGTGCCACAGAATTTCAGAGTTGCCACCAAAAACACTACCCTTCCAAGGGGA   2283
CYP52A3A 2322   CTTGAGATTGTACCCATCGGTTCCACACAACTTTAGAGTTGCTACCAGAAACACTACCCTCCCAAGAGGT   2391
CYP52A3B 2109   CTTGAGATTGTACCCATCTGTTCCACACAACTTCAGAGTTGCCACCAGAAACACTACCCTTCCAAGAGGC   2178
CYP52A5A 2230   CTTGCGTATTTACCCAAGTGTCCCAAGAAACTTCAGAATCGCCACCAAGAACACGACATTGCCAAGGGGC   2299
CYP52A5B 2269   CTTGCGTGTTTACCCAAGTGTCCCAAGAAACTTCAGAATCGCCACCAAGAATACAACATTGCCAAGGGGT   2338
CYP52A8A 1576   TTTGAGATTACACCCAAGTGTCCCAAGAAACGCAAGATTTGCGATTAAAGACACGACTTTACCAAGAGGC   1645
CYP52A8B 2129   GTTGAGATTACACCCAAGTGTCCCAAGAAACGCAAGATTTGCGATTAAAGACACGACTTTACCAAGAGGC   2198
CYP52D4A 1840   TCTTCGACTATACCCAAGTGTGCCTAGGAACGCGAGATTTGCTACGAGGAATACGACGCTTCCTCGTGGC   1909

CYP52A1A 2395   GGTGGTGCTAACGGTACCGACCCAATCTACATTCCTAAAGGCTCCACTGTTGCTTACGTTGTCTACAAGA   2464
CYP52A2A 2411   GGTGGTAAGGACGGGTTGTCTCCTGTTTTGGTGAGAAAGGGTCAGACCGTTATTTACGGTGTCTACGCAG   2480
CYP52A2B 2284   GGTGGTAAGGACGGGTTATCTCCTGTTTTGGTCAGAAAGGGTCAAACCGTTATGTACGGTGTCTACGCTG   2353
CYP52A3A 2392   GGTGGTGAAGATGGATACTCGCCAATTGTCGTCAAGAAGGGTCAAGTTGTCATGTACACTGTTATTGCTA   2461
CYP52A3B 2179   GGTGGTAAAGACGGATGCTCGCCAATTGTTGTCAAGAAGGGTCAAGTTGTCATGTACACTGTCATTGGTA   2248
CYP52A5A 2300   GGTGGTTCAGACGGTACCTCGCCAATCTTGATCCAAAAGGGAGAAGCTGTGTCGTATGGTATCAACTCTA   2369
CYP52A5B 2339   GGTGGTCCAGACGGTACCCAGCCAATCTTGATCCAAAAGGGAGAAGGTGTGTCGTATGGTATCAACTCTA   2408
CYP52A8A 1646   GGTGGCCCCAACGGCAAGGATCCTATCTTGATCAGGAAGGATGAGGTGGTGCAGTACTCCATCTCGGCAA   1715
CYP52A8B 2199   GGTGGCCCCAACGGCAAGGATCCTATCTTGATCAGAAAGAATGAGGTGGTGCAATACTCCATCTCGGCAA   2268
CYP52D4A 1910   GGAGGTCCAGATGGATCGTTTCCGATTTTGATAAGAAAGGGCCAGCCAGTGGGGTATTTCATTTGTGCTA   1979
```

FIG. 15H-I

```
CYP52A1A 2465  CCCACCGTTTGGAAGAATACTACGGTAAGGACGCTAACGACTTCAGACCAGAAAGATGGTTTGAACCATC  2534
CYP52A2A 2481  CCCACAGAAACCCAGCTGTTTACGGTAAGGACGCTCTTGAGTTTAGACCAGAGAGATGGTTTGAGCCAGA  2550
CYP52A2B 2354  CCCACAGAAACCCAGCTGTCTACGGTAAGGACGCCCTTGAGTTTAGACCAGAGAGGTGGTTTGAGCCAGA  2423
CYP52A3A 2462  CCCACAGAGACCCAAGTATCTACGGTGCCGACGCTGACGTCTTCAGACCAGAAAGATGGTTTGAACCAGA  2531
CYP52A3B 2249  CCCACAGAGACCCAAGTATCTACGGTGCCGACGCCGACGTCTTCAGACCAGAAAGATGGTTCGAGCCAGA  2318
CYP52A5A 2370  CTCATTTGGACCCTGTCTATTACGGCCCTGATGCTGCTGAGTTCAGACCAGAGAGATGGTTTGAGCCATC  2439
CYP52A5B 2409  CCCACTTAGATCCTGTCTATTATGGCCCTGATGCTGCTGAGTTCAGACCAGAGAGATGGTTTGAGCCATC  2478
CYP52A8A 1716  CTCAGACAAATCCTGCTTATTATGGCGCCGATGCTGCTGATTTTAGACCGGAAAGATGGTTTGAACCATC  1785
CYP52A8B 2269  CTCAGACAAATCCTGCTTATTATGGCGCCGATGCTGCTGATTTTAGACCGGAAAGATGGTTTGAGCCATC  2338
CYP52D4A 1980  CACACTTGAATGAGAAGGTATATGGGAATGATAGCCATGTGTTTCGACCGGAGAGATGGGCTGCGTTAGA  2049

CYP52A1A 2535  TACTAAGAAGTTGGGCTGGGCTTATGTTCCATTCAACGGTGGTCCAAGAGTCTGCTTGGGTCAACAATTC  2604
CYP52A2A 2551  GACAAAGAAGCTTGGCTGGGCCTTCCTCCCATTCAACGGTGGTCCAAGAATCTGTTTGGGACAGCAGTTT  2620
CYP52A2B 2424  GACAAAGAAGCTTGGCTGGGCCTTCCTTCCATTCAACGGTGGTCCAAGAATTTGCTTGGGACAGCAGTTT  2493
CYP52A3A 2532  AACTAGAAAGTTGGGCTGGGCATACGTTCCATTCAATGGTGGTCCAAGAATCTGTTTGGGTCAACAGTTT  2601
CYP52A3B 2319  AACTAGAAAGTTGGGCTGGGCATATGTTCCATTCAATGGTGGTCCAAGAATCTGTTTGGGTCAGCAGTTT  2388
CYP52A5A 2440  AACCAAAAAGCTCGGCTGGGCTTACTTGCCATTCAACGGTGGTCCAAGAATCTGTTTGGGTCAGCAGTTT  2509
CYP52A5B 2479  AACCAGAAAGCTCGGCTGGGCTTACTTGCCATTCAACGGTGGGCCACGAATCTGTTTGGGTCAGCAGTTT  2548
CYP52A8A 1786  AACTAGAAACTTGGGATGGGCTTTCTTGCCATTCAACGGTGGTCCAAGAATCTGTTTGGGACAACAGTTT  1855
CYP52A8B 2339  AACTAGAAACTTGGGATGGGCTTACTTGCCATTCAACGGTGGTCCAAGAATCTGCTTGGGACAACAGTTT  2408
CYP52D4A 2050  GGGCAAGAGTTTGGGCTGGTCGTATCTTCCATTCAACGGCGGCCCGAGAAGCTGCCTTGGTCAGCAGTTT  2119
```

FIG. 15H-2

```
CYP52A1A 2605  GCCTTGACTGAAGCTTCTTATGTGATCACTAGATTGGCCCAGATGTTTGAAACTGTCTCATCTGATCCAG  2674
CYP52A2A 2621  GCCTTGACAGAAGCTTCGTATGTCACTGTCAGGTTGCTCCAGGAGTTTGCACACTTGTCTATGGACCCAG  2690
CYP52A2B 2494  GCCTTGACAGAAGCTTCGTATGTCACTGTCAGATTGCTCCAAGAGTTTGGACACTTGTCTATGGACCCCA  2563
CYP52A3A 2602  GCCTTGACCGAAGCTTCATACGTCACTGTCAGATTGCTCCAGGAGTTTGCACACTTGTCTATGGACCCAG  2671
CYP52A3B 2389  GCCTTGACTGAAGCTTCATACGTCACTGTCAGATTGCTCCAAGAGTTTGGAAACTTGTCCCTGGATCCAA  2458
CYP52A5A 2510  GCCTTGACGGAAGCTGGCTATGTGTTGGTTAGATTGGTGCAAGAGTTCTCCCACGTTAGGCTGGACCCAG  2579
CYP52A5B 2549  GCCTTGACCGAAGCTGGTTACGTTTTGGTCAGATTGGTGCAAGAGTTCTCCCACATTAGGCTGGACCCAG  2618
CYP52A8A 1856  GCTTTGACTGAAGCCGGTTACGTTTTGGTTAGACTTGTTCAGGAGTTTCCAAACTTGTCACAAGACCCCG  1925
CYP52A8B 2409  GCTTTGACCGAAGCCGGTTACGTTTTGGTTAGACTTGTTCAGGAATTCCCTAGCTTGTCACAGGACCCCG  2478
CYP52D4A 2120  GCAATCCTTGAAGCTTCGTATGTTTTGGCTCGATTGACACAGTGCTACACGACGATACAGCTTAG---AA  2186
```

FIG. 15H-3

```
CYP52A1A 2675  GTCTCGAATACCCTCCACCAAAGTGTATTCACTTGACCATGAGTCACAACGATGGTGTCTTTGTCAAGAT  2744
CYP52A2A 2691  ACACCGAATATCCACCTAAGAAAATGTCGCATTTGACCATGTCGCTTTTCGACGGTGCCAATATTGAGAT  2760
CYP52A2B 2564  ACACCGAATATCCACCTAGGAAAATGTCGCATTTGACCATGTCCCTTTTCGACGGTGCCAACATTGAGAT  2633
CYP52A3A 2672  ACACCGAATATCCACCAAAATTGCAGAACACCTTGACCTTGTCGCTCTTTGATGGTGCTGATGTTAGAAT  2741
CYP52A3B 2459  ACGCTGAGTACCCACCAAAATTGCAGAACACCTTGACCTTGTCACTCTTTGATGGTGCTGACGTTAGAAT  2528
CYP52A5A 2580  ACGAGGTGTACCCGCCAAAGAGGTTGACCAACTTGACCATGTGTTTGCAGGATGGTGCTATTGTCAAGTT  2649
CYP52A5B 2619  ATGAAGTGTATCCACCAAAGAGGTTGACCAACTTGACCATGTGTTTGCAGGATGGTGCTATTGTCAAGTT  2688
CYP52A8A 1926  AAACCAAGTACCCACCACCTAGATTGGCACACTTGACGATGTGCTTGTTTGACGGTGCACACGTCAAGAT  1995
CYP52A8B 2479  AAACTGAGTACCCACCACCTAGATTGGCACACTTGACGATGTGCTTGTTTGACGGGGCATACGTCAAGAT  2548
CYP52D4A 2187  CTACCGAGTACCCACCAAAGAAACTCGTTCATCTCACGATGAGTCTTCTCAACGGGGTGTACATCCGAAC  2256

CYP52A1A 2745  GTAA-AGTAGTCGATGCTGGGTATTCGATTACATGT--GTATAGGAAGATTTTGGTTTTTTATTCGTTCT  2811
CYP52A2A 2761  GTATTAGAGGGTCATGTGTTATTTT-GATTGTTTA-----GTTTGTAATTACTGATTAGGTTAATTCATG  2824
CYP52A2B 2634  GTATTAGAGGATCATGTGTTATTTTTGATTGGTTTAGTCTGTTTGTAGCTATTGATTAGGTTAATTCACG  2703
CYP52A3A 2742  GTACTAAGGTTGCTTTTCCTTGCTAATTTTCTTCTGTATAGCTTGTGTATTTAAATTGAATCGGCAATTG  2811
CYP52A3B 2529  GTTCTAAGGTTGCTTATCCTTGCTAGTGTTATT---TATAGTTTGTGTATTTAAATTGAATCGGCGATTG  2595
CYP52A5A 2650  TGACTAGCGGCGTGGTGAATGCGTTTGATTTTGTA---GTTTCTGTTTGCAGTAATGAGATAACTATTCA  2716
CYP52A5B 2689  TGACTAGTA-CGTA-TGAGTGCGTTTGATTTTGTA---GTTTCTGTTTGCAGTAATGAGATAACTATTCA  2753
CYP52A8A 1996  GTCATAGGTTTCCC---CATACAAGTAGTTCAGTA---ATTATACACTGTTTTTACTTTCTCTTCATACC  2059
CYP52A8B 2549  GCAATAGGTTT------------------------------------TGGTTTGACTTTGTTTCCATA--  2580
CYP52D4A 2257  TAGAACTTGATTATGTGTTTATGGTTAATCGGGGCAAAGCACTGCAAGTCATTGATGTTTGTGGAAGCCC  2326
```

FIG. 15I-1

```
CYP52A1A 2812  TTTTTTTAATTTTTGTTAAATTAG-TTTAGAGATTTCATTAATACATAGATGGGTGCTATTTCCGAAACT  2880
CYP52A2A 2825  GATTGTTATTTATTGATAGGGGTT---------TGCGCGTGTTGCATTCACTTGGGATCGTTCCAGGTTG  2885
CYP52A2B 2704  GATTGTTATTTATTGATAGGGGGTGCGTGTGTGTGTGTGTGTTGCATTCACATGGGATCGTTCCAGGTTG  2773
CYP52A3A 2812  ATTTTTCTGATACCAATAACCGTA--------GTGCGATTTGACCAAAACCGTTCAAAGTTTTTGTTCTC  2873
CYP52A3B 2596  ATTTTTCTGGTACTAATAACTGTA--------GTGGGTTTTGACCAAAACCGTTCAAACTTTTTTTTTTT  2657
CYP52A5A 2717  GATAAGGCGAGTGGATGTACGTTT-TGTAAGAGTTT--CCT-TACAACCTTGGTGGGG-TGTGTGAGGTT  2781
CYP52A5B 2754  GATAAGGCGGGTGGATGTACGTTT-TGTAAGAGTTT--CCT-TACAACCCTGGTGGG--TGTGTGAGGTT  2817
CYP52A8A 2060  AAATGGACAAAAGTTTTAAGCATG-CCTAACAACGTGACCG-GACAATTGTGTCGCACTAGTATGTAACA  2127
CYP52A8B 2581  ---------------------------------------------------------------TGCAAGT  2587
CYP52D4A 2327  AGCATTGGTGTTCCGGAGCATCAATAACCAATGTCTTGAAGGGTTTGATTTTCTTGACCTTCTTCTTCCT  2396

CYP52A1A 2881  TTACTTCTATCC--CCTGTATCCCTTATTATCCCTCTCAGTCACATGATTGCTGTAATTGTCGTGCAGGA  2948
CYP52A2A 2886  ATGTTTCCTTCCATCCT--GTCGAGTCAAAAGGAGTTTTGTTTTGTAACTCCGGACGATGTTTTAAATAG  2953
CYP52A2B 2774  TTGTTTCCTTCCATCCT--GTTGAGTCAAAAGGAGTTTTGTTTTGTAACTCCGGACGATGTCTTAGATAG  2841
CYP52A3A 2874  TCGTTGACG------------TGCTCGCTCATCAGCACTGTTTGAAGACGAAAGA-GAAAATTTTTTGTA  2930
CYP52A3B 2658  TTTTCTTCCCCCTACCTTCGTTGCTCGCTCATCAGCACTGTTTGAAAACGAAAAAAGAAAATTTTTTGTA  2727
CYP52A5A 2782  GAGGTTGCATCTT-GGGGAGATTACACCTTTTG-CAGCTCTCCGTATACACTTGTACTCTTTGTAACCTC  2849
CYP52A5B 2818  G----CATCTTAG-GGAGAGATAGCACCTTTTG-CAGCTCTCCGTATACAGTTTTACTCTTTGTAACCTA  2881
CYP52A8A 2128  ATTGTAAAAATAG-TGTACACTAATTTGTGGTGGCCGGAGATAAATTACAGTTTGGTTTTGTGTAAACTC  2196
CYP52A8B 2588  AGTTCAGTAAT---TACACACTAATTTGTGGTGGCCGGCGATAAATTACCGTTTGGTTTTGTGTAAAAAT  2654
CYP52D4A 2397  GAGCTTCTTTCCG--TCAAACTTGTACAGAATGGCCATCATTTCAGGAACAACCA-CGTACGACGGCCGG  2463
```

FIG. 15I-2

```
CYP52A1A 2949  CACAAACTCCCTAACGGACTTAAACCATAAACAAGCTCAGAACCATAAGCCGACATCACTCCTTCTTCTC  3018
CYP52A2A 2954  AAGGTCGATCTCCATGTGATTGTTTTGACTGTTACTGTGATTATGTAATCTGCG-------GACGTTATA  3016
CYP52A2B 2842  AAGGTCGATCTCCATGTGATTGTTT-GACTGCTACTCTGATTATGTAATCTGTAAAGCCTAGACGTTATG  2910
CYP52A3A 2931  AACAACACTGTCCAAATTTACCCAACGTGAACCATTATG--CAAATGAGCGGCC---------CTTTCAA  2989
CYP52A3B 2728  AACAACATTGCCCAAACTTACCCAACGTGAACCATTATAACCAAATGAGCGGCG---------CTTTCAA  2788
CYP52A5A 2850  TATCAATCATGTGGGGGGGGGGGTTCATTGTTTGGC-CATGGTGGTGCATGTTAAATCCGCC-AACTACC  2917
CYP52A5B 2882  TGCCAATCATGTGG------GGATTCATTGTTTGCC-CATGGTGGTGCATGCAAAATCCCCCCAACTACC  2944
CYP52A8A 2197  GCGGATATCTCTGGC-----AGTTTCTCTTCTCCGC-AGCAGCTTTGCCACGGGTTTGCTCTGGGGCCAA  2260
CYP52A8B 2655  TCGGACATCTCTGGT-----GGTTTCCCTTCTCCGC-AGCAGCTTTGCCACGGGTTTGCTCTGCGGCCAA  2718
CYP52D4A 2464  TACCGCATCTGGAGTA---TCTCGCCGTCGTTCAAGTAG--CACGAAAACAGCAACGACGTCACCATCTG  2528
```

FIG. 15I-3

```
CYP52A1A 3019  TCTTCTCCAACCAATAGCATGGACAGACCCACCCTCCTATCCGAATCGAAGACCCTTATTGACTCCATAC  3088
CYP52A2A 3017  CAAGCATGTGATTGTGGTTTT------GCAGCCT-TTTGCACGACAAATGATCGTCAGACGATTACGTAA  3079
CYP52A2B 2911  CAAGCATGTGATTGTGGTTTTT-----GCAACCTGTTTGCACGACAAATGATCGACAGTCGATTACGTAA  2975
CYP52A3A 2990  CTGGTCGCTGGAAGCATTCGGG-----GATATCTACAACGCCCTTAAGTTTGAAACAGACATTGATTTAG  3054
CYP52A3B 2789  CTGGTCACTGGAGGCATTCGGG-----GATATCTACAACACCCTTAAGTTTGAGGAAGACATTGATTTAG  2853
CYP52A5A 2918  CAATCTCACATGAAACTCAAGCACACTAAAAAAAAAAAAGATGTTGGGGGAAAACTT-TGGTTTCCCTTC  2986
CYP52A5B 2945  CAATCTCACATGAAACTCAAGCACACTAGAAAAAAAA--GATGTTGCGTGGGTTCTT-TTGATG------  3005
CYP52A8A 2261  CAAATTCAAAAGGGGG-----------AGAAACTTAACACCCCTTATCTCTCCACTC-TAGGTTGTAGCT  2318
CYP52A8B 2719  CAAATTCGAAAGGGGGGGGGGGGGGGGAGAAAGTTAACACCCCCTGTTCC--CACCG-TAGGCTGTAGCT  2785
CYP52D4A 2529  CTTCCCAATCTTGACACCC--------ACAGATACCCCTGCGGCTTCATGGATCAAAAACGTCGGCAACC  2590

CYP52A1A 3089  CCACCTGGAAGCCCCTCAAGCCACACACGTCATCCAGCCCACCCATCACCACATCCCTCTACTCGACAAC  3158
CYP52A2A 3080  TCTTTGTTA-----GAGGGGTAAAAAAAACAAAATGGCAGCCAGAATTTCAAACATTCTGCAAACAATG  3144
CYP52A2B 2976  TCCATATTAT-TTAGAGGGGTAATAAAAAATAAA-TGGCAGCCAGAATTTCAAACATTTTGCAAACAATG  3043
CYP52A3A 3055  ACACCATAGA-TTTCAGCGGCATCAAGAATGACC----TTGCCCACATTTTGACGACCCCAACACCACTG  3119
CYP52A3B 2854  ACACCATAGA-TTTCAGCGGCATCAAGAATGACC----TTGTCCACATTTTGACAACCCCAACACCACTG  2918
CYP52A5A 2987  TTAGTAATT--AAACACTCTCACTCTCACTCTCACTCTCTCCACTCAGACAAACCAACCACCTGGGCTGC  3054
CYP52A5B 3006  TTGGGGAAA--ACTTTCGTTTCCTTTCTCAGTAATTAAACGTTCTCACTCAGACAAACCACCTGGGCTGC  3073
CYP52A8A 2319  CTTGTGGGG--ATGCAATTGTCGTACGTTTTTATGTTTTGTCTAGACTTTGATGATTACGTTGGATTTC  2386
CYP52A8B 2786  CTTGTGGGGGGATGTAATTGTCGTACGTTTTC-ATGTTTGGCCCAGACTTTGATGATTACGTAGGCTTTC  2854
CYP52D4A 2591  CCGCGTATATGTCCATGTAATTCTCCATGGCCACCT--CCATCAACACACTGATGGAGCGACTGACGGTG  2658
```

FIG. 15J-1

```
CYP52A1A 3159  GTCCAAAGACGGCGAGTTCTGGTGTGCCCGGAAATCAGCCATCCCGGCCACATACAAGCAGCCGTTGATT  3228
CYP52A2A 3145  CAAAAAATGGAAACTC--CAACAGACAAAA-AAAAAAACTCCGCAGCACTCCGAACCCACAGAACAATG  3211
CYP52A2B 3044  CAAAAGATGAGAAACTC--CAACAGAAAAAATAAAAAAACTCCGCAGCACTCCGAACCAACAAAACAATG  3111
CYP52A3A 3120  GAAGAATCACGCCAGA----AACTAGGCGATGGATCCAAGCCTGTGACCTTGCCCAATGGAGACGAAGTG  3185
CYP52A3B 2919  GAAGAATCGCGCCAGA----AACTAGGCGATGGATCCAAGCCTGTGGCCTTGCCCAATGGAGACGAAGTG  2984
CYP52A5A 3055  AGACAACCAGAAAAAAAAAGAACAAAATCCAGATAGAAAAACAAAGGGCT-GGACAACCATAAAT-AAAC  3122
CYP52A5B 3074  AGACAACCAGAAAAAAA------CAAAATCCAGATAGAAGAAGAAAGGGCT-GGACAACCATAAAT-AAAC  3135
CYP52A8A 2387  TTATGTCTGAGGCGTG----CTTGAAAGAAGTGTCAAAATGTGACAGGCG-ACGCTATTCGACAT-GAAC  2450
CYP52A8B 2855  TTATGTCTAAGGCGTG----CTTGACACAAGTGTCAAAAGGTGACAGGCG-ACGTTATTCGACAT-GAAC  2918
CYP52D4A 2659  CCACCACTGCCCTCGG------TTGAGTCAAGGCAGTATGATGCCGGGATCCAGTACTCCAATGGGAACC  2722

CYP52A1A 3229  GCGTGCATACTCGGCGAGCCCACAATGGGAGCCACGCATTCGGACCATGAAGCAAAGTACATTCACGAGA  3298
CYP52A2A 3212  GGG----CGCCAGAATTATTGACTATTGTGACTTTTTTA-----------CGCTAACGCTCATTGCAGTG  3266
CYP52A2B 3112  GGGG--GCGCCAGAATTATTGACTATTGTGACTTTTTTTT--ATTTTTTCCGTTAACTTTCATTGCAGTG  3177
CYP52A3A 3186  GAGTTGAACCAAGCGTTCCTAGAAGTTACCACATTATTGTCGAATGAGTTTGACTTGGACCAATTGAACG  3255
CYP52A3B 2985  GAGTTGAACCAAGCGTTCCTAGAAGTTACCACATTATTGTCGAACGAGTTTGACTTGGACCAATTGAACG  3054
CYP52A5A 3123  AATCTAGGGTCTACTCCATCTTCCACTGTTTCTTCTTCTTCAGACTTAGCT-AACAAACAACTCACTTCA  3191
CYP52A5B 3136  AACCTAGGGTCCACTCCATCTTTCACT---TCTTCTTCTTCAGACTTATCT-AACAAACGACTCACTTCA  3201
CYP52A8A 2451  GCGAAAGGGTTATTTGCATCAATACGAG--GGGCTGACTCTAGTCTAGG---ATGGCAGTCCTAGGTTGC  2515
CYP52A8B 2919  GCAAAAGGGTAATTTGCATCGATACGAG--GGGTTGCCTCTGGTCTAAG---AAGGACCCCCCAGGTTGC  2983
CYP52D4A 2723  TCT-----GCACGGTGTCGCTGCAGTTTTTGAGGCGTATTTCGA--------TCCATGATCGTTCTTTGG  2779
```

FIG. 15J-2

```
CYP52A1A 3299  TCACGGGTGTTTCAG-TGTCGCAGATTGAGAAGTTCGACGATGGATGGAAGTACGATCTCGTTGCGGATT  3367
CYP52A2A 3267  TAGTGCGTCTTACACGG-------GGTATTGCTTTCTACAATGCAAGGGCA-CAGTTGAAGGTTTGCACC  3328
CYP52A2B 3178  AAGTGTGTTACACGGGGTGGTGATGGTGTTGGTTTCTACAATGCAAGGGCA-CAGTTGAAGGTTTCCACA  3246
CYP52A3A 3256  CGGCAGAGTTGTTATACTA-CGCTGGCGACATATCCTACAAGAAGGGCACATCAATCGCAGACAGTGCCA  3324
CYP52A3B 3055  CGGCCGAGTTGTTATACTA-CGCCGGCGACATATCCTACAAGAAGGGCACATCAATTGCCGACAGTGCCA  3123
CYP52A5A 3192  CCATGGATTACGCAGGCATCACGCGTGGCTCCATCAGAGG-CGAGGCCTTGAAGAAACTCG--CAGAATT  3258
CYP52A5B 3202  CCATGGATTACGCAGGTATCACGCGTGGGTCCATCAGAGG-CGAAGCCTTGAAGAAACTCG--CCGAGTT  3268
CYP52A8A 2516  AAACATGTTGCACCA-TATCCCTCCTGGAGTTGGTCGAC--CTCGCCTACGCC-ACCCTCA--GCGATCG  2579
CYP52A8B 2984  AAACATGTTGCACTG-CATCCCACTCAGAGTTGGTCGAC--CACGCCTACGCTTACCCTCA--GCGATCG  3048
CYP52D4A 2780  TGCTGTAGTATAACGAGCT--CTTGGTGTCCTTGAAATGGAACAGGTTGGATGTGTTGTTGAGTTTGTCT  2847
```

FIG. 15J-3

```
CYP52A1A 3368 ACGACTTCGGTGGGTTGTTATCTAAACGAAGATTCTATGAGACGCAGCATGTGTTTCGGTTCGAGGATTG 3437
CYP52A2A 3329 TAACGTTGCCCCGTGTCAACTCAATTTGAC-----------G--AGTAACTTCCTAAGCTCGAATTATGC 3385
CYP52A2B 3247 TAACGTTGCACCATATCAACTCAATTTATC-----------CTCATTCATGTGATAAAAGAAGAGCCAAA 3305
CYP52A3A 3325 GATTGTCTTATTATTTGAGAGCAAACTAC---------------ATCTTGAACATACTTGGGTATTTGAT 3379
CYP52A3B 3124 GATTGTCTTACTATTTGAGAGCAAACTAC---------------ATCTTGAACATACTTGGGTACTTTAT 3178
CYP52A5A 3259 G-ACCATCCAGAACCAGCCATCCAGCT------TGAAAGAAATCAACACCGGCATCCAGAAGGACGACTT 3321
CYP52A5B 3269 G-ACCATCCAGAACCAGCCATCCAGCT------TGAAAGAAATCAACACCGGCATCCAGAAGGACGACTT 3331
CYP52A8A 2580 GCACTTTCCGTTGTTCAATATTTCTC------------------CTTCCCATTGTTCCAGGGGTTA--TC 2629
CYP52A8B 3049 GCACTTTCCGTTGCTCAATATTTCTCT------CCCCCCTGCTTCCCCCCATTGTTCCAGGGATTA--TC 3110
CYP52D4A 2848 GCGTGCTTGGTTTGCAAGTCTTCGATCG----------------AGCGTAGTGAGTAGACAGTTGGCGGG 2901

CYP52A1A 3438 TGCGTACGTCATGAGTGTGCCTTTTGATGGACCCAAGGAGGAAGGTTACGTGGTTGGGACGTACAGATCC 3507
CYP52A2A 3386 AGCT-CGTGCGTCAACCTATGTGCAGGAAAGAAAAAATCCAAAAA--AATCGAAA-ATGCGACTTTCGAT 3451
CYP52A2B 3306 AGGT-AAT-TGGCAGACCCCCCAAGGGGAACACGGAGTAGAAAGC--AATGGAAACACGCCCATGACAGT 3371
CYP52A3A 3380 TTCG-AAGCAGCGATTGGATTTGATAGTCACGGACAACGACGCGT--TGTTTGATAGTATTTTGAAAAGT 3446
CYP52A3B 3179 TTCG-AAGCAGCGATTGGATGTGATAGTCACCGACAACAACGCGT--TGTTTGATAATATTTTGAAAAGT 3245
CYP52A5A 3322 TGCC-AAGTTGTTGTCTGCCACCCCGAAAATCCCCACCAAGCACA--AGTTGAACGGCAACCACGAATT- 3387
CYP52A5B 3332 TGCC-AAGTTGTTGTCTTCCACCCCGAAAATCCACACCAAGCACA--AGTTGAATGGCAACCACGAATT- 3397
CYP52A8A 2630 AACA-ACGTTGCCGGCCTCCTC------------CCCAAATTA-----------CAAGAAAAATAAATT- 2674
CYP52A8B 3111 AACA-ACGTTGCCGGTCTCCTCTCCCCCCCCTCCCCCCAGTTAT-------GTACAAGAAAATTAAATT- 3171
CYP52D4A 2902 GGTGGTGGCTCGGGCTTTATTCTGTGTTTGTGTTTCCTTCTTAGT--CTTGGAATGACGCTGTTATCGAC 2969
```

FIG. 15K-1

```
CYP52A1A 3508  ATTGAAAGGTTGAGCTGGGGTAAAGACGGGGACGTGGA-GTGGACCATGG---CGACGACGTCGGATCCT  3573
CYP52A2A 3452  TTTGAATAAACCAAAAAGAAAAATGTCGCACTTTTTTC-----TCGCTCTCGCTCTCTCGACCCAAATCA  3516
CYP52A2B 3372  GCCATTTAGCCCACA---ACACATCTAGTATTCTTTTT-----TTTTTTTGTGCGCAGGTGCACACCTGG  3433
CYP52A3A 3447  TTTGAAAAGATCTAC----AAGTTGATAAGCGTGTTGA-----ACGATATGATTGACAAGCAAAAGGTGA  3507
CYP52A3B 3246  TTTGAAAAGATCTAC----AAGTTGATAAGCGCGTTGA-----ACGATATGATTGACAAGCAAAAGGTGA  3306
CYP52A5A 3388  GTCTGAGGTCGCCATTGCCAAAAAGGAGTACGAGGTGTTGATTGCCTTGAGCGACGCCACAAAAGACCCA  3457
CYP52A5B 3398  GTCCGAAGTCGCCATTGCCAAAAAGGAGTACGAGGTGTTGATTGCCTTGAGCGACGCCACGAAAGAACCA  3467
CYP52A8A 2675  GTCGCACGGCACCGATCTGTCAAAGATACAGATAA--------ACCTTAAATCTGCAAAAACAAGACCCC  2736
CYP52A8B 3172  GTCGCACGGCACCGATACGTCAAAGATACAGAGAA--------ACCTTAA----------------TCC  3216
CYP52D4A 2970  GGTTCGTAGTATAAGTAGCGCCAATATGAGAATGTATA-----TCCGCATCACCCAAGACTCTTCAGCCT  3034

CYP52A1A 3574  GGTGGGTTTATCCCGCA-ATGGATAACTCGATTGAGCA-TCCCTGGAGCAATCGCAAAAGATGTGCCTAG  3641
CYP52A2A 3517  CAACAAATCCTCGCGCGCAGTATTTCGACGAAAC--CACAACAAATAAAAAAAACAAATTCTACACCACT  3584
CYP52A2B 3434  ACTTTAGTTATTGCCC-CATAAAGTTAACAATCT--CACCTTTGGCTCTCCCAGTGTCTCCGCCTCCAGA  3500
CYP52A3A 3508  CAAGCGACATCAACAGTCTAGCATTCATCAATTG--CATCAACTACTCGAGAGGTCAACTATTCTCCGCA  3575
CYP52A3B 3307  CAAGCGACATCAACAGTCTAGCATTTATCAACTG--CATCAACTACTCGAGGGGTCAACTATTCTCCGCA  3374
CYP52A5A 3458  ATCAAAGTGACCTCCCAGATCAAGATCTTGATTGACAAGTTCAAGGTGTACTTGT---TTGAGTTGCCTG  3524
CYP52A5B 3468  ATCAAAGTCACCTCCCAGATCAAGATCTTGATTGACAAGTTCAAGGTGTACTTGT---TTGAGTTGCCCG  3534
CYP52A8A 2737  TCCCCATAGCCTAGAAGCACCAGCAAGATGATGGAGCAACTCCTCCAGTACTGGTACATCGCACTCTCTG  2806
CYP52A8B 3217  CTCCCATAGCCTAGAAGCATCAAAAAGATGATTGAGCAACTCCTCCAGTACTGGTACATTGCACTCCCTG  3286
CYP52D4A 3035  GTTACAACGACTGAGGCTGTTGGCCGTGTGACCAATTGGTTTCTTTGGTGACCTAGATTGGTCCCGCAGG  3104
```

FIG. 15K-2

```
CYP52A1A 3642  TG---TATTAAACTACATACAGAAATAAAAACGTGTCTTGATTCATTGGTTT---GGTTCTTGTTGGGTT  3705
CYP52A2A 3585  T----CTTTTTCTTCACCAGTCAACAAAAAACAACAAATTATACACCATTTCAACGATTTTTGCTCTTAT  3650
CYP52A2B 3501  TG---CTCGTTTTACACCCTCGAGCTAACGACAACACAACACCCATGAGGGGAATGGGCAAAGTT-----  3562
CYP52A3A 3576  CA---CGAACTTTTGGG-ACTGGTTTTGTTTGGATTGGTCGACATCTATTTCAACCAGTTTGGCACATTA  3641
CYP52A3B 3375  CA---CGAACTTTTGGG-ACTGGTTTTGTTTGGATTGGTTGACAACTATTTCAACCAGTTTGGCTCATTA  3440
CYP52A5A 3525  AC---CAGAAGTTCTCCTACTCCATCGTGTCCAACTCCGTCAACATCGCCCCC-TGGACCTTGCTCGGGG  3590
CYP52A5B 3535  AC---CAGAAGTTCTCCTACTCCATCGTGTCCAACTCCGTTAACATTGCCCCC-TGGACCTTGCTCGGTG  3600
CYP52A8A 2807  TA---TGGTTCATCCTTCGCTACTTGGCTTCCCACGCACGAGCCGTCTACTTG-CGCCACAAGCTCGGCG  2872
CYP52A8B 3287  TA---TGGTTCATTCTCCGCTACGTGGCTTCCCACGCACGAACCATCTACTTG-CGCCACAAGCTCGGCG  3352
CYP52D4A 3105  GAAAGCAAGGGCTGCTAGGGGGGCATACCAAACAAGGTCGTGTAATCAGTATCTATGGTGCTACCATGTG  3174
```

FIG. 15K-3

```
CYP52A1A 3706  CCGAGCCAATATTTCACATCATCTCCTAAATTCTCCAAGAATCCCAACGTAGCGTAGTCCAGCACGCCCT  3775
CYP52A2A 3651  AAATGCTATATAATGGTTTAATTCAACTCAGGTATGTTTAT-TTTACTGTTTTCAGCTCAAGTATGT--T  3717
CYP52A2B 3563  AAACACTTTTGGTTTCAATGATTCCTATTTGCTACTCTCTTGTTTTGTGTTTTGATTTGCACCATGT--G  3630
CYP52A3A 3642  GACAACTACAAGAAGGTATTGGCATTGATACTGAAGAACATCAGCGATGAAGACATCTTGATCATAC--A  3709
CYP52A3B 3441  GACAACTACAAGAAAGTATTGGCATTGATACTGAAGAACATCAGTGATGAAGATATCTTGATCGTAC--G  3508
CYP52A5A 3591  AGAAGTTGACCACGGGCTTGATCAACTTGGCCTTCCAGAACAACAAGCAGCACTTGGACGAGGTCATT-G  3659
CYP52A5B 3601  AGAAGTTGACCACGGGCTTGATCAACTTGGCGTTCCAGAACAACAAGCAGCACTTGGACGAAGTCATC-G  3669
CYP52A8A 2873  CGGCGCCATTCACGCACACCCAGTACGACGGCTGGTATGGGTTCAAGTTTGGGCGGGAGTTTCTCAA--G  2940
CYP52A8B 3353  CGGCGCCGTTCACGCACACCCAGTACGACGGATGGTATGGGTTCAAGTTTGGGCGGGAGTTTCTCAA--G  3420
CYP52D4A 3175  TGTGGTTGGGGGGAAATTCCCGCATTTTTGTGTAACGAAAGTTCTAGAAAGTTCTCGTGGGTTCTGAG-A  3243

CYP52A1A 3776  CTGAGATCTTATTTAATATCGACTTCTCAACCACCGGTGGAATC--CCGTTCAGACCATTGTTACCTGTA  3843
CYP52A2A 3718  CAAATACTAACTACTTTTGATGTTTGTCGCTTTTCTAGAATCAAAACAACGCCCACAACACGCCGAGCTT  3787
CYP52A2B 3631  AAATAAACGACAATTATATATACCTTT---TCGTCTGTCCTC----CAATGTCT-CTTTTTGCTGCCATT  3692
CYP52A3A 3710  CTTCCTCCCATCGACACTACAATTGTTTAAGCTGGTGTTGGACAA-GAAAGACGACGCTGCAGTTGAACA  3778
CYP52A3B 3509  CTTCCTCCCATCGACACTACAATTGTTTAAGCTGGTGTTGGATAA-GAAAGACGACGCCACTGTTGACCA  3557
CYP52A5A 3660  ACATCTTCAACGAGTTCATCGACAAGTTCTTTGGCAACACGGAG--CCGCAATTGAC-----CAACTTCT  3722
CYP52A5B 3670  ACATCTTCAACGAGTTCATCGACAAGTTCTTTGGCAACACAGAG--CCGCAATTGAC-----CAACTTCT  3732
CYP52A8A 2941  GCGAAGAAGATCGGGCGGCAGACGGACTTGGTGCATGCGCGGTT--CCGTGGCGG-------CATGGACA  3001
CYP52A8B 3421  GCGAAGAAGATTGGAAGGCAGACGGACTTGGTGCATGCGCGGTT--CCGTGGAGGGGG----CATGGATA  3484
CYP52D4A 3244  ATCTGCTGGAACCATCCACCCGCATTTCCGTTGCCAAAGTGGGAA-GAGCAATCAACCCACCCTGCTTTG  3312
```

FIG. 15L-1

```
CYP52A1A 3844  GTGTGTTTGCTCTTGTTCTTGATGACAATGATGTATTTGTCACGATACCTGAAATAATAAAACATCCAGT  3913
CYP52A2A 3788  GTCGAATAGACGGTTTGTTTACTCATTAGATGGTCCCAGATTACTTTTCAAGCCAAAGTCTCT-CGAGTT  3856
CYP52A2B 3693  TTGCTTTTTGCTTTTTGCTTTTGCACT---CTCTCCCACTCCCACAATCAGTGCAGCAACACA-CAA  3755
CYP52A3A 3779  GTTCTACAAGTACATCACTTCAACAGT--GTCACGAGACTACAACTCCAACATCGGCTCCACAGCCAAAG  3846
CYP52A3B 3578  GTTCTACAAGTACATCACCTCAACAGT--GTCGCAAGACTACAACTCCAACATCGGAGCCACAGCCAAAG  3645
CYP52A5A 3723  TGACCTTGTGCGGTGTGTTGGACGGGTTGATTGACCATGCC-AACTTCTTGAGCGTGTCCTCGCGGACCT  3791
CYP52A5B 3733  TGACCTTGTCCGGTGTGTTGGACGGGTTGATTGACCATGCC-AACTTCTTGAGCGTGTCCTCCAGGACCT  3801
CYP52A8A 3002  CCTTCTCGAGCTACACTTTCGGCATCCATATCATCCTTACC-CGGGACCCGGAGAACATCAAGGCGGTCT  3070
CYP52A8B 3485  CTTTCTCGAGCTATACTTTCGGCATCCATATCATTCTTACT-CGGGACCCGGAGAACATCAAGGCGGTCT  3553
CYP52D4A 3313  CCCAATCAGCCATTCCCCTGGGAATATAAATTCAAC  3348

CYP52A1A 3914  CATTGAGCTTATTACTCGTGAACTTATGAAAGAACTCATTCAAGCCGTTCCCAAAAAACCCAGAATTGAA  3983
CYP52A2A 3857  TTGTTTGCTGTTTCCCCAATTCCTAACTATGAAGGGTTTTATAAGGTCCAAAGACCCCAAGGCATAGTT  3926
CYP52A2B 3756  3755
CYP52A3A 3847  ATGATATCGATTTGTCCAAAACCAAACTCAGTGGCTTTGAGGTGTTGACGAGTT  3900
CYP52A3B 3646  ATGATATCGATTTGTCCAAAGCC  3663
CYP52A5A 3792  TCAAGATCTTCTTGAACTTGGACTCGTATGTGGAC  3826
CYP52A5B 3802  TCAAGATCTTCTTGAACTTGGACTCGTTTGTGGACAACTCGGACTTCTTGAACGACGTGGAGAACTACTC  3871
CYP52A8A 3071  TGGCGACGCAGTTCGATGACTTCTCGCTCGGTGGCAGGATCAGGTTCTTGAAGCCGTTGTTGGGGTATGG  3140
DYP52A8B 3554  TGGCGACGCAGTTCGATGACTTTTCG  3579
CYP52D4A 3349  3348
```

FIG. 15L-2

```
CYP52A1A 3984  GATCTTGCTCAACTGGTCATGCAAGTAGTAGATCGCCATGATCTGATACTTTACCAAGCTATCCTCTCCA  4053
CYP52A2A 3927  TTTTTGGTTCCTTCTTGTCGTG                                                  3948
CYP52A2B 3756                                                                          3755
CYP52A3A 3901                                                                          3900
CYP52A3B 3669                                                                          3668
CYP52A5A 3827                                                                          3826
CYP52A5B 3872  CGACTTTTTGTACGACGAGCCGAACGAGTACCAGAACTT                                 3910
CYP52A8A 3141  GATATTCACGTT                                                            3152
CYP52A8B 3580                                                                          3579
CYP52D4A 3349                                                                          3348
```

FIG. 15L-3

```
CYP52A1A 4054  AGTTCTCCCACGTACGGCAAGTACGGCAACGAGCTCTGGAAGCTTTGTTGTTTGGGGTCATA  4115
CYP52A2A 3949                                                                  3948
CYP52A2B 3756                                                                  3755
CYP52A3A 3901                                                                  3900
CYP52A3B 3669                                                                  3668
CYP52A5A 3827                                                                  3826
CYP52A5B 3911                                                                  3910
CYP52A8A 3153                                                                  3152
CYP52A8B 3580                                                                  3579
CYP52D4A 3349                                                                  3348
```

FIG. 15M

```
CYP52A1A     1       MATQEIIDSVLPYL-------TKWYTVITAAVLVFLISTNIKNYV    38
CYP52A2A     1       MTVHDIIATY----------FTKWYVIVPLALIAYRVLDYFGRY     35
CYP52A2B     1       MTAQDIIATY----------ITKWYVIVPLALIAYRVLDYFGRY     35
CYP52A3A     1  MSSSPSFAQEVLATTSPYIEYFLDNYTRWYYFIPLVLLSLNFISLLHTRY    50
CYP52A3B     1  MSSSPSFAQEVLATTSPYIEYFLDNYTRWYYFIPLVLLSLNFISLLHTKY    50
CYP52A5A     1            MIEQLLEY----------WYVVVPVLYIIKQLLAYTKTRV    30
CYP52A5B     1            MIEQILEY----------WYIVVPVLYIIKQLIAYSKTRV    30
CYP52A8A     1            MLDQILHY----------WYIVLPLLAIINQIVAHVRTNY    30
CYP52A8B     1            MLDQIFHY----------WYIVLPLLVIIKQIVAHARTNY    30
CYP52D4A     1           MAISSLLSWD---------VICVVFICVCVYFGYEYCYTKY    32

CYP52A1A    39  KAKKLKCVDPPYLKDAGLTGILSLIAAIKAKNDGRLANFAD---EVFDEY    85
CYP52A2A    36  LMYKLGAKPFFQKQTDGCFGFKAPLELLKKKSDGTLIDFTL---QRIHDL    82
CYP52A2B    36  LMYKLGAKPFFQKQTDGYFGFKAPLELLKKKSDGTLIDFTL---ERIQAL    82
CYP52A3A    51  LERRFHAKPLGNFVRDPTFGIATPLLLIYLKSKGTVMKFAWGLWNNKYIV   100
CYP52A3B    51  LERRFHAKPLGNVVLDPTFGIATPLILIYLKSKGTVMKFAWSFWNNKYIV   100
CYP52A5A    31  LMKKLGAAPVTNKLYDNAFGIVNGWKALQFKKEGRAQEYND---YKFDHS    77
CYP52A5B    31  LMKQLGAAPITNQLYDNVFGIVNGWKALQFKKEGRAQEYND---HKFDSS    77
CYP52A8A    31  LMKKLGAKPFTHVQRDGWLGFKFGREFLKAKSAGRLVDLII---SRFHDN    77
CYP52A8B    31  LMKKLGAKPFTHVQLDGWFGFKFGREFLKAKSAGRQVDLII---SRFHDN    77
CYP52D4A    33  LMHKHGAREIENVINDGFFGFRLPLLLMRASNEGRLIEFSV---KRFESA    79
```

FIG. 16A-1

| | | | |
|---|---|---|---|
| CYP52A1A | 86 | PN--HTFYLSVAGALKIVMTVDPENIKAVLATQFTDFSLGTRHAHFAPLL | 133 |
| CYP52A2A | 83 | DRPDIPTFTFPVFSINLVNTLEPENIKAILATQFNDFSLGTRHSHFAPLL | 132 |
| CYP52A2B | 83 | NRPDIPTFTFPIFSINLISTLEPENIKAILATQFNDFSLGTRHSHFAPLL | 132 |
| CYP52A3A | 101 | RDPKYKTTGLRIVGLPLIETMDPENIKAVLATQFNDFSLGTRHDFLYSLL | 150 |
| CYP52A3B | 101 | KDPKYKTTGLRIVGLPLIETIDPENIKAVLATQFNDFSLGTRHDFLYSLL | 150 |
| CYP52A5A | 78 | KNPSVGTYVSILFGTRIVVTKDPENIKAILATQFGDFSLGKRHTLFKPLL | 127 |
| CYP52A5B | 78 | KNPSVGTYVSILFGTKIVVTKDPENIKAILATQFGDFSLGKRHALFKPLL | 127 |
| CYP52A8A | 78 | ED----TFSSYAFGNHVVFTRDPENIKALLATQFGDFSLGSRVKFFKPLL | 123 |
| CYP52A8B | 78 | ED----TFSSYAFGNHVVFTRDPENIKALLATQFGDFSLGSRVKFFKPLL | 123 |
| CYP52D4A | 80 | PHPQNKTLVNRALSVPVILTKDPVNIKAMLSTQFDDFSLGLRLHQFAPLL | 129 |

| | | | |
|---|---|---|---|
| CYP52A1A | 134 | GDGIFTLDGEGWKHSRAMLRPQFARDQIGHVKALEPHIQIMAKQIKLNQG | 183 |
| CYP52A2A | 133 | GDGIFTLDGAGWKHSRSMLRPQFAREQISHVKLLEPHVQVFFKHVRKAQG | 182 |
| CYP52A2B | 133 | GDGIFTLDGAGWKHSRSMLRPQFAREQISHVKLLEPHMQVFFKHVRKAQG | 182 |
| CYP52A3A | 151 | GDGIFTLDGAGWKHSRTMLRPQFAREQVSHVKLLEPHVQVFFKHVRKHRG | 200 |
| CYP52A3B | 151 | GDGIFTLDGAGWKHSRTMLRPQFAREQVSHVKLLEPHVQVFFKHVRKHRG | 200 |
| CYP52A5A | 128 | GDGIFTLDGEGWKHSRAMLRPQFAREQVAHVTSLEPHFQLLKKHILKHKG | 177 |
| CYP52A5B | 128 | GDGIFTLDGEGWKHSRSMLRPQFAREQVAHVTSLEPHFQLLKKHILKHKG | 177 |
| CYP52A8A | 124 | GYGIFTLDAEGWKHSRAMLRPQFAREQVAHVTSLEPHFQLLKKHILKHKG | 173 |
| CYP52A8B | 124 | GYGIFTLDGEGWKHSRAMLRPQFAREQVAHVTSLEPHFQLLKKHILKHKG | 173 |
| CYP52D4A | 130 | GKGIFTLDGPEWKQSRSMLRPQFAKDRVSHILDLEPHFVLLRKHIDGHNG | 179 |

FIG. 16A-2

```
CYP52A1A   184  KTFDIQELFFRFTVDTATEFLFGESVHSLYDEKLGIPTP-NEIPGRENFA   232
CYP52A2A   183  KTFDIQELFFRLTVDSATEFLFGESVESLRDESIGMSINALDFDGKAGFA  232
CYP52A2B   183  KTFDIQELFFRLTVDSATEFLFGESVESLRDESIGMSINALDFDGKAGFA  232
CYP52A3A   201  QTFDIQELFFRLTVDSATEFLFGESAESLRDESIGLTPTTKDFDGRRDFA  250
CYP52A3B   201  QTFDIQELFFRLTVDSATEFLFGESAESLRDDSVGLTPTTKDFEGRGDFA  250
CYP52A5A   178  EYFDIQELFFRFTVDSATEFLFGESVHSLKDESIGINQDDIDFAGRKDFA  227
CYP52A5B   178  EYFDIQELFFRFTVDSATEFLFGESVHSLKDETIGINQDDIDFAGRKDFA  227
CYP52A8A   174  EYFDIQELFFRFTVDSATEFLFGESVHSLKDEEIGYDTKDMSEERRR-FA  222
CYP52A8B   174  EYFDIQELFFRFTVDSATEFLFGESVHSLRDEEIGYDTKDMAEERRK-FA  222
CYP52D4A   180  DYFDIQELYFRFSMDVATGFLFGESVGSLKDE------D-------ARFL  216

CYP52A1A   233  AAFNVSQHYLATRSYSQTFYFLTNPKEFRDCNAKVHHLAKYFVNKALNFT  282
CYP52A2A   233  DAFNYSQNYLASRAVMQQLYWVLNGKKFKECNAKVHKFADYYVNKALDLT  282
CYP52A2B   233  DAFNYSQNYLASRAVMQQLYWVLNGKKFKECNAKVHKFADYYVSKALDLT  282
CYP52A3A   251  DAFNYSQTYQAYRFLLQQMYWILNGSEFRKSIAVVHKFADHYVQKALELT  300
CYP52A3B   251  DAFNYSQTYQAYRFLLQQMYWILNGAEFRKSIAIVHKFADHYVQKALELT  300
CYP52A5A   228  ESFNKAQEYLAIRTLVQTFYWLVNNKEFRDCTKLVHKFTNYYVQKALDAS  277
CYP52A5B   228  ESFNKAQEYLSIRILVQTFYWLINNKEFRDCTKLVHKRTNYYVQKALDAT  277
CYP52A8A   223  DAFNKSQVYVATRVALQNLYWLVNNKEFKECNDIVHKFTNYYVQKALDAT  272
CYP52A8B   223  DAFNKSQVYLSTRVALQTLYWLVNNKEFKECNDIVHKFTNYYVQKALDAT  272
CYP52D4A   217  EAFNESQKYLATRATLHELYFLCDGFRFRQYNKVVRKFCSQCVHKALDVA  266
```

FIG. 16B-1

```
CYP52A1A   283  PEELEEKSKSGYVFLYELVKQTRDPKVLQDQLLNIMVAGRDTTAGLLSFA  332
CYP52A2A   283  PEQLE-K-QDGYVFLYELVKQTRDKQVLRDQLLNIMVAGRDTTAGLLSFV  330
CYP52A2B   283  PEQLE-K-QDGYVFLYELVKQTRDRQVLRDQLLNIMVAGRDTTAGLLSFV  330
CYP52A3A   301  DDDLQ-K-QDGYVFLYELAKQTRDPKVLRDQLLNILVAGRDTTAGLLSFV  348
CYP52A3B   301  DDDLQ-K-QDGYVFLYELAKQTRDPKVLRDQLLNILVAGRDTTAGLLSFV  348
CYP52A5A   278  PEELE-K-QSGYVFLYELVKQTRDPNVLRDQSLNILLAGRDTTAGLLSFA  325
CYP52A5B   278  PEELE-K-QGGYVFLYELVKQTRDPKVLRDQSLNILLAGRDTTAGLLSFA  325
CYP52A8A   273  PEELE-K-QGGYVFLYELVKQTRDPKVLRDQSLNILLAGRDTTAGLLSFA  320
CYP52A8B   273  PEELE-K-QGGYVFLYELAKQTKDPNVLRDQSLNILLAGRDTTAGLLSFA  320
CYP52D4A   267  PEDTS-----EYVFLRELVKHTRDPVVLQDQALNVLLAGRDTTASLLSFA  311

CYP52A1A   333  LFELARHPEMWSKLREEIEVNFGVGEDSRVEEITFEALKRCEYLKAILNE  382
CYP52A2A   331  FFELARNPEVTNKLREEIEDKFGLGENASVEDISFESLKSCEYLKAVLNE  380
CYP52A2B   331  FFELARNPEVTNKLREEIEDKFGLGENARVEDISFESLKSCEYLKAVLNE  380
CYP52A3A   349  FYELSRNPEVFAKLREEVENRFGLGEEARVEEISFESLKSCEYLKAVINE  398
CYP52A3B   349  FYELSRNPEVFAKLREEVENRFGLGEEARVEEISFESLKSCEYLKAVINE  398
CYP52A5A   326  VFELARHPEIWAKLREEIEQQFGLGEDSRVEEITFESLKRCEYLKAFLNE  375
CYP52A5B   326  VFELARNPHIWAKLREEIEQQFGLGEDSRVEEITFESLKRCEYLKAFLNE  375
CYP52A8A   321  VFELARNPHIWAKLREEIEQQFGLGEDSRVEEITFESLKRCEYLKAVLNE  370
CYR52A8B   321  VFELARNPHIWAKLREEIESHFGLGEDSRVEEITFESLKRCEYLKAVLNE  370
CYP52D4A   312  TFELARNDHMWRKLREEVILTMGPSSD----EITVAGLKSCRYLKAILNE  357
```

FIG. 16B-2

```
CYP52A1A   383  TLRMYPSVPVNFRTATRDTTLPRGGGANGTDPIYIPKGSTVAYVVYKTHR  432
CYP52A2A   381  TLRLYPSVPQNFRVATKNTTLPRGGGKDGLSPVLVRKGQTVIYGVYAAHR  430
CYP52A2B   381  TLRLYPSVPQNFRVATKNTTLPRGGGKDGLSPVLVRKGQTVMYGVYAAHR  430
CYP52A3A   399  TLRLYPSVPHNFRVATRNTTLPRGGGEDGYSPIVVKKGQVVMYTVIATHR  448
CYP52A3B   399  ALRLYPSVPHNFRVATRNTTLPRGGGKDGCSPIVVKKGQVVMYTVIGTHR  448
CYP52A5A   376  TLRIYPSVPRNFRIATKNTTLPRGGGSDGTSPILIQKGEAVSYGINSTHL  425
CYP52A5B   376  TLRVYPSVPRNFRIATKNTTLPRGGGPDGTQPILIQKGEGVSYGINSTHL  425
CYP52A8A   371  TLRLHPSVPRNARFAIKDTTLPRGGGPNGKDPILIRKDEVVQYSISATQT  420
CYP52A8B   371  TLRLHPSVPRNARFAIKDTTLPRGGGPNGKDPILIRKNEVVQYSISATQT  420
CYP52D4A   358  TLRLYPSVPRNARFATRNTTLPRGGGPDGSFPILIRKGQPVGYFICATHL  407

CYP52A1A   433  LEEYYGKDANDFRPERWFEPSTKKLGWAYVPFNGGPRVCLGQQFALTEAS  482
CYP52A2A   431  NPAVYGKDALEFRPERWFEPETKKLGWAFLPFNGGPRICLGQQFALTEAS  480
CYP52A2B   431  NPAVYGKDALEFRPERWFEPETKKLGWAFLPFNGGPRICLGQQFALTEAS  480
CYP52A3A   449  DPSIYGADADVFRPERWFEPETRKLGWAYVPFNGGPRICLGQQFALTEAS  498
CYP52A3B   449  DPSIYGADADVFRPERWFEPETRKLGWAYVPFNGGPRICLGQQFALTEAS  498
CYP52A5A   426  DPVYYGPDAAEFRPERWFEPSTKKLGWAYLPFNGGPRICLGQQFALTEAG  475
CYP52A5B   426  DPVYYGPDAAEFRPERWFEPSTRKLGWAYLPFNGGPRICLGQQFALTEAG  475
CYP52A8A   421  NPAYYGADAADFRPERWFEPSTRNLGWAFLPFNGGPRICLGQQFALTEAG  470
CYP52A8B   421  NPAYYGADAADFRPERWFEPSTRNLGWAYLPFNGGPRICLGQQFALTEAG  470
CYP52D4A   408  NEKVYGNDSHVFRPERWAALEGKSLGWSYLPFNGGPRSCLGQQFAILEAS  457
```

FIG. 16C-1

| | | | |
|---|---|---|---|
| CYP52A1A | 483 | YVITRLAQMFETVSSDPGLEYPPPKCIHLTMSHNDGVFVKM | 523 |
| CYP52A2A | 481 | YVTVRLLQEFAHLSMDPDTEYPPKKMSHLTMSLFDGANIEMY | 522 |
| CYP52A2B | 481 | YVTVRLLQEFGHLSMDPNTEYPPRKMSHLTMSLFDGANIEMY | 522 |
| CYP52A3A | 499 | YVTVRLLQEFAHLSMDPDTEYPPKLQNTLTLSLFDGADVRMY | 540 |
| CYP52A3B | 499 | YVTVRLLQEFGNLSLDPNAEYPPKLQNTLTLSLFDGADVRMF | 540 |
| CYP52A5A | 476 | YVLVRLVQEFSHVRLDPDEVYPPKRLTNLTMCLQDGAIVKFD | 517 |
| CYP52A5B | 476 | YVLVRLVQEFSHIRLDPDEVYPPKRLTNLTMCLQDGAIVKFD | 517 |
| CYP52A8A | 471 | YVLVRLVQEFPNLSQDPETKYPPPRLAHLTMCLFDGAHVKMS | 512 |
| CYP52A8B | 471 | YVLVRLVQEFPSLSQDPETEYPPPRLAHLTMCLFDGAYVKMQ | 512 |
| CYP52D4A | 458 | YVLARLTQCYTTIQLR-TTEYPPKKLVHLTMSLLNGVYIRTRT | 499 |

FIG. 16C-2

Sequence Range: 1 to 1712

| | | | | | | | |
|---|---|---|---|---|---|---|---|
| 10 | 20 | 30 | 40 | 50 | 50 | 70 | 80 |
| GGTACCGAGC | TCACGAGTTT | TGGGATTTTC | GAGTTTGGAT | TGTTTCCTTT | GTTGATTGAA | TTGACGAAAC | CAGAGGTTTT |
| 90 | 100 | 110 | 120 | 130 | 140 | 150 | 160 |
| CAAGACAGAT | AAGATTGGGT | TTATCAAAAC | GCAGTTTGAA | ATATTCCAGT | TGGTTTCCAA | GATATCTTGA | AGAAGATTGA |
| 170 | 180 | 190 | 200 | 210 | 220 | 230 | 240 |
| CGATTTGAAA | TTTGAAGAAG | TGGAGAAGAT | CTGGTTTGGA | TTGTTGGAGA | ATTTCAAGAA | TCTCAAGATT | TACTCTAACG |
| 250 | 260 | 270 | 280 | 290 | 300 | 310 | 320 |
| ACGGGTACAA | CGAGAATTGT | ATTGAATTGA | TCAAGAACAT | GATCTTGGTG | TTACAGAACA | TCAAGTTCTT | GGACCAGACT |
| 330 | 340 | 350 | 360 | 370 | 380 | 390 | 400 |
| GAGAATGCCA | CAGATATACA | AGGCGTCATG | TGATAAAATG | GATGAGATTT | ATCCCACAAT | TGAAGAAAGA | GTTTATGGAA |
| 410 | 420 | 430 | 440 | 450 | 460 | 470 | 480 |
| AGTGGTCAAC | CAGAAGCTAA | ACAGGAAGAA | GCAAACGAAG | AGGTGAAACA | AGAAGAAGAA | GGTAAATAAG | TATTTTGTAT |
| 490 | 500 | 510 | 520 | 530 | 540 | 550 | 560 |
| TATATAACAA | ACAAAGTAAG | GAATACAGAT | TTATACAATA | AATTGCCATA | CTAGTCACGT | GAGATATCTC | ATCCATTCCC |
| 570 | 580 | 590 | 600 | 610 | 620 | 630 | 640 |
| CAACTCCCAA | GAAAAAAAAA | AAGTGAAAAA | AAAAATCAAA | CCCAAAGATC | AACCTCCCCA | TCATCATCGT | CATCAAACCC |

FIG. 23A

```
         650        660        670        680        690        700        710        720
CCAGCTCAAT TCGCAATGGT TAGCACAAAA ACATACACAG AAAGGGCATC AGCACACCCC TCCAAGGTTG CCCAACGTTT
                M  V   S  I  K   T  Y  T   E  R  A  S   A  H  P   S  K  V   A  Q  R  L>

         730        740        750        760        770        780        790        800
ATTCCGCTTA ATGGAGTCCA AAAAGACCAA CCTCTGCGCC TCGATCGACG TGACCACAAC CGCCGAGTTC CTTTCGCTCA
 F  R  L   M  E  S   K  K  T  N   L  C  A   S  I  D   V  T  T  T   A  E  F   L  S  L>

         810        820        830        840        850        860        870        880
TCGACAAGCT CGGTCCCCAC ATCTGTCTCG TGAAGACGCA CATCGATATC ATCTCAGACT TCAGCTACGA GGGCACGATT
I  D  K  L   G  P  H   I  C  L   V  K  T  H   I  D  I   I  S  D   F  S  Y  E   G  T  I>

         890        900        910        920        930        940        950        960
GAGCCGTTGC TTGTGCTTGC AGAGCGCCAC GGGTTCTTGA TATTCGAGGA CAGGAAGTTT GCTGATATCG GAAACACCGT
 E  P  L   L  V  L  A   E  R  H   G  F  L   I  F  E  D   R  K  F   A  D  I   G  N  T  V>

         970        980        990       1000       1010       1020       1030       1040
GATGTTGCAG TACACCTCGG GGGTATACCG GATCGCGGCG TGGAGTGACA TCACGAACGC GCACGGAGTG ACTGGGAAGG
 M  L  Q   Y  T  S   G  V  Y  R   I  A  A   W  S  D   I  T  N  A   H  G  V   T  G  K>

        1050       1060       1070       1080       1090       1100       1110       1120
GCGTCGTTGA AGGGTTGAAA CGCGGTGCGG AGGGGGTAGA AAAGGAAAGG GGCGTGTTGA TGTTGGCGGA GTTGTCGAGT
G  V  V  E   G  L  K   R  G  A   E  G  V  E   K  E  R   G  V  L   M  L  A  E   L  S  S>

        1130       1140       1150       1160       1170       1180       1190       1200
AAAGGCTCGT TGGCGCATGG TGAATATACC CGTGAGACGA TCGAGATTGC GAAGAGTGAT CGGGAGTTCG TGATTGGGTT
 K  G  S   L  A  H  G   E  Y  T   R  E  T   I  E  I  A   K  S  D   R  E  F   V  I  G  F>
```

FIG. 23B

```
      1210       1220       1230       1240       1250       1260       1270       1280
CATCGCGCAG CGGGACATGG GGGGTAGAGA AGAAGGGTTT GATTGGATCA TCATGACGCC TGGTGTGGGG TTGGATGATA
  I  A  Q   R  D  M   G  G  R  E   E  G  F   D  W  I   I  M  T  P   G  V  G   L  D  D>

      1290       1300       1310       1320       1330       1340       1350       1360
AAGGCGATGC GTTGGGCCAG CAGTATAGGA CTGTTGATGA GGTGGTTCTG ACTGGTACCG ATGTGATTAT TGTCGGGAGA
K  G  D  A   L  G  Q   Q  Y  R   T  V  D  E   V  V  L   T  G  T   D  V  I  I   V  G  R>

      1370       1380       1390       1400       1410       1420       1430       1440
GGGTTGTTTG GAAAAGGAAG AGACCCTGAG GTGGAGGGAA AGAGATACAG GGATGCTGGA TGGAAGGCAT ACTTGAAGAG
 G  L  F    G  K  G  R   D  P  E   V  E  G   K  R  Y  R   D  A  G   W  K  A   Y  L  K  R>

      1450       1460       1470       1480       1490       1500       1510       1520
AACTGGTCAG TTAGAATAAA TATTGTAATA AATAGGTCTA TATACATACA CTAAGCTTCT AGGACGTCAT TGTAGTCTTC
  T  G  Q   L  E  >

      1530       1540       1550       1560       1570       1580       1590       1600
GAAGTTGTCT GCTAGTTTAG TTCTCATGAT TTCGAAAACC AATAACGCAA TGGATGTAGC AGGGATGGTG GTTAGTGCGT

      1610       1620       1630       1640       1650       1660       1670       1680
TCCTGACAAA CCCAGAGTAC GCCGCCTCAA ACCACGTCAC ATTCGCCCTT TGCTTCATCC GCATCACTTG CTTGAAGGTA

      1690       1700       1710
TCCACGTACG AGTTGTAATA CACCTTGAAG AA
```

FIG. 23C

<u>GC parameters</u>

Column : HP-INNOWAX capillary column, 30m X 0.32mm, 0.5 μm film thickness
Split Ratio : 1:100
Column Head Pressure : 13.5 psig
Injector Temperature : 240°C
FID Detector Temp. : 250°C
Temp. Prog. : 90°C for 0 min. to 190°C @ 7°C/min. for 0 min. to 235°C @ 12°C/min. for 30 min.

CYTOCHROME P450 MONOOXYGENASE CYP52A2A FROM *CANDIDA TROPICALIS*

CROSS REFERENCE TO RELATED APPLICATIONS

The present application is a continuation of U.S. application Ser. No. 09/976,800, filed Oct. 12, 2001 now abandoned, which is a divisional application of U.S. Ser. No. 09/302,620, filed Apr. 30, 1999, now U.S. Pat. No. 6,331,420, issued Dec. 18, 2001, which claims priority to U.S. Provisional Application Ser. No. 60/123,555, filed Mar. 10, 1999, U.S. Provisional Application Ser. No. 60/103,099, filed Oct. 5, 1998, and U.S. Provisional Application Ser. No. 60/083,798, filed May 1, 1998.

BACKGROUND

1. Field of the Invention

The present invention relates to novel genes which encode enzymes of the ω-hydroxylase complex in yeast *Candida tropicalis* strains. In particular, the invention relates to novel genes encoding the cytochrome P450 and NADPH reductase enzymes of the ω-hydroxylase complex in yeast *Candida tropicalis,* and to a method of quantitating the expression of genes.

2. Description of the Related Art

Aliphatic dioic acids are versatile chemical intermediates useful as raw materials for the preparation of perfumes, polymers, adhesives and macrolid antibiotics. While several chemical routes to the synthesis of long-chain alpha, ω-dicarboxylic acids are available, the synthesis is not easy and most methods result in mixtures containing shorter chain lengths. As a result, extensive purification steps are necessary. While it is known that long-chain dioic acids can also be produced by microbial transformation of alkanes, fatty acids or esters thereof, chemical synthesis has remained the most commercially viable route, due to limitations with the current biological approaches.

Several strains of yeast are known to excrete alpha, ω-dicarboxylic acids as a byproduct when cultured on alkanes or fatty acids as the carbon source. In particular, yeast belonging to the Genus *Candida,* such as *C. albicans, C. cloacae, C. guillermondii, C. intermedia, C. lipolytica, C. maltosa, C. parapsilosis* and *C. zeylenoides* are known to produce such dicarboxylic acids (*Agr. Biol. Chem.* 35: 2033–2042 (1971)). Also, various strains of *C. tropicalis* are known to produce dicarboxylic acids ranging in chain lengths from $C_{11}$ through $C_{18}$ (Okino et al., B M Lawrence, B D Mookherjee and B J Willis (eds), in *Flavors and Fragrances: A World Perspective.* Proceedings of the $10^{th}$ International Conference of Essential Oils, Flavors and Fragrances, Elsevier Science Publishers BV Amsterdam (1988)), and are the basis of several patents as reviewed by Bühler and Schindler, in *Aliphatic Hydrocarbons in Biotechnology,* H. J. Rehm and G. Reed (eds), Vol. 169, Verlag Chemie, Weinheim (1984).

Studies of the biochemical processes by which yeasts metabolize alkanes and fatty acids have revealed three types of oxidation reactions: α-oxidation of alkanes to alcohols, ω-oxidation of fatty acids to alpha, ω-dicarboxylic acids and the degradative β-oxidation of fatty acids to $CO_2$ and water. The first two types of oxidations are catalyzed by microsomal enzymes while the last type takes place in the peroxisomes. In *C. tropicalis,* the first step in the ω-oxidation pathway is catalyzed by a membrane-bound enzyme complex (ω-hydroxylase complex) including a cytochrome P450 monooxygenase and a NADPH cytochrome reductase. This hydroxylase complex is responsible for the primary oxidation of the terminal methyl group in alkanes and fatty acids (Gilewicz et al., *Can. J. Microbiol.* 25:201 (1979)). The genes which encode the cytochrome P450 and NADPH reductase components of the complex have previously been identified as P450ALK and P450RED respectively, and have also been cloned and sequenced (Sanglard et al., *Gene* 76:121–136 (1989)). P450ALK has also been designated P450ALK1. More recently, ALK genes have been designated by the symbol CYP and RED genes have been designated by the symbol CPR. See, e.g., Nelson, *Pharmacogenetics* 6(1):1–42 (1996), which is incorporated herein by reference. See also Ohkuma et al., *DNA and Cell Biology* 14:163–173 (1995), Seghezzi et al., *DNA and Cell Biology,* 11:767–780 (1992) and Kargel et al., *Yeast* 12:333–348 (1996), each incorporated herein by reference. For example, P450ALK is also designated CYP52 according to the nomenclature of Nelson, supra. Fatty acids are ultimately formed from alkanes after two additional oxidation steps, catalyzed by alcohol oxidase (Kemp et al., *Appl. Microbiol. and Biotechnol.* 28:370–374 (1988)) and aldehyde dehydrogenase. The fatty acids can be further oxidized through the same or similar pathway to the corresponding dicarboxylic acid. The ω-oxidation of fatty acids proceeds via the ω-hydroxy fatty acid and its aldehyde derivative, to the corresponding dicarboxylic acid without the requirement for CoA activation. However, both fatty acids and dicarboxylic acids can be degraded, after activation to the corresponding acyl-CoA ester through the β-oxidation pathway in the peroxisomes, leading to chain shortening. In mammalian systems, both fatty acid and dicarboxylic acid products of ω-oxidation are activated to their CoA-esters at equal rates and are substrates for both mitochondrial and peroxisomal β-oxidation (*J. Biochem.,* 102:225–234 (1987)). In yeast, β-oxidation takes place solely in the peroxisomes (*Agr. Biol. Chem.* 49:1821–1828 (1985)).

It has recently been determined that certain eukaryotes, e.g., certain yeast, do not adhere, in some respects, to the "universal" genetic code which provides that particular codons (triplets of nucleic acids) code for specific amino acids. Indeed, the genetic code is "universal" because it is virtually the same in all living organisms. Certain *Candida* sp. are now known to translate the CTG codon (which, according to the "universal" code designates leucine) as serine. See, e.g., Ueda et al., *Biochemic* (1994) 76, 1217–1222, where *C. tropicalis, C. cylindracea, C. guilliermodii* and *C. lusitaniae* are shown to adhere to the "non-universal" code with respect to the CTG codon. Accordingly, nucleic acid sequences may code for one amino acid sequence in "universal" code organisms and a variant of that amino acid sequence in "non-universal" code organisms depending on the number of CTG codons present in the nucleic acid coding sequence. The difference may become evident when, in the course of genetic engineering, nucleic acid encoding a protein is transferred from a "non-universal" code organism to a "universal" code organism or vice versa. Obviously, there will be a different amino acid sequence depending on which organism is used to express the protein.

The production of dicarboxylic acids by fermentation of unsaturated $C_{14}$-$C_{16}$ monocarboxylic acids using a strain of the species *C. tropicalis* is disclosed in U.S. Pat. No. 4,474,882. The unsaturated dicarboxylic acids correspond to the starting materials in the number and position of the double bonds. Similar processes in which other special microorganisms are used are described in U.S. Pat. Nos.

3,975,234 and 4,339,536, in British Patent Specification 1,405,026 and in German Patent Publications 21 64 626, 28 53 847, 29 37 292, 29 51 177, and 21 40 133.

Cytochromes P450 (P450s) are terminal monooxidases of a multicomponent enzyme system as described above. They comprise a superfamily of proteins which exist widely in nature having been isolated from a variety of organisms as described e.g., in Nelson, supra. These organisms include various mammals, fish, invertebrates, plants, mollusk, crustaceans, lower eukaryotes and bacteria (Nelson, supra). First discovered in rodent liver microsomes as a carbon-monoxide binding pigment as described, e.g., in Garfinkel, *Arch. Biochem. Biophys.* 77:493–509 (1958), which is incorporated herein by reference, P450s were later named based on their absorption at 450 nm in a reduced-CO coupled difference spectrum as described, e.g., in Omura et al., *J. Biol. Chem.* 239:2370–2378 (1964), which is incorporated herein by reference.

P450s catalyze the metabolism of a variety of endogenous and exogenous compounds (Nelson, supra). Endogenous compounds include steroids, prostanoids, eicosanoids, fat-soluble vitamins, fatty acids, mammalian alkaloids, leukotrines, biogenic amines and phytolexins (Nelson, supra). P450 metabolism involves such reactions as epoxidation, hydroxylation, dealkylation, N-hydroxylation, sulfoxidation, desulfuration and reductive dehalogenation. These reactions generally make the compound more water soluble, which is conductive for excretion, and more electrophilic. These electrophilic products can have detrimental effects if they react with DNA or other cellular constituents. However, they can react through conjugation with low molecular weight hydrophilic substances resulting in glucoronidation, sulfation, acetylation, amino acid conjugation or glutathione conjugation typically leading to inactivation and elimination as described, e.g., in Klaasen et al., *Toxicology,* 3$^{rd}$ ed, Macmillan, New York, 1986, incorporated herein by reference.

P450s are heme thiolate proteins consisting of a heme moiety bound to a single polypeptide chain of 45,000 to 55,000 Da. The iron of the heme prosthetic group is located at the center of a protoporphyrin ring. Four ligands of the heme iron can be attributed to the porphyrin ring. The fifth ligand is a thiolate anion from a cysteinyl residue of the polypeptide. The sixth ligand is probably a hydroxyl group from an amino acid residue, or a moiety with a similar field strength such as a water molecule as described, e.g., in Goeptar et al., *Critical Reviews in Toxicology* 25(1):25–65 (1995), incorporated herein by reference.

Monooxygenation reactions catalyzed by cytochromes P450 in a eukaryotic membrane-bound system require the transfer of electrons from NADPH to P450 via NADPH-cytochrome P450 reductase (CPR) as described, e.g., in Taniguchi et al., *Arch. Biochem. Biophys.* 232:585 (1984), incorporated herein by reference. CPR genes are now also referred to as NCP genes. See, e.g., Debacker et al., *Antimicrobial Agents and Chemotherapy,* 45:1660 (2001). CPR is a flavoprotein of approximately 78,000 Da containing 1 mol of flavin adenine dinucleotide (FAD) and 1 mol of flavin mononucleotide (FMN) per mole of enzyme as described, e.g., in Potter et al., *J. Biol. Chem.* 258:6906 (1983), incorporated herein by reference. The FAD moiety of CPR is the site of electron entry into the enzyme, whereas FMN is the electron-donating site to P450 as described, e.g., in Vermilion et al., *J. Biol. Chem.* 253:8812 (1978), incorporated herein by reference. The overall reaction is as follows:

$$H^-+RH+NADPH+O_2 \rightarrow ROH+NADP^-+H_2O$$

Binding of a substrate to the catalytic site of P450 apparently results in a conformational change initiating electron transfer from CPR to P450. Subsequent to the transfer of the first electron, $O_2$ binds to the $Fe_2^-$-P450 substrate complex to form $Fe_3^-$-P450-substrate complex. This complex is then reduced by a second electron from CPR, or, in some cases, NADH via cytochrome b5 and NADH-cytochrome b5 reductase as described, e.g., in Guengerich et al., *Arch. Biochem. Biophys.* 205:365 (1980), incorporated herein by reference. One atom of this reactive oxygen is introduced into the substrate, while the other is reduced to water. The oxygenated substrate then dissociates, regenerating the oxidized form of the cytochrome P450 as described, e.g., in Klassen, Amdur and Doull, *Casarett and Doull's Toxicology,* Macmillan, New York (1986), incorporated herein by reference.

The P450 reaction cycle can be short-circuited in such a way that $O_2$ is reduced to $O_2^-$ and/or $H_2O_2$ instead of being utilized for substrate oxygenation. This side reaction is often referred to as the "uncoupling" of cytochrome P450 as described, e.g., in Kuthen et al., *Eur. J. Biochem.* 126:583 (1982) and Poulos et al., *FASEB*J. 6:674 (1992), both of which are incorporated herein by reference. The formation of these oxygen radicals may lead to oxidative cell damage as described, e.g., in Mukhopadhyay, *J. Biol. Chem.* 269 (18):13390–13397 (1994) and Ross et al., *Biochem. Pharm.* 69(7):979–989 (1925), both of which are incorporated herein by reference. It has been proposed that cytochrome b5's effect on P450 binding to the CPR results in a more stable complex which is less likely to become "uncoupled" as described, e.g., in Yamazaki et al., *Arch. Biochem. Biophys.* 325(2):174–182 (1996), incorporated herein by reference.

P450 families are assigned based upon protein sequence comparisons. Notwithstanding a certain amount of heterogeneity, a practical classification of P450s into families can be obtained based on deduced amino acid sequence similarity. P450s with amino acid sequence similarity of between about 40–80% are considered to be in the same family, with sequences of about >55% belonging to the same subfamily. Those with sequence similarity of about <40% are generally listed as members of different P450 gene families (Nelson, supra). A value of about >97% is taken to indicate allelic variants of the same gene, unless proven otherwise based on catalytic activity, sequence divergence in non-translated regions of the gene sequence, or chromosomal mapping.

The most highly conserved region is the HR2 consensus containing the invariant cysteine residue near the carboxyl terminus which is required for heme binding as described, e.g., in Gotoh et al. *J. Biochem.* 93:807–817 (1983) and Motohashi et al., *J. Biochem.* 101:879–997 (1987), both of which are incorporated herein by reference. Additional consensus regions, including the central region of helix I and the transmembrane region, have also been identified, as described, e.g, in Goeptar et al., supra and Kalb et al., *PNAS.* 85:7221–7225 (1988), incorporated herein by reference, although the HR2 cysteine is the only invariant amino acid among P450s.

Short chain (≦C12) aliphatic dicarboxylic acids (diacids) are important industrial intermediates in the manufacture of diesters and polymers, and find application as thermoplastics, plasticizing agents, lubricants, hydraulic fluids, agricultural chemicals, pharmaceuticals, dyes, surfactants, and adhesives. The high price and limited availability of short chair diacids are due to constraints imposed by the existing chemical synthesis.

Long-chain diacids (aliphatic α, ω-dicarboxylic acids with carbon numbers of 12 or greater, hereafter also referred to as diacids) ($HOOC—(CH_2)_n—COOH$) are a versatile family of chemicals with demonstrated and potential utility in a variety of chemical products including plastics, adhesives, and fragrances. Unfortunately, the full market potential of diacids has not been realized because chemical processes produce only a limited range of these materials at a relatively high price. In addition, chemical processes for the production of diacids have a number of limitations and disadvantages. All the chemical processes are restricted to the production of diacids of specific carbon chain lengths. For example, the dodecanedioic acid process starts with butadiene. The resulting product diacids are limited to multiples of four-carbon lengths and, in practice, only dodecanedioic acid is made. The dodecanedioic process is based on nonrenewable petrochemical feedstocks. The multireaction conversion process produces unwanted byproducts, which result in yield losses, $NO_x$ pollution and heavy metal wastes.

Long-chain diacids offer potential advantages over shorter chain diacids, but their high selling price and limited commercial availability prevent widespread growth in many of these applications. Biocatalysis offers an innovative way to overcome these limitations with a process that produces a wide range of diacid products from renewable feedstocks. However, there is no commercially viable bioprocess to produce long chain diacids from renewable resources.

SUMMARY OF THE INVENTION

An isolated nucleic acid is provided which encodes s CPRA protein having the amino acid sequence set forth in SEQ ID NO: 83 or SEQ ID NO: 117. An isolated nucleic acid is also provided which includes a coding region defined by nucleotides 1006–3042 as set forth in SEQ ID NO:81. An isolated protein is provided which includes an amino acid sequence as set forth in SEQ ID NO: 83 or SEQ ID NO: 117. A vector is provided which includes a nucleotide sequence encoding CPRA protein including an amino acid sequence as set forth in SEQ ID NO: 83 or SEQ ID NO: 117. A host cell is provided which is transfected or transformed with the nucleic acid encoding CPRA protein having an amino acid sequence as set forth in SEQ ID NO: 83 or SEQ ID NO: 117. A method of producing a CPRA protein including an amino acid sequence as set forth in SEQ ID NO: 83 or SEQ ID NO: 117 is also provided which includes a) transforming a suitable host cell with a DNA sequence that encodes the protein having the amino acid sequence as set forth in SEQ ID NO: 83 or SEQ ID NO: 117; and b) culturing the cell under conditions favoring the expression of the protein.

An isolated nucleic acid is provided which encodes a CPRB protein having the amino acid sequence set forth in SEQ ID NO: 84 or SEQ ID NO: 118. An isolated nucleic acid is provided which includes a coding region defined by nucleotides 1033–3069 as set forth in SEQ ID NO: 82. An isolated protein is provided which includes an amino acid sequence as set forth in SEQ ID NO: 84 or SEQ ID NO: 118. A vector is provided which includes a nucleotide sequence encoding CPRB protein including an amino acid sequence as set forth in SEQ ID NO: 84 or SEQ ID NO: 118. A host cell is provided which is transfected or transformed with the nucleic acid encoding CPRB protein having an amino acid sequence as set forth in SEQ ID NO: 84 or SEQ ID NO: 118. A method of producing a CPRB protein including an amino acid sequence as set forth in SEQ ID NO: 84 or SEQ ID NO: 118 is provided which includes a) transforming a suitable host cell with a DNA sequence that encodes the protein having the amino acid sequence as set forth in SEQ ID NO: 84 or SEQ ID NO: 118; and b) culturing the cell under conditions favoring the expression of the protein.

An isolated nucleic acid is provided which encodes a CYP52A1A protein having the amino acid sequence set forth in SEQ ID NO: 95 or SEQ ID NO: 110. An isolated nucleic acid is provided which includes a coding region defined by nucleotides 1177–2748 as set forth in SEQ ID NO: 85. An isolated protein is provided which includes an amino acid sequence as set forth in SEQ ID NO: 95 or SEQ ID NO: 110. A vector is provided which includes a nucleotide sequence encoding CYP52A1A protein including an amino acid sequence as set forth in SEQ ID NO: 95 or SEQ ID NO: 110. A host cell is provided which is transfected or transformed with the nucleic acid encoding CYP52A1A protein having an amino acid sequence as set forth in SEQ ID NO: 95 or SEQ ID NO: 110. A method of producing a CYP52A1A protein including an amino acid sequence as set forth in SEQ ID NO: 95 or SEQ ID NO: 110 is provided which includes a) transforming a suitable host cell with a DNA sequence that encodes the protein having the amino acid sequence as set forth in SEQ ID NO: 95 or SEQ ID NO: 110; and b) culturing the cell under conditions favoring the expression of the protein.

An isolated nucleic acid encoding a CYP52A2A protein is provided which has the amino acid sequence set forth in SEQ ID NO: 96. An isolated nucleic acid is provided which includes a coding region defined by nucleotides 1199–2767 as set forth in SEQ ID NO: 86. An isolated protein is provided which includes an amino acid sequence as set forth in SEQ ID NO: 96. A vector is provided which includes a nucleotide sequence encoding CYP52A2A protein including an amino acid sequence as set forth in SEQ ID NO: 96. A host cell is provided which is transfected or transformed with the nucleic acid encoding CYP52A2A protein having an amino acid sequence as set forth in SEQ ID NO: 96. A method of producing a CYP52A2A protein including an amino acid sequence as set forth in SEQ ID NO: 96 is provided which includes a) transforming a suitable host cell with a DNA sequence that encodes the protein having the amino acid sequence as set forth in SEQ ID NO: 96; and b) culturing the cell under conditions favoring the expression of the protein.

An isolated nucleic acid encoding a CYP52A2B protein is provided which has the amino acid sequence set forth in SEQ ID NO: 97. An isolated nucleic acid is provided which includes a coding region defined by nucleotides 1072–2640 as set forth in SEQ ID NO: 87. An isolated protein is provided which includes an amino acid sequence as set forth in SEQ ID NO: 97. A vector is provided which includes a nucleotide sequence encoding CYP52A2B protein including an amino acid sequence as set forth in SEQ ID NO: 97. A host cell is provided which is transfected or transformed with the nucleic acid encoding CYP52A2B protein having an amino acid sequence as set forth in SEQ ID NO: 97. A method of producing a CYP52A2B protein including an amino acid sequence as set forth in SEQ ID NO: 97 is provided which includes a) transforming a suitable host cell with a DNA sequence that encodes the protein having the amino acid sequence as set forth in SEQ ID NO: 97; and b) culturing the cell under conditions favoring the expression of the protein.

An isolated nucleic acid encoding a CYP52A3A protein is provided which has the amino acid sequence set forth in SEQ ID NO: 98. An isolated nucleic acid is provided which includes a coding region defined by nucleotides 1126–2748 as set forth in SEQ ID NO: 88. An isolated protein is provided which includes an amino acid sequence as set forth in SEQ ID NO: 98. A vector is provided which includes a nucleotide sequence encoding CYP52A3A protein including an amino acid sequence as set forth in SEQ ID NO: 98. A host cell is provided which is transfected or transformed with the nucleic acid encoding CYP52A3A protein having an amino acid sequence as set forth in SEQ ID NO: 98. A method of producing a CYP52A3A protein including an amino acid sequence as set forth in SEQ ID NO: 98 is provided which includes a) transforming a suitable host cell with a DNA sequence that encodes the protein having the amino acid sequence as set forth in SEQ ID NO: 98; and b) culturing the cell under conditions favoring the expression of the protein.

An isolated nucleic acid encoding a CYP52A3B protein is provided having the amino acid sequence as set forth in SEQ ID NO: 99 or SEQ ID NO: 111. An isolated nucleic acid is provided which includes a coding region defined by nucleotides 913–2535 as set forth in SEQ ID NO: 89. An isolated protein is provided which includes an amino acid sequence as set forth in SEQ ID NO: 99 or SEQ ID NO: 111. A vector is provided which includes a nucleotide sequence encoding CYP52A3B protein including an amino acid sequence as set forth in SEQ ID NO: 99 or SEQ ID NO: 111. A host cell is provided which is transfected or transformed with the nucleic acid encoding CYP52A3B protein having an amino acid sequence as set forth in SEQ ID NO: 99 or SEQ ID NO: 111. A method of producing a CYP52A3B protein including an amino acid sequence as set forth in SEQ ID NO: 99 or SEQ ID NO: 111 is provided which includes a) transforming a suitable host cell with a DNA sequence that encodes the protein having the amino acid sequence as set forth in SEQ ID NO: 99 or SEQ ID NO: 111; and b) culturing the cell under conditions favoring the expression of the protein.

An isolated nucleic acid encoding a CYP52A5A protein is provided having the amino acid sequence set forth in SEQ ID NO: 100 or SEQ ID NO: 112. An isolated nucleic acid is provided which includes a coding region defined by nucleotides 1103–2656 as set forth in SEQ ID NO: 90. An isolated protein is provided which includes an amino acid sequence as set forth in SEQ ID NO: 100 or SEQ ID NO: 112. A vector is provided which includes a nucleotide sequence encoding CYP52A5A protein including an amino acid sequence as set forth in SEQ ID NO: 100 or SEQ ID NO: 112. A host cell is provided which is transfected or transformed with the nucleic acid encoding CYP52A5A protein having an amino acid sequence as set forth in SEQ ID NO: 100 or SEQ ID NO: 112. A method of producing a CYP52A5A protein including an amino acid sequence as set forth in SEQ ID NO: 100 or SEQ ID NO: 112 is provided which includes a) transforming a suitable host cell with a DNA sequence that encodes the protein having the amino acid sequence as set forth in SEQ ID NO: 100 or SEQ ID NO: 112; and b) culturing the cell under conditions favoring the expression of the protein.

An isolated nucleic acid encoding a CYP52A5B protein is provided having the amino acid sequence as set forth in SEQ ID NO: 101 or SEQ ID NO: 113. An isolated nucleic acid is provided which includes a coding region defined by nucleotides 1142–2695 as set forth in SEQ ID NO: 91. An isolated protein is provided which includes an amino acid sequence as set forth in SEQ ID NO: 101 or SEQ ID NO: 113. A vector is provided which includes a nucleotide sequence encoding CYP52A5B protein including the amino acid sequence as set forth in SEQ ID NO: 101 or SEQ ID NO: 113. A host cell is provided which is transfected or transformed with the nucleic acid encoding CYP52A5B protein having the amino acid sequence as set forth in SEQ ID NO: 101 or SEQ ID NO: 113. A method of producing a CYP52A5B protein including an amino acid sequence as set forth in SEQ ID NO: 101 or SEQ ID NO: 113 is provided which includes a) transforming a suitable host cell with a DNA sequence that encodes the protein having the amino acid sequence as set forth in SEQ ID NO: 101 or SEQ ID NO: 113; and b) culturing the cell under conditions favoring the expression of the protein.

An isolated nucleic acid encoding a CYP52A8A protein is provided having the amino acid sequence set forth in SEQ ID NO: 102 or SEQ ID NO: 114. An isolated nucleic acid is provided which includes a coding region defined by nucleotides 464–2002 as set forth in SEQ ID NO: 92. An isolated protein is provided which includes an amino acid sequence as set forth in SEQ ID NO: 102 or SEQ ID NO: 114. A vector is provided which includes a nucleotide sequence encoding CYP52A8A protein including an amino acid sequence as set forth in SEQ ID NO: 102 or SEQ ID NO: 114. A host cell is provided which is transfected or transformed with the nucleic acid encoding CYP52A8A protein having an amino acid sequence as set forth in SEQ ID NO: 102 or SEQ ID NO: 114. A method of producing a CYP52A8A protein including an amino acid sequence as set forth in SEQ ID NO: 102 or SEQ ID NO: 114 is provided which includes a) transforming a suitable host cell with a DNA sequence that encodes the protein having the amino acid sequence as set forth in SEQ ID NO: 102 or SEQ ID NO: 114; and b) culturing the cell under conditions favoring the expression of the protein.

An isolated nucleic acid encoding a CYP52A8B protein is provided having the amino acid sequence set forth in SEQ ID NO: 103 or SEQ ID NO: 115. An isolated nucleic acid is provided which includes a coding region defined by nucleotides 1017–2555 as set forth in SEQ ID NO: 93. An isolated protein is provided which includes an amino acid sequence as set forth in SEQ ID NO: 103 or SEQ ID NO: 115. A vector is provided which includes a nucleotide sequence encoding CYP52A8B protein including an amino acid sequence as set forth in SEQ ID NO: 103 or SEQ ID NO: 115. A host cell is provided which is transfected or transformed with the nucleic acid encoding CYP52A8B protein having an amino acid sequence as set forth in SEQ ID NO: 103 or SEQ ID NO: 115. A method of producing a CYP52A8B protein including an amino acid sequence as set forth in SEQ ID NO: 103 or SEQ ID NO: 115 is provided which includes a) transforming a suitable host cell with a DNA sequence that encodes the protein having the amino acid sequence as set forth in SEQ ID NO: 103 or SEQ ID NO: 115; and b) culturing the cell under conditions favoring the expression of the protein.

An isolated nucleic acid encoding a CYP52D4A protein is provided having the amino acid sequence set forth in SEQ ID NO: 104 or SEQ ID NO: 116. An isolated nucleic acid is provided including a coding region defined by nucleotides 767–2266 as set forth in SEQ ID NO: 94. An isolated protein is provided which includes an amino acid sequence as set forth in SEQ ID NO: 104 or SEQ ID NO: 116. A vector is provided which includes a nucleotide sequence encoding CYP52D4A protein including an amino acid sequence as set forth in SEQ ID NO: 104 or SEQ ID NO: 116. A host cell is provided which is transfected or transformed with the nucleic acid encoding CYP52D4A protein having an amino acid sequence as set forth in SEQ ID NO: 104 or SEQ ID NO: 116. A method of producing a CYP52D4A protein including an amino acid sequence as set forth in SEQ ID NO: 104 or SEQ ID NO: 116 is provided which includes a) transforming a suitable host cell with a DNA sequence that encodes the protein having the amino acid sequence as set forth in SEQ ID NO: 104 or SEQ ID NO: 116; and b) culturing the cell under conditions favoring the expression of the protein.

A method for discriminating members of a gene family by quantifying the amount of target mRNA in a sample is provided which includes a) providing an organism containing a target gene; b) culturing the organism with an organic substrate which causes upregulation in the activity of the target gene; c) obtaining a sample of total RNA from the organism at a first point in time; d) combining at least a portion of the sample of the total RNA with a known amount of competitor RNA to form an RNA mixture, wherein the competitor RNA is substantially similar to the target mRNA but has a lesser number of nucleotides compared to the target mRNA; e) adding reverse transcriptase to the RNA mixture in a quantity sufficient to form corresponding target DNA and competitor DNA; (f) conducting a polymerase chain reaction in the presence of at least one primer specific for at least one substantially non-homologous region of the target DNA within the gene family, the primer also specific for the competitor DNA; g) repeating steps (c–f) using increasing amounts of the competitor RNA while maintaining a substantially constant amount of target RNA; h) determining the point at which the amount of target DNA is substantially equal to the amount of competitor DNA; i) quantifying the results by comparing the ratio of the concentration of unknown target to the known concentration of competitor; and j) obtaining a sample of total RNA from the organism at another point in time and repeating steps (d–i).

A method for increasing production of a dicarboxylic acid is provided which includes a) providing a host cell having a naturally occurring number of CPRA genes; b) increasing, in the host cell, the number of CPRA genes which encode a CPRA protein having the amino acid sequence as set forth in SEQ ID NO: 83 or SEQ ID NO: 117; c) culturing the host cell in media containing an organic substrate which upregulates the CPRA gene, to effect increased production of dicarboxylic acid.

A method for increasing the production of a CPRA protein having an amino acid sequence as set forth in SEQ ID NO: 83 or SEQ ID NO: 117 is provided which includes a) transforming a host cell having a naturally occurring amount of CPRA protein with an increased copy number of a CPRA gene that encodes the CPRA protein having the amino acid sequence as set forth in SEQ ID NO: 83 or SEQ ID NO: 117; and b) culturing the cell and thereby increasing expression of the protein compared with that of a host cell containing a naturally occurring copy number of the CPRA gene.

A method for increasing production of a dicarboxylic acid is provided which includes a) providing a host cell having a naturally occurring number of CPRB genes; b) increasing, in the host cell, the number of CPRB genes which encode a CPRB protein having the amino acid sequence as set forth in SEQ ID NO: 84 or SEQ ID NO: 118; c) culturing the host cell in media containing an organic substrate which upregulates the CPRB gene, to effect increased production of dicarboxylic acid.

A method for increasing the production of CPRB protein having an amino acid sequence as set forth in SEQ ID NO: 84 or SEQ ID NO: 118 is provided which includes a) transforming a host cell having a naturally occurring amount of CPRB protein with an increased copy number of a CPRB gene that encodes the CPRB protein having the amino acid sequence as set forth in SEQ ID NO: 84 or SEQ ID NO: 118; and b) culturing the cells and thereby increasing expression of the protein compared with that of a host cell containing a naturally occurring copy number of the CPRB gene.

A method for increasing production of a dicarboxylic acid is provided which includes a) providing a host cell having a naturally occurring number of CYP52A1A genes; b) increasing, in the host cell, the number of CYP52A1A genes which encode a CYP52A1A protein having the amino acid sequence as set forth in SEQ ID NO: 95 or SEQ ID NO: 110; c) culturing the host cell in media containing an organic substrate which upregulates the CPY52A1A gene, to effect increased production of dicarboxylic acid.

A method for increasing the production of a CYP52A1A protein having an amino acid sequence as set forth in SEQ ID NO: 95 or SEQ ID NO: 110 is provided which includes a) transforming a host cell having a naturally occurring amount of CYP52A1A protein with an increased copy number of a CYP52A1A gene that encodes the CYP52A1A protein having the amino acid sequence as set forth in SEQ ID NO: 95 or SEQ ID NO: 110; and b) culturing the cell and thereby increasing expression of the protein compared with that of a host cell containing a naturally occurring copy number of the CYP52A1A gene.

A method for increasing production of a dicarboxylic acid is provided which includes a) providing a host cell having a naturally occurring number of CYP52A1A genes; b) increasing, in the host cell, the number of CYP52A2A genes which encode a CYP52A2A protein having the amino acid sequence as set forth in SEQ ID NO: 96; c) culturing the host cell in media containing an organic substrate which upregulates the CYP52A2A gene, to effect increased production of dicarboxylic acid.

A method for increasing the production of a CYP52A2A protein having an amino acid sequence as set forth in SEQ ID NO: 96 is provided which includes a) transforming a host cell having a naturally occurring amount of CYP52A2A protein with an increased copy number of a CYP52A2A gene that encodes the CYP52A2A protein having the amino acid sequence as set forth in SEQ ID NO: 96; and b) culturing the cell and thereby increasing expression of the protein compared with that of a host cell containing a naturally occurring copy number of the CYP52A2A gene.

A method for increasing production of a dicarboxylic acid is provided which includes a) providing a host cell having a naturally occurring number of CYP52A2B genes; b) increasing, in the host cell, the number of CYP52A2B genes which encode a CYP52A2B protein having the amino acid sequence as set forth in SEQ ID NO: 97; c) culturing the host cell in media containing an organic substrate which upregulates the CYP52A2B gene, to effect increased production of dicarboxylic acid.

A method for increasing the production of a CYP52A2B protein having an amino acid sequence as set forth in SEQ ID NO: 97 is provided which includes a) transforming a host cell having a naturally occurring amount of CYP52A2B protein with an increased copy number of a CYP52A2B gene that encodes the CYP52A2B protein having the amino acid sequence as set forth in SEQ ID NO: 97; and b) culturing the cell and thereby increasing expression of the protein compared with that of a host cell containing a naturally occurring copy number of the CYP52A2B gene.

A method for increasing production of a dicarboxylic acid is provided which includes a) providing a host cell having a naturally occurring number of CYP52A3A genes; b) increasing, in the host cell, the number of CYP52A3A genes which encode a CYP52A3A protein having the amino acid sequence as set forth in SEQ ID NO: 98; c) culturing the host cell in media containing an organic substrate which upregulates CYP52A3A gene, to effect increased production of dicarboxylic acid.

A method for increasing the production of a CYP52A3A protein having an amino acid sequence as set forth in SEQ ID NO: 98 is provided which includes a) transforming a host cell having a naturally occurring amount of CYP52A3A protein with an increased copy number of a CYP52A3A gene that encodes the CYP52A3A protein having the amino acid sequence as set forth in SEQ ID NO: 98; and b) culturing the cell and thereby increasing expression of the protein compared with that of a host cell containing a naturally occurring copy number of the CYP52A3A gene.

A method for increasing production of a dicarboxylic acid is provided which includes a) providing a host cell having a naturally occurring number of CYP52A3B genes; b) increasing, in the host cell, the number of CYP52A3B genes which encode a CYP52A3B protein having the amino acid sequence as set forth in SEQ ID NO: 99 or SEQ ID NO: 111; c) culturing the host cell in media containing an organic substrate which upregulates the CYP52A3B gene, to effect increased production of dicarboxylic acid.

A method for increasing the production of a CYP52A3B protein having an amino acid sequence as set forth in SEQ ID NO: 99 or SEQ ID NO: 111 is provided which includes a) transforming a host cell having a naturally occurring amount of CYP52A3B protein with an increased copy number of a CYP52A3B gene that encodes the CYP52A3B protein having the amino acid sequence as set forth in SEQ ID NO: 99 or SEQ ID NO: 111; and b) culturing the cell and thereby increasing expression of the protein compared with that of a host cell containing a naturally occurring copy number of the CYP52A3B gene.

A method for increasing production of a dicarboxylic acid is provided which includes a) providing a host cell having a naturally occurring number of CYP52A5A genes; b) increasing, in the host cell, the number of CYP52A5A genes which encode a CYP52A5A protein having the amino acid sequence as set forth in SEQ ID NO: 100 or SEQ ID NO: 112; c) culturing the host cell in media containing an organic substrate which upregulates the CYP52A5A gene, to effect increased production of dicarboxylic acid.

A method for increasing the production of a CYP52A5A protein having an amino acid sequence as set forth in SEQ ID NO: 100 or SEQ ID NO: 112 is provided which includes a) transforming a host cell having a naturally occurring amount of CYP52A5A protein with an increased copy number of a CYP52A5A gene that encodes the CYP52A5A protein having the amino acid sequence as set forth in SEQ ID NO: 100 or SEQ ID NO: 112; and b) culturing the cell and thereby increasing expression of the protein compared with that of a host cell containing a naturally occurring copy number of the CYP52A5A gene.

A method for increasing production of a dicarboxylic acid is provided which includes a) providing a host cell having a naturally occurring number of CYP52A5B genes: b) increasing, in the host cell, the number of CYP52A5B genes which encode a CYP52A5B protein having the amino acid sequence as set forth in SEQ ID NO: 1010 or SEQ ID NO: 113; c) culturing the host cell in media containing an organic substrate which upregulates the CYP52A5B gene, to effect increased production of dicarboxylic acid.

A method for increasing the production of a CYP52A5B protein having an amino acid sequence as set forth in SEQ ID NO: 101 or SEQ ID NO: 113 is provided which includes a) transforming a host cell having a naturally occurring amount of CYP52A5B protein with an increased copy number of a CYP52A5B gene that encodes the CYP52A5B protein having the amino acid sequence as set forth in SEQ ID NO: 101 or SEQ ID NO: 113; and b) culturing the cell and thereby increasing expression of the protein compared with that of a host cell containing a naturally occurring copy number of the CYP52A5B gene.

A method for increasing production of a dicarboxylic acid is provided which includes a) providing a host cell having a naturally occurring number of CYP52A8A genes; b) increasing, in the host cell, the number of CYP52A8A genes which encode a CYP52A8A protein having the amino acid sequence as set forth in SEQ ID NO: 102 or SEQ ID NO: 114; c) culturing the host cell in media containing an organic substrate which upregulates the CYP52A8A gene, to effect increased production of dicarboxylic acid.

A method for increasing the production of a CYP52A8A protein having an amino acid sequence as set forth in SEQ ID NO: 102 or SEQ ID NO; 114 is provided which includes a) transforming a host cell having a naturally occurring amount of CYP52A8A protein with an increased copy number of a CYP52A8A gene that encodes the CYP52A8A protein having the amino acid sequence as set forth in SEQ ID NO: 102 or SEQ ID NO: 114; and b) culturing the cell and thereby increasing expression of the protein compared with that of a host cell containing a naturally occurring copy number of the CYP52A8A gene.

A method for increasing production of a dicarboxylic acid is provided which includes a) providing a host cell having a naturally occurring number of CYP52A8B genes; b) increasing, in the host cell, the number of CYP52A8B genes which encode a CYP52A8B protein having the amino acid sequence as set forth in SEQ ID NO: 103 or SEQ ID NO: 115; c) culturing the host cell in media containing an organic substrate which upregulates the CYP52A8B gene, to effect increased production of dicarboxylic acid.

A method for increasing the production of a CYP52A8B protein having an amino acid sequence as set forth in SEQ ID NO: 103 or SEQ ID NO: 115 is provided which includes a) transforming a host cell having a naturally occurring amount of CYP52A8B protein with an increased copy number of a CYP52A8B gene that encodes the CYP52A8B protein having the amino acid sequence as set forth in SEQ ID NO: 103 or SEQ ID NO: 115; and b) culturing the cell and thereby increasing expression of the protein compared with that of a host cell containing a naturally occurring copy number of the CYP52A8B gene.

A method for increasing production of a dicarboxylic acid is provided which includes a) providing a host cell having a naturally occurring number of CYP52D4A genes; b) increasing, in the host cell, the number of CYP52D4A genes which encode a CYP52D4A protein having the amino acid sequence as set forth in SEQ ID NO: 104 or SEQ ID NO: 116; c) culturing the host cell in media containing an organic substrate which upregulates the CYP52D4A gene, to effect increased production of dicarboxylic acid.

A method for increasing the production of a CYP52D4A protein having an amino acid sequence as set forth in SEQ ID NO: 104 or SEQ ID NO: 116 is provided which includes a) transforming a host cell having a naturally occurring amount of CYP52D4A protein with an increased copy number of a CYP52D4A gene that encodes the CYP52D4A protein having the amino acid sequence as set forth in SEQ ID NO: 104 or SEQ ID NO: 116; and b) culturing the cell and thereby increasing expression of the protein compared with that of a host cell containing a naturally occurring copy number of the CYP52D4A gene.

BRIEF DESCRIPTION OF THE DRAWINGS

FIG. 3 is a double stranded DNA sequence of a portion of the 5 prime coding region of the CYP52A5A gene (SEQ ID NO: 36), the non-coding or antisense sequence (SEQ ID NO: 108), primer 7581-97F (SEQ ID NO: 47) and primer 7581-97M (SEQ ID NO: 48).

FIG. 8 is a diagrammatic representation of the plasmid pHKM11 containing the CYP52A1A gene (SEQ ID NO: 85) present in the pBK-CMV vector. A detailed restriction map of only the sequenced region is shown at the top. The bar indicates the open reading frame. The direction of transcription is indicated by an arrow under the open reading frame.

FIGS. 13A-I through 13D-2 show the complete DNA sequences including regulatory and coding regions for the CPRA gene (SEQ ID NO: 81) and CPRB gene (SEQ ID NO: 82) from *C. tropicalis* ATCC 20336. FIGS. 13A-I through 13D-2 show regulatory and coding region alignment of these sequences. Asterisks indicate conserved nucleotides. The start codons are underlined and the last amino acid coding codons immediately before the stop codon are underlined.

FIGS. 14A through 14B shows the amino acid sequence of the CPRA (SEQ ID NO: 83) and CPRB (SEQ ID NO: 84) proteins from *C. tropicalis* ATCC 20336 and alignment of these amino acid sequences. Asterisks indicate residues which are not conserved.

FIGS. 15A-1 through 15M show the complete DNA sequences including regulatory and coding regions for the following genes from *C. tropicalis* ATCC 20366: CYP52A1A (SEQ ID NO: 85), CYP52A2A (SEQ ID NO: 86), CYP52A2B (SEQ ID NO: 87), CYP52A3A (SEQ ID NO: 88), CYP52A3B (SEQ ID NO: 89), CYP52A5A (SEQ ID NO: 90), CYP52A5B (SEQ ID NO: 91), CYP52A8A (SEQ ID NO: 92), CYP52A8B (SEQ ID NO: 93), and CYP52D4A (SEQ ID NO: 94). FIGS. 15A-1 through 15M show regulatory and coding region alignment of these sequences. Asterisks indicate conserved nucleotides. The start codons are underlined and the last amino acid coding codons immediately before the stop codon are underlined.

FIGS. 16A-1 through 16C-2 show the amino acid sequences encoding the CPY52A1A (SEQ ID NO: 95), CYP52A2A (SEQ ID NO: 96), CYP52A2B (SEQ ID NO: 97), CYP52A3A (SEQ ID NO: 98), CYP52A3B (SEQ ID NO: 99), CYP52A5A (SEQ ID NO: 100), CYP52A5B (SEQ ID NO: 101), CYP52A8A (SEQ ID NO: 102), CYP52A8B (SEQ ID NO: 103) and CYP52D4A (SEQ ID NO: 104) proteins from *C. tropicalis* ATCC 20336. Asterisks indicate identical residues and dots indicate conserved residues.

FIGS. 23A–23C show the complete DNA sequence (SEQ ID NO: 105) encoding URA3A from *C. tropicalis* ATCC 20336 and the amino acid sequence of the encoded protein (SEQ ID NO: 106).

DESCRIPTION OF THE PREFERRED EMBODIMENTS

Figure 1:
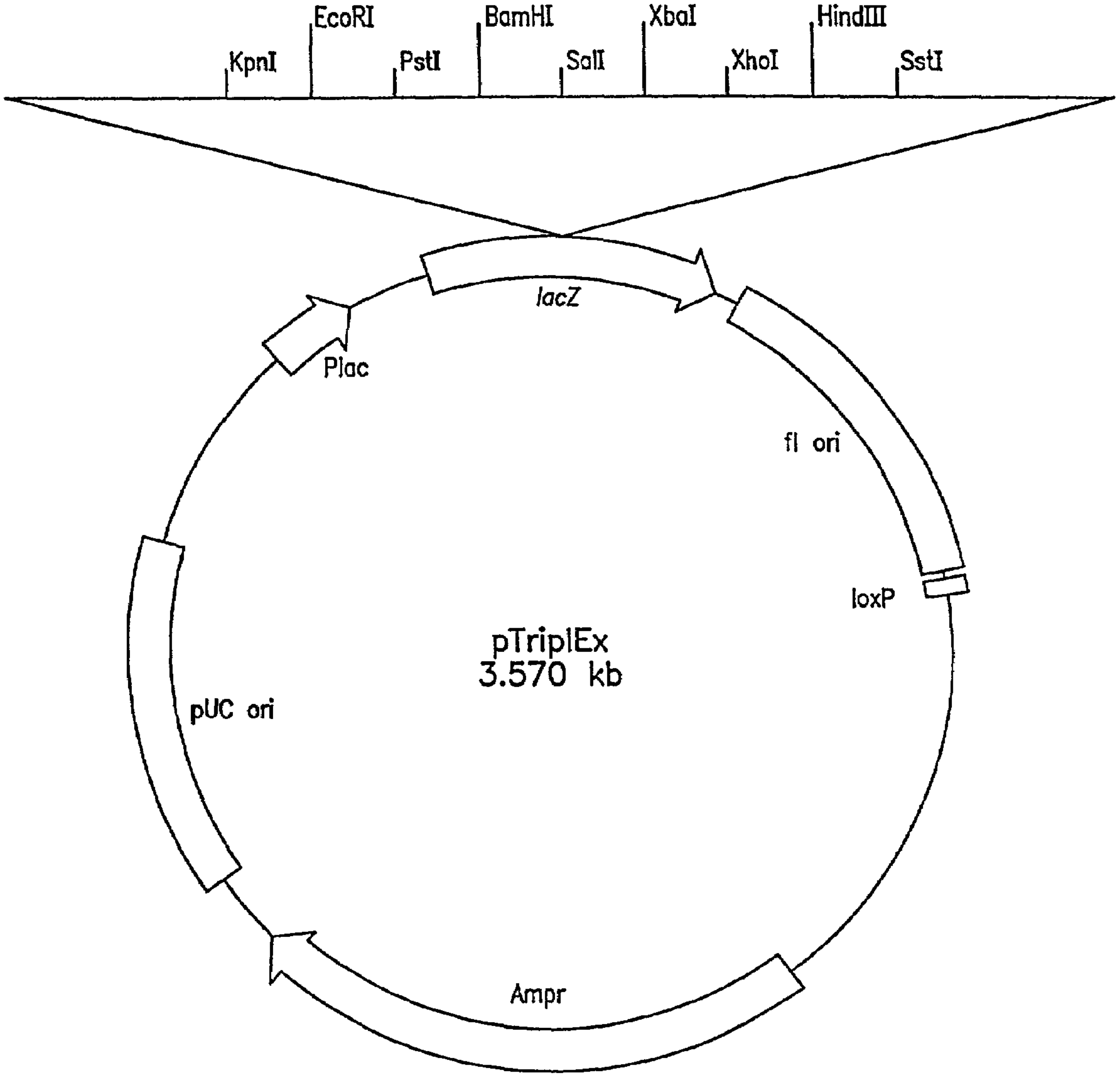
FIG. 1 is a schematic representation of cloning vector pTriplEx from Clontech™ Laboratories, Inc. Selected restriction sites within the multiple cloning site are shown.

Diacid productivity is improved according to the present invention by selectively increasing enzymes which are known to be important to the oxidation of organic substrates such as fatty acids composing the desired feed. According to the present invention, ten CYP genes and two CPR genes of *C. tropicalis* have been identified and characterized that relate to participation in the ω-hydroxylase complex catalyzing the first step in the ω-oxidation pathway. In addition, a novel quantitative competitive reverse transcription polymerase chain reaction (QC-RT-PCR) assay is used to measure gene expression in the fermentor under conditions of induction by one or more organic substrates as defined herein. Based upon QC-RT-PCR results, three CYP genes, CYP52A1, CYP52A2 and CYP52A5, have been identified as being of greater importance for the ω-oxidation of long chain fatty acids. Amplification of the CPR gene copy number improves productivity. The QC-RT-PCR assay indicates that both CYP and CPR genes appear to be under tight regulatory control.

In accordance with the present invention, a method for discriminating members of a gene family by quantifying the amount of target mRNA in a sample is provided which includes a) providing an organism containing a target gene; b) culturing the organism with an organic substrate which causes upregulation in the activity of the target gene; c) obtaining a sample of total RNA from the organism at a first point in time; d) combining at least a portion of the sample of the total RNA with a known amount of competitor RNA to form an RNA mixture, wherein the competitor RNA is substantially similar to the target mRNA but has a lesser number of nucleotides compared to the target mRNA; e) adding reverse transcriptase to the RNA mixture in a quantity sufficient to form corresponding target DNA and competitor DNA; (f) conducting a polymerase chain reaction in the presence of at least one primer specific for at least one substantially non-homologous region of the target DNA within the gene family, the primer also specific for the competitor DNA; g) repeating steps (c–f) using increasing amounts of the competitor RNA while maintaining a substantially constant amount of target RNA; h) determining the point at which the amount of target DNA is substantially equal to the amount of competitor DNA; i) quantifying the results by comparing the ratio of the concentration of unknown target to the known concentration of competitor; and j) obtaining a sample of total RNA from the organism at another point in time and repeating steps (d–i).

In addition, modification of existing promoters and/or the isolation of alternative promoters provides increased expression of CYP and CPR genes. Strong promoters are obtained from at least four sources: random or specific modifications of the CYP52A2 promoter, CYP52A5 promoter, CYP52A1 promoter, the selection of a strong promoter from available *Candida* β-oxidation genes such as POX4 and POX5, or screening to select another suitable *Candida* promoter.

Promoter strength can be directly measured using QT-RT-PCR to measure CYP and CPR gene expression in *Candida* cells isolated from fermentors. Enzymatic assays and antibodies specific for CYP and CPR proteins are used to verify that increased promoter strength is reflected by increased synthesis of the corresponding enzymes. Once a suitable promoter is identified, it is fused to the selected CYP and CPR genes and introduced into *Candida* for construction of a new improved production strain. It is contemplated that the coding region of the CYP and CPR genes can be fused to suitable promoters or other regulatory sequences which are well known to those skilled in the art.

In accordance with the present invention, studies on *C. tropicalis* ATCC 20336 have identified six unique CYP genes and four potential alleles. QC-RT-PCR analyses of cells isolated during the course of the fermentation bioconversions indicate that at least three of the CYP genes are induced by fatty acids and at least two of the CYP genes are induced by alkanes. See FIG. 34. Two of the CYP genes are highly induced indicating participation in the ω-hydroxylase complex which catalyzes the rate limiting step in the oxidation of fatty acids to the corresponding diacids.

The biochemical characterizations of each P450 enzyme herein is used to tailor the *C. tropicalis* host for optimal diacid productivity and is used to select P450 enzymes to be amplified based upon the fatty acid content of the feedstream. CYP gene(s) encoding P450 enzymes that have a low specific activity for the fatty acid or alkane substrate of choice are targeted for inactivation, thereby reducing the physiological load on the cell.

Since it has been demonstrated that CPR can be limiting in yeast systems, the removal of non-essential P450s from the system can free electrons that are being used by non-essential P450s and make them available to the P450s important for diacid productivity. Moreover, the removal of non-essential P450s can make available other necessary but potentially limiting components of the P450 system (i.e., available membrane space, heme and/or NADPH).

Diacid productivity is thus improved by selective integration, amplification, and over expression of CYP and CPR genes in the *C. tropicalis* production host.

It should be understood that host cells into which one or more copies of desired CYP and/or CPR genes have been introduced can be made to include such genes by any technique known to those skilled in the art. For example, suitable host cells include procaryotes such as *Bacillus* sp., *Pseudomous* sp., *Actinomycetes* sp., *Eschericia* sp., *Mycobacterium* sp., and eukaryotes such as yeast, algae, insect cells, plant cells and and filamentous fungi. Suitable host cells are preferably yeast cells such as *Yarrowia, Bebaromyces, Saccharomyces, Schizosaccharomyces,* and *Pichia* and more preferably those of the *Candida* genus. Preferred species of *Candida* are *tropicalis, maltosa, apicola, paratropicalis, albicans, cloacae, guillermondii, intermedia, lipolytica, parapsilosis* and *zeylenoides.* Certain preferred stains of *Candida tropicalis* are listed in U.S. Pat. No. 5,254,466, incorporated herein by reference.

Vectors such as plasmids, phagemids, phages or cosmids can be used to transform or transfect suitable host cells. Host cells may also be transformed by introducing into a cell a linear DNA vector(s) containing the desired gene sequence. Such linear DNA may be advantageous when it is desirable to avoid introduction of non-native (foreign) DNA into the cell. For example, DNA consisting of a desired target gene(s) flanked by DNA sequences which are native to the cell can be introduced into the cell by electroporation, lithium acetate transformation, spheroplasting and the like. Flanking DNA sequences can include selectable markers and/or other tools for genetic engineering.

It should be understood that, depending on whether a transformed organism utilizes the universal genetic code or the non-universal genetic code known, e.g., in connection with *C. tropicalis,* slight differences can be manifest in the amino acid sequences of protein-products. Thus, nucleotide sequences containing a CTG codon produce proteins containing a CTG encoded leucine in prokaryotes such as *E. coli* and a CTG encoded serine in non-universal coding eukaryotes such as *C. tropicalis.* For example, the CYP52A1A gene contains one CTG codon starting at position 1354 which is translated as a leucine in *E. coli* and a serine in *C. tropicalis,* leading to two versions of the CYP52A1A protein (SEQ ID NO: 95 and SEQ ID NO: 110); the CYP52A3B gene contains one CTG codon starting at position 2449 which is translated as a leucine in *E. coli* and a serine in *C. tropicalis,* leading to two versions of the CYP52A3B protein (SEQ ID NO: 99 and SEQ ID NO: 111); the CYP52A5A gene contains two CTG codons starting, respectively, at positions 1883 and 2570, which are translated as leucine in *E. coli* and serine in *C. tropicalis,* leading to two versions of the CYP52A5A protein (SEQ ID NO: 100 and SEQ ID NO: 112); the CYP52A5B gene contains two CTG codons starting, respectively, at positions 1922 and 2609, which are translated as leucine in *E. coli* and serine in *C. tropicalis,* leading to two versions of the CYP52A5B protein (SEQ ID NO: 101 and SEQ ID NO: 113); the CYP52A8A gene contains one CTG codon starting at position 659, which is translated as a leucine in *E. coli* and a serine in *C. tropicalis,* leading to two versions of the CYP52A8B protein (SEQ ID NO: 103 and SEQ ID NO: 115); the CYP52D4A gene contains three CTG codons starting, respectively, at positions 1247, 1412 and 1757, which are translated as leucine in *E. coli* and as serine in *C. tropicalis,* leading to two versions of the CYP5234A protein (SEQ ID NO: 104 and SEQ ID NO: 116); the CPRA (NCP1A) gene contains one CTG codon starting at position 1153 which is translated as a leucine in *E. coli* and as a serine in *C. tropicalis,* leading to two versions of the CPRA (NCP1A) protein (SEQ ID NO: 83 and SEQ ID NO: 117); the CPRG (NCP1B) gene contains one CTG codon starting at position 1180 which is translated as a leucine in *E. coli* and as a serine in *C. tropicalis,* leading to two versions of the CPRB (NCP1B) protein (SEQ ID NO: 84 and SEQ ID NO: 118).

A suitable organic substrate herein can be any organic compound that is biooxidizable to a mono- or polycarboxylic acid. Such a compound can be any saturated or unsaturated aliphatic compound or any carbocyclic or heterocyclic aromatic compound having at least one terminal methyl group, a terminal carboxyl group and/or a terminal functional group which is oxidizable to a carboxyl group by biooxidation. A terminal functional group which is a derivative of a carboxyl group may be present in the substrate molecule and may be converted to a carboxyl group by a reaction other than biooxidation. For example, if the terminal group is an ester that neither the wild-type *C. tropicalis* nor the genetic modifications described herein will allow hydrolysis of the ester functionality to a carboxyl group, then a lipase can be added during the fermentation step to liberate free fatty acids. Suitable organic substrates include, but are not limited to, saturated fatty acids, unsaturated fatty acids, alkanes, alkenes, alkynes and combinations thereof.

Alkanes are a type of saturated organic substrate which are useful herein. The alkanes can be linear or cyclic, branched or straight chain, substituted or unsubstituted. Particularly preferred alkanes are those having from about 4 to about 25 carbon atoms, examples of which include but are not limited to butane, hexane, octane, nonane, dodecane, tridecane, tetradecane, octadecane and the like.

Examples of unsaturated organic substrates which can be used herein include but are not limited to internal olefins such as 2-pentene, 2-hexene, 3-hexene, 9-octadecene and the like; unsaturated carboxylic acids such as 2-hexenoic acid and esters thereof, oleic acid and esters thereof including triglyceryl esters having a relatively high oleic acid content, erucic acid and esters thereof including triglyceryl esters having a relatively high erucic acid content, ricinoleic acid and esters thereof including triglyceryl esters having a relatively high ricinoleic acid content, linoleic acid and esters thereof including triglyceryl esters having a relatively high linoleic acid content; unsaturated alcohols such as 3-hexen-1-ol, 9-octadecen-1-ol and the like; unsaturated aldehydes such as 3-hexen-1-al, 9-octadecen-1-al and the like. In addition to the above, an organic substrate which can be used herein include alicyclic compounds having at least one internal carbon-carbon double bond and at least one terminal methyl group, a terminal carboxyl group and/or a terminal functional group which is oxidizable to a carboxyl group by biooxidation. Examples of such compounds include but are not limited to 3,6-dimethyl, 1,4-cyclohexadiene; 3-methylcyclohexene; 3-methyl-1, 4-cyclohexadiene and the like.

Examples of the aromatic compounds that can be used herein include but are not limited to arenes such as o-, m-, p-xylene; o-, m-, p-methyl benzoic acid; dimethyl pyridine, and the like. The organic substrate can also contain other functional groups that are biooxidizable to carboxyl groups such as an aldehyde or alcohol group. The organic substrate can also contain other functional groups that are not biooxidizable to carboxyl groups and do not interfere with the biooxidation such as halogens, ethers, and the like.

Examples of saturated fatty acids which may be applied to cells incorporating the present CYP and CPR genes include caproic, enanthic, caprylic, pelargonic, capric, undecylic, lauric, myristic, pentadecanoic, palmitic, margaric, stearic, arachidic, behenic acids and combinations thereof. Examples of unsaturated fatty acids which may be applied to cells incorporating the present CYP and CPR genes include palmitoleic, oleic, erucic, linoleic, linolenic acids and combinations thereof. Alkanes and fractions of alkanes may be applied which include chain links from C12 to C24 in any combination. An example of a preferred fatty acid mixtures are Emersol® 267 and Tallow, both commercially available from Henkel Chemicals Group, Cincinnati, Ohio. The typical fatty acid composition of Emersol® 267 and Tallow is as follows:

| | TALLOW | E267 |
|---|---|---|
| C14:0 | 3.5% | 2.4% |
| C14:1 | 1.0% | 0.7% |
| C15:0 | 0.5% | — |
| C16:0 | 25.5% | 4.6% |
| C16:1 | 4.0% | 5.7% |
| C17:0 | 2.5% | — |
| C17:1 | — | 5.7% |
| C18:0 | 19.5% | 1.0% |
| C18:1 | 41.0% | 69.9% |
| C18:2 | 2.5% | 8.8% |
| C18:3 | — | 0.3% |
| C20:0 | 0.5% | — |
| C20:1 | — | 0.9% |

The following examples are meant to illustrate but not to limit the invention. All relevant microbial strains and plasmids are described in Table 1 and Table 2, respectively.

TABLE 1

List of *Escherichia coli* and *Candida tropicalis* strains

| *E. Coli* STRAIN | GENOTYPE | SOURCE |
|---|---|---|
| XL1Blue-MRF' | endA1, gyrA96, hsdR17, lac$^-$, recA1, relA1, supE44, thi-1, [F' lacI$^q$Z M15, proAB, Tn10] | Stratagene, La Jolla, CA |
| BM25.8 | SupE44, thi (lac-proAB) [F' traD36, proAB$^+$, lacI$^q$Z M15] λimm434 (kan$^R$)P1 (cam$^R$) hsdR ($r_{k12}$- $m_{k12}$-) | Clontech, Palo Alto, CA |
| XLOLR | (mcrA)183 (mcrCB-hsdSMR-mrr)173 endA1 thi-1 recA1 gyrA96 relA1 lac [F' proAB lacI$^q$Z M15 Tn10 (Tet$^r$) Su (nonsuppressing λ$^r$(lambda resistant) | Stratagene, La Jolla, CA |
| *C. tropicalis* STRAIN | GENOTYPE | SOURCE |
| ATCC20336 | Wild-type | American Type Culture Collection, Rockville, MD |
| ATCC750 | Wild-type | American Type Culture Collection, Rockville, MD |
| ATCC 20962 | ura3A/ura3B, pox4A::ura3A/pox4B::ura3A, pox5::ura3A/pox5::URA3A | Henkel |
| H5343 ura- | ura3A/ura3B, pox4A::ura3A/pox4B::ura3A, pox5::ura3A/pox5::URA3A, ura3- | Henkel |
| HDC1 | ura3A/ura3B, pox4A::ura3A/pox4B::ura3A, pox5:ura3A/pox5::URA3A, ura3::URA3A-CYP52A2A | Henkel |
| HDC5 | ura3A/ura3B, pox4A::ura3A/pox4B::ura3A, pox5::ura3A/pox5::URA3A, ura3::URA3A-CYP52A3A | Henkel |
| HDC10 | ura3A/ura3B, pox4A::ura3A/pox4B::ura3A, pox5::ura3A/pox5::URA3A, ura3::URA3A-CPRB | Henkel |
| HDC15 | ura3A/ura3B, pox4A::ura3A/pox4B::ura3A, pox5::ura3A/pox5::URA3A, ura3::URA3A-CYP52A5A | Henkel |
| HDC20 | ura3A/ura3B, pox4A::ura3A/pox4B::ura3A, pox5::ura3A/pox5::URA3A, ura3::URA3A-CYP52A2A + CPR B (CYP and CPR have opposite 5' to 3' orientation with respect to each other) | Henkel |
| HDC23 | ura3A/ura3B, pox4A::ura3A/pox4B::ura3A, pox5::ura3A/pox5::URA3A, ura3::URA3A-CYP52A2A + CPR B (CYP and CPR have same 5' to 3' orientation with respect to each other) | Henkel |

TABLE 2

List of plasmids isolated from genomic libraries and constructed for use in gene integrations.

| Plasmid | Base vector | Insert | Insert Size | Plasmid size | Description |
|---|---|---|---|---|---|
| pURAin | pNEB193 | URA3A | 1706 bp | 4399 bp | pNEB193 with the URA3A gene inserted in the AscI - PmeI site, generating a PacI site |
| pURA 2in | pURAin | CYP52A2A | 2230 bp | 6629 bp | pURAin containing a PCR CYP52A2A allele containing PacI restriction sites |
| pURA REDB in | pURAin | CPRB | 3266 bp | 7665 bp | pURAin containing a PCR CPRB allele containing PacI restriction sites |
| pHKM1 | pTriplEx | Truncated CPRA gene | Approx. 3.8 kb | Approx. 7.4 kb | A truncated CPRA gene obtained by first screening library containing the 5' untranslated region and 1.2 kb open reading frame |
| pHKM4 | PTriplEx | Truncated CPRA gene | Approx. 5 kb | Approx. 8.6 kb | A truncated CPRA gene obtained by screening second library containing the 3' untranslated region end sequence |
| pHKM9 | pBC-CMV | CPRB gene | Approx. 5.3 kb | Approx. 9.8 kb | CPRB allele isolated from the third library |
| pHKM11 | pBC-CMV | CYP52A1A | Approx. 5 kb | Approx. 9.5 kb | CYP52A1A isolated from the third library |
| pHKM12 | pBC-CMV | CYP52A8A | Approx. 7.5 kb | Approx. 12 kb | CYP52A8A isolated from the third library |
| pHKM13 | pBC-CMV | CYP52D4A | Approx. 7.3 kb | Approx. 11.8 kb | CYP52D4A isolated from the third library |
| pHKM14 | pBC-CMV | CYP52A2B | Approx. 6 kb | Approx. 10.5 kb | CYP52A2B isolated from the third library |
| pHKM15 | pBC-CMV | CYP52A8B | Approx. 6.6 kb | Approx. 11.1 kb | CYP52A8B isolated from the third library |
| pPAL3 | pTriplEx | CYP52A5A | 4.4 kb | Approx. 8.1 kb | CYP52A5A isolated from the 1st library |
| pPA5 | pTriplEx | CYP52A5B | 4.1 kb | Approx. 7.8 kb | CYP52A5B isolated from the 2nd library |
| pPA15 | pTriplEx | CYP52A2A | 6.0 kb | Approx. 9.7 kb | CYP52A2A isolated from the 2nd library |
| pPA57 | pTriplEx | CYP52A3A | 5.5 kb | Approx. 9.2 kb | CYP52A3A isolated from the 2nd library |
| pPA62 | pTriplEx | CYP52A3B | 6.0 kb | Approx. 9.7 kb | CYP52A3B isolated from the 2nd library |

EXAMPLE 1

Purification of Genomic DNA from *Candida tropicalis* ATCC 20336

A. Construction of Genomic Libraries 50 ml of YEPD broth (see Table 9) was inoculated with a single colony of *C. tropicalis* 20336 from YEPD agar plate and grown overnight at 30° C. 5 ml of the overnight culture was inoculated into 100 ml of fresh YEPD broth and incubated at 30° C. for 4 to 5 hr with shaking. Cells were harvested by centrifugation, washed twice with sterile distilled water and resuspended in 4 ml of spheroplasting buffer (1 M Sorbitol, 50 mM EDTA, 14 mM mercaptoethanol) and incubated for 30 min at 37° C. with gentle shaking. 0.5 ml of 2 mg/ml zymolyase (ICN Pharmaceuticals, Inc., Irvine, Calif.) was added and incubated at 37° C. with gentle shaking for 30 to 60 min. Spheroplast formation was monitored by SDS lysis. Spheroplasts were harvested by brief centrifugation (4,000 rpm, 3 min) and were washed once with the spheroplast buffer without mercaptoethanol. Harvested spheroplasts were then suspended in 4 ml of lysis buffer (0.2 M tris/pH 8.0, 50 mM EDTA, 1% SDS) containing 100 μg/ml RNase (Qiagen Inc., Chatsworth, Calif.) and incubated at 37° C. for 30 to 60 min.

Proteins were denatured and extracted twice with an equal volume of chloroform/isoamyl alcohol (24:1) by gently mixing the two phases by hand inversions. The two phases were separated by centrifugation at 10,000 rpm for 10 min and the aqueous phase containing the high-molecular weight DNA was recovered. To the aqueous layer NaCl was added to a final concentration of 0.2 M and the DNA was precipitated by adding 2 vol of ethanol. Precipitated DNA was spooled with a clean glass rod and resuspended in TE buffer (10 mM Tris/pH 8.0, 1 mM EDTA) and allowed to dissolve overnight at 4° C. To the dissolved DNA, RNase free of any DNase activity (Qiagen Inc., Chatsworth, Calif.) was added to a final concentration of 50 μg/ml and incubated at 37° C. for 30 min. Then protease (Qiagen Inc., Chatsworth, Calif.) was added to a final concentration of 100 μg/ml and incubated at 55 to 60° C. for 30 min. The solution was extracted once with an equal volume of phenol/chloroform/isoamyl alcohol (25:24:1) and once with equal volume of chloroform/isoamyl alcohol (24:1). To the aqueous phase 0.1 vol of 3 M sodium acetate and 2 volumes of ice cold ethanol (200 proof) were added and the high molecular weight DNA was spooled with a glass rod and dissolved in 1 to 2 ml of TE buffer.

B. Genomic DNA Preparation for PCR Amplification of CYP and CPR Genes

Five 5 ml of YPD medium was inoculated with a single colony and grown at 30° C. overnight. The culture was centrifuged for 5 min at 1200×g. The supernatant was removed by aspiration and 0.5 ml of a sorbitol solution (0.9 M sorbitol, 0.1 M Tris-Cl pH 8.0, 0.1 M EDTA) was added to the pellet. The pellet was resuspended by vortexing and 1 μl of 2-mercaptoethanol and 50 μl of a 10 μg/ml zymolyase solution were added to the mixture. The tube was incubated at 37° C. for 1 hr on a rotary shaker (200 rpm). The tube was then centrifuged for 5 min at 1200×g and the supernatant was removed by aspiration. The protoplast pellet was resuspended in 0.5 ml 1×TE (10 mM Tris-Cl pH 8.0, 1 mM EDTA) and transferred to a 1.5 ml microcentrifuge tube. The protoplasts were lysed by the addition of 50 μl 10% SDS followed by incubation at 65° C. for 20 min. Next, 200 μl of 5M potassium acetate was added and after mixing, the tube was incubated on ice for at least 30 min. Cellular debris was removed by centrifugation at 13,000×g for 5 min. The supernatant was carefully removed and transferred to a new microfuge tube. The DNA was precipitated by the addition of 1 ml 100% (200 proof) ethanol followed by centrifugation for 5 min at 13,000×g. The DNA pellet was washed with 1 ml 70% ethanol followed by centrifugation for 5 min at 13,000×g. After partially drying the DNA under a vacuum, it was resuspended in 200 μl of 1×TE. The DNA concentration was determined by ratio of the absorbance at 260 nm/280 nm ($A_{260/280}$).

EXAMPLE 2

Construction of *Candida tropicalis* 20336 Genomic Libraries

Three genomic libraries of *C. tropicalis* were constructed, two at Clontech Laboratories, Inc., (Palo Alto, Calif.) and one at Henkel Corporation (Cincinnati, Ohio).

A. Clontech Libraries

The first Clontech library was made as follows: Genomic DNA was prepared from *C. tropicalis* 20336 as described above, partially digested with EcoRI and size fractionated by gel electrophoresis to eliminate fragments smaller than 0.6 kb. Following size fractionation, several ligations of the EcoRI genomic DNA fragments and lambda (λ) TriplEx™ vector (FIG. 1) arms with EcoRI sticky ends were packaged into λ phage heads under conditions designed to obtain one million independent clones. The second genomic library was constructed as follows: Genomic DNA was digested partially with Sau3A1 and size fractionated by gel electrophoresis. The DNA fragments were blunt ended using standard protocols as described, e.g., in Sambrook et al, *Molecular Cloning: A Laboratory Manual,* 2ed. Cold Spring Harbor Press, USA (1989), incorporated herein by reference. The strategy was to fill in the Sau3A1 overhands with Klenow polymerase (Life Technologies, Grand Island, N.Y.) followed by digestion with S1 nuclease (Life Technologies, Grand Island, N.Y.). After S1 nuclease digestion the fragments were end filled one more time with Klenow polymerase to obtain the final blunt-ended DNA fragments. EcoRI linkers were ligated to these blunt-ended DNA fragments followed by ligation into the λTriplEx vector. The resultant library contained approximately $2\times10^6$ independent clones with an average insert size of 4.5 kb.

B. Henkel Library

Figure 2A:
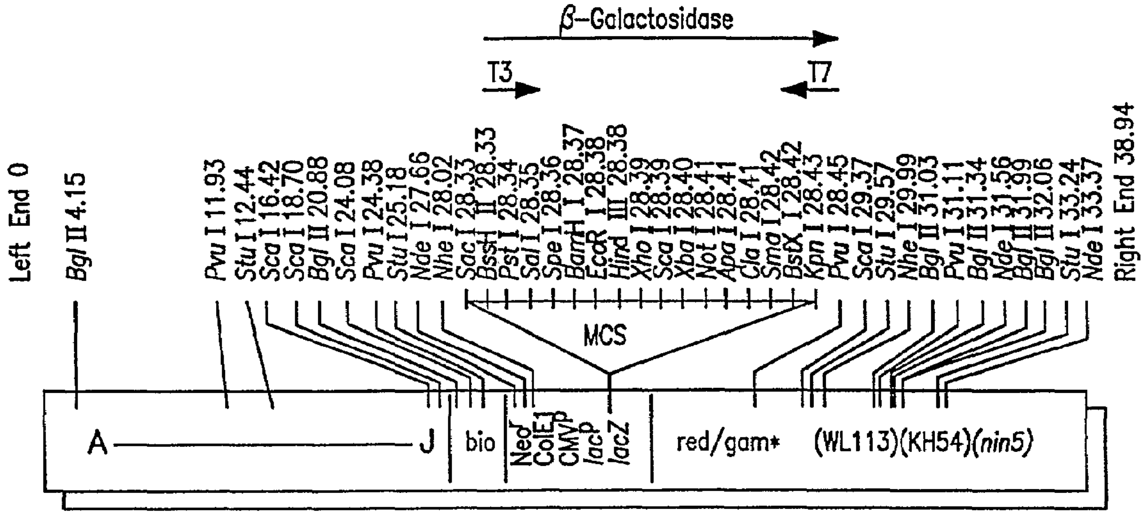
FIG. 2A is a map of the ZAP Express™ vector.
Figure 2B:
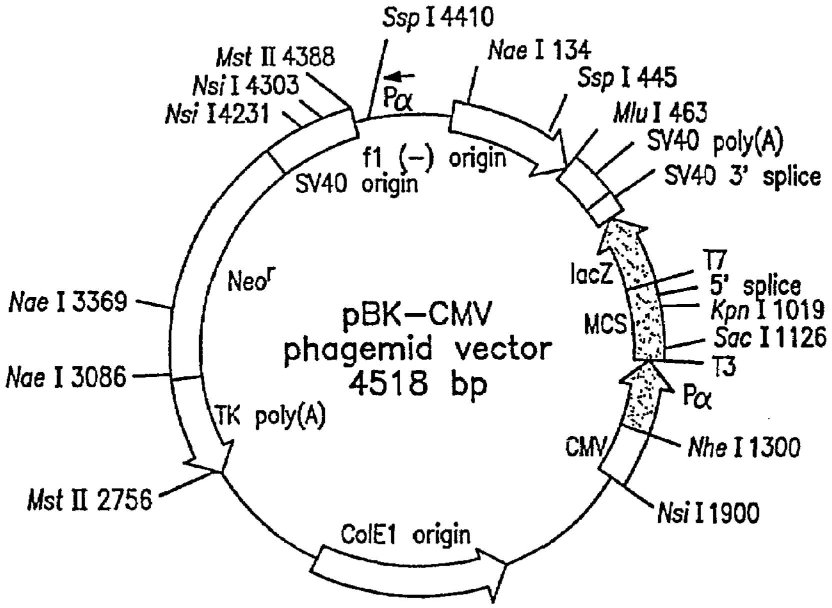
FIG. 2B is a schematic representation of cloning phagemid vector pBK-CMV.

The third genomic library was constructed at Henkel Corporation using λZAP Express™ vector (Stratagene, La Jolla, Calif.) (FIG. 2). Genomic DNA was partially digested with Sau3A1 and fragments in the range of 6 to 12 kb were purified from an agarose gel after electrophoresis of the digested DNA. These DNA fragments were then ligated to BamHI digested λZAP Express™ vector arms according to manufacturers protocols. Three ligations were set up to obtain approximately $9.8\times10^5$ independent clones. All three libraries were pooled and amplified according to manufacturer instructions to obtain high-titre (>$10^9$ plaque forming units/ml) stock for long-term storage. The titre of packaged phage library was ascertained after infection of *E. coli* XL1Blue-MRF' cells. *E. coli XL*1Blue-MRF' were grown overnight in either in LB medium or NZCYM (Table 9) containing 10 mM $MgSO_4$ and 0.2% maltose at 37° C. or 30° C., respectively with shaking. Cells were then centrifuged and resuspended in 0.5 to 1 volume of 10 mM $MgSO_4$. 200 μl of this *E. coli* culture was mixed with several dilutions of packaged phage library and incubated at 37° C. for 15 min. To this mixture 2.5 ml of LB top agarose or NZCYM top agarose (maintained at 60° C.) (see Table 9) was added and plated on LB agar or NCZYM agar (see Table 9) present in 82 mm petri dishes. Phage were allowed to propagate overnight at 37° C. to obtain discrete plaques and the phage titre was determined.

EXAMPLE 3

Screening of Genomic Libraries

Both λTriplEx™ and λZAP Express™ vectors are phagemid vectors that can be propagated either as phage or plasmid DNA (after conversion of phage to plasmid). Therefore, the genomic libraries constructed in these vectors can be screened either by plaque hybridization (screening of lambda form of library) or by colony hybridization (screening plasmid form of library after phage to plasmid conversion). Both vectors are capable of expressing the cloned genes and the main difference is the mechanism of excision of plasmid from the phage DNA. The cloning site in λTriplEx™ is located within a plasmid which is present in the phage and is flanked by loxP site (FIG. 1). When λTriplEx™ is introduced into *E. coli* strain BM25.8 (supplied by Clontech), the Cre recombinase present in BM25.8 promotes the excision and circularization of plasmid pTriplEx from the phage λTriplEx™ at the loxP sites. The mechanism of excision of plasmid pBK-CMV from phage λZAP Express™ is different. It requires the assistance of a helper phage such as ExAssist™ (Stratagene) and an *E. coli* strain such as XLOR (Stratagene). Both pTriplEx and pBK-CMV can replicate autonomously in *E. coli.*

A. Screening Genomic Libraries (Plasmid Form)

1) Colony Lifts

A single colony of *E. coli* BM25.8 was inoculated into 5 ml of LB containing 50 μg/ml kanaycin, 10 mM $MgSO_4$ and 0.1% maltose and grown overnight at 31° C., 250 rpm. To 200 μl of this overnight culture (~$4\times10^8$ cells) 1 μl of phage library (2–$5\times10^6$ plaque forming units) and 150 μl LB broth were added and incubated at 31° C. for 30 min after which 400 μl of LB broth was added and incubated at 31° C., 225 rpm for 1 h. This bacterial culture was diluted and plated on LB agar containing 50 μg/ml ampicillin (Sigma Chemical Company, St. Louis, Mo.) and kanamycin (Sigma Chemical Company) to obtain 500 to 600 colonies/plate. The plates were incubated at 37° C. for 6 to 7 hrs until the colonies became visible. The plates were then stored at 4° C. for 1.5 h before placing a Colony/Plaque Screen™ Hybridization Transfer Membrane disc (DuPont NEN Research Products, Boston, Mass.) on the plate in contact with bacterial colonies. The transfer of colonies to the membrane was allowed to proceed for 3 to 5 min. The membrane was then lifted and placed on a fresh LB agar (see Table 9) plate containing 200 μg/ml of chloramphenicol with the side exposed to the bacterial colonies facing up. The plates containing the membranes were then incubated at 37° C. overnight in order to allow full development of the bacterial colonies. The LB agar plates from which colonies were initially lifted were incubated at 37° C. overnight and stored at 4° C. for future use. The following morning the membranes containing bacterial colonies were lifted and placed on two sheets of Whatman 3M (Whatman, Hillsboro, Oreg.) paper saturated with 0.5 N NaOH and left at room temperature (RT) for 3 to 6 min to lyse the cells. Additional treatment of membranes was as described in the protocol provided by NEN Research Products.

2) DNA Hybridizations

Membranes were dried overnight before hybridizing to oligonucleotide probes prepared using a non-radioactive ECL™ 3'-oligolabelling and detection system from Amersham Life Sciences (Arlington Heights, Ill.). DNA labeling, prehybridization and hybridizations were performed according to manufacturer's protocols. After hybridization, membranes were washed twice at room temperature in 5 X SSC, 0.1% SDS (in a volume equivalent to 2 ml/$cm^2$ of membrane) for 5 min each followed by two washes at 50° C. in 1X SSC, 0.1% SDS (in a volume equivalent to 2 ml/$cm^2$ of membrane) for 15 min each. The hybridization signal was then generated and detected with Hyperfilm ECL™ (Amersham) according to manufacturer's protocols. Membranes were aligned to plates containing bacterial colonies from which colony lifts were performed and colonies corresponding to positive signals on X-ray were then isolated and propagated in LB broth. Plasmid DNA's were isolated from these cultures and analyzed by restriction enzyme digestions and by DNA sequencing.

B. Screening Genomic Libraries (Plaque Form)

1) λ Library Plating

*E. coli* XL1Blue-MRF' cells were grown overnight in LB medium (25 ml) containing 10 mM $MgSO_4$ and 0.2% maltose at 37° C., 250 rpm. Cells were then centrifuged (2,200×g for 10 min) and resuspended in 0.5 volumes of 10 mM $MgSO_4$. 500 μl of this *E. coli* culture was mixed with a phage suspension containing 25,000 amplified lambda phage particles and incubated at 37° C. for 15 min. To this mixture 6.5 ml of NZCYM top agarose (maintained at 60° C.) (see Chart) was added and plated on 80–100 ml NCZYM agar (see Chart) present in a 150 mm petridish. Phage were allowed to propagate overnight at 37° C. to obtain discrete plaques. After overnight growth plates were stored in a refrigerator for 1–2 hr before plaque lifts were performed.

2) Plaque Lift and DNA Hybridizations

Magna Lift™ nylon membranes (Micron Separations, Inc., Westborough, Mass.) were placed on the agar surface in complete contact with λ plaques and transfer of plaques to nylon membranes was allowed to proceed for 5 min at RT. After plaque transfer the membrane was placed on 2 sheets of Whatman 3M™ (Whatman, Hillsboro, Oreg.) filter paper saturated with a 0.5 N NaOH, 1.0 M NaCl solution and left for 10 min at RT to denature DNA. Excess denaturing solution was removed by blotting briefly on dry Whatman 3M paper. Membranes were then transferred to 2 sheets of Whatman 3M™ paper saturated with 0.5 M Tris-HCl (pH 8.0), 1.5 M NaCl and left for 5 min to neutralize. Membranes were then briefly washed in 200–500 ml of 2 X SSC, dried by air and baked for 30–40 min at 80° C. The membranes were then probed with labelled DNA.

Membranes were prewashed with a 200–500 ml solution of 5 X SSC, 0.5% SDS, 1 mM EDTA (pH 8.0) for 1–2 hr at 42° C. with shaking (60 rpm) to get rid of bacterial debris from the membranes. The membranes were prehybridized for 1–2 hr at 42° C. with (in a volume equivalent to 0.125–0.25 ml/$cm^2$ of membrane) ECL Gold™ buffer (Amersham) containing 0.5 M NaCl and 5% blocking reagent. DNA fragments that were used as probes were purified from agarose gel using a QIAEX II™ gel extraction kit (Qiagen Inc., Chatsworth, Calif.) according to manufacturers protocol and labeled using an Amersham ECL™ direct nucleic acid labeling kit (Amersham). Labeled DNA (5–10 ng/ml hybridization solution) was added to the prehybridized membranes and the hybridization was allowed to proceed overnight. The following day membranes were washed with shaking (60 rpm) twice at 42° C. for 20 min each time in (in a volume equivalent to 2 ml/$cm^2$ of membrane) a buffer containing either 0.1 (high stringency) or 0.5 (low stringency) X SSC, 0.4% SDS and 360 g/l urea. This was followed by two 5 min washes at room temperature in (in a volume equivalent to 2 ml/$cm^2$ of membrane) 2 X SSC. Hybridization signals were generated using the ECL™ nucleic acid detection reagent and detected using Hyperfilm ECL™ (Amersham).

Agar plugs which contained plaques corresponding to positive signals on the X-ray film were taken from the master plates using the broad-end of Pasteur pipet. Plaques were selected by aligning the plates with the x-ray film. At this stage, multiple plaques were generally taken. Phage particles were eluted from the agar plugs by soaking in 1 ml SM buffer (Sambrook et al., supra) overnight. The phage eluate was then diluted and plated with freshly grown *E. coli* XL1Blue-MRF' cells to obtain 100–500 plaques per 85 mm NCZYM agar plate. Plaques were transferred to Magna Lift nylon membranes as before and probed again using the same probe. Single well-isolated plaques corresponding to signals on X-ray film were picked by removing agar plugs and eluting the phage by soaking overnight in 0.5 ml SM buffer.

Conversion of λ Clones to Plasmid Form

The lambda clones isolated were converted to plasmid form for further analysis. Conversion from the plaque to the plasmid form was accomplished by infecting the plaques into *E. coli* strain BM25.8. The *E. coli* strain was grown overnight at 31° C., 250 rpm in LB broth containing 10 mM $MgSO_4$ and 0.2% maltose until the $OD_{600}$ reached 1.1–1.4. Ten milliliters of the overnight culture was removed and mixed with 100 μl of 1 M $MgCl_2$. A 200 μl volume of cells was removed, mixed with 150 μl of eluted phage suspension and incubated at 31° C. for 30 min. LB broth (400 μl) was added to the tube and incubation was continued at 31° C. for 1 hr with shaking, 250 rpm. 1–10 μl of the infected cell suspension was plated on LB agar containing 100 μg/ml ampicillin (Sigma, St. Louis, Mo.). Well-isolated colonies were picked and grown overnight in 5 ml LB broth containing 100 μg/ml ampicillin at 37° C., 250 rpm. Plasmid DNA was isolated from these cultures and analyzed. To convert the λZAP Express™ vector to plasmid form *E. coli* strains XL1Blue-MRF' and XLOR were used. The conversion was performed according to the manufacturer's (Stratagene) protocols for single-plaque excision.

EXAMPLE 4

Transformation of *C. tropicalis* H5343 $ura^-$

A. Transformation of *C. tropicalis* H5343 by Electroporation 5 ml of YEPD was inoculated with *C. tropicalis* H5343 ura- from a frozen stock and incubated overnight on a New Brunswick shaker at 30° C. and 170 rpm. The next day, 10 μl of the overnight culture was inoculated into 100 ml YEPD and growth was continued at 30° C., 170 rpm. The following day the cells were harvested at an $OD_{600}$ of 1.0 and the cell pellet was washed one time with sterile ice-cold water. The cells were resuspended in ice-cold sterile 35% Polyethylene glycol (4,000 MW) to a density of $5\times10^8$ cells/ml. A 0.1 ml volume of cells were utilized for each electroporation. The following electroporation protocol was followed: 1.0 μg of transforming DNA was added to 0.1 ml cells, along with 5 μg denatured, sheared calf thymus DNA and the mixture was allowed to incubate on ice for 15 min. The cell solution was then transferred to an ice-cold 0.2 cm electroporation cuvette, tapped to make sure the solution was on the bottom of the cuvette and electroporated. The cells were electroporated using an Invitrogen electroporator (Carlsbad, Calif.) at 450 Volts, 200 Ohms and 250 μF. Following electroporation, 0.9 ml SOS media (1M Sorbitol, 30% YEPD, 10 mM $CaCl_2$) was added to the suspension. The resulting culture was grown for 1 hr at 30° C., 170 rpm. Following the incubation, the cells were pelleted by centrifugation at 1500×g for 5 min. The electroporated cells were resuspended in 0.2 ml of 1M sorbitol and plated on synthetic complete media minus uracil (SC-uracil) (Nelson, supra). In some cases the electroporated cells were plated directly onto SC-uracil. Growth of transformants was monitored for 5 days. After three days, several transformants were picked and transferred to SC-uracil plates for genomic DNA preparation and screening.

B. Transformation of *C. tropicalis* Using Lithium Acetate

The following protocol was used to transform *C. tropicalis* in accordance with the procedures described in *Current Protocols in Molecular Biology,* Supplement 5, 13.7.1 (1989), incorporated herein by reference.

5 ml of YEPD was inoculated with *C. tropicalis* H5343 ura- from a frozen stock and incubated overnight on a New Brunswick shaker at 30° C. and 170 rpm. The next day, 10 μl of the overnight culture was inoculated into 50 ml YEPD and growth was continued at 30° C., 170 rpm. The following day the cells were harvested at an $OD_{600}$ of 1.0. The culture was transferred to a 50 ml polypropylene tube and centrifuged at 1000×g for 10 min. The cell pellet was resuspended in 10 ml sterile TE (10 mM Tris-Cl and 1 mM EDTA, pH 8.0). The cells were again centrifuged at 1000×g for 10 min and the cell pellet was resuspended in 10 ml of a sterile lithium acetate solution [LiAc (0.1 M lithium acetate, 10 mM Tris-Cl, pH 8.0, 1 mM EDTA)]. Following centrifugation at 1000×g for 10 min., the pellet was resuspended in 0.5 ml LiAc. This solution was incubated for one hour at 30° C. while shaking gently at 50 rpm. A 0.1 ml aliquot of this suspension was incubated with 5 μg of transforming DNA at 30° C. with no shaking for 30 min. A 0.7 ml PEG solution (40% wt/vol polyethylene glycol 3340, 0.1 M lithium acetate, 10 mM Tris-Cl, pH 8.0, 1 mM EDTA) was added and incubated at 30° C. for 45 min. The tubes were then placed at 42° C. for 5 min. A 0.2 ml aliquot was plated on synthetic complete media minus uracil (SC-uracil) (Kaiser et al. *Methods in Yeast Genetics,* Cold Spring Harbor Laboratory Press, USA, 1994, incorporated herein by reference). Growth of transformants was monitored for 5 days. After three days, several transformants were picked and transferred to SC-uracil plates for genomic DNA preparation and screening.

EXAMPLE 5

Plasmid DNA Isolation

Plasmid DNA were isolated from *E. coli* cultures using Qiagen plasmid isolation kit (Qiagen Inc., Chatsworth, Calif.) according to manufacturer's instructions.

EXAMPLE 6

DNA Sequencing and Analysis

DNA sequencing was performed at Sequetech Corporation (Mountain View, Calif.) using Applied Biosystems automated sequencer (Perkin Elmer, Foster City, Calif.). DNA sequences were analyzed with MacVector and GeneWorks software packages (Oxford Molecular Group, Campbell, Calif.).

EXAMPLE 7

PCR Protocols

PCR amplification was carried out in a Perkin Elmer Thermocycler using the AmpliTaqGold enzyme (Perkin Elmer Cetus, Foster City, Calif.) kit according to manufacturer's specifications. Following successful amplification, in some cases, the products were digested with the appropriate enzymes and gel purified using QiaexII (Qiagen, Chatsworth, Calif.) as per manufacturer instructions. In specific cases the Ultma Taq polymerase (Perkin Elmer Cetus, Foster City, Calif.) or the Expand Hi-Fi Taq polymerase (Boehringer Mannheim, Indianapolis, Ind.) were used per manufacturer's recommendations or as defined in Table 3.

TABLE 3

PCR amplification conditions used with different primer combinations.

| PRIMER COMBINATION | Taq | TEMPLATE DENATURING CONDITION | ANNEALING TEMP/TIME | EXTENSION TEMP/TIME | CYCLE Number |
|---|---|---|---|---|---|
| 3674-41-1/41-2/41-4 + 3674-41-4 | Ampli-Taq Gold | 94 C./30 sec | 55 C./30 sec | 72 C./1 min | 30 |
| URA Primer 1a URA Primer 1b | Ampli-Taq Gold | 95 C./1 min | 70 C./1 min | 72 C./2 min | 35 |
| URA Primer 2a URA Primer 2b | Ampli-Taq Gold | 95 C./1 min | 70 C./1 min | 72 C./2 min | 35 |
| CYP2A#1 CYP2A#2 | Ampli-Taq Gold | 95 C./1 min | 70 C./1 min | 72 C./2 min | 35 |

TABLE 3-continued

PCR amplification conditions used with different primer combinations.

| PRIMER COMBINATION | Taq | TEMPLATE DENATURING CONDITION | ANNEALING TEMP/TIME | EXTENSION TEMP/TIME | CYCLE Number |
|---|---|---|---|---|---|
| CYP3A#1 CYP3A#2 | Ultma Taq | 95 C./1 min | 70 C./1 min | 72 C./1 min | 30 |
| CPR B#1 | Expand | 94 C./15 sec | 50 C./30 sec | 68 C./3 min | 10 |
| CPR B#2 | Hi-Fi Taq | 94 C./15 sec | 50 C./30 sec | 68 C./3 min + 20 sec/cycle | 15 |
| CYP5A#1 | Expand | 94 C./15 sec | 50 C./30 sec | 68 C./3 min | 10 |
| CYP5A#2 | Hi-Fi Taq | 94 C./15 sec | 50 C./30 sec | 68 C./3 min + 20 sec/cycle | 15 |

Table 4 below contains a list of primers (SEQ ID NOS: 1–35) used for PCR amplification to construct gene integration vectors or to generate probes for gene detection and isolation.

TABLE 4

Primer table for PCR amplification to construct gene integration vectors, to generate probes for gene isolation and detection and to obtain DNA sequence of constructs. (A-deoxyadenosine triphosphate [dATP], G-deoxyguanosine triphosphate [dGTP], C-deoxycytosine triphosphate [dCTP], T-deoxythymidine triphosphate [dTTP], Y- dCTP or dTTP, R- dATP or dGTP, W- dATP or dTTP, M- dATP or dCTP, N- dATP or dCTP or dGTP or dTTP).

| Target gene(s) | Patent Primer Name | Lab Primer Name | Sequence (5' to 3') | PCR Product Size |
|---|---|---|---|---|
| CYP52A2 A | CYP2A#1 | 3659-72M | *CCTTAATTAA*ATGCACGAAGCGGAGATAAAAG (SEQ ID NO: 1) | 2230 bp |
| | CYP2A#2 | 3659-72N | *CCTTAATTAA*GCATAAGCTTGCTCGAGTCT (SEQ ID NO: 2) | |
| CYP52A3 A | CYP3A#1 | 3659-72O | *CCTTAATTAA*ACGCAATGGGAACATGGAGTG (SEQ ID NO: 3) | 2154 bp |
| | CYP3A#2 | 3659-72P | *CCTTAATTAA*TCGCACTACGGTTATTGGTATCAG (SEQ ID NO: 4) | |
| CYP52A5 A | CYP5A#1 | 3659-72K | *CCTTAATTAA*TCAAAGTACGTTCAGGCGG (SEQ ID NO: 5) | 3298 bp |
| | CYP5A#2 | 3659-72L | *CCTTAATTAA*GGCAGACAACAACTTGGCAAAGTC (SEQ ID NO: 6) | |
| CPRB | CPRB#1 | 3698-20A | *CCTTAATTAA*GAGGTCGTTGGTTGAGTTTTC (SEQ ID NO: 7) | 3266 bp |
| | CPRB#2 | 3698-20B | *CCTTAATTAA*TTGATAATGACGTTGCGGG (SEQ ID NO: 8) | |
| URA3A | URA Primer 1a | 3698-7C | *AGGCGCGCC*GGAGTCCAAAAAGACCAACCTCTG (SEQ ID NO: 9) | 956 bp |
| | URA Primer 1b | 3698-7D | *CCTTAATTAA*TACGTGGATACCTTCAAGCAAGTG (SEQ ID NO: 10) | |
| URA3A | URA Primer 2a | 3698-7A | *CCTTAATTAA*GCTCACGAGTTTTGGGATTTTCGA G (SEQ ID NO: 11) | 750 bp |
| | URA Primer 2b | 3698-7B | *GGGTTTAAAC*CGCAGAGGTTGGTCTTTTTGGAC TC (SEQ ID NO: 12) | |
| | | | *GGGTTTAAAC* - Pme I restriction site (SEQ ID NO: 13) | |
| | | | *AGGCGCGCC* - AscI restriction site (SEQ ID NO: 14) | |
| | | | *CCTTAATTAA* - PacI restriction site (SEQ ID NO: 15) | |
| CPR | FMN1 | 3674-41-1 | TCYCAAACWGGTACWGCWGAA (SEQ ID NO: 16) | |
| CPR | FMN2 | 3674-41-2 | GGTTTGGGTAAYTCWACTTAT (SEQ ID NO: 17) | |
| CPR | FAD | 3674-41-3 | CGTTATTAYTCYATTTCTTC (SEQ ID NO: 18) | |
| CPR | NADPH | 3674-41-4 | GCMACACCRGTACCTGGACC (SEQ ID NO: 19) | |
| CPR | PRK1.F3 | PRK1.F3 | ATCCCAATCGTAATCAGC (SEQ ID NO: 20) | |

TABLE 4-continued

Primer table for PCR amplification to construct gene integration vectors, to generate probes for gene isolation and detection and to obtain DNA sequence of constructs. (A-deoxyadenosine triphosphate [dATP], G-deoxyguanosine triphosphate [dGTP], C-deoxycytosine triphosphate [dCTP], T-deoxythymidine triphosphate [dTTP], Y- dCTP or dTTP, R- dATP or dGTP, W- dATP or dTTP, M- dATP or dCTP, N- dATP or dCTP or dGTP or dTTP).

| Target gene(s) | Patent Primer Name | Lab Primer Name | Sequence (5' to 3') | PCR Product Size |
|---|---|---|---|---|
| CPR | PRK1.F5 | PRK1.F5 | ACTTGTCTTCGTTTAGCA (SEQ ID NO: 21) | |
| CPR | PRK4.R20 | PRK4.R20 | CTACGTCTGTGGTGATGC (SEQ ID NO: 22) | |
| CYP | UCup1 | UCup1 | CGNGAYACNACNGCNGG (SEQ ID NO: 23) | |
| CYP | UCup2 | UCup2 | AGRGAYACNACNGCNGG (SEQ ID NO: 24) | |
| CYP | UCdown1 | UCdown1 | AGNGCRAAYTGYTGNCC (SEQ ID NO: 25) | |
| CYP | UCdown2 | UCdown2 | YAANGCRAAYTGYTGNCC (SEQ ID NO: 26) | |
| CYP | HemeB1 | HemeB1 | ATTCAACGGTGGTCCAAGAATCTGTTTGG (SEQ ID NO: 27) | |
| CYP | 2,3,5P | 2,3,5P | GAGCTATGTTGAGACCACAGTTTGC (SEQ ID NO: 28) | |
| CYP | 2,3,5M | 2,3,5M | CTTCAGTTAAAGCAAATTGTTTGGCC (SEQ ID NO: 29) | |
| pTriplEx vector | Triplex5' | Triplex5' | CTCGGGAAGCGCGCCATTGTGTTGG (SEQ ID NO: 30) | |
| pTriplEx vector | Triplex3' | Triplex3' | TAATACGACTCACTATAGGGCGAATTGGC (SEQ ID NO: 31) | |
| CYP | Cyp52a | Cyp52a | TGRYTCAAACCATCTYTCTGG (SEQ ID NO: 32) | |
| CYP | Cyp52b | Cyp52b | GGACCGGCGTTAAAGGG (SEQ ID NO: 33) | |
| CYP | Cyp52c | Cyp52c | CATAGTCGWATYATGCTTAGACC (SEQ ID NO: 34) | |
| CYP | Cyp52d | Cyp52d | GGACCACCATTGAATGG (SEQ ID NO: 35) | |

EXAMPLE 8

Yeast Colony PCR Procedure for Confirmation of Gene Integration into the Genome of *C. tropicalis*

Single yeast colonies were removed from the surface of transformation plates, suspended in 50 μl of spheroplasting buffer (50 mM KCl, 10 mM Tris-HCl, pH 8.3, 1.0 mg/ml Zymolyase, 5% glycerol) and incubated at 37° C. for 30 min. Following incubation, the solution was heated for 10 min at 95° C. to lyse the cells. Five μl of this solution was used as a template in PCR. Expand Hi-Fi Taq polymerase (Boehringer Mannheim, Indianapolis, Ind.) was used in PCR coupled with a gene-specific primer (gene to be integrated) and a URA3 primer. If integration did occur, amplification would yield a PCR product of predicted size confirming the presence of an integrated gene.

EXAMPLE 9

Fermentation Method for Gene Induction Studies

A fermentor was charged with a semi-synthetic growth medium having the composition 75g/l glucose (anhydrous), 6.7 g/l Yeast Nitrogen Base (Difco Laboratories), 3 g/l yeast extract, 3 g/l ammonium sulfate, 2 g/l monopotassium phosphate, 0.5 g/l sodium chloride. Components were made as concentrated solutions for autoclaving then added to the fermentor upon cooling: final pH approximately 5.2. This charge was inoculated with 5–10% of an overnight culture of *C. tropicalis* ATCC 10962 prepared in YM medium (Difco Laboratories) as described in the methods of Examples 17 and 20 of U.S. Pat. No. 5,254,466, which is incorporated herein by reference. *C. tropicalis* ATCC 20962 is a POX 4 and POX 5 disrupted *C. tropicalis* ATCC 20336. Air and agitation were supplied to maintain the dissolved oxygen at greater than about 40% of saturation versus air. The pH was maintained at about 5.0 to 8.5 by the addition of 5N caustic soda on pH control. Both a fatty acid feedstream (commercial oleic acid in this example) having a typical composition: 2.4% $C_{14}$; 0.7% $C_{14.1}$; 4.6% $C_{16}$; 5.7% $C_{16.1}$; 5.7% $C_{17:1}$; 1.0% $C_{18}$; 69.9% $C_{18:1}$; 8.8% $C_{18.2}$; 0.30% $C_{18:3}$; 0.90% $C_{20:1}$ and a glucose co-substrate feed were added in a feedbatch mode beginning near the end of exponential growth. Caustic was added on pH control during the bioconversion of fatty acids to diacids to maintain the pH in the desired range. Typically, samples for gene induction studies were collected just prior to starting the fatty acid feed and over the first 10 hours of bioconversion. Determination of fatty acid and diacid content was determined by a standard methyl ester protocol using gas liquid chromatography (GLC). Gene induction was measured using the QC-RT-PCR protocol described in this application.

EXAMPLE 10

RNA Preparation

The first step of this protocol involves the isolation of total cellular RNA from cultures of *C. tropicalis*. The cellular RNA was isolated using the Qiagen RNeasy Mini Kit (Qiagen Inc., Chatsworth, Calif.) as follows: 2 ml samples of

*C. tropicalis* cultures were collected from the fermentor in a standard 2 ml screw capped Eppendorf style tubes at various times before and after the addition of the fatty acid or alkane substrate. Cell samples were immediately frozen in liquid nitrogen or a dry-ice/alcohol bath after their harvesting from the fermentor. To isolate total RNA from the samples, the tubes were allowed to thaw on ice and the cells pelleted by centrifugation in a microfuge for 5 minutes (min) at 4° C. and the supernatant was discarded while keeping the pellet ice-cold. The microfuge tubes were filled ⅔ full with ice-cold Zirconia/Silica beads (0.5 mm diameter, Biospec Products, Bartlesville, Okla.) and the tube filled to the top with ice-cold RLT* lysis buffer (* buffer included with the Qiagen RNeasy Mini Kit). Cell rupture was achieved by placing the samples in a mini bead beater (Biospec Products, Bartlesville, Okla.) and immediately homogenized at full speed for 2.5 min. The samples were allowed to cool in a ice water bath for 1 minute and the homogenization/cool process repeated two more times for a total of 7.5 min homogenization time in the beadbeater. The homogenized cells samples were microfuged at full speed for 10 min and 700 μl of the RNA containing supernatant removed and transferred to a new eppendorf tube. 700 μl of 70% ethanol was added to each sample followed by mixing by inversion. This and all subsequent steps were performed at room temperature. Seven hundred microliters of each ethanol treated sample were transferred to a Qiagen RNeasy spin column, followed by centrifugation at 8,000×g for 15 sec. The flow through was discarded and the column reloaded with the remaining sample (700 μl) and recentrifuged at 8,000×g for 15 sec. The column was washed once with 700 μl of buffer RW1*, and centrifuged at 8,000×g for 15 sec and the flow through discarded. The column was placed in a new 2 ml collection tube and washed with 500 μl of RPE* buffer and the flow through discarded. The RPE* wash was repeated with centrifugation at 8,000×g for 2 min and the flow through discarded. The spin column was transferred to a new 1.5 ml collection tube and 100 μl of RNase free water added to the column followed by centrifugation at 8,000×g for 15 seconds. An additional 75 μl of RNase free water was added to the column followed by centrifugation at 8,000×g for 2 min. RNA eluted in the water flow through was collected for further purification.

The RNA eluate was then treated to remove contaminating DNA. Twenty microliters of 10X DNase 1 buffer (0.5 M tris (pH 7.5), 50 mM $CaCl_2$, 100 mM $MgCl_2$), 10 μl of RNase-free DNase I (2 Units/μl, Ambion Inc., Austin, Tex.) and 40 units Rnasin (Promega Corporation, Madison, Wis.) were added to the RNA sample. The mixture was then incubated at 37° C. for 15 to 30 min. Samples were placed on ice and 250 μl Lysis buffer RLT* and 250 μl ethanol (2000 proof) added. The samples were then mixed by inversion. The samples were transferred to Qiagen RNeasy spin columns and centrifuged at 8,000×g for 15 sec and the flow through discarded. Columns were placed in new 2 ml collection tubes and washed twice with 500 μl of RPE* wash buffer and the flow through discarded. Columns were transferred to new 1.5 ml eppendorf tubes and RNA was eluated by the addition of 100 μl of DEPC treated water followed by centrifugation at 8,000×g for 15 sec. Residual RNA was collected by adding an additional 50 μl of RNase free water to the spin column followed by centrifugation at full speed for 2 min. 10 μl of the RNA preparation was removed and quantified by the ($A_{260/280}$) method. RNA was stored at −70° C. Yields were found to be 30–100 μg total RNA per 2.0 ml of fermentation broth.

EXAMPLE 11

Quantitative Competitive Reverse Transcription Polymerase Chain Reaction (QC-RT-PCR) Protocol QC-RT-PCR is a technique used to quantitate the amount of a specific RNA in a RNA sample. This technique employs the synthesis of a specific DNA molecule that is complementary to an RNA molecule in the original sample by reverse transcription and its subsequent amplification by polymerase chain reaction. By the addition of various amounts of a competitor RNA molecule to the sample one can determine the concentration of the RNA molecule of interest (in this case the mRNA transcripts of the CYP and CPR genes). The levels of specific mRNA transcripts were assayed over time in response to the addition of fatty acid and/or alkane substrates to the growth medium of fermentation grown *C. tropicalis* cultures for the identification and characterization of the genes involved in the oxidation of these substrates. This approach can be used to identify the CYP and CPR genes involved in the oxidation of any given substrate based upon their transcriptional regulation.

A. Primer Design

The first requirement for QC-RT-PCR is the design of the primer pairs to be used in the reverse transcription and subsequent PCR reactions. These primers need to be unique and specific to the gene of interest. As there is a family of genetically similar CYP genes present in *C. tropicalis* 20336, care had to be taken to design primer pairs that would be discriminating and only amplify the gene of interest, in this example the CYP52A5 gene. In this manner, unique primers directed to substantially non-homologous (aka variable) regions within target members of a gene family are constructed. What constitutes substantially non-homologous regions is determined on a case by case basis. Such unique primers should be specific enough to anneal the non-homologous region of the target gene without annealing to other non-target members of the gene family. By comparing the known sequences of the members of a gene family, non-homologous regions are identified and unique primers are constructed which will anneal to those regions. It is contemplated that non-homologous regions herein would typically exhibit less than about 85% homology but can be more homologous depending on the positions which are conserved and stringency of the reaction. After conducting PCR, it may be helpful to check the reaction product to assure it represents the unique target gene product. If not, the reaction conditions can be altered in terms of stringency to focus the reaction to the desired target. Alternatively a new primer or new non-homologous region can be chosen. Due to the high level of homology between the genes of the CYP52A family, the most variable 5 prim region of the CYP52A5 coding sequence was targeted for the design of the primer pairs. In FIG. 3, a portion of the 5 prime coding region for the CYP52A5A (SEQ ID NO: 36) allele of *C. tropicalis* 20336 is shown. The boxed sequences in FIG. 3 are the sequences of the forward and backwards primers (SEQ ID NOS: 47 and 48) used to quantitate expression of both alleles of this gene. The actual reverse primer (SEQ ID NO: 48) contains one less adenine than that shown in FIG. 3. Primers used to measure the expression of specific *C. tropicalis* 20336 genes using the QC-RT-PCR protocol are listed in Table 5 (SEQ ID NOS: 37–58).

TABLE 5

Primer used to measure *C. tropicalis* gene expression in the QC-RT-PCR reactions.

| Primer Name | Direction | Target | Sequence |
|---|---|---|---|
| 3737-89F | F | CYP52A1A | CCGATGAAGTTTTCGACGAGTACCC (SEQ ID NO: 37) |
| 3737-89B | B | CYP52A1A | AAGGCTTTAACGTGTCCAATCTGGTC (SEQ ID NO: 38) |
| alk2aF1 | F | CYP52A2A | ATTATCGCCACATACTTCACCAAATGG (SEQ ID NO: 39) |
| alk2aB5 | B | CYP52A2A | CGAGATCGTGGATACGCTGGAGTG (SEQ ID NO: 40) |
| 7581-178-3 | F | CYP52A3A | GCCACTCGGTAACTTTGTCAGGGAC (SEQ ID NO: 41) |
| 7581-178-4 | B | CYP52A3A | CATTGAACTGAGTAGCCAAAACAGCC (SEQ ID NO: 42) |
| 3737-50F | F | CYP52A3A & CYP52A3B | CCTACGTTTGGTATCGCTACTCCGTTG (SEQ ID NO: 43) |
| 3737-50B | B | CYP52A3A & CYP52A3B | TTTCCAGCCAGCACCGTCCAAG (SEQ ID NO: 44) |
| 3737-175F | F | CYP52D4A | GCAGAGCCGATCTATGTTGCGTCC (SEQ ID NO: 45) |
| 3737-175B | B | CYP52D4A | TCATTGAATGCTTCCAGGAACCTCG (SEQ ID NO: 46) |
| 7581-97-F | F | CYP52A5A & CYP52A5B | AAGAGGGCAGGGCTCAAGAG (SEQ ID NO: 47) |
| 7581-97-M | B | CYP52A5A & CYP52A5B | TCCATGTGAAGATCCCATCAC (SEQ ID NO: 48) |
| 4P-2 | F | CYP52A8A | CTTGAAGGCCGTGTTGAACG (SEQ ID NO: 49) |
| 4M-1 | B | CYP52A8A | CAGGATTTGTCTGAGTTGCCG (SEQ ID NO: 50) |
| 3737-52F | F | POX4A & POX4B | CCATTGCCTTGAGATACGCCATTGGTAG (SEQ ID NO: 51) |
| 3737-52B | B | POX4A & POX4B | AGCCTTGGTGTCGTTCTTTTCAACGG (SEQ ID NO: 52) |
| 3737-53F | F | POX5A | TTGGGTTTGTTTGTTTCCTGTGTCCG (SEQ ID NO: 53) |
| 3737-53B | B | POX5A | CCTTTGACCTTCAATCTGGCGTAGACG (SEQ ID NO: 54) |
| F33 | F | CPRA | GGTTTGCTGAATACGCTGAAGGTGATG (SEQ ID NO: 55) |
| B63 | B | CPRA | TGGAGCTGAACAACTCTCTCGTCTCGG (SEQ ID NO: 56) |
| 3737-133F | F | CPRA & CPRB | TTCCTCAACACGGACAGCGG (SEQ ID NO: 57) |
| 3737-133B | B | CPRA & CPRB | AGTCAACCAGGTGTGGAACTCGTC (SEQ ID NO: 58) |

F-Forward
B-Backward

B. Design and Synthesis of the Competitor DNA Template

The competitor RNA is synthesized in vitro from a competitor DNA template that has the T7 polymerase promoter and preferably carries a small deletion of e.g., about 10 to 25 nucleotides relative to the native target RNA sequence. The DNA template for the in-vitro synthesis of the competitor RNA is synthesized using PCR primers that are between 46 and 60 nucleotides in length. In this example, the primer pairs for the synthesis of the CYP52A5 competitor DNA are shown in Tables 6 and 7 (SEQ ID NOS: 59 AND 60).

TABLE 6

Forward and Reverse primers used to synthesize the competitor RNA template for the QC-RT-PCR measurement of *CYP52A5A* gene expression.

| | | |
|---|---|---|
| Forward Primer | *CYP52A5A* | GGATCCTAATACGACTCACTATAGGGAGG AAGAGGGCAGGGCTCAAGAG (SEQ ID NO:59) |
| Reverse Primer | *CYP52A5A* | TCCATGTGAAGATCCCATCACGAGTGTGC CTCTTGCCCAAAG (SEQ ID NO:60) |

TABLE 7

Primers for the synthesis of the QC-RT-PCR competitor RNA templates

| Primer Name | Direction | Target | Sequence 5'–3' |
|---|---|---|---|
| 3737-89C | F | CYP52A1A | GGATCCTAATACGACTCACTATAGGGAGGCCGAT GAAGTTTTCGACGAGTACCC (SEQ ID NO: 61) |
| 3737-89D | B | CYP52A1A | AAGGCTTTAACGTGTCCAATCTGGTC AACATAGCTCTGGAGTGCTTCCAACC (SEQ ID NO: 62) |
| 7581-137-A | F | CYP52A2A | GGATCCTAATACGACTCACTATAGGGAGGATTAT CGCCACATACTTCACCAAATGG (SEQ ID NO: 63) |
| 7581-137-B | B | CYP52A2A | CGAGATCGTGGATACGCTGGAGTGCGTCGCTCTT CTTCTTCAACAATTCAAG (SEQ ID NO: 64) |
| 7581-137-D | B | CYP52A3A | CATTGAACTGAGTAGCCAAAACAGCCCATGGTTT CAATCAATGGGAGGC (SEQ ID NO: 65) |
| 7581-137-C | F | CYP52A3A | GGATCCTAATACGACTCACTATAGGGAGGGCCAC TCGGTAACTTTGTCAGGGAC (SEQ ID NO: 66) |
| 3737-50-D | F | CYP52A3A & CYP52A3B | GGATCCTAATACGACTCACTATAGGGAGGCCTAC GTTTGGTATCGCTACTCCGTTG (SEQ ID NO: 67) |
| 3737-50-C | B | CYP52A3A & CYP52A3B | TTTCCAGCCAGCACCGTCCAAGCAACAAGGAGTA CAAGAAATCGTGTC (SEQ ID NO: 68) |
| 3737-175C | F | CYP52D4A | GGATCCTAATACGACTCACTATAGGGAGGGCAGA GCCGATCTATGTTGCGTCC (SEQ ID NO: 69) |
| 3737-175D | B | CYP52D4A | TCATTGAATGCTTCCAGGAACCTCGCCACATCCAT CGAGAACCGG (SEQ ID NO: 70) |
| 7581-97-A | F | CYP52A5A & CYP52A5B | GGATCCTAATACGACTCACTATAGGGAGGAAGAG GGCAGGGCTCAAGAG (SEQ ID NO: 59) |
| 7581-97-B | B | CYP52A5A & CYP52A5B | TCCATGTGAAGATCCCATCACGAGTGTGCCTCTT GCCCAAAG (SEQ ID NO: 60) |
| 4P-2/T7 | F | CYP52A8A | GGATCCTAATACGACTCACTATAGGGAGGCTTGA AGGCCGTGTTGAACG (SEQ ID NO: 71) |
| 4M-3/4M-1 | B | CYP52A8A | CAGGATTTGTCTGAGTTGCCGCCTGATCAAGATA GGATCCTTGCCG (SEQ ID NO: 72) |
| 3737-26-D | F | CPRA | GGATCCTAATACGACTCACTATAGGGAGGGGTTT GCTGAATACGCTGAAGGTGATG (SEQ ID NO: 73) |
| 3737-26-C | B | CPRA | TGGAGCTGAACAACTCTCTCGTCTCGGGTGGTCG AATGGACCCTTGGTCAAG (SEQ ID NO: 74) |
| 3737-133C | F | CPRA & CPRB | GGATCCTAATACGACTCACTATAGGGAGGTTCCT CAACACGGACAGCGG (SEQ ID NO: 75) |
| 3737-133D | B | CPRA & CPRB | AGTCAACCAGGTGTGGAACTCGTCGGTGGCAACA ATGAAAAACACCAAG (SEQ ID NO: 76) |
| 3737-52-C | F | POX4A & POX4B | GGATCCTAATACGACTCACTATAGGGAGGCCATT GCCTTGAGATACGCCATTGGTAG (SEQ ID NO: 77) |
| 3737-52-D | B | POX4A & POX4B | AGCCTTGGTGTCGTTCTTTTCAACGGAAGGTGGT CTCGATGGTGTGTTCAACC (SEQ ID NO: 78) |
| 3737-53-C | F | POX5A | GGATCCTAATACGACTCACTATAGGGAGGTTGGG TTTGTTTGTTTCCTGTGTCCG (SEQ ID NO: 79) |
| 3737-53-D | B | POX5A | CCTTTGACCTTCAATCTGGCGTAGACGCAGCACC ACCGATCCACCACTTG (SEQ ID NO: 80) |

F = Forward
B = Backward

The forward primer (SEQ ID NO: 59) contains the T7 promoter consensus sequence "GGATCCTAATACGA CTCACTATAGGG AGG" (SEQ ID NO: 109) fused to the primer 7581-97-F sequence (SEQ ID NO: 47). The Reverse Primer (SEQ ID NO: 60) contains the sequence of primer 7581-97M (SEQ ID NO: 48) followed by the 20 bases of upstream sequence with a 18 base pair deletion between the two blocks of the CYP52A5 sequence. The forward primer was used with the corresponding reverse primer to synthesize the competitor DNA template. The primer pairs were combined in a standard Taq Gold polymerase PCR reaction according to the manufacturer's recommended conditions (Perkin-Elmer/Applied Biosystems, Foster City, Calif.). The PCR reaction mix contained a final concentration of 250 nM each primer and 10 ng *C. tropicalis* chromosomal DNA for template. The reaction mixture was placed in a thermocycler for 25 to 35 cycles using the highest annealing temperature possible during the PCR reactions to assure a homogeneous PCR product (in this case 62° C.). The PCR products were either gel purified or filtered purified to remove un-incorporated nucleotides and primers. The competitor template DNA was then quantified using the ($A_{260/280}$) method. Primers used in QC-RT-PCR experiments for the synthesis of various competitive DNA templates are listed in Table 7 (SEQ ID NOS: 61–80).

C. Synthesis of the Competitor RNA

Competitor template DNA was transcribed In-Vitro to make the competitor RNA using the Megascript T7 kit from Ambion Biosciences (Ambion Inc., Austin, Tex.). 250 nanograms (ng) of competitor DNA template and the in-vitro transcription reagents are mixed according to the directions provided by the manufacturer. The reaction mixture was incubated for 4 hours at 37° C. The resulting RNA preparations were then checked by gel electrophoresis for the conditions giving the highest yields and quality of competitor RNA. This often required optimization according to the manufacturer's specifications. The DNA template was then removed using DNase I as described in the Ambion kit. The RNA competitor was then quantified by the ($A_{260/280}$) method. Serial dilution's of the RNA (1 ng/μl to 1 femtogram (fg/μl) were made for use in the QC-RT-PCR reactions and the original stocks stored at −70° C.

D. QC-RT-PCR Reactions

QC-RT-PCR reactions were performed using rTth polymerase from Perkin-Elmer (Perkin-Elmer/Applied Biosystems, Foster City, Calif.) according to the manufacturer's recommended conditions. The reverse transcription reaction was performed in a 10 μl volume with a final concentrations of 200 μM for each dNTP, 1.25 units rTth polymerase, 1.0 mM $MnCl_2$, 1X of the 10X buffer supplied with the Enzyme from the manufacturer, 100 ng of total RNA isolated from a fermentor grown culture of *C. tropicalis* and 1.25 μM of the appropriate reverse primer. To quantitate CYP52A5 expression in *C. tropicalis* an appropriate reverse primer was 7581-97M (SEQ ID NO: 48). Several reaction mixes were prepared for each RNA sample characterized. To quantitate CYP52A5 expression a series of 8 to 12 of the previously described QC-RT-PCR reaction mixes were aliquoted to different reaction tubes. To each tube 1 μl of a serial dilution containing from 100 pg to 100 fg CYP52A5 competitor RNA per μl was added bringing the final reaction mixtures up to the final volume of 10 μl. The QC-RT-PCR reaction mixtures were mixed and incubated at 70° C. for 15 min according to the manufacturer's recommended times for reverse transcription to occur. At the completion of the 15 minute incubation, the sample temperature was reduced to 4° C. to stop the reaction and 40 μl of the PCR reaction mix added to the reaction to bring the total volume up to 50 μl. The PCR reaction mix consists of an aqueous solution containing 0.3125 μM of the forward primer 7581-97F (SEQ ID NO: 47), 3.125 mM MgCl, and 1X chelating buffer supplied with the enzyme from Perkin-Elmer. The reaction mixtures were placed in a thermocycler (Perkin-Elmer GeneAmp PCR System 2400, Perkin-Elmer/Applied Biosystems, Foster City, Calif.) and the following PCR cycle performed: 94° C. for 1 min. followed by 94° C. for 10 seconds followed by 58° C. for 40 seconds for 17 to 22 cycles. The PCR reaction was completed with a final incubation at 58° C. for 2 min followed by 4° C. In some reactions were no detectable PCR products were produced the samples were returned the thermocycler for additional cycles, this process was repeated until enough PCR products were produced to quantify using HPLC. The number of cycles necessary to produce enough PCR product is a function of the amount of the target mRNA in the 100 ng of total cellular RNA. In cultures where the CYP52A5 gene is highly expressed there is sufficient CYP52A5 mRNA message present and less PCR cycles (≦17) are required to produce quantifiable amount of PCR product. The lower the concentrations of the target mRNA present the more PCR cycles are required to produce a detectable amount of product. These QC-RT-PCR procedures were applied to all the target genes listed in Table 5 using the respective primers indicated therein.

HPLC Quantification

Upon completion of the QC-RT-PCR reactions the samples were analyzed and quantitated by HPLC. Five to fifteen microliters of the QC-RT-PCR reaction mix was injected into a Waters Bio-Compatible 625 HPLC with an attached Waters 484 tunable detector. The detector was set to measure a wave length of 254 nm. The HPLC contained a Sarasep brand DNASep™ column (Sarasep, Inc., San Jose, Calif.) which was placed within the oven and the temperature set for 52° C. The column was installed according to the manufacturer's recommendation of having 30 cm. of heated PEEK tubing installed between the injector and the column. The system was configured with a Sarasep brand Guard column positioned before the injector. In addition, there was a 0.22 μm filter disk just before the column, within the oven. Two Buffers were used to create an elution gradient to resolve and quantitate the PCR products from the QC-RT-PCR reactions. Buffer-A consists of 0.1 M tri-ethyl ammonium acetate (TEAA) and 5% acetonitrile (volume to volume). Buffer-B consists of 0.1 M TEAA and 25% acetonitrile (volume to volume). The QC-RT-PCR samples were injected into the HPLC and the linear gradient of 75% buffer-A/25% buffer-B to 45% buffer-A/55% B was run over 6 min at a flow rate of 0.85 ml per minute. The QC-RT-PCR product of the competitor RNA being 18 base pairs smaller is eluted from the HPLC column before the QC-RT-PCR product from the CYP52A5 mRNA(U). The amount of the QC-RT-PCR products are plotted and quantitated with an attached Waters Corporation 745 data module. The log ratios of the amount of CYP52A5 mRNA QC-RT-PCR product (U) to competitor QC-RT-PCR product (C), as measured by peak areas, was plotted and the amount of competitor RNA required to equal the amount of CYP52A5 mRNA product determined. In the case of each of the target genes listed in Table 5, the competitor RNA contained fewer base pairs as compared to the native target mRNA and eluted before the native mRNA in a manner similar to that demonstrated by CYP52A5, HPLC quantification of the genes was conducted as above.

EXAMPLE 12

Evaluation of New Strains in Shake Flasks

Figure 35:
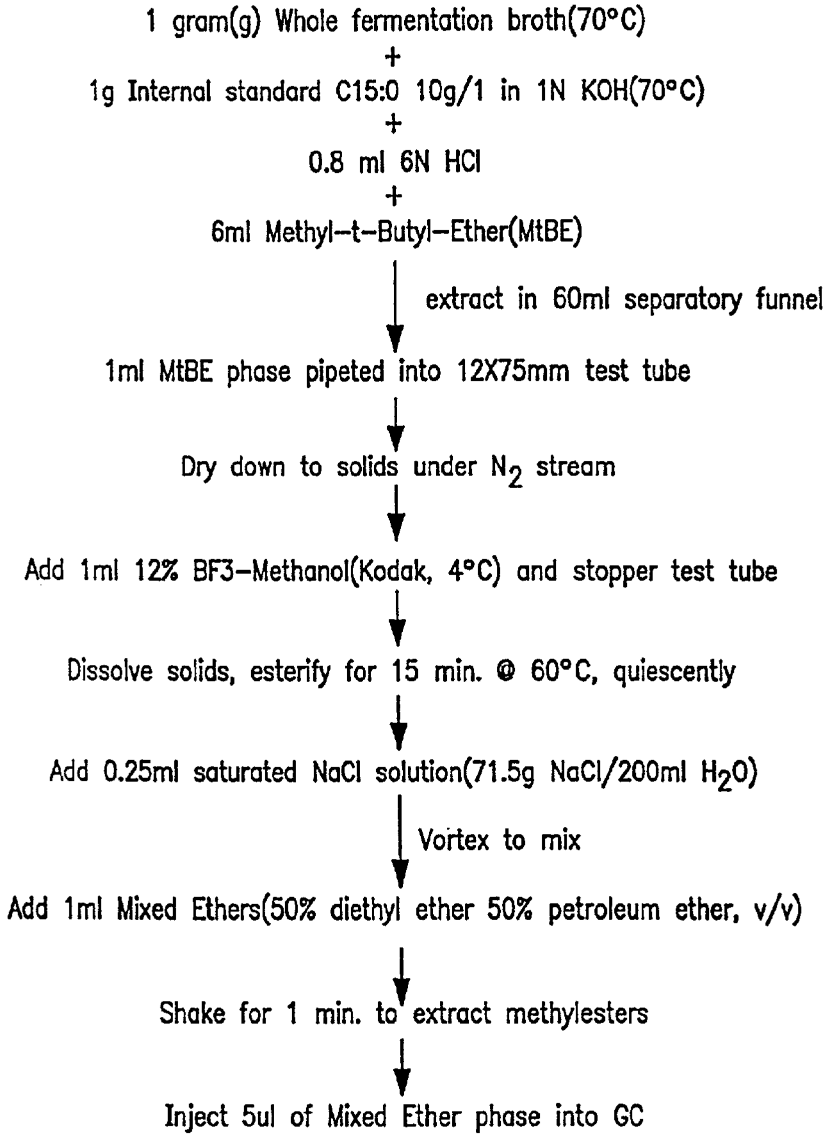
FIG. 35 depicts a scheme used for the extraction and analysis of diacids and monoacids from fermentation broths.

The CYP and CPR amplified strains such as strains HDC10, HDC15, HDC20 and HDC23 (Table 1) and H5343 were evaluated for diacid productionin shake flasks. A single colony for each strain was transferred from a YPD agar plate into 5 ml of YPD broth and grown overnight at 30° C., 250 rpm. An inoculum was then transferred into 50 ml of DCA2 medium (Table 9) and grown for 24 h at 30° C., 300 rpm. The cells were centrifuged at 5000 rpm for 5 min and resuspended in 50 ml of DCA3 medium (Table 9) and grown for 24 h at 30° C., 300 rpm. 3% oleic acid w/v was added after 24 h growth in DCA3 medium and the cultures were allowed to bioconvert oleic acid for 48 h. Samples were harvested and the diacid and monoacid concentrations were analyzed as per the scheme given in FIG. 35. Each strain was tested in duplicate and the results shown in Table 8 represent the average value from two flasks.

TABLE 8

Bioconversion of oleic acid by different recombinant strains of *Candida tropicalis*

| Strain | Conversion to Oleic diacid (%) | Specific Conversion (g diacid/g biomass |
|---|---|---|
| H5343 | 41.9 | 0.53 |
| HDC 10-2 | 50.5 | 0.85 |
| HDC 15 | 54.4 | 0.85 |
| HDC 20-1 | 45.1 | 0.72 |
| HDC 20-2 | 45.3 | 0.58 |
| HDC 23-2 | 55.2 | 0.84 |
| HDC 23-3 | 58.8 | 0.89 |

EXAMPLE 13

Figure 4:
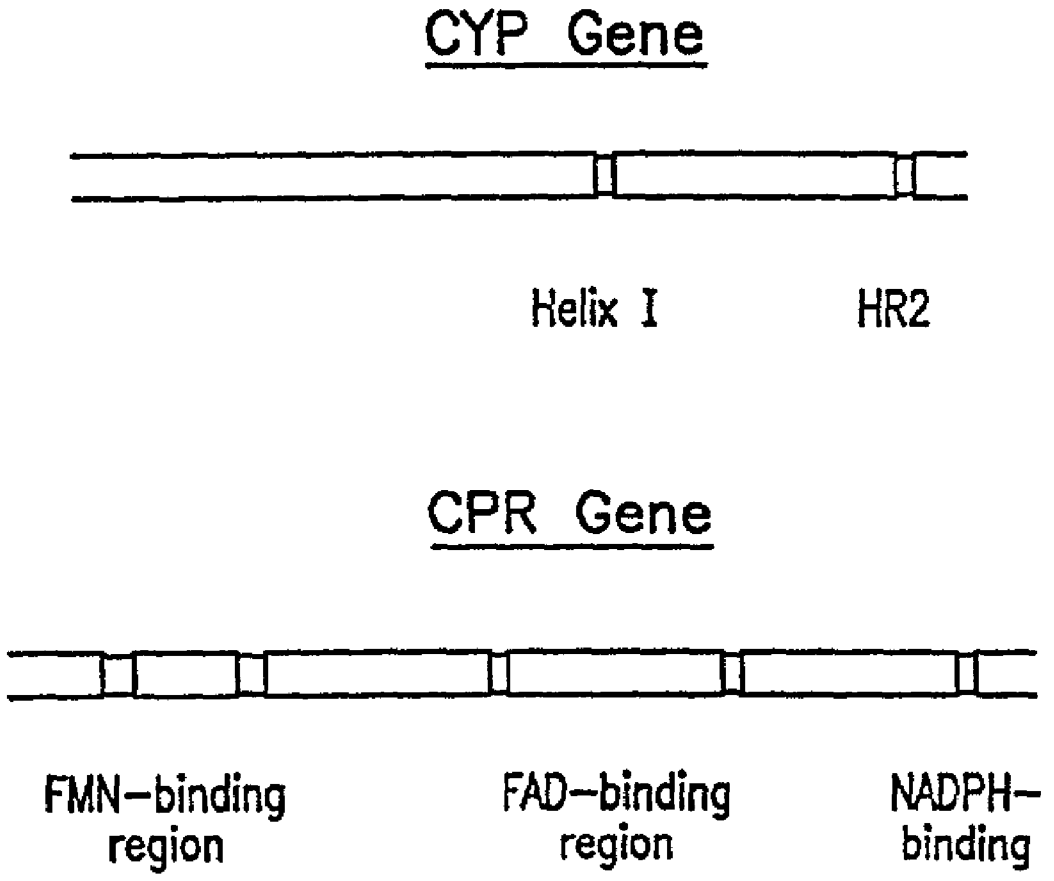
FIG. 4 is a diagrammatic representation of highly conserved regions of CYP and CPR gene protein sequences. helix I represents the putative substrate binding site and HR2 represents the heme binding region. The FMN, FAD and NADPHA binding regions are indicated below the CPR gene.

Cloning and Characterization of *C. tropicalis* 20336 Cytochrome P450 Monooxygenase (CYP) and Cytochrome P450 NADPH Oxidoreductase (CPR) Genes To clone CYP and CPR genes several different strategies were employed. Available CYP amino acid sequences were aligned and regions of similarity were observed (FIG. 4). These regions corresponded to described conserved regions seen in other cytochrome P450 families (Goeptar et al., supra and Kalb et al. supra). Proteins from eight eukaryotic cytochrome P450 families share a segmented region of sequence similarity. One region corresponded to the HR2 domain containing the invariant cysteine residue near the carboxyl terminus which is required for heme binding while the other region correspond to the central region of the I helix thought to be involved in substrate recognition (FIG. 4). Degenerate oligonucleotide primers corresponding to these highly conserved regions of the CYP52 gene family present in *Candida maltosa* and *Candida tropicalis* ATCC 750 were designed and used to amplify DNA fragments of CYP genes from *C. tropicalis* 20336 genomic DNA. These discrete PCR fragments were then used as probes to isolate full-length CYP genes from the *C. tropicalis* 20336 genomic libraries. In a few instances oligonucleotide primers corresponding to highly conserved regions were directly used as probes to isolate full-length CYP genes from genomic libraries. In the case of CPR a heterologous probe based upon the known DNA sequence for the CPR gene from *C. tropicalis* 750 was used to isolate the *C. tropicalis* 20336 CPR gene.

A. Cloning of the CPR Gene from *C. tropicalis* 20336

1) Cloning of the CPRA Allele

Approximately 25,000 phage particles from the first genomic library of *C. tropicalis* 20336 were screened with a 1.9 kb BamHI-NdeI fragment from plasmid pCU3RED (See Picattagio et al., Bio/Technology 10:894–898 (1992), incorporated herein by reference) containing most of the *C. tropicalis* 750 CPR gene. Five clones that hybridized to the probe were isolated and the plasmid DNA from these lambda clones was rescued and characterized by restriction enzyme analysis. The restriction enzyme analysis suggested that all five clones were identical but it was not clear that a complete CPR gene was present.

Figure 5:
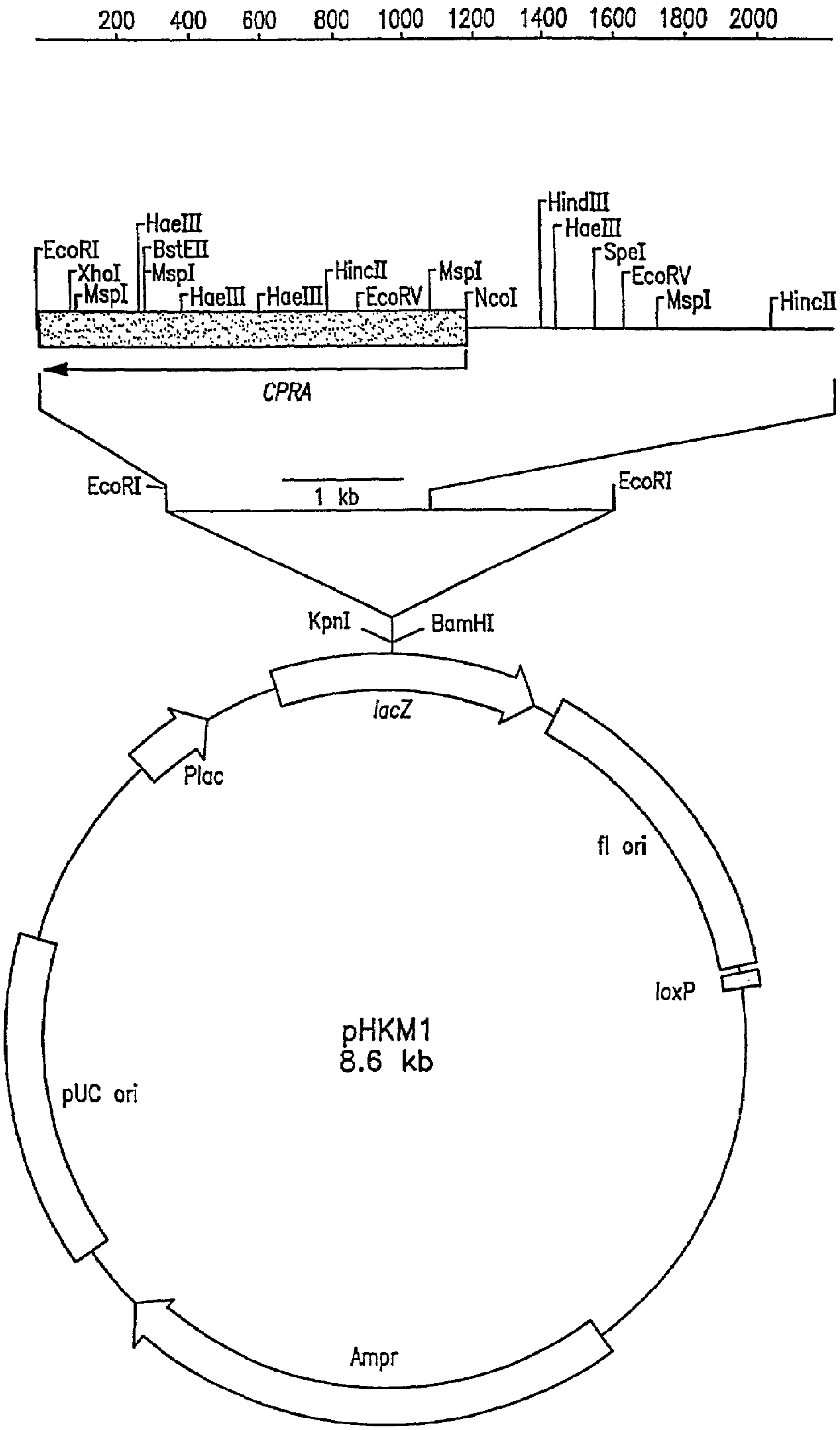
FIG. 5 is a diagrammatic representation of the plasmid pHKM1 containing the truncated CPRA gene present in the pTriplEx vector. A detailed restriction map of only the sequenced region is shown at the top. The bar indicates the open reading frame. The direction of transcription is indicated by an arrow under the open reading frame.

PCR analysis was used to determine if a complete CPR gene was present in any of the five clones. Degenerate primers were prepared for highly conserved regions of known CPR genes (See Sutter et al., *Biol. Chem.* 265: 16428–16436 (1990), incorporated herein by reference) (FIG. 4). Two Primers were synthesized for the FMN binding region (FMN1, SEQ ID NO: 16 and FMN2, SEQ ID NO: 17). One primer was synthesized for the FAD binding region (FAD, SEQ ID NO: 18), and one primer for the NADPH binding region (NADPH, SEQ ID NO: 19) (Table 4). These four primers were used in PCR amplification experiments using as a template plasmid DNA isolated from four of the five clones described above. The FMN (SEQ ID NOS: 16 and 17) and FAD (SEQ ID NO: 18) primers served as forward primers and the NADPH primer (SEQ ID NO: 19) as the reverse primer in the PCR reactions. When different combinations of forward and reverse primers were used, no PCR products were obtained from any of the plasmids. However, all primer combinations amplified expected size products with a plasmid containing the *C. tropicalis* 750 CPR gene (positive control). The most likely reason for the failure of the primer pairs to amplify a product, was that all four of clones contained a truncated CPR gene. One of the four clones (pHKM1) was sequenced using the Triplex 5' (SEQ ID NO: 30) and the Triplex 3' (SEQ ID NO: 31) primers (Table 4) which flank the insert and the multiple cloning site on the cloning vector, and with the degenerate primer based upon the NADPH binding site described above. The NADPH primer (SEQ ID NO: 19) failed to yield any sequence data and this is consistent with the PCR analysis. Sequences obtained with Triplex primers were compared with *C. tropicalis* 750 CPR sequence using the MacVector™ program (Oxford Molecular Group, Campbell, Calif.). Sequence obtained with the Triplex 3' primer (SEQ ID NO: 31) showed similarity to an internal sequence of the *C. tropicalis* 750 CPR gene confirming that pHKM1 contained a truncated version of a 20336 CPR gene. pHKM1 had a 3.8 kb insert which included a 1.2 kb coding region of the CPR gene accompanied by 2.5 kb of upstream DNA (FIG. 5). Approximately 0.85 kb of the 20336 CPR gene encoding the C-terminal portion of the CPR protein is missing from this clone.

Figure 6:
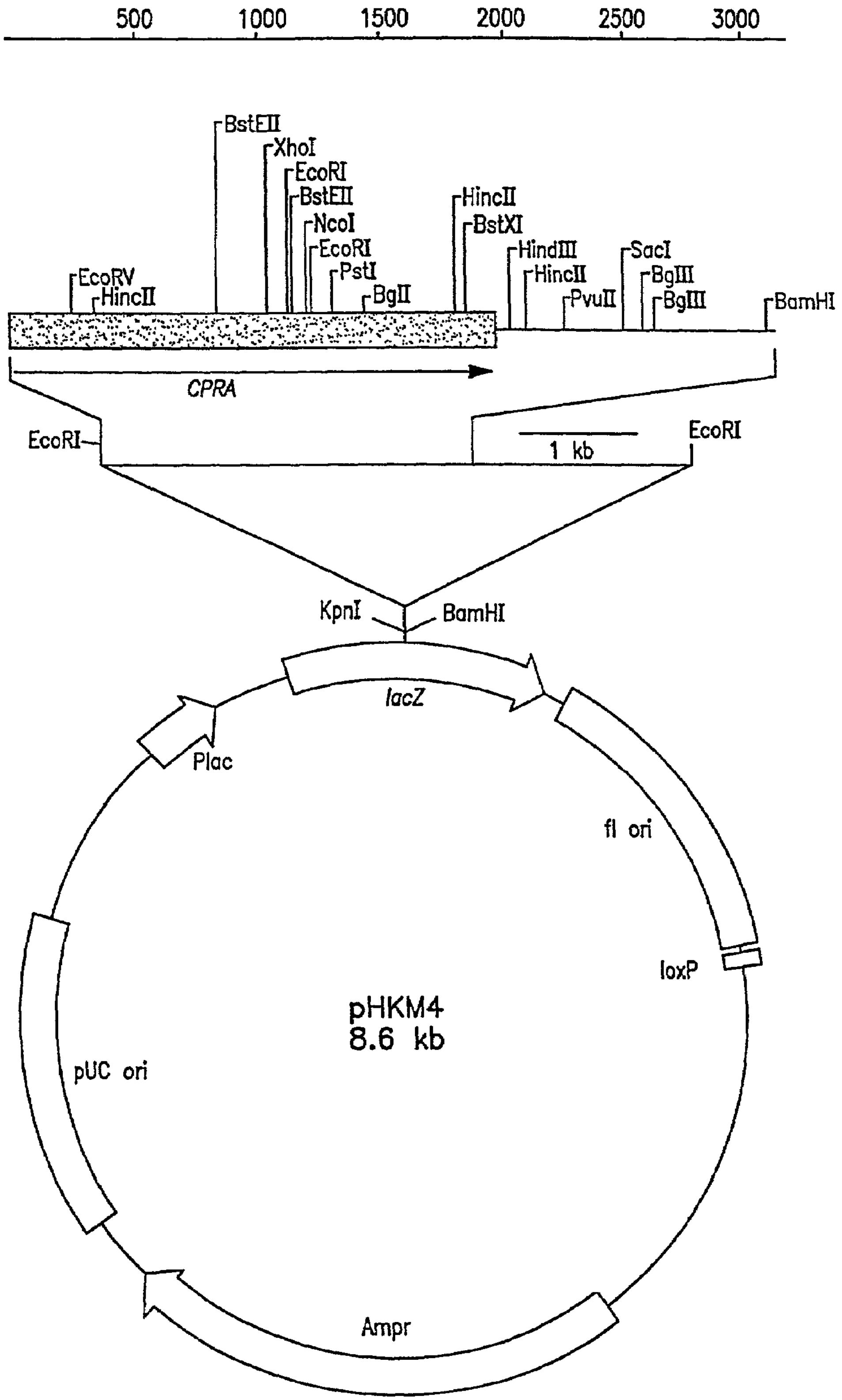
FIG. 6 is a diagrammatic representation of the plasmid pHKM4 containing the truncated CPRA gene present in the pTriplEx vector. A detailed restriction map of only the sequenced region is shown at the top. The bar indicates the open reading frame. The direction of transcription is indicated by an arrow under the open reading frame.

Since the first Clontech library yielded only a truncated CPR gene, the second library prepared by Clontech was screened to isolate a full-length CPR gene. Three putative CPR clones were obtained. The three clones, having inserts in the range of 5–7 kb, were designated pHKM2, pHKM3 and pHKM4. All three were characterized by PCR using the degenerate primers described above. Both pHKM2 and pHKM4 gave PCR products with two sets of internal primers. pHKM3 gave a PCR product only with the FAD (SEQ ID NO: 18) and NADPH (SEQ ID NO: 19) primers suggesting that this clone likely contained a truncated CPR gene. All three plasmids were partially sequenced using the two Triplex primers and a third primer whose sequence was selected from the DNA sequence near the truncated end of the CPR gene present in pHKM1. This analysis confirmed that both pHKM2 & 4 have sequences that overlap pHKM1 and that both contained the 3' region of CPR gene that is missing from pHKM1. Portions of inserts from pHKM1 and pHKM4 were sequenced and a full-length CPR gene was identified. Based on the DNA sequence and PCR analysis, it was concluded that pHKM1 contained the putative promoter region and 1.2 kb of sequence encoding a portion (5' end) of a CPR gene. pHKM4 had 1.1 kb of DNA that overlapped pHKM1 and contained the remainder (3' end) of a CPR gene along with a downstream untranslated region (FIG. 6). Together these two plasmids contained a complete CPRA gene with an upstream promoter region. CPRA is 4206 nucleotides in length (SEQ ID NO: 81) and includes a regulatory region and a protein coding region (defined by nucleotides 1006–3042) which is 2037 base pairs in length and codes for a putative protein of 679 amino acids (SEQ ID NO: 83) (FIGS. 13 and 14). In FIG. 13, the asterisks denote conserved nucleotides between CPRA and CPRB, bold denotes protein coding nucleotides, and the start and stop codons are underlined. The CPRA protein, when analyzed by the protein alignment program of the GeneWorks™ software package (Oxford Molecular Group, Campbell, Calif.), showed extensive homology to CPR proteins from *C. tropicalis* 750 and *C. maltosa.*

2) Cloning of the CPRB Allele

Figure 7:
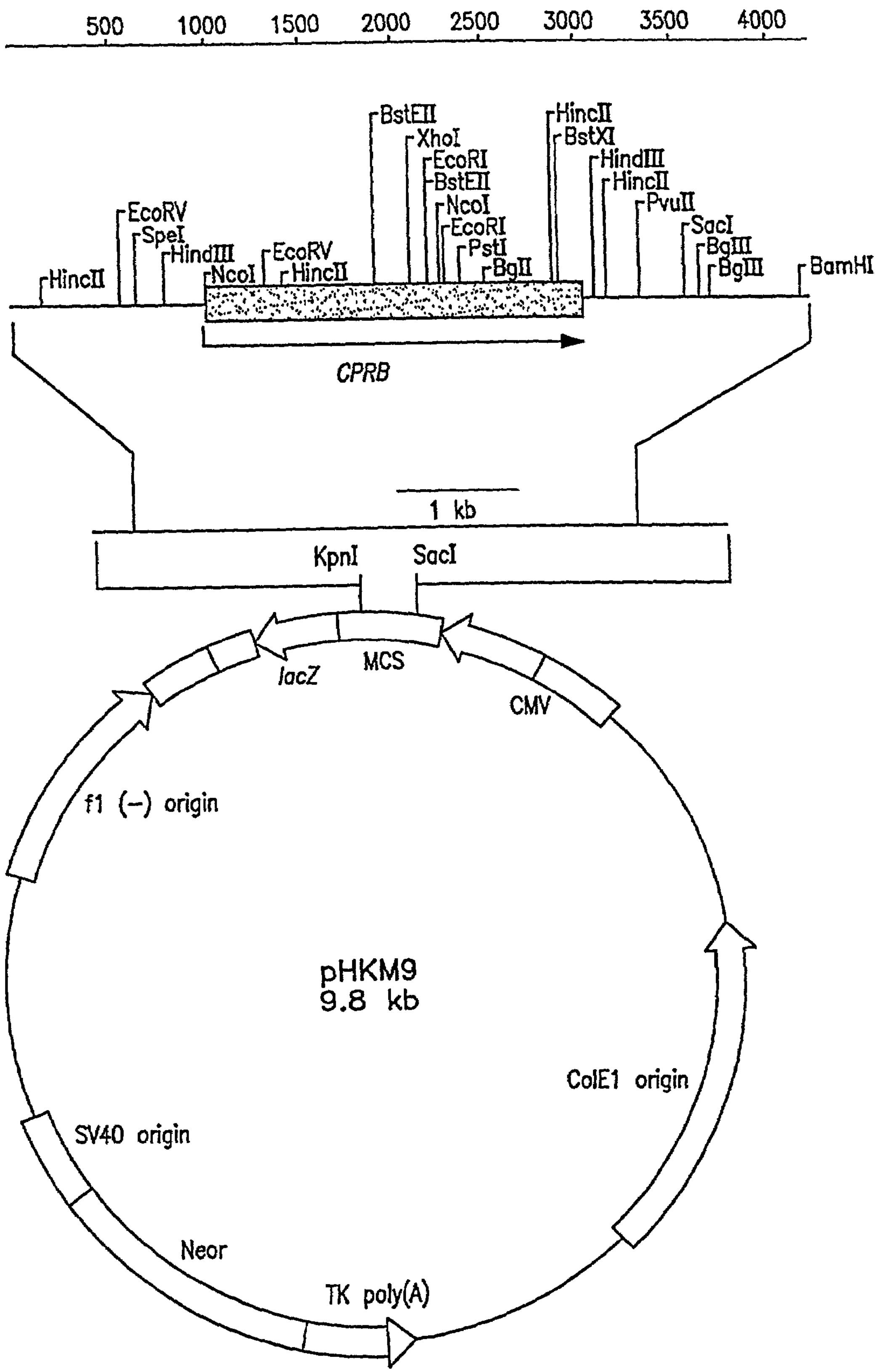
FIG. 7 is a diagrammatic representation of the plasmid pHKM9 containing the CPRB gene (SEQ ID NO: 82) present in the pBK-CMV vector. A detailed restriction map of only the sequenced region is shown at the top. The bar indicates the open reading frame. The direction of transcription is indicated by an arrow under the open reading frame.

To clone the second CPRB allele, the third genomic library, prepared by Henkel, was screened using DNA fragments from pHKM1 and pHKM4 as probes. Five clones were obtained and these were sequenced with the three internal primers used to sequence CPRA. These primers were designated PRK1.F3 (SEQ ID NO: 20), PRK1.F5 (SEQ ID NO: 21) and PRK4.R20 (SEQ ID NO: 22) (Table 4). and the two outside primers (M13–20 and T3 [Stratagene]) for the polylinker region present in the pBK-CMV cloning vector. Sequence analysis suggested that four of these clones, designated pHKM5 to 8, contained inserts which were identical to the CPRA allele isolated earlier. All four seemed to contain a full length CPR gene. The fifth clone was very similar to the CPRA allele, especially in the open reading frame region where the identity was very high. However, there were significant differences in the 5' and 3' untranslated regions. This suggested that the fifth clone was the allele to CPRA. The plasmid was designated pHKM9 (FIG. 7) and a 4.14 kb region of this plasmid was sequenced and the analysis of this sequence confirmed the presence of the CPRB allele (SEQ ID NO: 82), which includes a regulatory region and a protein coding region (defined by nucleotides 1033–3069) (FIG. 13). The amino acid sequence of the CPRB protein is set forth in SEQ ID NO: 84 (FIG. 14).

B. Cloning of *C. tropicalis* 20336 (CYP) Genes

1) Cloning of CYP52A2A, CYP52A3A & 3B and CYP52A5A & 5B

Figure 26:
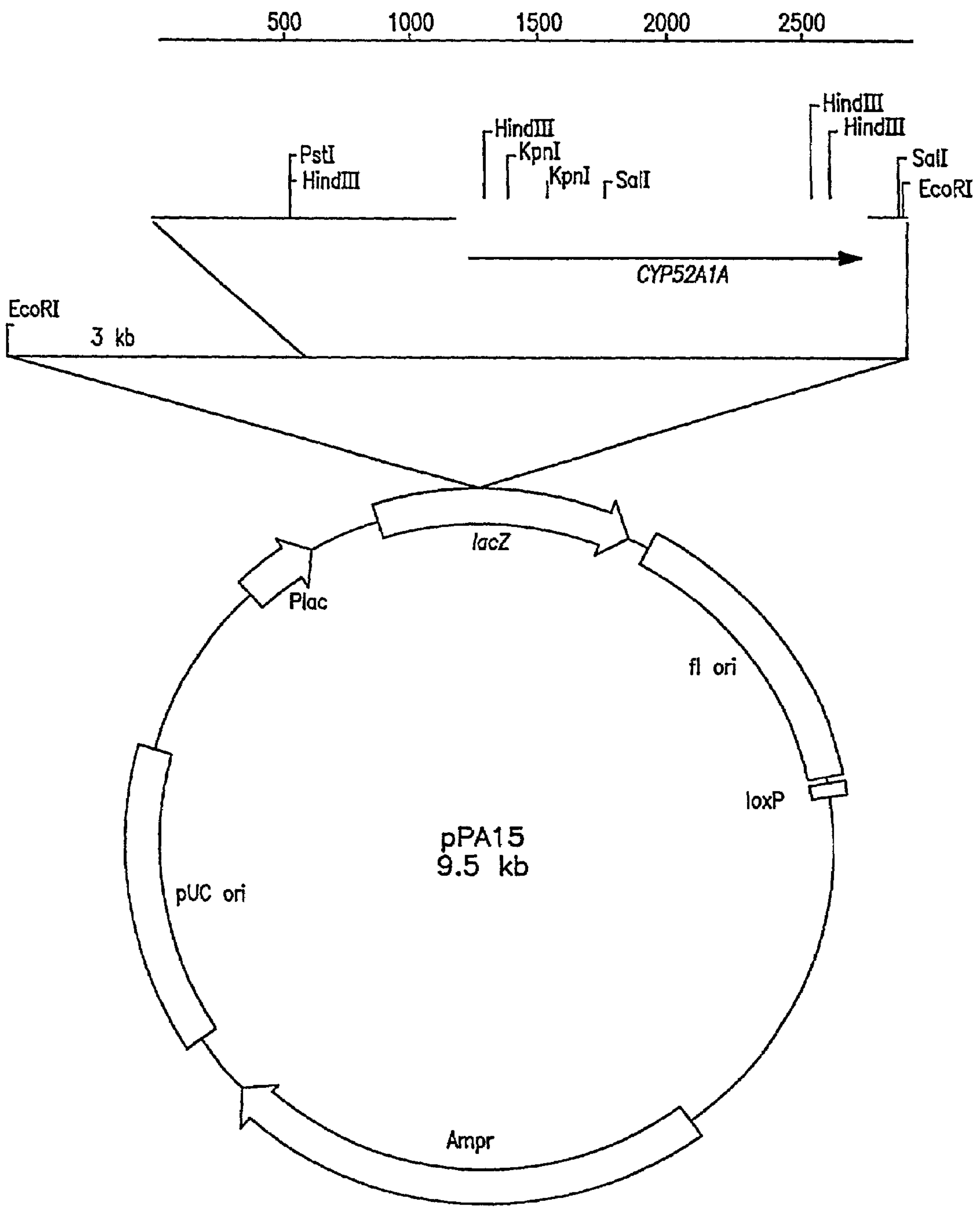
FIG. 26 is a diagrammatic representation of the plasmid pPA15 containing the truncated CYP52A2A gene present in the pTriplEx vector. A detailed restriction map of only the sequenced region is shown at the top. The bar indicates the open reading frame. The direction of transcription is indicated by an arrow under the open reading frame.
Figure 29:
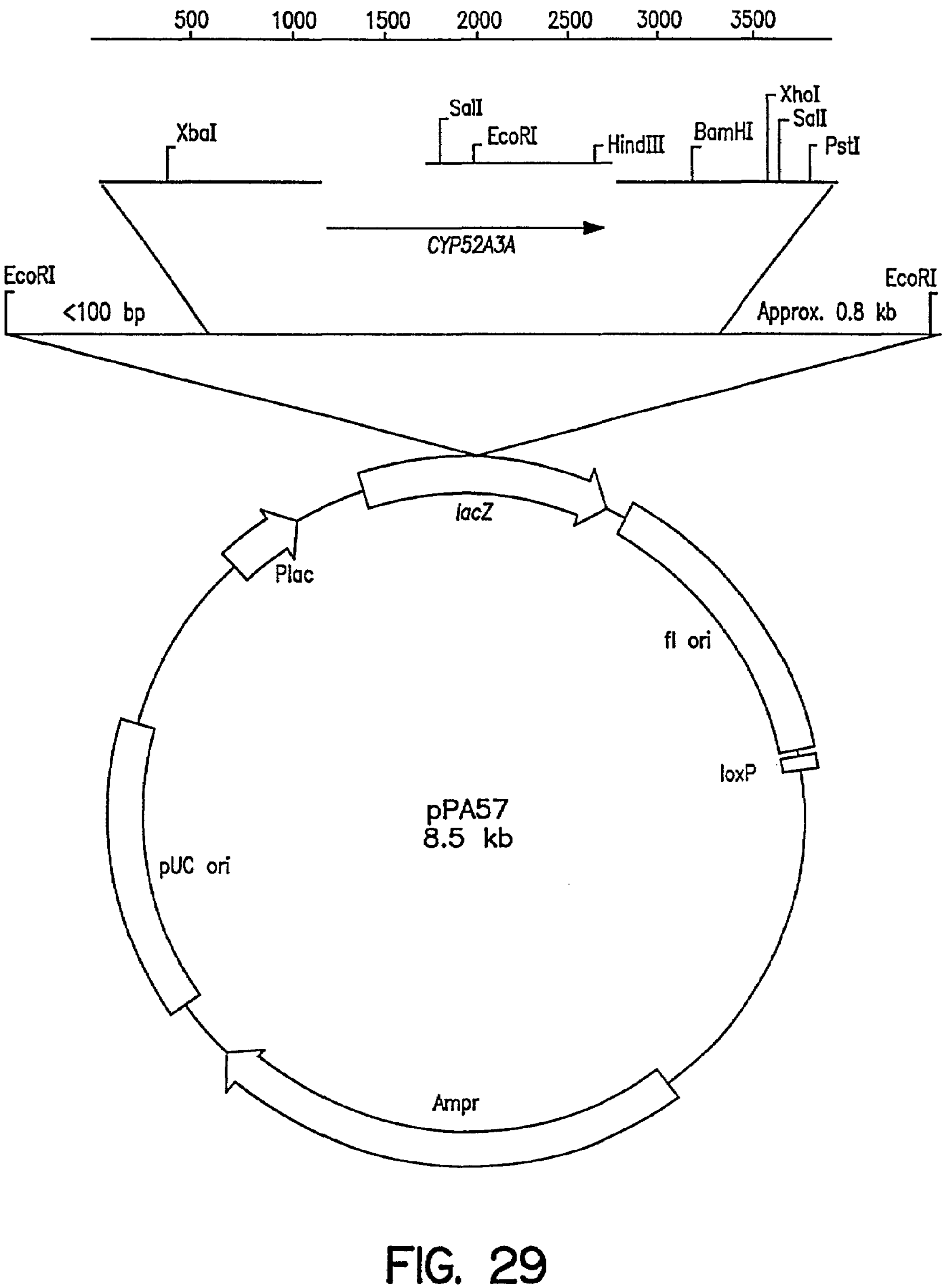
FIG. 29 is a diagrammatic representation of the plasmid pPA57 containing the truncated CYP52A3A gene present in the pTriplEx vector. A detailed restriction map of only the sequenced region is shown at the top. The bar indicates the open reading frame. The direction of transcription is indicated by an arrow under the open reading frame.
Figure 30:
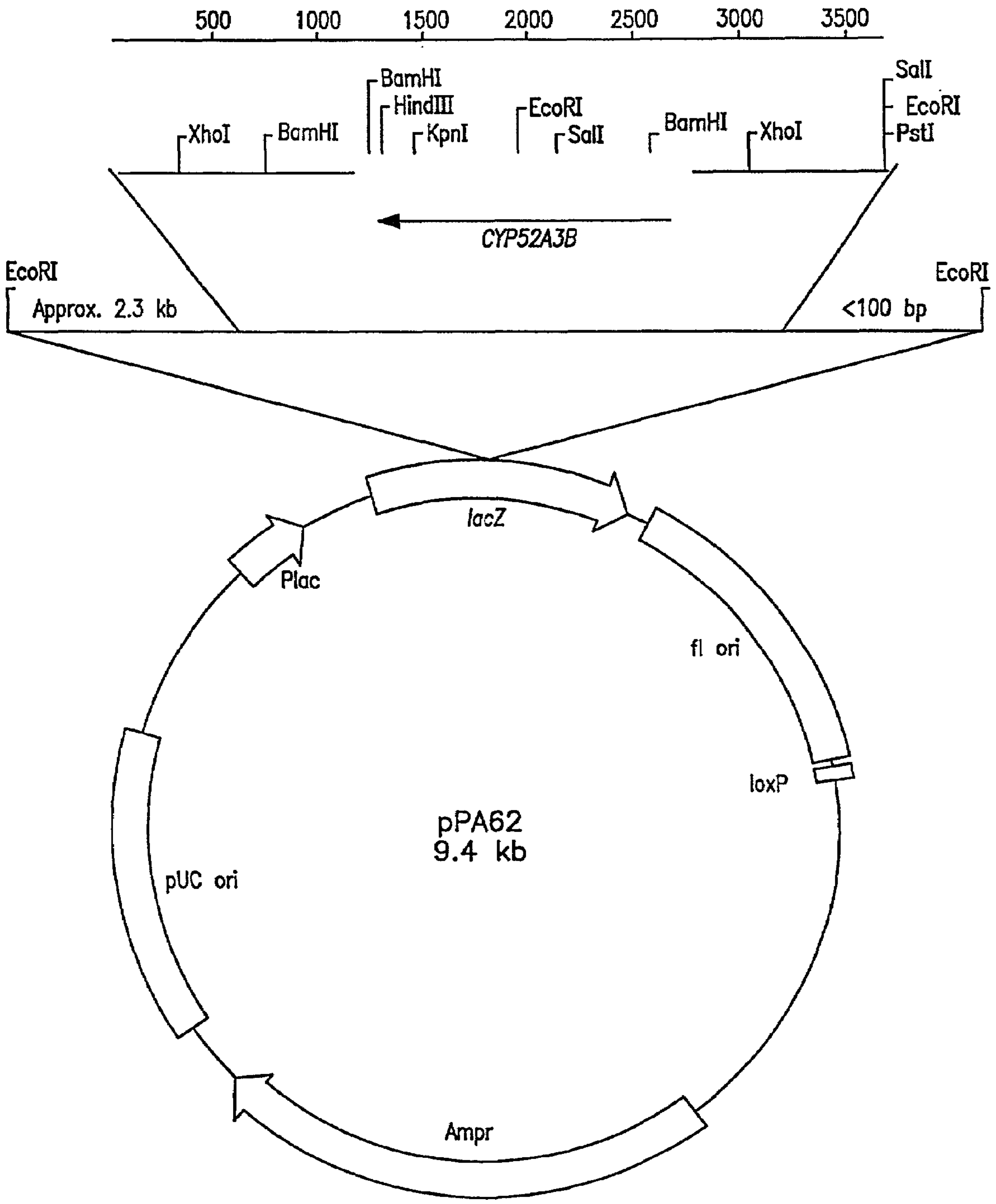
FIG. 30 is a diagrammatic representation of the plasmid pPA62 containing the truncated CYP52A3B gene present in the pTriplEx vector. A detailed restriction map of only the sequenced region is shown at the top. The bar indicates the open reading frame. The direction of transcription is indicated by an arrow under the open reading frame.
Figure 31:
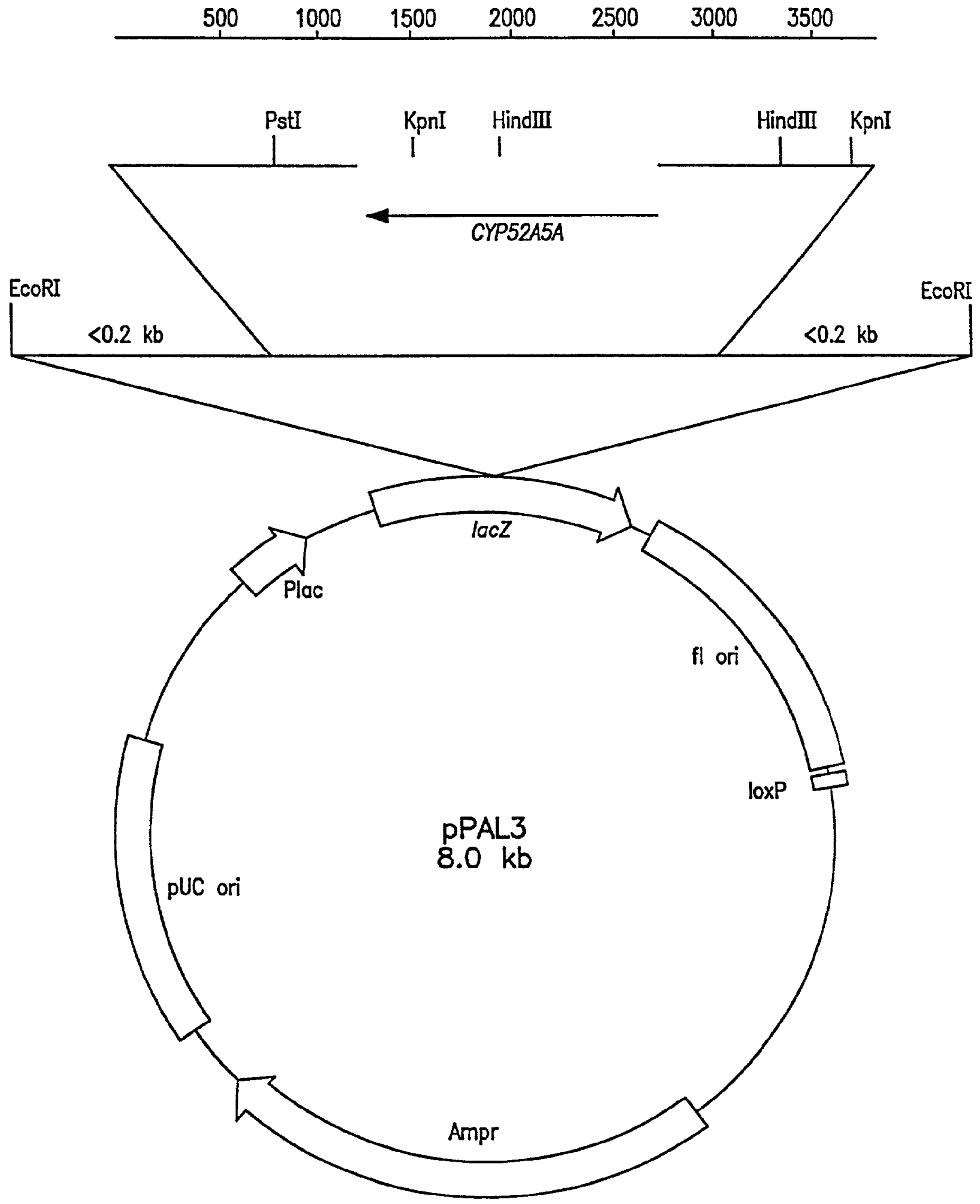
FIG. 31 is a diagrammatic representation of the plasmid pPAL3 containing the truncated CYP52A5A gene present in the pTriplEx vector. A detailed restriction map of only the sequenced region is shown at the top. The bar indicates the open reading frame. The direction of transcription is indicated by an arrow under the open reading frame.
Figure 32:
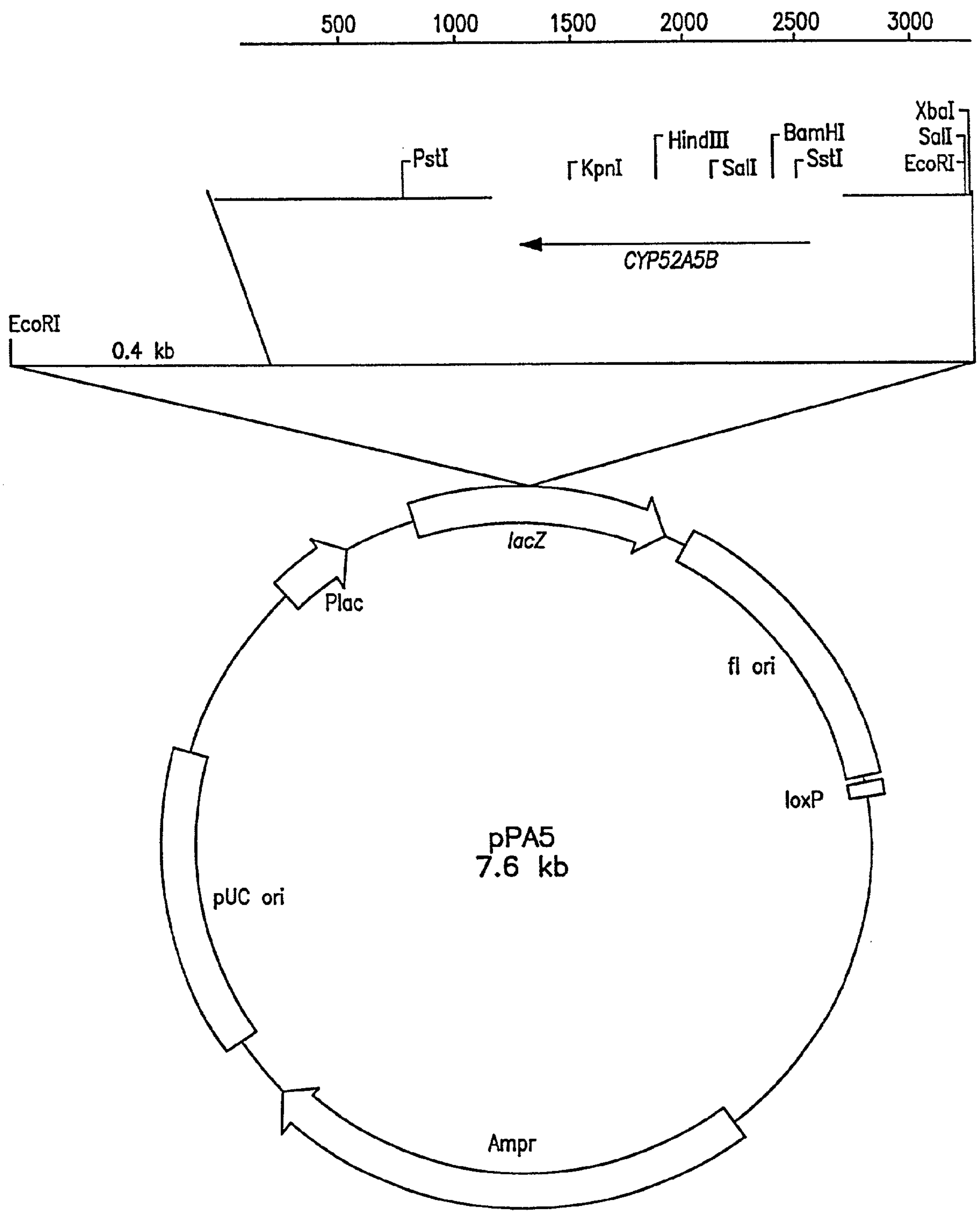
FIG. 32 is a diagrammatic representation of the plasmid pPA5 containing the truncated CYP52A5A gene present in the pTriplEx vector. A detailed restriction map of only the sequenced region is shown at the top. The bar indicates the open reading frame. The direction of transcription is indicated by an arrow under the open reading frame.

Clones carrying CYP52A2A, A3A, A3B, A5A and A5B genes were isolated from the first and second Clontech genomic libraries using an oligonucleotide probe (HemeB1, SEQ ID NO: 27) whose sequence was based upon the amino acid sequence for the highly conserved heme binding region present throughout the CYP52 family. The first and second libraries were converted to the plasmid form and screened by colony hybridizations using the HemeB1 probe (SEQ ID NO: 27) (Table 4). Several potential clones were isolated and the plasmid DNA was isolated from these clones and sequenced using the HemeB1 oligonucleotide (SEQ ID NO: 27) as a primer. This approach succeeded in identifying five CYP52 genes. Three of the CYP genes appeared unique, while the remaining two were classified as alleles. Based upon an arbitrary choice of homology to CYP52 genes from *Candida maltosa,* these five genes and corresponding plasmids were designated CYP52A2A (pPA15 [FIG. 26]), CYP52A3A (pPA57 [FIG. 29]), CYP52A3B (pPA62 [FIG. 30]), CYP52A5A (pPAL3 [(FIG. 31]) and CYP52A5B (pPA5 [FIG. 32]). The complete DNA sequence including regulatory and protein coding regions of these five genes was obtained and confirmed that all five were CYP52 genes (FIG. 15). In FIG. 15, the asterisks denote conserved nucleotides among the CYP genes. Bold indicates the protein coding nucleotides of the CYP genes, and the start and stop codons are underlined. The CYP52A2A gene as represented by SEQ ID NO: 86 has a protein coding region defined by nucleotides 1199–2767 and the encoded protein has an amino acid sequence as set forth in SEQ ID NO: 96. The CYP52A3A gene as represented by SEQ ID NO: 88 has a protein encoding region defined by nucleotides 1126–2748 and the encoded protein has an amino acid sequence as set forth in SEQ ID NO: 98. The CYP52A3B gene as represented by SEQ ID NO: 89 has a protein coding defined by nucleotides 913–2535 and the encoded protein has an amino acid sequence as set forth in SEQ ID NO: 99. The CYP52A5A gene as represented by SEQ ID NO: 90 has a protein coding region defined by nucleotides 1103–2656 and the encoded protein has an amino acid sequence as set forth in SEQ ID NO: 100. The CYP52A5B gene as represented by SEQ ID NO: 91 has a protein coding region defined by nucleotides 1142–2695 and the encoded protein has an amino acid sequence as set forth in SEQ ID NO: 101.

2) Cloning of CYP52A1A and CYP52A8A

Figure 17:
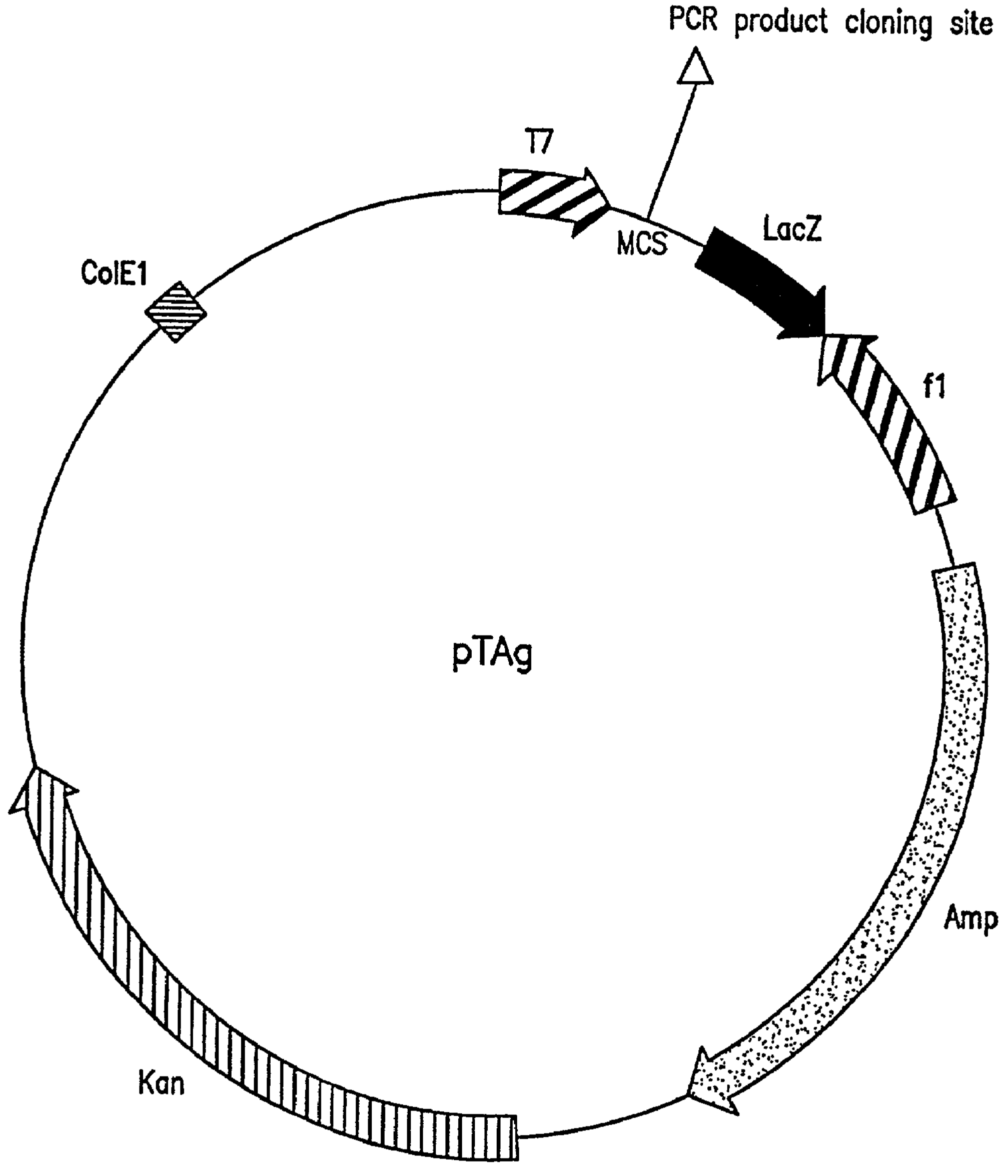
FIG. 17 is a diagrammatic representation of the pTAg PCR product cloning vector (commercially available from R&D Systems, Minneapolis, Minn.).

CYP52A1A and CYP52A8A genes were isolated from the third genomic library using PCR fragments as probes. The PCR fragment probe for CYP52A1 was generated after PCR amplification of 20336 genomic DNA with oligonucleotide primers that were designed to amplify a region from the Helix I region to the HR2 region using all available CYP52 genes from National Center for Biotechnology Information. Degenerate forward primers UCup1 (SEQ ID NO: 23) and UCup2 (SEQ ID NO: 24) were designed based upon an amino acid sequence (-RDTTAG-) from the Helix I region (Table 4). Degenerate primers UCdown1 (SEQ ID NO: 25) and UCdown2 (SEQ ID NO: 26) were designed based upon an amino acid sequence (-GQQFAL-) from the HR2 region (Table 4). For the reverse primers, the DNA sequence represents the reverse complement of the corresponding amino acid sequence. These primers were used in pairwise combinations in a PCR reaction with Stoffel Taw DNA polymerase (Perkin-Elmer Cetus, Foster City, Calif.) according to the manufacturer's recommended procedure. A PCR product of approximately 450 bp was obtained. This product was purified from agarose gel using Gene-clean™ (Bio 101, LaJolla, Calif.) and ligated to the pTAG™ vector (FIG. 17) (R&D systems, Minneapolis, Minn.) according to the recommendations of the manufacturer. No treatment was necessary to clone into pTAG because it employs the use of the TA cloning technique. Plasmids from several transformants were isolated and their inserts were characterized. One plasmid contained the PCR clone intact. The DNA sequence of the PCR fragment (designated 44CYP3, SEQ ID NO: 107) shared homology with the DNA sequences for the CYP52A1 gene of *C. maltosa* and the CYP52A3 gene of *C. tropicalis* 750. This fragment was used as a probe in isolating the *C. tropicalis* 20336 CYP52A1 homolog. The third genomic library was screened using the 44CYP3 PCR probe (SEQ ID NO: 107) and a clone (pHKM11) that contained a full-length CYP52 gene was obtained (FIG. 8). The clone contained a gene having regulatory and protein coding regions. An open reading frame of 1572 nucleotides encoded a CYP52 protein of 523 amino acids (FIGS. 15 and 16). This CYP52 gene was designated CYP52A1A (SEQ ID NO: 85) since its putative amino acid sequence (SEQ ID NO: 95) was most similar to the CYP52A1 protein of *C. maltosa.* The protein coding region of the CYP52A1A gene is defined by nucleotides 1177–2748 of SEQ ID NO: 85.

Figure 9:
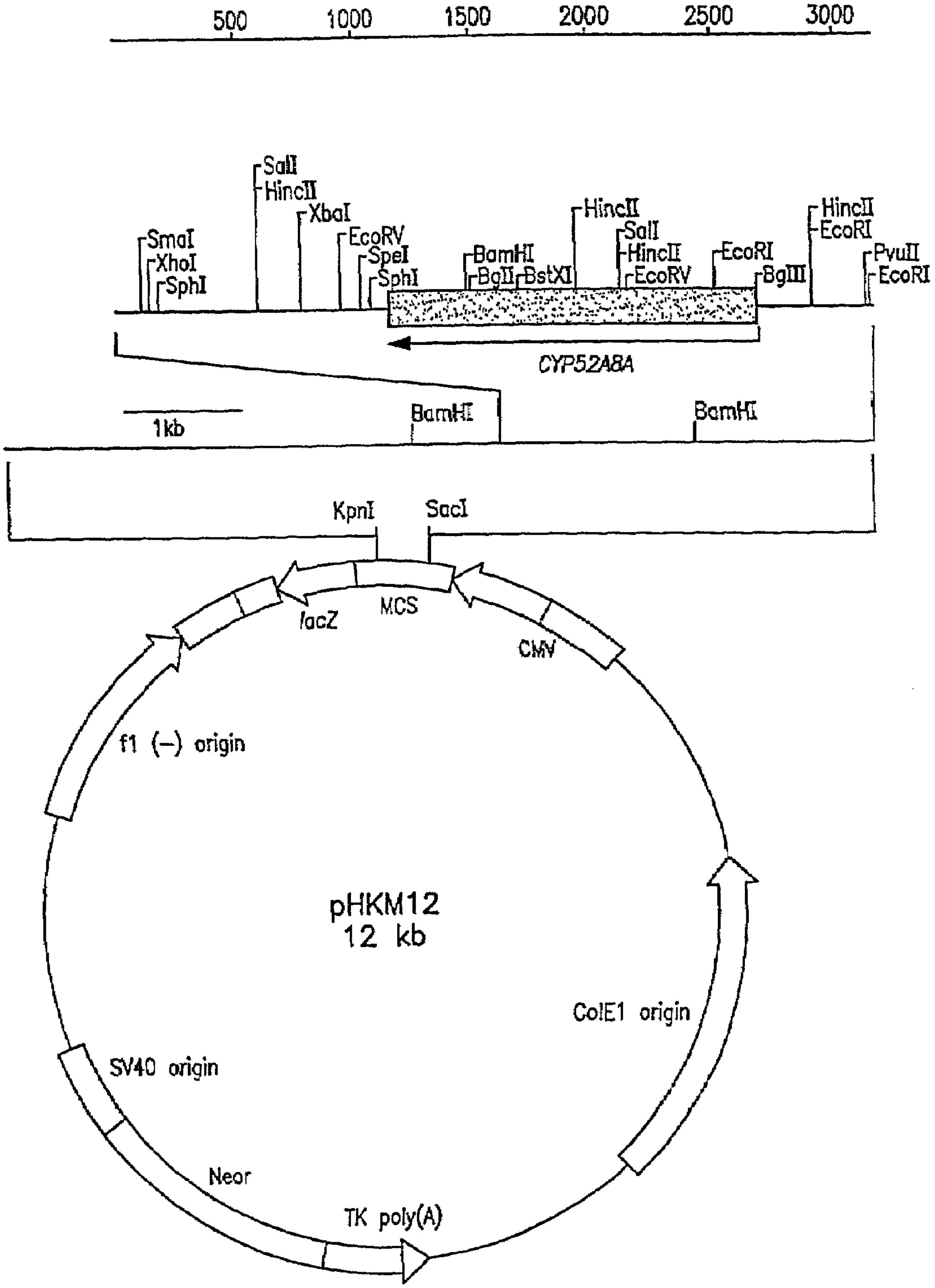
FIG. 9 is a diagrammatic representation of the plasmid pHKM12 containing the CYP52A8A gene (SEQ ID NO: 92) present in the pBK-CMV vector. A detailed restriction map of only the sequenced region is shown at the top. The bar indicates the open reading frame. The direction of transcription is indicated by an arrow under the open reading frame.

A similar approach was taken to clone CYP52A8A. A PCR fragment probe for CYP52A8 was generated using primers for highly conserved sequences of CYP52A3, CYP52A2 and CYP52A5 genes of *C. tropicalis* 750. The reverse primer (primer 2,3,5,M) (SEQ ID NO: 29) was designed based on the highly conserved heme binding region (Table 4). The design of the forward primer (primer 2,3,5,P) (SEQ ID NO: 28) was based upon a sequence conserved near the N-terminus of the CYP52A3, CYP52A2 and CYP52A5 genes from *C. tropicalis* 750 (Table 4). Amplification of 20336 genomic DNA with these two primers gave a mixed PCR product. One amplified PCR fragment was 1006 bp long (designated DCA1002). The DNA sequence for this fragment was determined and was found to have 85% identity to the DNA sequence for the CYP52D4 gene of *C. tropicalis* 750. When this PCR product was used to screen the third genomic library one clone (pHKM12) was identified that contained a full-length CYP52 gene along with 5' and 3' flanking sequences (FIG. 9). The CYP52 gene included regulatory and protein coding regions with an open reading frame of 1539 nucleotides long which encoded a putative CYP52 protein of 512 amino acids (FIGS. 15 and 16). This gene was designated as CYP52A8A (SEQ ID NO: 92) since its amino acid sequence (SEQ ID NO: 102) was most similar to the CYP52A8 protein of *C. maltosa.* The protein coding region of the CYP52A8A gene is defined by nucleotides 464–2002 of SEQ ID NO: 92. The amino acid sequence of the CYP52A8A protein is set forth in SEQ ID NO: 102.

3) Cloning of CYP52D4A

Figure 10:
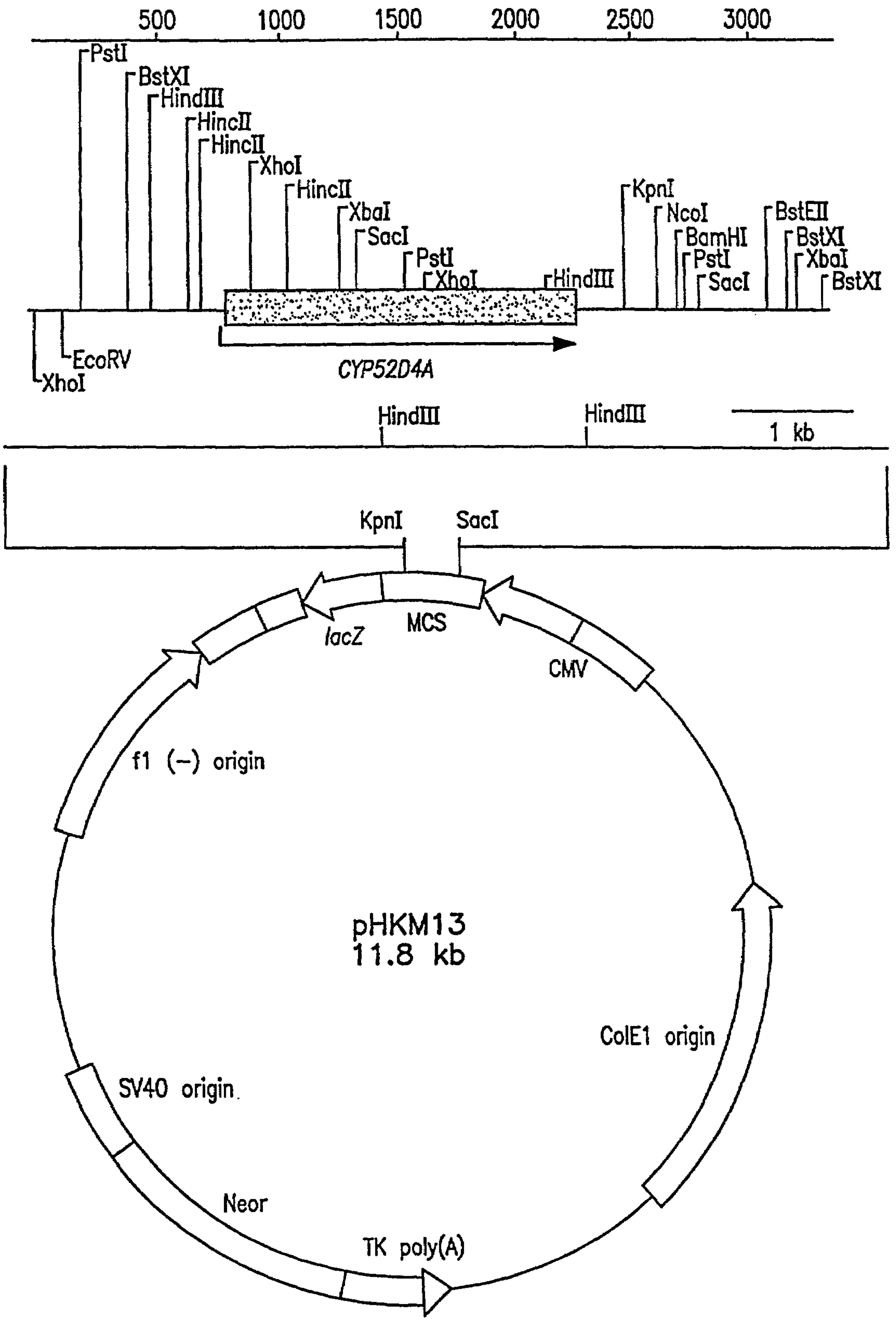
FIG. 10 is a diagrammatic representation of the plasmid pHKM13 containing the CPY52D4A gene (SEQ ID NO: 94) present in the pBK-CMV vector. A detailed restriction map of only the sequenced region is shown at the top. The bar indicates the open reading frame. The direction of transcription is indicated by an arrow under the open reading frame.
Figure 33:
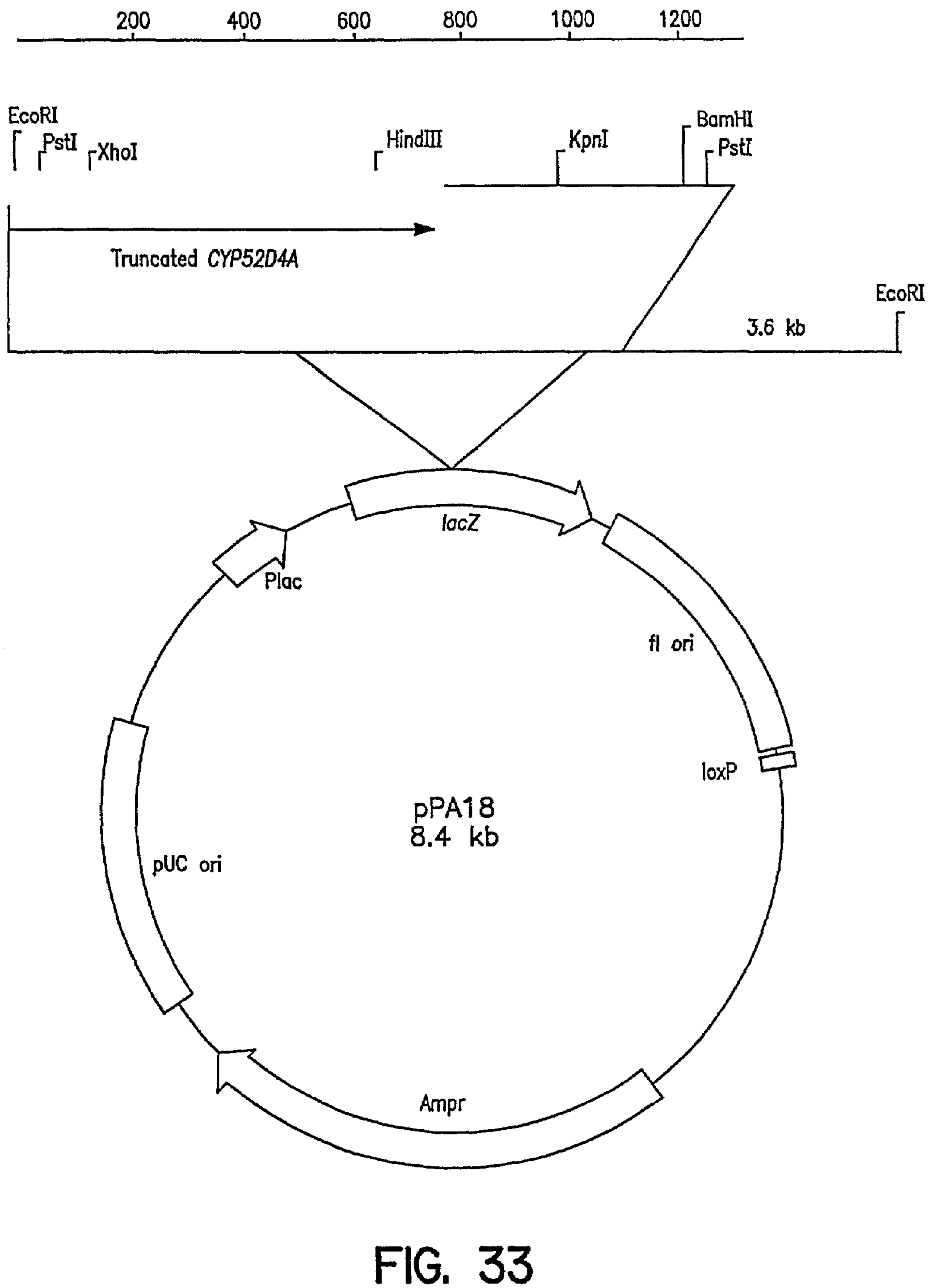
FIG. 33 is a diagrammatic representation of the plasmid pPA18 containing the truncated CYP52D4A gene present in the pTriplEx vector. A detailed restriction map of only the sequenced region is shown at the top. The bar indicates the open reading frame. The direction of transcription is indicated by an arrow under the open reading frame.

The screening of the second genomic library with the HemeB1 (SEQ ID NO: 27) primer (Table 4) yielded a clone carrying a plasmid (pPA18) that contained a truncated gene having homology with the CYP52D4 gene of *C. maltosa* (FIG. 33). A 1.3 to 1.5-kb EcoRI-SstI fragment from pPA18 containing part of the truncated CYP gene was isolated and used as a probe to screen the third genomic library for a full length CYP52 gene. One clone (pHKM13) was isolated and found to contain a full-length CYP gene with extensive 5' and 3' flanking sequences (FIG. 10). This gene has been designated as CYP52D4A (SEQ ID NO: 94) and the complete DNA including regulatory and protein coding regions (coding region defined by nucleotides 767–2266) and putative amino acid sequence (SEQ ID NO: 104) of this gene is shown in FIGS. 15 and 16. CYP52D4A (SEQ ID NO: 94) shares the greatest homology with the CYP52D4 gene of *C. maltosa.*

4) Cloning of CYP52A2B and CYP52A8B

Figure 11:
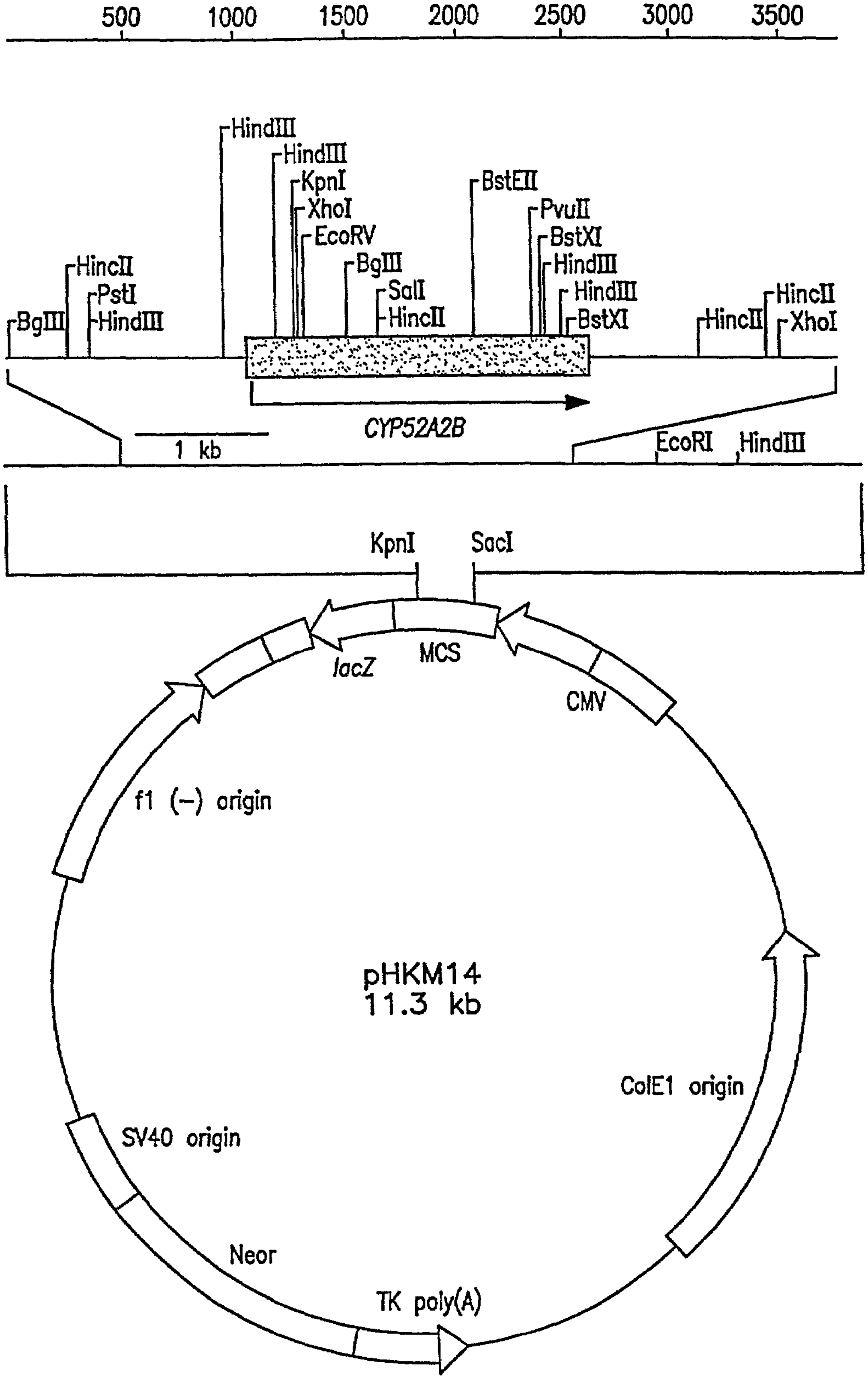
FIG. 11 is a diagrammatic representation of the plasmid pHKM14 containing the CYP52A2B gene (SEQ ID NO: 87) present in the pBK-CMV vector. A detailed restriction map of only the sequenced region is shown at the top. The bar indicates the open reading frame. The direction of transcription is indicated by an arrow under the open reading frame.
Figure 12:
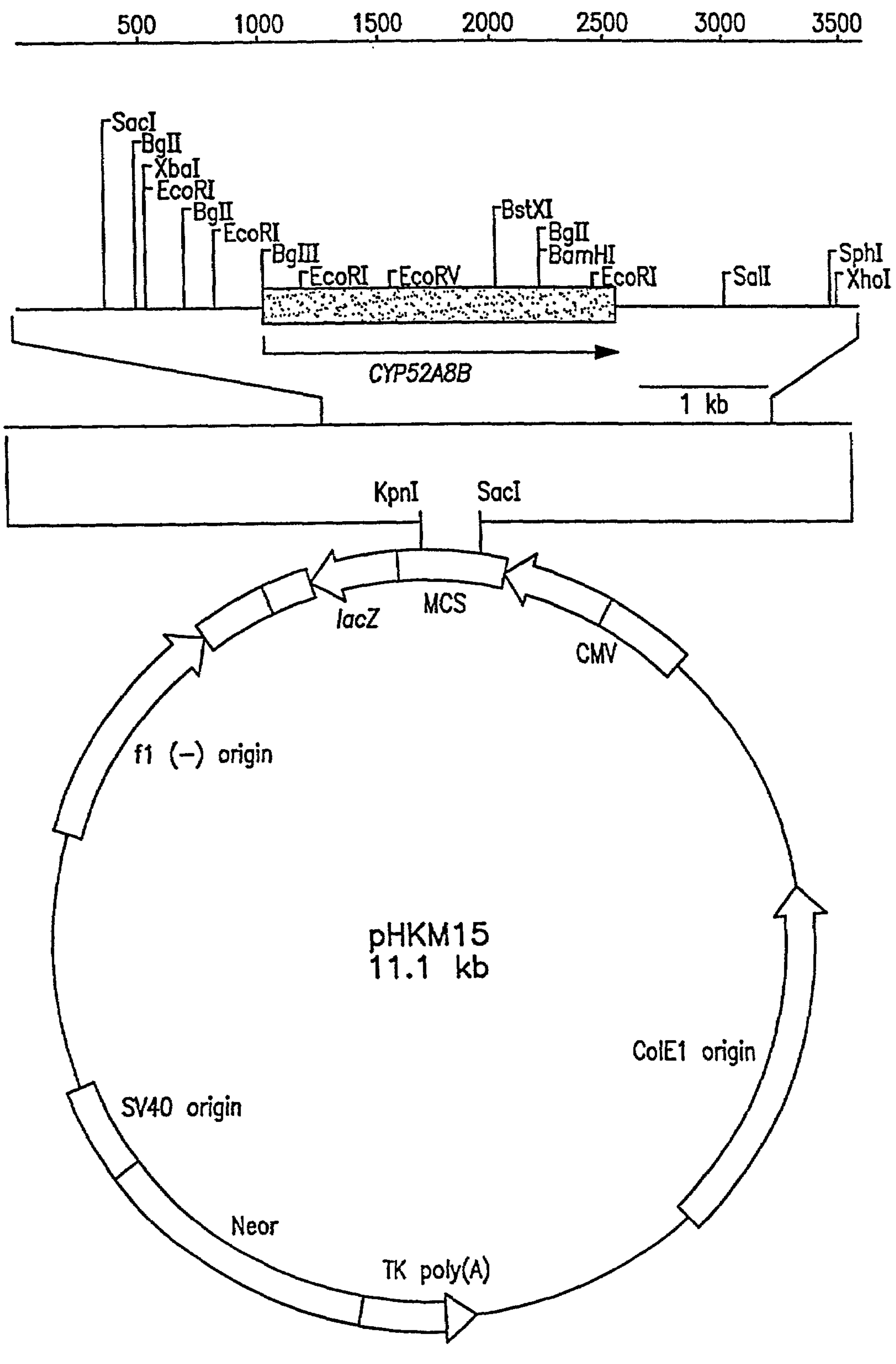
FIG. 12 is a diagrammatic representation of the plasmid pHKM15 containing the CYP52A8B gene (SEQ ID NO: 93) present in the pBK-CMV vector. A detailed restriction map of only the sequenced region is shown at the top. The bar indicates the open reading frame. The direction of transcription is indicated by an arrow under the open reading frame.

A mixed probe containing CYP52A1A, A2A, A3A, D4A, A5A and A8A genes was used to screen the third genomic library and several putative positive clones were identified. Seven of these were sequenced with the degenerate primers Cyp52a (SEQ ID NO: 32), Cyp52b (SEQ ID NO: 33), Cyp52c (SEQ ID NO: 34) and Cyp52d (SEQ ID NO: 35) shown in Table 4. These primers were designed from highly conserved regions of the four CYP52 subfamilies, namely CYP52A, B, C & D. Sequences from two clones, pHKM14 and pHKM15 (FIGS. 11 and 12), shared considerable homology with DNA sequence of the *C. tropicalis* 20336 CYP52A2 and CYP52A8 genes, respectively. The complete DNA (SEQ ID NO: 87) including regulatory and protein coding regions (coding region defined by nucleotides 1072–2640) and putative amino acid sequence (SEQ ID NO: 97) of the CYP52 gene present in pHKM14 suggested that it is CYP52A2B (FIGS. 15 and 16). The complete DNA (SEQ ID NO: 93) including regulatory and protein coding regions (coding region defined by nucleotides 1017–2555) and putative amino acid sequence (SEQ ID NO: 103) of the CYP52 gene present in pHKM15 suggested that it is CYP52A8B (FIGS. 15 and 16).

EXAMPLE 14

Figure 18:
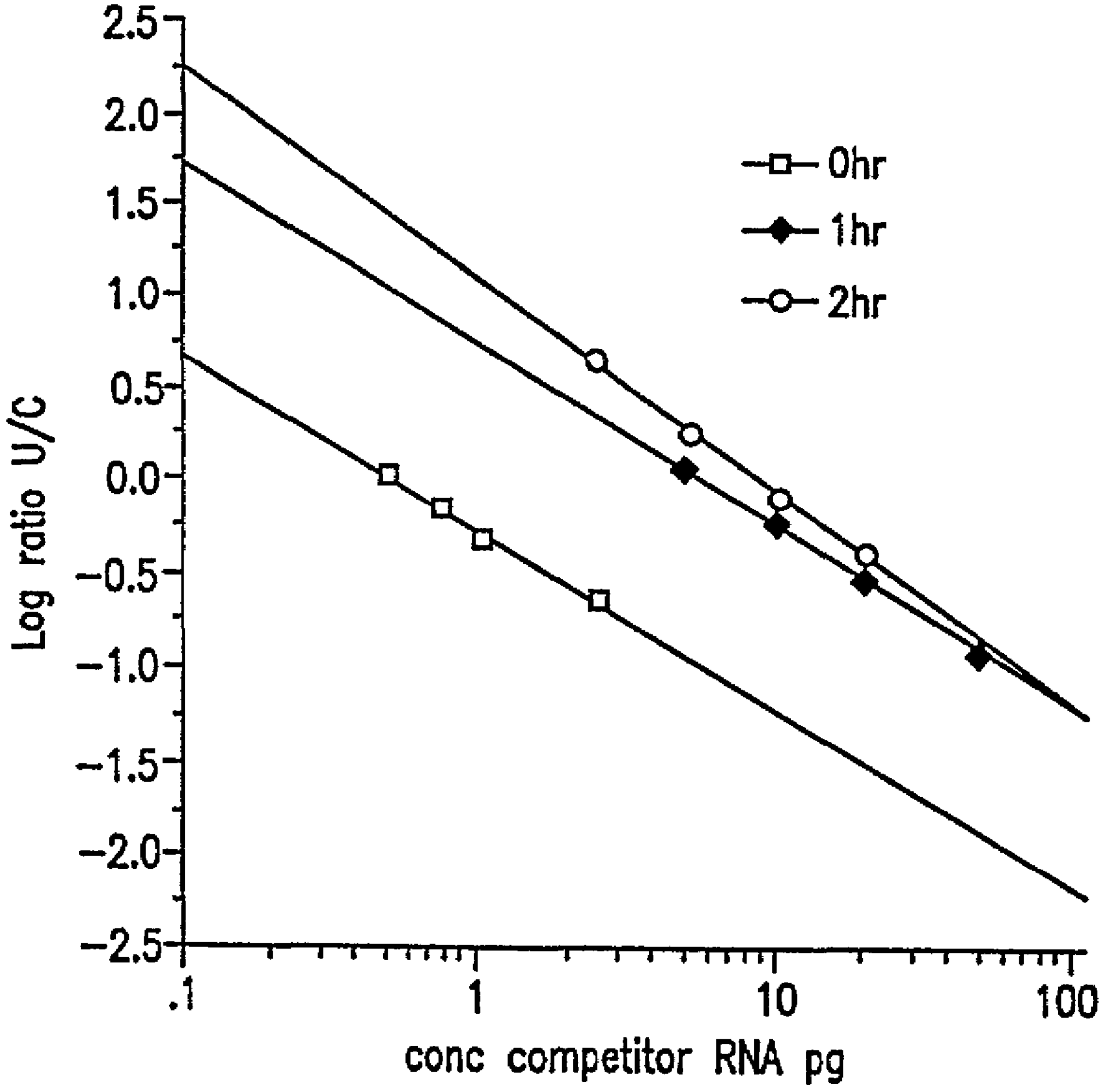
FIG. 18 is a plot of the log ratio (U/C) of unknown target DNA product to competitor DNA product versus the concentration of competitor mRNA. The plot is used to calculate the target messenger RNA concentration in a quantitative competitive reverse transcription polymerase chain reaction QC-RT-PCR).
Figure 19:
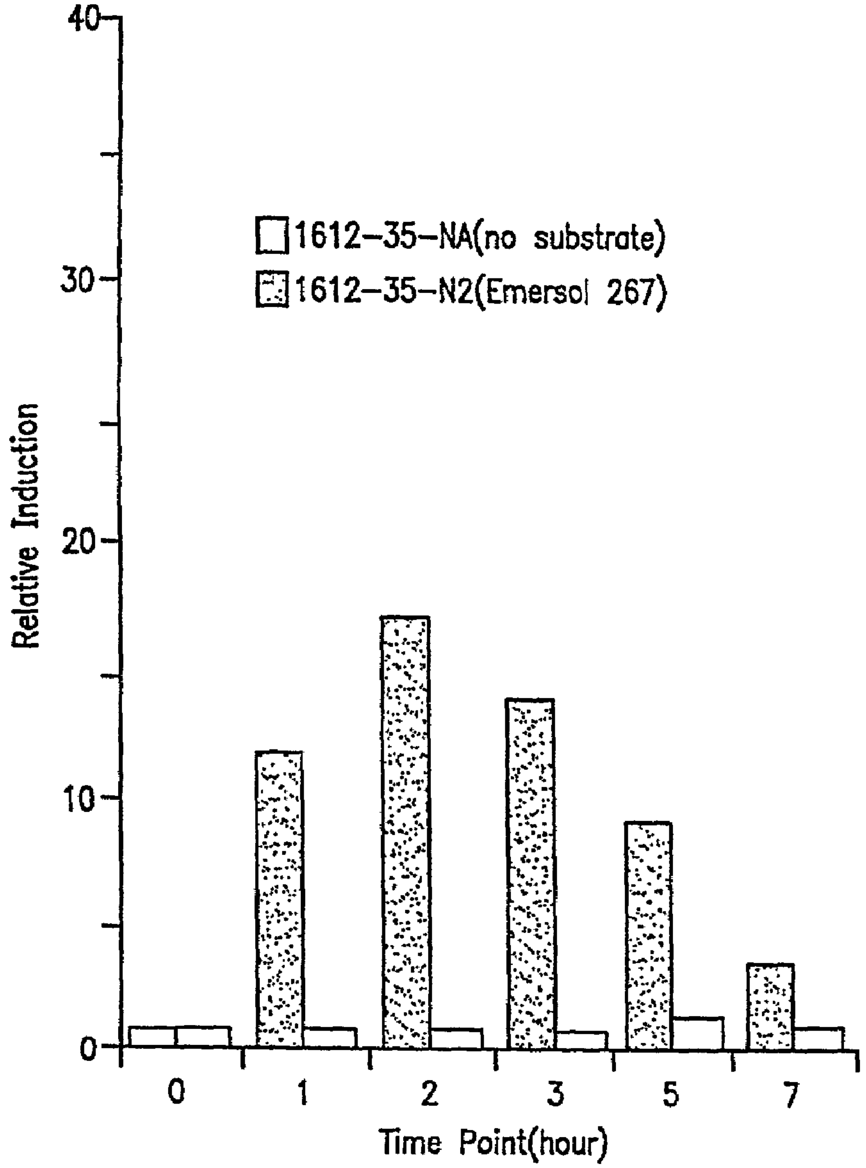
FIG. 19 is a graph showing the relative induction of *C. tropicalis* ATCC 20962 CYP52A5A (SEQ ID NO: 90) by the addition of the fatty acid substrate Emersol® 267 to the growth medium.

Identification of CYP and CPR Genes Induced by Selected Fatty Acid and Alkane Substrates Genes whose transcription is turned on by the presence of selected fatty acid or alkane substrates have been identified using the QC-RT-PCR assay. This assay was used to measure (CYP) and (CPR) gene expression in fermentor grown cultures *C. tropicalis* ATCC 20962. This method involves the isolation of total cellular RNA from cultures of *C. tropicalis* and the quantification of a specific mRNA within that sample through the design and use of sequence specific QC-RT-PCR primers and an RNA competitor. Quantification is achieved through the use of known concentrations of highly homologous competitor RNA in the QC-RT-PCR reactions. The resulting QC-RT-PCR amplified cDNA's are separated and quantitated through the use of ion pairing reverse phase HPLC. This assay was used to characterized the expression of CYP52 genes of *C. tropicalis* ATCC 20962 in response to various fatty acid and alkane substrates. Genes which were induced were identified by the calculation of their mRNA concentration at various times before and after induction. FIG. 18 provides an example of how the concentration of mRNA for CYP52A5 can be calculated using the QC-RT-PCR assay. The log ratio of unknown (U) to competitor product (C) is plotted versus the concentration of competitor RNA present in the QC-RT-PCR reactions. The concentration of competitor which results in a log ratio of U/C of zero, represents the point where the unknown messenger RNA concentration is equal to the concentration of the competitor. FIG. 18 allows for the calculation of the amount of CYP52A5 message present in 100 ng of total RNA isolated from cell samples taken at 0, 1, and 2 hours after the addition of Emersol® 267 in a fermentor run. From this analysis, it is possible to determine the concentration of the CYP52A5 mRNA present in 100 ng of total cellular RNA. In the plot contained in FIG. 18 it takes 0.46 pg of competitor to equal the number of mRNA's of CYP52A5 in 100 ng of RNA isolated from cells just prior (time 0) to the addition of the substrate, Emersol® 267. In cell samples taken at one and two hours after the addition of Emersol® 267 it takes 5.5 and 8.5 pg of competitor RNA, respectively. This result demonstrates that CYP52A5 (SEQ ID NOS: 90 and 91) is induced more than 18 fold within two hours after the addition of Emersol® 267. This type of analysis was used to demonstrate that CYP52A5 (SEQ ID NO: 90 and 91) is induced by Emersol® 267. FIG. 19 shows the relative amounts of CYP52A5 (SEQ ID NOS: 90 and 91) expression in fermentor runs with and without Emersol® 267 as a substrate. The differences in the CYP52A5 (SEQ ID NOS:

90 and 91) expression patterns are due to the addition of Emersol® 267 to the fermentation medium.

Figure 20:
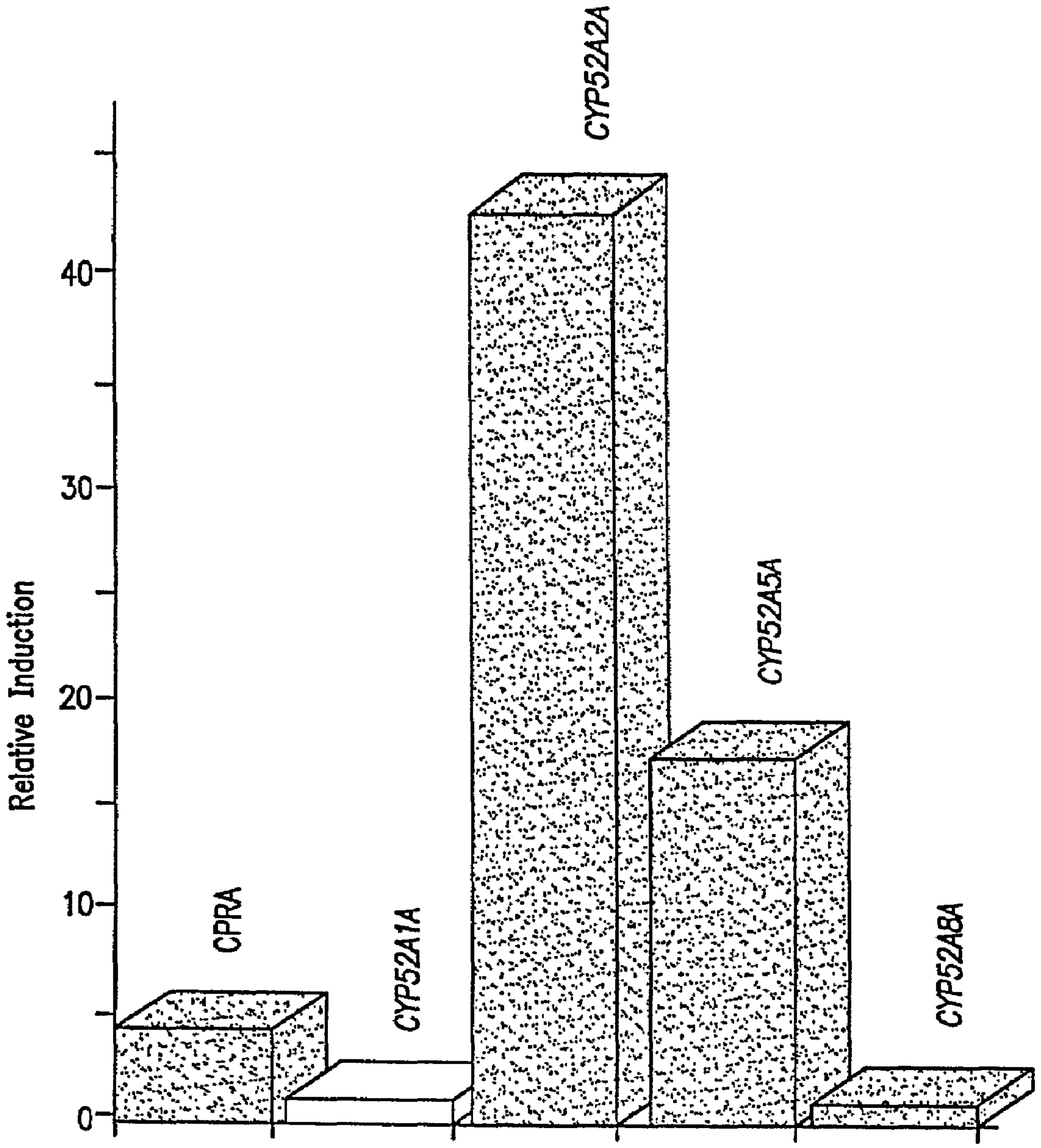
FIG. 20 is a graph showing the induction of *C. tropicalis* ATCC 20962 CYP52 and CPR genes by Emersol® 267. P450 genes CYP52A3A (SEQ ID NO: 88), CYP52A3B (SEQ ID NO: 89), and CYP52D4A (SEQ ID NO: 94) are expressed at levels below the detection level of the QC-RT-PCR assay.
Figure 34:
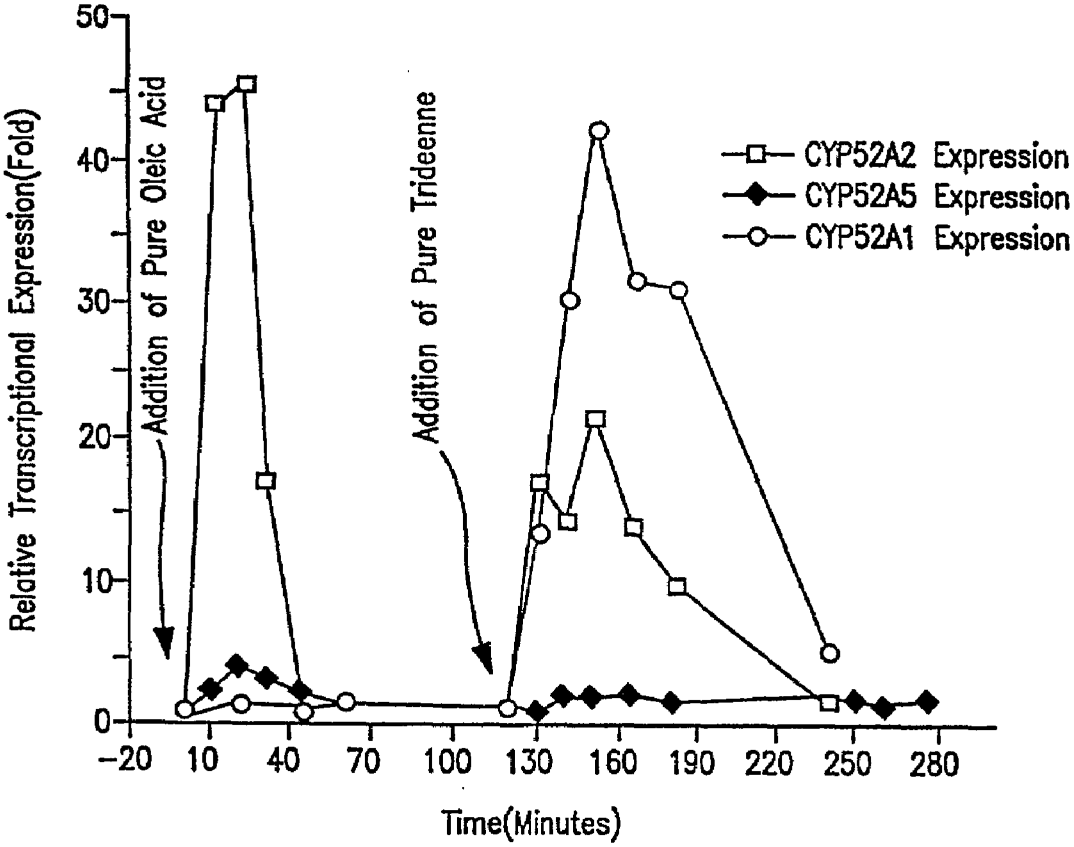
FIG. 34 is a graph showing the expression of CYP52A1 (SEQ ID NO: 85), CYP52A2 (SEQ ID NO: 86) and CYP52A5 genes (SEQ ID NOS: 90 and 91) from *C. tropicalis* 20962 in a fermentor run upon the addition of amounts of the substrate oleic acid or tridecane in a spiking experiment.
Figure 36:
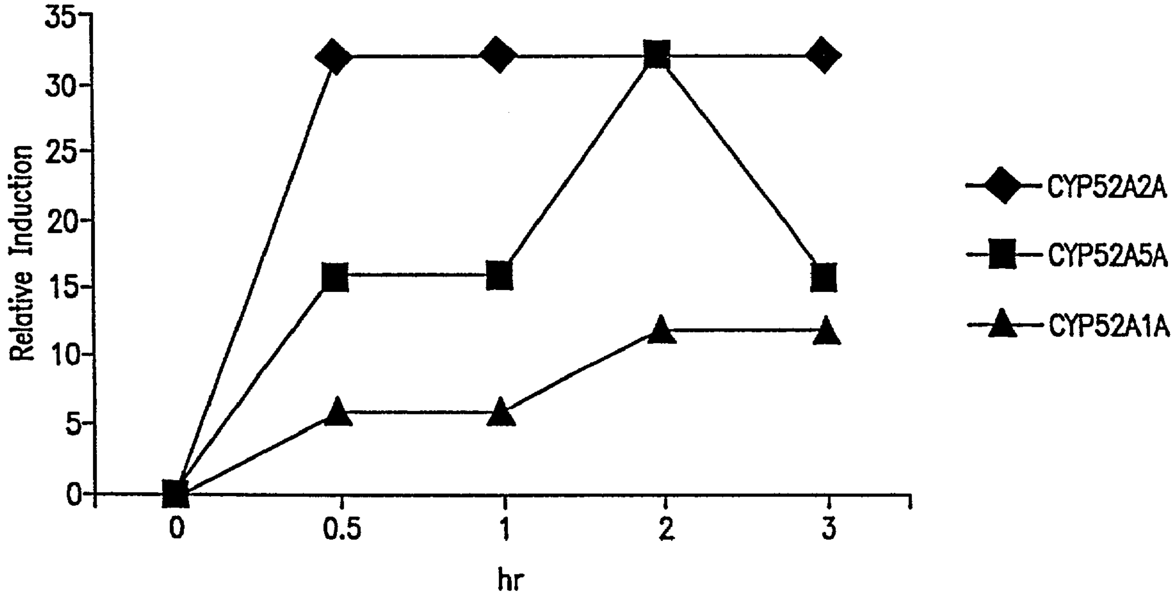
FIG. 36 is a graph showing the induction of expression of CYP52A1A, CYP52A2A and CYP52A5A in a fermentor run upon addition of the substrate octadecane. No induction of CYP52A3A or CYP52A3B was observed under these conditions.

This analysis clearly demonstrates that expression of CYP52A5 (SEQ ID NOS: 90 and 91) in *C. tropicalis* 20962 is inducible by the addition of Emersol® 267 to the growth medium. This analysis was performed to characterize the expression of CYP52A2A (SEQ ID NO: 86), CYP52A3AB (SEQ ID NOS: 88 and 89), CYP52A8A (SEQ ID NO: 92), CYP52A1A (SEQ ID NO: 85), CYP52D4A (SEQ ID NO: 94) and CPRB (SEQ ID NO: 82) in response to the presence of Emersol® 267 in the fermentation medium (FIG. 20). The results of these analysis' indicate, that like the CYP52A5 gene (SEQ ID NOS: 90 and 91) of *C. tropicalis* 20962, the CYP52A2A gene (SEQ ID NO: 86) is inducible by Emersol® 267. A small induction is observed for CYP52A1A (SEQ ID NO: 85) and CYP52A8A (SEQ ID NO: 92). In contrast, any induction for CYP52D4A (SEQ ID NO: 94), CYP52A3A (SEQ ID NO: 88), CYP52A3B (SEQ ID NO: 89) is below the level of detection of the assay. CPRB (SEQ ID NO: 82) is moderately induced by Emersol® 267, four to five fold. The results of these analysis are summarized in FIG. 20. FIG. 34 provides an example of selective induction of CYP52A genes. When pure fatty acid or alkanes are spiked into a fermentor containing *C. tropicalis* 20962 or a derivative thereof, the transcriptional activation of CYP52A genes was detected using the QC-RT-PCR assay. FIG. 34 shows that pure oleic acid (C18:1) strongly induces CYP52A2A (SEQ ID NO: 86) while inducing CYP52A5 (SEQ ID NOS: 90 and 91). In the same fermentor addition of pure alkane (tridecane) shows strong induction of both CYP52A2A (SEQ ID NO: 86) and CYP52A1A (SEQ ID NO: 85). However, tridecane did not induce CYP52A5 (SEQ ID NOS: 90 and 91). In a separate fermentation using ATCC 20962, containing pure octadecane as the substrate, induction of CYP52A2A, CYP52A5A and CYP52A1A is detected (see FIG. 36). The foregoing demonstrates selective induction of particular CYP genes by specific substrates, thus providing techniques for selective metabolic engineering of cell strains. For example, if tridecane modification is desired, organisms engineered for high levels of CYP52A2A (SEQ ID NO: 86) and CYP52A1A (SEQ ID NO: 85) activity are indicated. If oleic acid modification is desired, organism engineered for high levels of CYP52A2A (SEQ ID NO: 86) activity are indicated.

EXAMPLE 15

Integration of Selected CYP and CPR Genes into the Genome of *Candida tropicalis*

Figure 21:
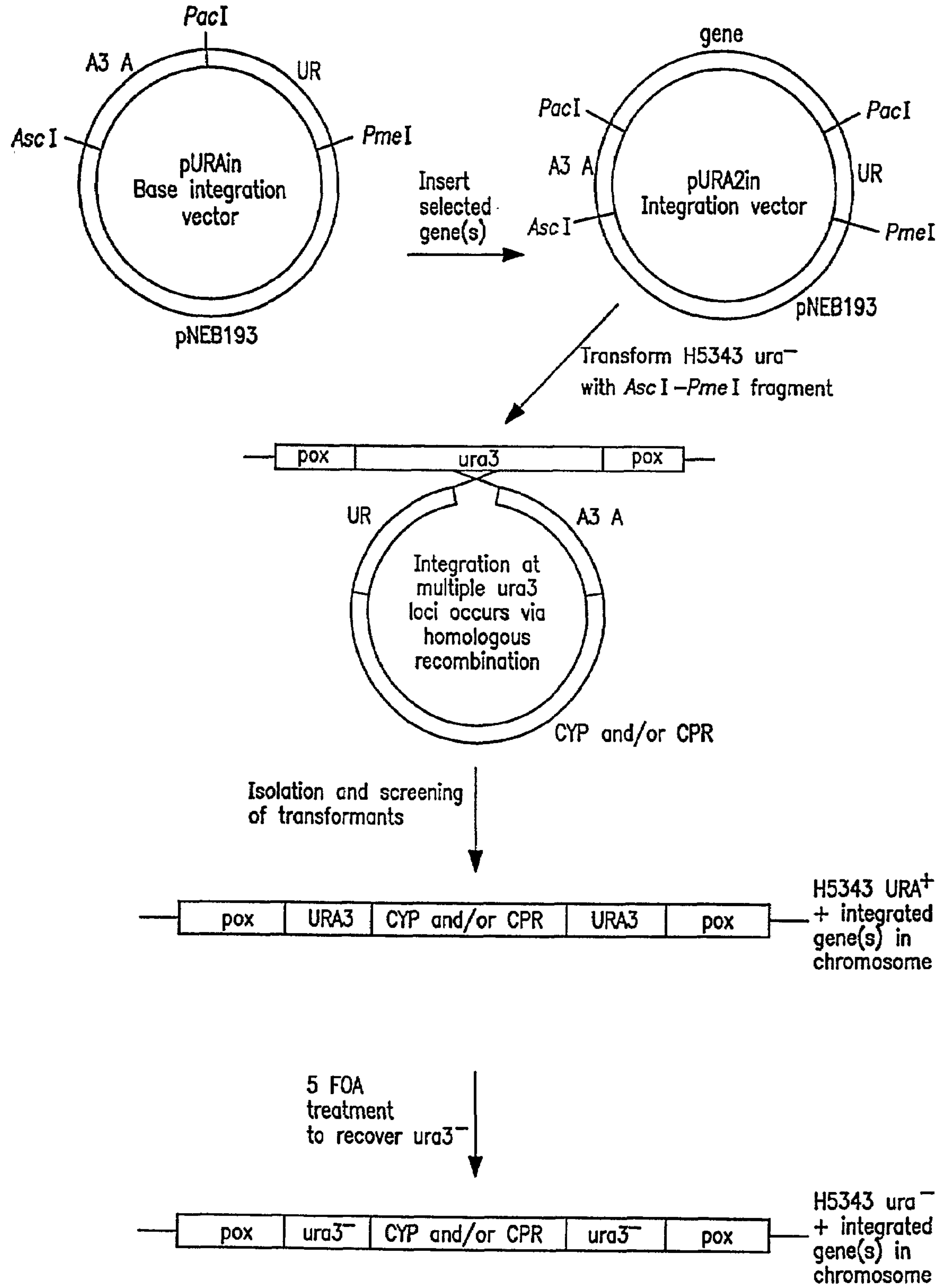
FIG. 21 is a scheme to integrate selected genes into the genome of *Candida tropicalis* strains and recovery of URA3A selectable marker.
Figure 22:
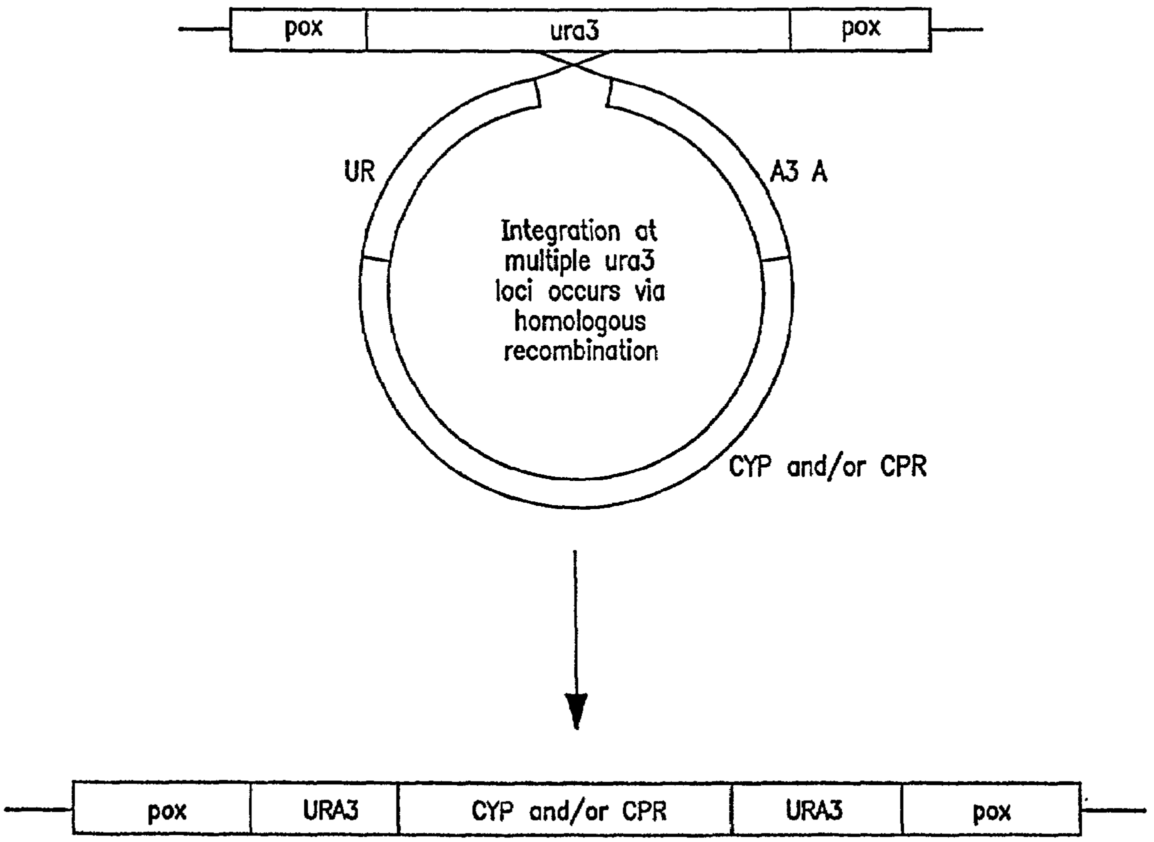
FIG. 22 is a schematic representation of the transformation of *C. tropicalis* H5343 ura3$^-$ with CYP and/or CPR genes. Only one URA3 locus needs to be functional. There are a total of 6 possible ura3 targets (5ura3A loci-2 pox4 disruptions, 2 pox 5 disruptions, 1 ura3A locus; and 1 urs3B locus).

In order to integrate selected genes into the chromosome of *C. tropicalis* 20336 or its descendants, there has to be a target DNA sequence, which may or may not be an intact gene, into which the genes can be inserted. There must also be a method to select for the integration event. In some cases the target DNA sequence and the selectable marker are the same and, if so, then there must also be a method to regain use of the target gene as a selectable marker following the integration event. In *C. tropicalis* and its descendants, one gene which fits these criteria is URA3A, encoding orotidine-5'-phosphate decarboxylase. Using it as a target for integration, ura variants of *C. tropicalis* can be transformed in such a way as to regenerate a $URA^+$ genotype via homologous recombination (FIG. 21). Depending upon the design of the integration vector, one or more genes can be integrated into the genome at the same time. Using a split URA3A gene oriented as shown in FIG. 22, homologous integration would yield at least one copy of the gene(s) of interest which are inserted between the split portions of the URA3A gene. Moreover, because of the high sequence similarity between URA3A and URA3B genes, integration of the construct can occur at both the URA3A and URA3B loci. Subsequently, an oligonucleotide designed with a deletion in a portion of the URA gene based on the identical sequence across both the URA3A and URA3B genes, can be utilized to yield *C. tropicalis* transformants which are once again $ura^-$ but which still carry one or more newly integrated genes of choice (FIG. 21). $ura^-$ variants of *C. tropicalis* can also be isolated via other methods such as classical mutagenesis or by spontaneous mutation. Using well established protocols, selection of $ura^-$ strains can be facilitated by the use of 5-fluoroorotic acid (5-FOA) as described, e.g., in Boeke et al., *Mol. Gen. Genet.* 197:345–346, (1984), incorporated herein by reference. The utility of this approach for the manipulation of *C. tropicalis* has been well documented as described, e.g., in Picataggio et al., *Mol. and Cell. Biol.* 11:4333–4339 (1991); Rohrer et al., *Appl. Microbiol. Biotechnol.* 36:650–654 (1992); Picataggio et al., *Bio/Technology* 10:894–898 (1992); U.S. Pat. No. 5,684,247; U.S. Pat. No. 5,620,878; U.S. Pat. No. 5,204,252; U.S. Pat. No. 5,254,466, all of which are incorporated herein by reference.

A. Construction of a URA Integration Vector, pURAin

Figure 24:
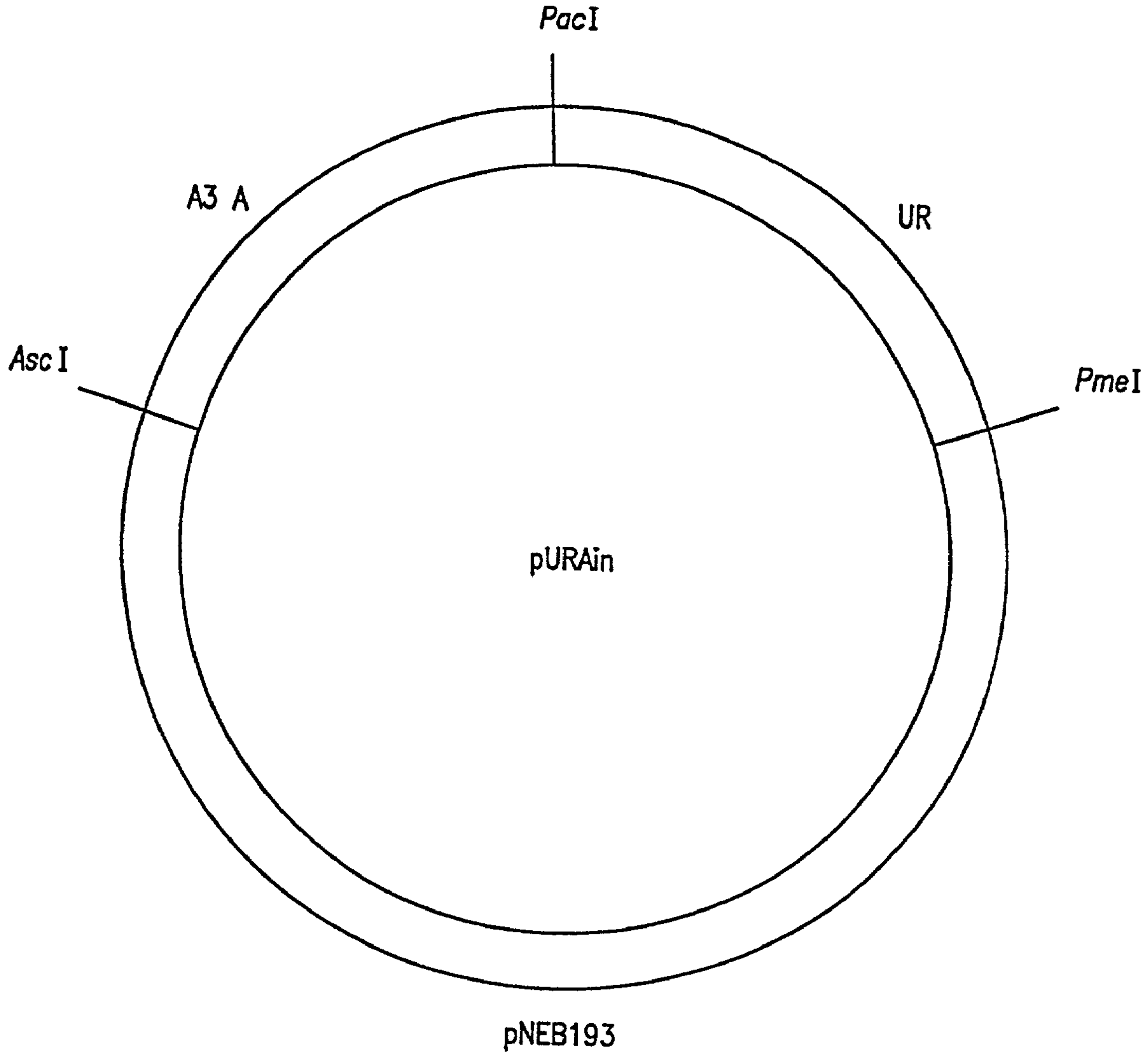
FIG. 24 is a schematic representation of the plasmid pURAin, the base vector for integrating selected genes into the genome of *C. tropicalis*. The detailed construction of pURAin is described in the text.
Figure 25:
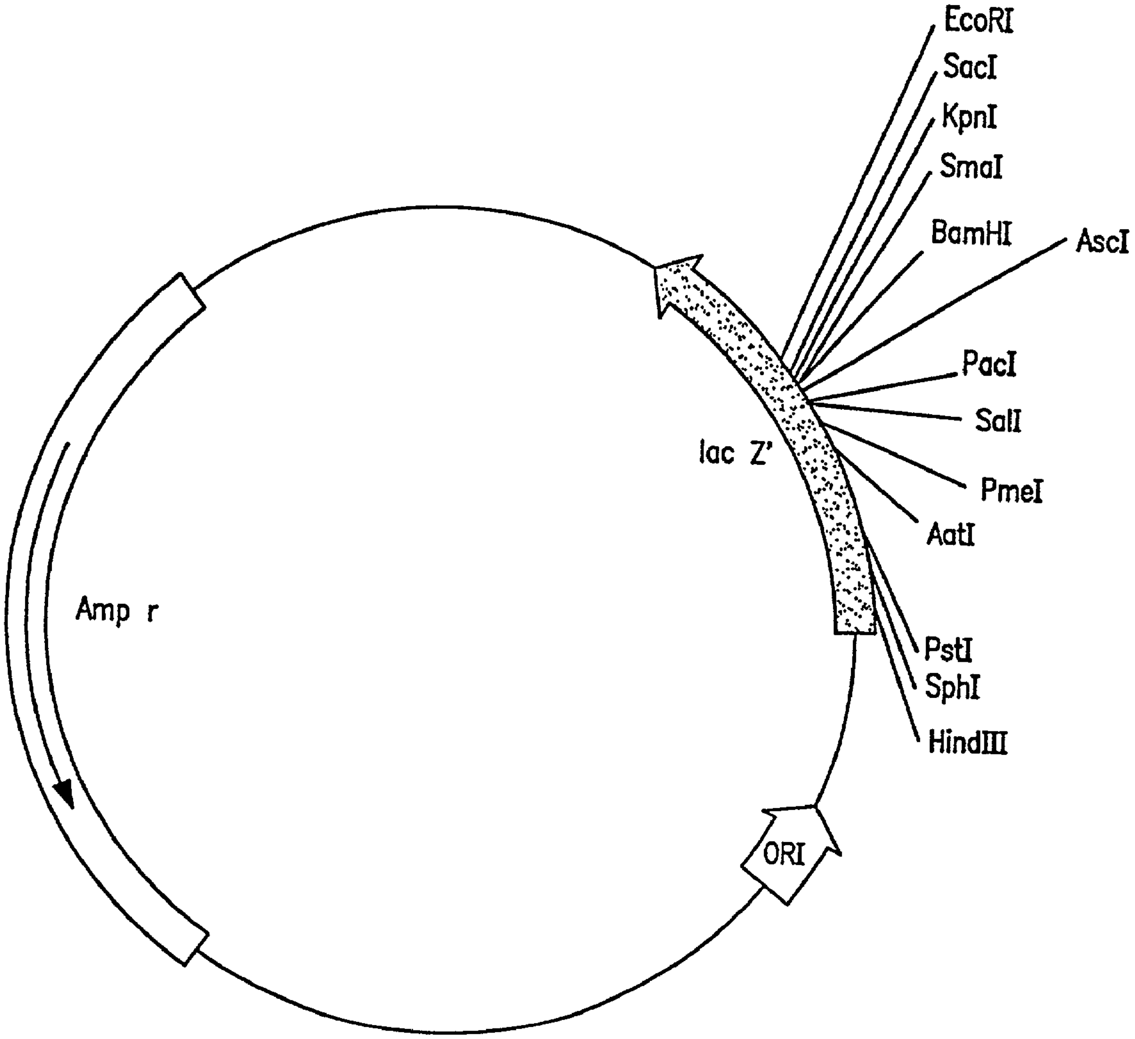
FIG. 25 is a schematic representation of the plasmid pNEB193 cloning vector (commercially available from New England Biolabs, Beverly, Mass.).

Primers were designed and synthesized based on the 1712 bp sequence of the URA3A gene of *C. tropicalis* 20336 (see FIG. 23). The nucleotide sequence of the URA3A gene of *C. tropicalis* 20336 is set forth in SEQ ID NO: 105 and the amino acid sequence of the encoded protein is set forth in SEQ ID NO: 106. URA3A Primer Set #1a (SEQ ID NO: 9) and #1b (SEQ ID NO: 10) (Table 4) was used in PCR with *C. tropicalis* 20336 genomic DNA to amplify URA3A sequences between nucleotide 733 and 1688 as shown in FIG. 23. The primers are designed to introduce unique 5' AscI and 3' PacI restriction sites into the resulting amplified URA3A fragment. AscI and PacI sites were chosen because these sites are not present within CYP or CPR genes identified to date. URA3A Primer Set #2 was used in PCR with *C. tropicalis* 20336 genomic DNA as a template, to amplify URA3A sequences between nucleotide 9 and 758 as shown in FIG. 23. URA3A Primer set #2a (SEQ ID NO: 11) and #2b (SEQ ID NO: 12) (Tabl e4) was designed to introduce unique 5' PacI and 3' PmeI restriction sites into the resulting amplified URA3A fragment. The PmeI site is also not present within CYP and CPR genes identified to date. PCR fragments of the URA3A gene were purified, restricted with AscI, PacI and PmeI restriction enzymes and ligated to a gel purified, QiaexII cleaned AscI-PmeI digest of plasmid pNEB193 (FIG. 25) purchased from New England Biolabs (Beverly, Mass.). The ligation was performed with an equimolar number of DNA termini at 16° C. for 16 hr using T4 DNA ligase (New England Biolabs). Ligations were transformed into *E. coli* XL1-Blue cells (Stratagene, LaJolla, Calif.) according to manufacturers recommendations. White colonies were isolated, grown, plasmid DNA isolated and digested with AscI-PmeI to confirm insertion of the modified URA3A into pNEB193. The resulting base integration vector was named pURAin (FIG. 24).

B. Amplification of CYP52A2A, CYP52A3A, CYP52A5A and CPRB from *C. tropicalis* 20336 Genomic DNA The genes encoding CYP52A2A, (SEQ ID NO: 86) and CYP52A3A (SEQ ID NO: 88) from *C. tropicalis* 20336 were amplified from genomic clones (pPA15 and pPA57, respectively) (FIGS. 26 and 29) via PCR using primers (Primer CYP2A#1, SEQ ID NO: 1 and Primer CYP2A#2, SEQ ID NO: 2 for CYP52A2A) (Primer CYP3A#1, SEQ ID NO: 3 and Primer CYP3A#2, SEQ ID NO: 4 for CYP52A3A) to introduce PacI cloning sites. These PCR primers were designed based upon the DNA sequence determined for CYP52A2A (SEQ ID NO: 86) (FIG. 15). The AmpliTaq Gold PCR kit (Perkin Elmer Cetus, Foster City, Calif.) was used according to manufacturers specifications. The CYP52A2A PCR amplification product was 2,230 base pairs in length, yielding 496 bp of DNA upstream of the CYP52A2A start codon and 168 bp downstream of the stop codon for the CYP52A2A ORF. The CYP52A3A PCR amplification product was 2154 base pairs in length, yielding 437 bp of DNA upstream of the CYP52A3A start codon and 97 bp downstream of the stop codon for the CYP52A3A ORF. The CYP52A3A PCR amplification product was 2154 base pairs in length, yielding 437 bp of DNA upstream of the CYP52A3A start codon and 97 bp downstream of the stop codon for the CYP52A3A ORF.

The gene encoding CYP52A5A (SEQ ID NO: 90) from *C. tropicalis* 20336 was amplified from genomic DNA via PCR using primers (Primer CYP 5A#1, SEQ ID NO: 5 and Primer CYP 5A#2, SEQ ID NO: 6) to introduce PacI cloning sites. These PCR primers were designed based upon the DNA sequence determined for CYP52A5A (SEQ ID NO: 90). The Expand Hi-Fi Taq PCR kit (Boehringer Mannheim, Indianapolis, Ind.) was used according to manufacturers specifications. The CYP52A5A PCR amplification product was 3,298 base pairs in length.

The gene encoding CPRB (SEQ ID NO: 82) from *C. tropicalis* 20336 was amplified from genomic DNA via PCR using primers (CPR B#1, SEQ ID NO: 7 and CPR B#2, SEQ ID NO: 8) based upon the DNA sequence determined for CPRB (SEQ ID NO: 82) (FIG. 13). These primers were designed to introduce unique PacI cloning sites. The Expand Hi-Fi Taq PCR kit (Boehringer Mannheim, Indianapolis, Ind.) was used according to manufacturers specifications. The CPRB PCR product was 3266 bp in length, yielding 747 bp of DNA upstream of the CPRB start codon and 493 bp downstream of the stop codon for the CPRB ORF. The resulting PCR products were isolated via agarose gel electrophoresis, purified using QiaexII and digested with PacI. The PCR fragments were purified, desalted and concentrated using a Microcon 100 (Amicon, Beverly, Mass.).

The above described amplification procedures are applicable to the other genes listed in Table 5 using the respectively indicated primers.

C. Cloning of CYP and CPR Genes into pURAin

The next step was to clone the selected CYP and CPR genes into the pURAin integration vector. In a preferred aspect of the present invention, no foreign DNA other than that specifically provided by synthetic restriction site sequences are incorporated into the DNA which was cloned into the genome of *C. tropicalis,* i.e., with the exception of restriction site DNA only native *C. tropicalis* DNA sequences are incorporated into the genome. pURAin was digested with PacI, Qiaex II cleaned, and dephosphorylated with Shrimp Alkaline Phosphatase (SAP) (United States Biochemical, Cleveland, Ohio) according to the manufacturer's recommendations. Approximately 500 ng of PacI linearized pURAin was dephosphorylated or 1 hr at 37° C. using SAP at a concentration of 0.2 Units of enzyme per 1 pmol of DNA termini. The reaction was stopped by heat inactivation at 65° C. for 20 min.

Figure 27:
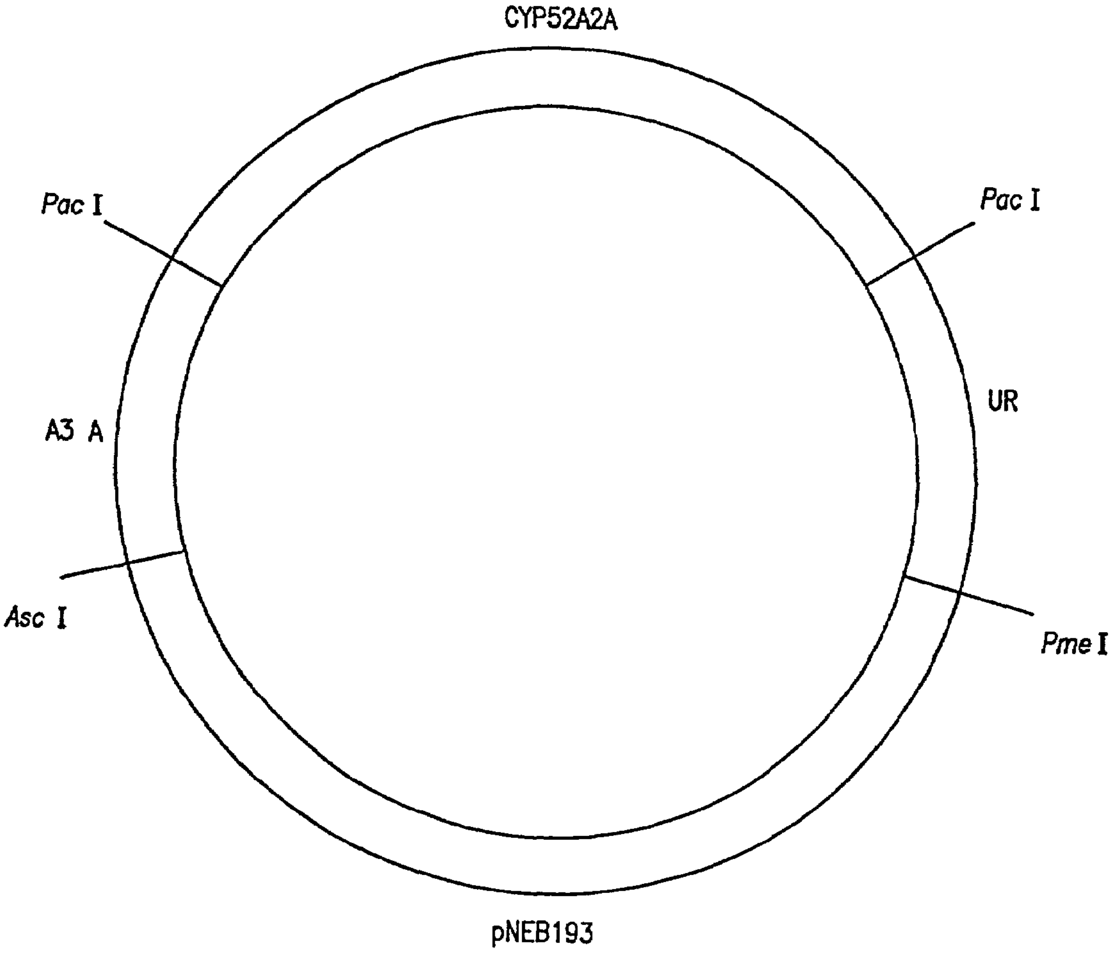
FIG. 27 is a schematic representation of pURA2in, the base vector is constructed in pNEB193 which contains the 8 bp recognition sequences for Asc I, Pac I and Pme I. URA3A (SEQ ID NO: 105) and CYP52A2A (SEQ ID NO: 86) do not contain these 8 bp recognition sites. URA3A is inverted so that the transforming fragment will attempt to recircularize prior to integration. A Asc I/Pme I fragment was used to transform H5343 ura.

The CYP52A2A PacI fragment derived using the primer shown in Table 4 was ligated to plasmid pURAin which had also been digested with PacI. PacI digested pURAin was dephosphorylated, and ligated to the CYP52A2A ULTMA PCR product as described previously. The ligation mixture was transformed into *E. coli* XL1 Blue MRF' (Stratagene) and 2 resistant colonies were selected and screened for correct constructs which should contain vector sequence, the inverted URA3A gene, and the amplified CYP52A2A gene (SEQ ID NO: 86) of 20336. AscI-PmeI digestion identified one of the two constructs, plasmid pURA2in, as being correct (FIG. 27). This plasmid was sequenced and compared to CYP52A2A (SEQ ID NO: 86) to confirm that PCR did not introduce DNA base changes that would result in an amino acid change.

Prior to its use, the CPRB PacI fragment derived using the primers shown in Table 4 was sequenced and compared to CPRB (SEQ ID NO: 82) to confirm that PCR did not introduce DNA base pair changes that would result in an amino acid change. Following confirmation, CPRB (SEQ ID NO: 82) was ligated to plasmid pURAin which had also been digested with PacI. PacI digested pURAin was dephosphorylated, and ligated to the CPR Expand Hi-Fi PCR product as described previously. The ligation mixture was transformed into *E. coli* XL1 Blue MRF' (Stratagene) and several resistant colonies were selected and screened for correct constructs which should contain vector sequence, the inverted URA3A gene, and the amplified CPRB gene (SEQ ID NO: 82) of 20336. AscI-PmeI digestion confirmed a successful construct, pURAREDBin.

In a manner similar to the above, each of the other CYP and CPR genes disclosed herein are cloned into pURAin. PacI fragments of these genes, whose sequences are given in FIGS. 13 and 15, are derivable by methods known to those skilled in the art.

1) Construction of Vectors Used to Generate HDC 20 and HDC 23

A previously constructed integration vector containing CPRB (SEQ ID NO: 82), pURAREDBin, was chosen as the starting vector. This vector was partially digested with PacI and the linearized fragment was gel-isolated. The active PacI was destroyed by treatment with T4 DNA polymerase and the vector was re-ligated. Subsequent isolation and complete digestion of this new plasmid yielded a vector now containing only one active PacI site. This fragment was gel-isolated, dephosphorylated and ligated to the CYP52A2A PacI fragment. Vectors that contain the CYP52A2A (SEQ ID NO: 86) and CPRB (SEQ ID NO: 82) genes oriented in the same direction, pURAin CPR 2A S, as well as opposite directions (5' ends connected), pURAin CPR 2A O, were generated.

D. Confirmation of CYP Integration (FIG. 21 for Integration Scheme) into the Genome of *C. tropicalis*

Figure 28:
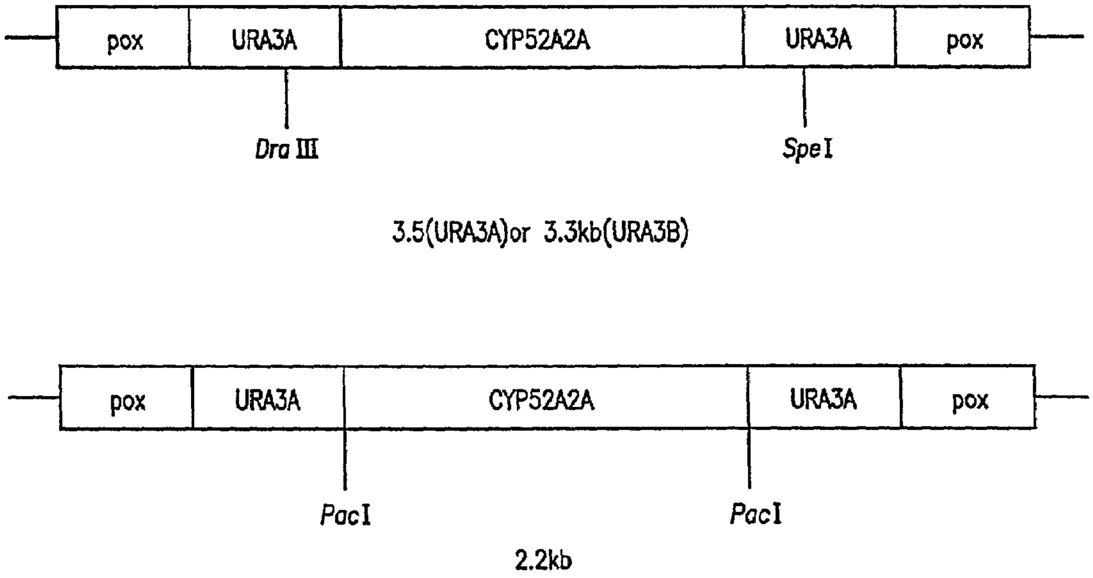
FIG. 28 shows a scheme to detect integration of CYP52A2A gene (SEQ ID NO: 86) into the genome of H5343 ura. In all cases, hybridization band intensity could reflect the number of integrations.

Based on the construct, pURA2in, used to transform H5343 ura, a scheme to detect integration was devised. Genomic DNA from transformants was digested with Dra III and Spe I which are enzymes that cut within the URA3A, and URA3B genes but not within the integrated CYP52A2A gene. Digestion of genomic DNA where an integration had occurred at the URA3A or URA3B loci would be expected to result in a 3.5 kb or a 3.3 kb fragment, respectively (FIG. 28). Moreover, digestion of the same genomic DNA with PacI would yield a 2.2 kb fragment characteristic for the integrated CYP52A2A gene (FIG. 28). Southern hybridizations of these digests with fragments of the CYP52A2A gene were used to screen for these integration events. Intensity of the band signal from the Southern using PacI digestion was used as a measure of the number of integration events, ((i.e. the more copies of the CYP52A2A gene (SEQ ID NO: 86) which are present, the stronger the hybridization signal)).

*C. tropicalis* H5343 transformed URA prototrophs were grown at 30° C., 170 rpm, in 10 ml SC-uracil media for preparation of genomic DNA. Genomic DNA was isolated by the method described previously. Genomic DNA was digested with SpeI and DraIII. A 0.95% agarose gel was used to prepare a Southern hybridization blot. The DNA from the gel was transferred to a MagnaCharge nylon filter membrane (MSI Technologies, Westboro, Mass.) according to the alkaline transfer method of Sambrook et al., supra. For the Southern hybridization, a 2.2 kb CYP52A2A DNA fragment was used as a hybridization probe, 300 ng of CYP52A2A DNA was labeled using a ECL Direct labeling and detection system (Amersham) and the Southern was processed according to the ECL kit specifications. The blot was processed in a volume of 30 ml of hybridization fluid corresponding to 0.125 ml/$cm^2$. Following a prehybridization at 42° C. for 1 hr, 300 ng of CYP52A2A probe was added and the hybridization continued for 16 hr at 42° C. in primary wash containing urea. Two 5 min secondary washes at RT were conducted, followed by detection according to directions. The blots were exposed for 16 hours (hr) as recommended.

Integration was confirmed by the detection of a SpeI-DraIII 3.5 kb fragment from the genomic DNA of the transformants but not with the *C. tropicalis* 20336 control. Subsequently, a PacI digestion of the genomic DNA of the positive transformants, followed by a Southern hybridization using an CYP52A2A gene probe, confirmed integration by the detection of a 2.2 kb fragment. The resulting CYP52A2A integrated strain was named HDC1 (see Table 1).

In a manner similar to the above, each of the genes contained in the PacI fragments which are described in Section 3c above were confirmed for integration into the genome of *C. tropicalis.*

Transformants generated by transformation with the vectors, pURAin CPR 2A S or pURAin CPR 2A O, were analyzed by Southern hybridization for integration of both the CYP52A2A (SEQ ID NO: 86) and CPRB (SEQ ID NO: 82) genes tandemly. Three strains were generated in which the CYP52A2A (SEQ ID NO: 86) and CPRB (SEQ ID NO: 82) genes integrated are in the opposite orientation (HDC 20-1, HDC 20-2 and HDC 20-3) and three were generated with the CYP52A2A (SEQ ID NO: 86) and CPRB (SEQ ID NO: 82) genes integrated in the same orientation (HDC 23-1, HDC 23-2 and HDC 23-3), Table 1.

E. Confirmation of CPRB Integration into H5343 ura

Seven transformants were screened by colony PCR using CPRB primer #2 (SEQ ID NO: 8) and a URA3A-specific primer. In five of the transformants, successful integration was detected by the presence of a 3899 bp PCR product. This 3899 bp PCR product represents the CPRB gene adjacent to the URA3A gene in the genome of H5343 thereby confirming integration. The resulting CPRB integrated strains were named HDC10-1 and HDC10-2 (see Table 1).

F. Strain Evaluation

As determined by quantitative PCR, when compared to parent H5343, HDC10-1 contained three additional copies of the reductase gene and HDC10-2 contained four additional copies of the reductase gene. Evaluations of HDC20-1, HDC20-2 and HDC20-3 based on Southern hybridization data indicates that HDC20-1 contained multiple integrations, i.e., 2 to 3 times that of HDC20-2 or HDC20-3. Evaluations of HDC23-1, HDC23-2, and HDC23-3 based on Southern hybridization data indicates that HDC23-3 contained multiple integrations, i.e., 2 to 3 times that of HDC23-1 or HDC23-2. The data in Table 8 indicates that the integration of components of the ω-hydroxylase complex have a positive effect on the improvement of *Candida tropicalis* ATCC 20962 as a biocatalyst. The results indicate that CYP52A5A (SEQ ID NO: 90) is an important gene for the conversion of oleic acid to diacid. Surprisingly, tandem integrations of CYP and CPR genes oriented in the opposite direction (HDC 20 strains) seem to be less productive than tandem integrations oriented in the same direction (HDC 23 strains), Tables 1 and 8.

TABLE 9

| Media Composition | |
|---|---|
| LB Broth | |
| Bacto Tryptone | 10 g |
| Bacto Yeast Extract | 5 g |
| Sodium Chloride | 10 g |
| Distilled Water | 1,000 ml |
| LB Agar | |
| Bacto Tryptone | 10 g |
| Bacto Yeast Extract | 5 g |
| Sodium Chloride | 10 g |
| Agar | 15 g |
| Distilled Water | 1,000 ml |
| LB Top Agarose | |
| Bacto Tryptone | 10 g |
| Bacto Yeast Extract | 5 g |
| Sodium Chloride | 10 g |
| Agarose | 7 g |
| Distilled Water | 1,000 ml |
| NZCYM Broth | |
| Bacto Casein Digest | 10 g |
| Bacto Casamino Acids | 1 g |
| Bacto Yeast Extract | 5 g |
| Sodium Chloride | 5 g |
| Magnesium Sulfate (anhydrous) | 0.98 g |
| Distilled Water | 1,000 ml |
| NZCYM Agar | |
| Bacto Casein Digest | 10 g |
| Bacto Casamino Acids | 1 g |
| Bacto Yeast Extract | 5 g |
| Sodium Chloride | 5 g |
| Magnesium Sulfate (anhydrous) | 0.98 g |
| Agar | 15 g |
| Distilled Water | 1,000 ml |
| NZCYM Top Agarose | |
| Bacto Casein Digest | 10 g |
| Bacto Casamino Acids | 1 g |
| Bacto Yeast Extract | 5 g |
| Sodium Chloride | 5 g |
| Magnesium Sulfate (anhydrous) | 0.98 g |
| Agarose | 7 g |
| Distilled Water | 1,000 ml |
| YEPD Broth | |
| Bacto Yeast Extract | 10 g |
| Bacto Peptone | 20 g |
| Glucose | 20 g |
| Distilled Water | 1,000 ml |
| YEPD Agar* | |
| Bacto Yeast Extract | 10 g |
| Bacto Peptone | 20 g |
| Glucose | 20 g |
| Agar | 20 g |
| Distilled Water | 1,000 ml |
| SC - uracil* | |
| Bacto-yeast nitrogen base without amino acids | 6.7 g |
| Glucose | 20 g |
| Bacto-agar | 20 g |
| Drop-out mix | 2 g |

TABLE 9-continued

| | |
|---|---|
| Distilled water | 1,000 ml |
| | g/l |
| DCA2 medium | |
| Peptone | 3.0 |
| Yeast Extract | 6.0 |
| Sodium Acetate | 3.0 |
| Yeast Nitrogen Base (Difco) | 6.7 |
| Glucose (anhydrous) | 50.0 |
| Potassium Phosphate (dibasic, trihydrate) | 7.2 |
| Potassium Phosphate (monobasic, anhydrous) | 9.3 |
| DCA3 medium | |
| 0.3 M Phosphate buffer containing, pH 7.5 | |
| Glycerol | 50 |
| Yeast Nitrogen base (Difco) | 6.7 |

Drop-out mix

| | | | |
|---|---|---|---|
| Adenine | 0.5 g | Alanine | 2 g |
| Arginine | 2 g | Asparagine | 2 g |
| Aspartic acid | 2 g | Cysteine | 2 g |
| Glutamine | 2 g | Glutamic acid | 2 g |
| Glycine | 2 g | Histidine | 2 g |
| Inositol | 2 g | Isoleucine | 2 g |
| Leucine | 10 g | Lysine | 2 g |
| Methionine | 2 g | para-Aminobenzoic acid | 0.2 g |
| Phenylalanine | 2 g | Proline | 2 g |
| Serine | 2 g | Threonine | 2 g |
| Tryptophan | 2 g | Tyrosine | 2 g |
| Valine | 2 g | | |

*See Kaiser et al., Methods in Yeast Genetics, Cold Spring Harbor Laboratory Press, USA (1994), incorporated herein by reference.

It will be understood that various modifications may be made to the embodiments and/or examples disclosed herein. Thus, the above description should not be construed as limiting, but merely as exemplifications of preferred embodiments. Those skilled in the art will envision other modifications within the scope and spirit of the claims appended hereto.

What is claimed is:

1. An isolated cytochrome P450 monooxygenase protein consisting of the amino acid sequence SEQ ID NO: 96.

* * * * *

```
                              SEQUENCE LISTING

<160> NUMBER OF SEQ ID NOS: 118

<210> SEQ ID NO 1
<211> LENGTH: 32
<212> TYPE: DNA
<213> ORGANISM: Artificial Sequence
<220> FEATURE:
<223> OTHER INFORMATION: Description of Artificial Sequence: Primer

<400> SEQUENCE: 1

ccttaattaa atgcacgaag cggagataaa ag                                     32


<210> SEQ ID NO 2
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 2

ccttaattaa gcataagctt gctcgagtct                                        30


<210> SEQ ID NO 3
<211> LENGTH: 31
<212> TYPE: DNA
<213> ORGANISM: Artificial Sequence
<220> FEATURE:
<223> OTHER INFORMATION: Description of Artificial Sequence: Primer

<400> SEQUENCE: 3

ccttaattaa acgcaatggg aacatggagt g                                      31


<210> SEQ ID NO 4
<211> LENGTH: 34
<212> TYPE: DNA
<213> ORGANISM: Artificial Sequence
<220> FEATURE:
<223> OTHER INFORMATION: Description of Artificial Sequence: Primer
```

-continued

<400> SEQUENCE: 4
ccttaattaa tcgcactacg gttattggta tcag 34

<210> SEQ ID NO 5
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 5
ccttaattaa tcaaagtacg ttcaggcgg 29

<210> SEQ ID NO 6
<211> LENGTH: 34
<212> TYPE: DNA
<213> ORGANISM: Artificial Sequence
<220> FEATURE:
<223> OTHER INFORMATION: Description of Artificial Sequence: Primer

<400> SEQUENCE: 6
ccttaattaa ggcagacaac aacttggcaa agtc 34

<210> SEQ ID NO 7
<211> LENGTH: 31
<212> TYPE: DNA
<213> ORGANISM: Artificial Sequence
<220> FEATURE:
<223> OTHER INFORMATION: Description of Artificial Sequence: Primer

<400> SEQUENCE: 7
ccttaattaa gaggtcgttg gttgagtttt c 31

<210> SEQ ID NO 8
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 8
ccttaattaa ttgataatga cgttgcggg 29

<210> SEQ ID NO 9
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 9
aggcgcgccg gagtccaaaa agaccaacct ctg 33

<210> SEQ ID NO 10
<211> LENGTH: 34
<212> TYPE: DNA
<213> ORGANISM: Artificial Sequence
<220> FEATURE:
<223> OTHER INFORMATION: Description of Artificial Sequence: Primer

<400> SEQUENCE: 10
ccttaattaa tacgtggata ccttcaagca agtg 34

<210> SEQ ID NO 11
<211> LENGTH: 35

-continued

<212> TYPE: DNA
<213> ORGANISM: Artificial Sequence
<220> FEATURE:
<223> OTHER INFORMATION: Description of Artificial Sequence: Primer

<400> SEQUENCE: 11
ccttaattaa gctcacgagt tttgggattt tcgag 35

<210> SEQ ID NO 12
<211> LENGTH: 35
<212> TYPE: DNA
<213> ORGANISM: Artificial Sequence
<220> FEATURE:
<223> OTHER INFORMATION: Description of Artificial Sequence: Primer

<400> SEQUENCE: 12
gggtttaaac cgcagaggtt ggtctttttg gactc 35

<210> SEQ ID NO 13
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 13
gggtttaaac 10

<210> SEQ ID NO 14
<211> LENGTH: 9
<212> TYPE: DNA
<213> ORGANISM: Artificial Sequence
<220> FEATURE:
<223> OTHER INFORMATION: Description of Artificial Sequence: Primer

<400> SEQUENCE: 14 aggcgcgcc 9

<210> SEQ ID NO 15
<211> LENGTH: 10
<212> TYPE: DNA
<213> ORGANISM: Artificial Sequence
<220> FEATURE:
<223> OTHER INFORMATION: Description of Artificial Sequence: Primer

<400> SEQUENCE: 15
ccttaattaa 10

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: misc_feature
<222> LOCATION: (3)..(4)
<223> OTHER INFORMATION: y=dCTP or dTTP
<220> FEATURE:
<221> NAME/KEY: misc_feature
<222> LOCATION: (9)..(10)
<223> OTHER INFORMATION: w=dATP or dTTP
<220> FEATURE:
<221> NAME/KEY: misc_feature
<222> LOCATION: (15)..(16)
<223> OTHER INFORMATION: w=dATP or dTTP
<220> FEATURE:
<221> NAME/KEY: misc_feature
<222> LOCATION: (18)..(19)

-continued

<223> OTHER INFORMATION: w=dATP or dTTP

<400> SEQUENCE: 16
tcycaaacwg gtacwgcwga a 21

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: misc_feature
<222> LOCATION: (12)..(13)
<223> OTHER INFORMATION: y=dCTP or dTTP
<220> FEATURE:
<221> NAME/KEY: misc_feature
<222> LOCATION: (15)..(16)
<223> OTHER INFORMATION: w=dATP or dTTP

<400> SEQUENCE: 17
ggtttgggta aytcwactta t 21

<210> SEQ ID NO 18
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 18
cgttattatc atttcttc 18

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: misc_feature
<222> LOCATION: (3)..(4)
<223> OTHER INFORMATION: m=dATP or dCTP
<220> FEATURE:
<221> NAME/KEY: misc_feature
<222> LOCATION: (9)..(10)
<223> OTHER INFORMATION: r=dATP or dGTP

<400> SEQUENCE: 19
gcmacaccrg tacctggacc 20

<210> SEQ ID NO 20
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 20
atcccaatcg taatcagc 18

<210> SEQ ID NO 21
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 21

-continued

```
acttgtcttc gtttagca                                                18


<210> SEQ ID NO 22
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 22

ctacgtctgt ggtgatgc                                                18


<210> SEQ ID NO 23
<211> LENGTH: 17
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: misc_feature
<222> LOCATION: (3)..(4)
<223> OTHER INFORMATION: n=dATP or dCTP or dGTP or dTTP
<220> FEATURE:
<221> NAME/KEY: misc_feature
<222> LOCATION: (6)..(7)
<223> OTHER INFORMATION: Y=dCTP or dTTP
<220> FEATURE:
<221> NAME/KEY: misc_feature
<222> LOCATION: (9)..(10)
<223> OTHER INFORMATION: n=dATP or dCTP or dGTP or dTTP
<220> FEATURE:
<221> NAME/KEY: misc_feature
<222> LOCATION: (12)..(13)
<223> OTHER INFORMATION: n=dATP or dCTP or dGTP or dTTP
<220> FEATURE:
<221> NAME/KEY: misc_feature
<222> LOCATION: (15)..(16)
<223> OTHER INFORMATION: n=dATP or dCTP or dGTP or dTTP

<400> SEQUENCE: 23

cgngayacna cngcngg                                                 17


<210> SEQ ID NO 24
<211> LENGTH: 17
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: misc_feature
<222> LOCATION: (3)..(4)
<223> OTHER INFORMATION: r=dATP or dTTP
<220> FEATURE:
<221> NAME/KEY: misc_feature
<222> LOCATION: (6)..(7)
<223> OTHER INFORMATION: y=dCTP or dTTP
<220> FEATURE:
<221> NAME/KEY: misc_feature
<222> LOCATION: (9)..(10)
<223> OTHER INFORMATION: n=dATP or dCTP or dGTP or dTTP
<220> FEATURE:
<221> NAME/KEY: misc_feature
<222> LOCATION: (12)..(13)
<223> OTHER INFORMATION: n=dATP or dCTP or dGTP or dTTP
<220> FEATURE:
<221> NAME/KEY: misc_feature
<222> LOCATION: (15)..(16)
<223> OTHER INFORMATION: n=dATP or dCTP or dGTP or dTTP

<400> SEQUENCE: 24

agrgayacna cngcngg                                                 17
```

-continued

<210> SEQ ID NO 25
<211> LENGTH: 17
<212> TYPE: DNA
<213> ORGANISM: Artificial Sequence
<220> FEATURE:
<223> OTHER INFORMATION: Description of Artifiical Sequence: Primer
<220> FEATURE:
<221> NAME/KEY: misc_feature
<222> LOCATION: (3)..(4)
<223> OTHER INFORMATION: n=dATP or dCTP or dGTP or dTTP
<220> FEATURE:
<221> NAME/KEY: misc_feature
<222> LOCATION: (6)..(7)
<223> OTHER INFORMATION: r=dATP or dGTP
<220> FEATURE:
<221> NAME/KEY: misc_feature
<222> LOCATION: (9)..(10)
<223> OTHER INFORMATION: y=dCTP or dTTP
<220> FEATURE:
<221> NAME/KEY: misc_feature
<222> LOCATION: (12)..(13)
<223> OTHER INFORMATION: y=dCTP or dTTP
<220> FEATURE:
<221> NAME/KEY: misc_feature
<222> LOCATION: (15)..(16)
<223> OTHER INFORMATION: n=dATP or dCTP or dGTP or dTTP

<400> SEQUENCE: 25
agngcraayt gytgncc 17

<210> SEQ ID NO 26
<211> LENGTH: 18
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: misc_feature
<222> LOCATION: (1)..(2)
<223> OTHER INFORMATION: y=dCTP or dTTP
<220> FEATURE:
<221> NAME/KEY: misc_feature
<222> LOCATION: (4)..(5)
<223> OTHER INFORMATION: n=dATP or dCTP or dGTP or dTTP
<220> FEATURE:
<221> NAME/KEY: misc_feature
<222> LOCATION: (7)..(8)
<223> OTHER INFORMATION: r=dATP or dGTP
<220> FEATURE:
<221> NAME/KEY: misc_feature
<222> LOCATION: (10)..(11)
<223> OTHER INFORMATION: y=dCTP or dTTP
<220> FEATURE:
<221> NAME/KEY: misc_feature
<222> LOCATION: (13)..(14)
<223> OTHER INFORMATION: y=dCTP or dTTP
<220> FEATURE:
<221> NAME/KEY: misc_feature
<222> LOCATION: (16)..(17)
<223> OTHER INFORMATION: n=dATP or dCTP or dGTP or dTTP

<400> SEQUENCE: 26
yaangcraay tgytgncc 18

<210> SEQ ID NO 27
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 27
attcaacggt ggtccaagaa tctgtttgg 29

-continued

<210> SEQ ID NO 28
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 28
gagctatgtt gagaccacag tttgc 25

<210> SEQ ID NO 29
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 29
cttcagttaa agcaaattgt ttggcc 26

<210> SEQ ID NO 30
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 30
ctcgggaagc gcgccattgt gttgg 25

<210> SEQ ID NO 31
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 31
taatacgact cactataggg cgaattggc 29

<210> SEQ ID NO 32
<211> LENGTH: 21
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: misc_feature
<222> LOCATION: (3)..(4)
<223> OTHER INFORMATION: r=dATP or dGTP
<220> FEATURE:
<221> NAME/KEY: misc_feature
<222> LOCATION: (4)..(5)
<223> OTHER INFORMATION: y=dCTP or dTTP
<220> FEATURE:
<221> NAME/KEY: misc_feature
<222> LOCATION: (16)..(17)
<223> OTHER INFORMATION: y=dCTP or dTTP

<400> SEQUENCE: 32
tgrytcaaac catctytctg g 21

<210> SEQ ID NO 33
<211> LENGTH: 17
<212> TYPE: DNA
<213> ORGANISM: Artificial Sequence
<220> FEATURE:

-continued

<223> OTHER INFORMATION: Description of Artificial Sequence: Primer

<400> SEQUENCE: 33
ggaccggcgt taaaggg 17

<210> SEQ ID NO 34
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 34
catagtcgwa tyatgcttag acc 23

<210> SEQ ID NO 35
<211> LENGTH: 17
<212> TYPE: DNA
<213> ORGANISM: Artificial Sequence
<220> FEATURE:
<223> OTHER INFORMATION: Description of Artificial Sequence: Primer

<400> SEQUENCE: 35
ggaccaccat tgaatgg 17

<210> SEQ ID NO 36
<211> LENGTH: 540
<212> TYPE: DNA
<213> ORGANISM: Candida tropicalis

<400> SEQUENCE: 36
atgattgaac aactcctaga atattggtat gtcgttgtgc cagtgttgta catcatcaaa 60
caactccttg catacacaaa gactcgcgtc ttgatgaaaa agttgggtgc tgctccagtc 120
acaaacaagt tgtacgacaa cgctttcggt atcgtcaatg gatggaaggc tctccagttc 180
aagaaagagg gcagggctca agagtacaac gattacaagt ttgaccactc caagaaccca 240
agcgtgggca cctacgtcag tattcttttc ggcaccagga tcgtcgtgac caaagatcca 300
gagaatatca aagctatttt ggcaacccag tttggtgatt tttctttggg caagaggcac 360
actcttttta agcctttgtt aggtgatggg atcttcacat tggacggcga aggctggaag 420
cacagcagag ccatgttgag accacagttt gccagagaac aagttgctca tgtgacgtcg 480
ttggaaccac acttccagtt gttgaagaag catattctta agcacaaggg tgaatacttt 540

<210> SEQ ID NO 37
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 37
ccgatgaagt tttcgacgag taccc 25

<210> SEQ ID NO 38
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 38
aaggctttaa cgtgtccaat ctggtc 26

-continued

<210> SEQ ID NO 39
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 39
attatcgcca catacttcac caaatgg 27

<210> SEQ ID NO 40
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 40
cgagatcgtg gatacgctgg agtg 24

<210> SEQ ID NO 41
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 41
gccactcggt aactttgtca gggac 25

<210> SEQ ID NO 42
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 42
cattgaactg agtagccaaa acagcc 26

<210> SEQ ID NO 43
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 43
cctacgtttg gtatcgctac tccgttg 27

<210> SEQ ID NO 44
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 44
tttccagcca gcaccgtcca ag 22

<210> SEQ ID NO 45
<211> LENGTH: 24
<212> TYPE: DNA
<213> ORGANISM: Artificial Sequence
<220> FEATURE:

-continued

<223> OTHER INFORMATION: Description of Artificial Sequence: Primer

<400> SEQUENCE: 45
gcagagccga tctatgttgc gtcc 24

<210> SEQ ID NO 46
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 46
tcattgaatg cttccaggaa cctcg 25

<210> SEQ ID NO 47
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 47
aagagggcag ggctcaagag 20

<210> SEQ ID NO 48
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 48
tccatgtgaa gatcccatca c 21

<210> SEQ ID NO 49
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 49
cttgaaggcc gtgttgaacg 20

<210> SEQ ID NO 50
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 50
caggatttgt ctgagttgcc g 21

<210> SEQ ID NO 51
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 51
ccattgcctt gagatacgcc attggtag 28

-continued

<210> SEQ ID NO 52
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 52
agccttggtg tcgttctttt caacgg 26

<210> SEQ ID NO 53
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 53
ttgggtttgt ttgtttcctg tgtccg 26

<210> SEQ ID NO 54
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 54
cctttgacct tcaatctggc gtagacg 27

<210> SEQ ID NO 55
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 55
gtttgctgaa tacgctgaag gtgatg 26

<210> SEQ ID NO 56
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 56
tggagctgaa caactctctc gtctcgg 27

<210> SEQ ID NO 57
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 57
ttcctcaaca cggacagcgg 20

<210> SEQ ID NO 58
<211> LENGTH: 24
<212> TYPE: DNA
<213> ORGANISM: Artificial Sequence
<220> FEATURE:
<223> OTHER INFORMATION: Description of Artificial Sequence: Primer -continued

<400> SEQUENCE: 58
agtcaaccag gtgtggaact cgtc 24

<210> SEQ ID NO 59
<211> LENGTH: 49
<212> TYPE: DNA
<213> ORGANISM: Artificial Sequence
<220> FEATURE:
<223> OTHER INFORMATION: Description of Artificial Sequence: Primer

<400> SEQUENCE: 59
ggatcctaat acgactcact atagggagga agagggcagg gctcaagag 49

<210> SEQ ID NO 60
<211> LENGTH: 42
<212> TYPE: DNA
<213> ORGANISM: Artificial Sequence
<220> FEATURE:
<223> OTHER INFORMATION: Description of Artificial Sequence: Primer

<400> SEQUENCE: 60
tccatgtgaa gatcccatca cgagtgtgcc tcttgcccaa ag 42

<210> SEQ ID NO 61
<211> LENGTH: 54
<212> TYPE: DNA
<213> ORGANISM: Artificial Sequence
<220> FEATURE:
<223> OTHER INFORMATION: Description of Artificial Sequence: Primer

<400> SEQUENCE: 61
ggatcctaat acgactcact atagggaggc cgatgaagtt ttcgacgagt accc 54

<210> SEQ ID NO 62
<211> LENGTH: 52
<212> TYPE: DNA
<213> ORGANISM: Artificial Sequence
<220> FEATURE:
<223> OTHER INFORMATION: Description of Artificial Sequence: Primer

<400> SEQUENCE: 62
aaggctttaa cgtgtccaat ctggtcaaca tagctctgga gtgcttccaa cc 52

<210> SEQ ID NO 63
<211> LENGTH: 56
<212> TYPE: DNA
<213> ORGANISM: Artificial Sequence
<220> FEATURE:
<223> OTHER INFORMATION: Description of Artificial Sequence: Primer

<400> SEQUENCE: 63
ggatcctaat acgactcact atagggagga ttatcgccac atacttcacc aaatgg 56

<210> SEQ ID NO 64
<211> LENGTH: 52
<212> TYPE: DNA
<213> ORGANISM: Artificial Sequence
<220> FEATURE:
<223> OTHER INFORMATION: Description of Artificial Sequence: Primer

<400> SEQUENCE: 64
cgagatcgtg gatacgctgg agtgcgtcgc tcttcttctt caacaattca ag 52

<210> SEQ ID NO 65
<211> LENGTH: 49

-continued

<212> TYPE: DNA
<213> ORGANISM: Artificial Sequence
<220> FEATURE:
<223> OTHER INFORMATION: Description of Artificial Sequence: Primer

<400> SEQUENCE: 65
cattgaactg agtagccaaa acagcccatg gtttcaatca atgggaggc 49

<210> SEQ ID NO 66
<211> LENGTH: 54
<212> TYPE: DNA
<213> ORGANISM: Artificial Sequence
<220> FEATURE:
<223> OTHER INFORMATION: Description of Artificial Sequence: Primer

<400> SEQUENCE: 66
ggatcctaat acgactcact atagggaggg ccactcggta actttgtcag ggac 54

<210> SEQ ID NO 67
<211> LENGTH: 56
<212> TYPE: DNA
<213> ORGANISM: Artificial Sequence
<220> FEATURE:
<223> OTHER INFORMATION: Description of Artificial Sequence: Primer

<400> SEQUENCE: 67
ggatcctaat acgactcact atagggaggc ctacgtttgg tatcgctact ccgttg 56

<210> SEQ ID NO 68
<211> LENGTH: 48
<212> TYPE: DNA
<213> ORGANISM: Artificial Sequence
<220> FEATURE:
<223> OTHER INFORMATION: Description of Artificial Sequence: Primer

<400> SEQUENCE: 68
tttccagcca gcaccgtcca agcaacaagg agtacaagaa atcgtgtc 48

<210> SEQ ID NO 69
<211> LENGTH: 53
<212> TYPE: DNA
<213> ORGANISM: Artificial Sequence
<220> FEATURE:
<223> OTHER INFORMATION: Description of Artificial Sequence: Primer

<400> SEQUENCE: 69
ggatcctaat acgactcact atagggaggg cagagccgat ctatgttgcg tcc 53

<210> SEQ ID NO 70
<211> LENGTH: 45
<212> TYPE: DNA
<213> ORGANISM: Artificial Sequence
<220> FEATURE:
<223> OTHER INFORMATION: Description of Artificial Sequence: Primer

<400> SEQUENCE: 70
tcattgaatg cttccaggaa cctcgccaca tccatcgaga accgg 45

<210> SEQ ID NO 71
<211> LENGTH: 49
<212> TYPE: DNA
<213> ORGANISM: Artificial Sequence
<220> FEATURE:
<223> OTHER INFORMATION: Description of Artificial Sequence: Primer

<400> SEQUENCE: 71

-continued ggatcctaat acgactcact atagggaggc ttgaaggccg tgttgaacg 49

<210> SEQ ID NO 72
<211> LENGTH: 46
<212> TYPE: DNA
<213> ORGANISM: Artificial Sequence
<220> FEATURE:
<223> OTHER INFORMATION: Description of Artificial Sequence: Primer

<400> SEQUENCE: 72
caggatttgt ctgagttgcc gcctgatcaa gataggatcc ttgccg 46

<210> SEQ ID NO 73
<211> LENGTH: 56
<212> TYPE: DNA
<213> ORGANISM: Artificial Sequence
<220> FEATURE:
<223> OTHER INFORMATION: Description of Artificial Sequence: Primer

<400> SEQUENCE: 73
ggatcctaat acgactcact atagggaggg gtttgctgaa tacgctgaag gtgatg 56

<210> SEQ ID NO 74
<211> LENGTH: 52
<212> TYPE: DNA
<213> ORGANISM: Artificial Sequence
<220> FEATURE:
<223> OTHER INFORMATION: Description of Artificial Sequence: Primer

<400> SEQUENCE: 74
tggagctgaa caactctctc gtctcgggtg gtcgaatgga cccttggtca ag 52

<210> SEQ ID NO 75
<211> LENGTH: 49
<212> TYPE: DNA
<213> ORGANISM: Artificial Sequence
<220> FEATURE:
<223> OTHER INFORMATION: Description of Artificial Sequence: Primer

<400> SEQUENCE: 75
ggatcctaat acgactcact atagggaggt tcctcaacac ggacagcgg 49

<210> SEQ ID NO 76
<211> LENGTH: 49
<212> TYPE: DNA
<213> ORGANISM: Artificial Sequence
<220> FEATURE:
<223> OTHER INFORMATION: Description of Artificial Sequence: Primer

<400> SEQUENCE: 76
agtcaaccag gtgtggaact cgtcggtggc aacaatgaaa aacaccaag 49

<210> SEQ ID NO 77
<211> LENGTH: 57
<212> TYPE: DNA
<213> ORGANISM: Artificial Sequence
<220> FEATURE:
<223> OTHER INFORMATION: Description of Artificial Sequence: Primer

<400> SEQUENCE: 77
ggatcctaat acgactcact atagggaggc cattgccttg agatacgcca ttggtag 57

<210> SEQ ID NO 78
<211> LENGTH: 53
<212> TYPE: DNA
<213> ORGANISM: Artificial Sequence -continued
<220> FEATURE:
<223> OTHER INFORMATION: Description of Artificial Sequence: Primer

<400> SEQUENCE: 78
agccttggtg tcgttctttt caacggaagg tggtctcgat ggtgtgttca acc 53

<210> SEQ ID NO 79
<211> LENGTH: 55
<212> TYPE: DNA
<213> ORGANISM: Artificial Sequence
<220> FEATURE:
<223> OTHER INFORMATION: Description of Artificial Sequence: Primer

<400> SEQUENCE: 79
ggatcctaat acgactcact atagggaggt tgggtttgtt tgtttcctgt gtccg 55

<210> SEQ ID NO 80
<211> LENGTH: 50
<212> TYPE: DNA
<213> ORGANISM: Artificial Sequence
<220> FEATURE:
<223> OTHER INFORMATION: Description of Artificial Sequence: Primer

<400> SEQUENCE: 80
cctttgacct tcaatctggc gtagacgcag caccaccgat ccaccacttg 50

<210> SEQ ID NO 81
<211> LENGTH: 4206
<212> TYPE: DNA
<213> ORGANISM: Candida tropicalis

<400> SEQUENCE: 81
catcaagatc atctatgggg ataattacga cagcaacatt gcagaaagag cgttggtcac 60
aatcgaaaga gcctatggcg ttgccgtcgt tgaggcaaat gacagcacca acaataacga 120
tggtcccagt gaagagcctt cagaacagtc cattgttgac gcttaaggca cggataatta 180
cgtggggcaa aggaacgcgg aattagttat ggggggatca aaagcggaag atttgtgttg 240
cttgtgggtt ttttccttta tttttcatat gatttctttg cgcaagtaac atgtgccaat 300
ttagtttgtg attagcgtgc cccacaattg gcatcgtgga cgggcgtgtt ttgtcatacc 360
ccaagtctta actagctcca cagtctcgac ggtgtctcga cgatgtcttc ttccacccct 420
cccatgaatc attcaaagtt gttgggggat ctccaccaag ggcaccggag ttaatgctta 480
tgtttctccc actttggttg tgattggggt agtctagtga gttggagatt ttcttttttt 540
cgcaggtgtc tccgatatcg aaatttgatg aatatagaga gaagccagat cagcacagta 600
gattgccttt gtagttagag atgttgaaca gcaactagtt gaattacacg ccaccacttg 660
acagcaagtg cagtgagctg taaacgatgc agccagagtg tcaccaccaa ctgacgttgg 720
gtggagttgt tgttgttgtt gttggcaggg ccatattgct aaacgaagac aagtagcaca 780
aaacccaagc ttaagaacaa aaataaaaaa aattcatacg acaattccaa agccattgat 840
ttacataatc aacagtaaga cagaaaaaac tttcaacatt tcaaagttcc ctttttccta 900
ttacttcttt tttttcttct ttccttcttt ccttctgttt ttcttacttt atcagtcttt 960
tacttgtttt tgcaattcct catcctcctc ctactcctcc tcaccatggc tttagacaag 1020
ttagatttgt atgtcatcat aacattggtg gtcgctgtag ccgcctattt tgctaagaac 1080
cagttccttg atcagcccca ggacaccggg ttcctcaaca cggacagcgg aagcaactcc 1140
agagacgtct tgctgacatt gaagaagaat aataaaaaca cgttgttgtt gtttgggtcc 1200

-continued

```
cagacgggta cggcagaaga ttacgccaac aaattgtcca gagaattgca ctccagattt   1260
ggcttgaaaa cgatggttgc agatttcgct gattacgatt gggataactt cggagatatc   1320
accgaagaca tcttggtgtt tttcattgtt gccacctatg gtgagggtga acctaccgat   1380
aatgccgacg agttccacac ctggttgact gaagaagctg acactttgag taccttgaaa   1440
tacaccgtgt tcgggttggg taactccacg tacgagttct tcaatgccat tggtagaaag   1500
tttgacagat tgttgagcga gaaaggtggt gacaggtttg ctgaatacgc tgaaggtgat   1560
gacggtactg gcaccttgga cgaagatttc atggcctgga aggacaatgt ctttgacgcc   1620
ttgaagaatg atttgaactt tgaagaaaag gaattgaagt acgaaccaaa cgtgaaattg   1680
actgagagag acgacttgtc tgctgctgac tcccaagttt ccttgggtga gccaaacaag   1740
aagtacatca actccgaggg catcgacttg accaagggtc cattcgacca cacccaccca   1800
tacttggcca gaatcaccga gacgagagag ttgttcagct ccaaggacag acactgtatc   1860
cacgttgaat ttgacatttc tgaatcgaac ttgaaataca ccaccggtga ccatctagct   1920
atctggccat ccaactccga cgaaaacatt aagcaatttg ccaagtgttt cggattggaa   1980
gataaactcg acactgttat tgaattgaag gcgttggact ccacttacac catcccattc   2040
ccaaccccaa ttacctacgg tgctgtcatt agacaccatt tagaaatctc cggtccagtc   2100
tcgagacaat tctttttgtc aattgctggg tttgctcctg atgaagaaac aaagaaggct   2160
tttaccagac ttggtggtga caagcaagaa ttcgccgcca aggtcacccg cagaaagttc   2220
aacattgccg atgccttgtt atattcctcc aacaacgctc catggtccga tgttcctttt   2280
gaattcctta ttgaaaacgt tccacacttg actccacgtt actactccat ttcgtcttcg   2340
tcattgagtg aaaagcaact catcaacgtt actgcagttg ttgaagccga agaagaagct   2400
gatggcagac cagtcactgg tgttgtcacc aacttgttga agaacgttga aattgtgcaa   2460
aacaagactg gcgaaaagcc acttgtccac tacgatttga gcggcccaag aggcaagttc   2520
aacaagttca agttgccagt gcatgtgaga agatccaact ttaagttgcc aaagaactcc   2580
accaccccag ttatcttgat tggtccaggt actggtgttg ccccattgag aggttttgtc   2640
agagaaagag ttcaacaagt caagaatggt gtcaatgttg gcaagacttt gttgttttat   2700
ggttgcagaa actccaacga ggactttttg tacaagcaag aatgggccga gtacgcttct   2760
gttttgggtg aaaactttga gatgttcaat gccttctcca gacaagaccc atccaagaag   2820
gtttacgtcc aggataagat tttagaaaac agccaacttg tgcacgagtt gttgactgaa   2880
ggtgccatta tctacgtctg tggtgatgcc agtagaatgg ctagagacgt gcagaccaca   2940
atttccaaga ttgttgctaa aagcagagaa attagtgaag acaaggctgc tgaattggtc   3000
aagtcctgga aggtccaaaa tagataccaa gaagatgttt ggtagactca aacgaatctc   3060
tctttctccc aacgcattta tgaatcttta ttctcattga agctttacat atgttctaca   3120
ctttattttt tttttttttt ttattattat attacgaaac ataggtcaac tatatatact   3180
tgattaaatg ttatagaaac aataactatt atctactcgt ctacttcttt ggcattgaca   3240
tcaacattac cgttcccatt accgttgccg ttggcaatgc cgggatattt agtacagtat   3300
ctccaatccg gatttgagct attgtagatc agctgcaagt cattctccac cttcaaccag   3360
tacttatact tcatctttga cttcaagtcc aagtcataaa tattacaagt tagcaagaac   3420
ttctggccat ccacgatata gacgttattc acgttattat gcgacgtatg gatgtggtta   3480
tccttattga acttctcaaa cttcaaaaac aaccccacgt cccgcaacgt cattatcaac   3540
gacaagttct ggctcacgtc gtcggagctc gtcaagttct caattagatc gttcttgtta   3600
```

-continued

```
ttgatcttct ggtactttct caattgctgg aacacattgt cctcgttgtt caaatagatc   3660
ttgaacaact ttttcaacgg gatcaacttc tcaatctggg ccaagatctc cgccgggatc   3720
ttcagaaaca agtcctgcaa cccctggtcg atggtctccg ggtacaacaa gtccaagggg   3780
cagaagtgtc taggcacgtg tttcaactgg ttcaacgaac atgttcgaca gtagttcgag   3840
ttatagttat cgtacaacca ttttggtttg atttcgaaaa tgacggagct gatgccatca   3900
ttctcctggt tcctctcata gtacaactgg cacttcttcg agaggctcaa ttcctcgtag   3960
ttcccgtcca agatattcgg caacaagagc ccgtaccgct cacggagcat caagtcgtgg   4020
ccctggttgt tcaacttgtt gatgaagtcc gaggtcaaga caatcaactg gatgtcgatg   4080
atctggtgcg ggaacaagtt cttgcatttt agctcgatga agtcgtacaa ctcacacgtc   4140
gagatatact cctgttcctc cttcaagagc cggatccgca agagcttgtg cttcaagtag   4200
tcgttg                                                              4206
```

<210> SEQ ID NO 82
<211> LENGTH: 4145
<212> TYPE: DNA
<213> ORGANISM: Candida tropicalis

<400> SEQUENCE: 82

```
tatatgatat atgatatatc ttcctgtgta attattattc gtattcgtta atacttacta     60
catttttttt tctttattta tgaagaaaag gagagttcgt aagttgagtt gagtagaata    120
ggctgttgtg catacgggga gcagaggaga gtatccgacg aggaggaact gggtgaaatt    180
tcatctatgc tgttgcgtcc tgtactgtac tgtaaatctt agatttccta gaggttgttc    240
tagcaaataa agtgtttcaa gatacaattt tacaggcaag ggtaaaggat caactgatta    300
gcggaagatt ggtgttgcct gtggggttct tttatttttc atatgatttc tttgcgcgag    360
taacatgtgc caatctagtt tatgattagc gtacctccac aattggcatc ttggacgggc    420
gtgttttgtc ttaccccaag ccttatttag ttccacagtc tcgacggtgt ctcgccgatg    480
tcttctccca cccctcgcag gaatcattcg aagttgttgg gggatctcct ccgcagttta    540
tgttcatgtc tttcccactt tggttgtgat tggggtagcg tagtgagttg gtgattttct    600
tttttcgcag gtgtctccga tatcgaagtt tgatgaatat aggagccaga tcagcatggt    660
atattgcctt tgtagataga gatgttgaac aacaactagc tgaattacac accaccgcta    720
aacgatgcgc acagggtgtc accgccaact gacgttgggt ggagttgttg ttggcagggc    780
catattgcta aacgaagaga agtagcacaa aacccaaggt taagaacaat taaaaaaatt    840
catacgacaa ttccacagcc atttacataa tcaacagcga caaatgagac agaaaaaact    900
ttcaacattt caaagttccc tttttcctat tacttctttt tttctttcct tcctttcatt    960
tcctttcctt ctgcttttat tactttacca gtcttttgct tgtttttgca attcctcatc   1020
ctcctcctca ccatggcttt agacaagtta gatttgtatg tcatcataac attggtggtc   1080
gctgtggccg cctattttgc taagaaccag ttccttgatc agccccagga caccgggttc   1140
ctcaacacgg acagcggaag caactccaga gacgtcttgc tgacattgaa gaagaataat   1200
aaaaacacgt tgttgttgtt tgggtcccag accggtacgg cagaagatta cgccaacaaa   1260
ttgtcaagag aattgcactc cagatttggc ttgaaaacca tggttgcaga tttcgctgat   1320
tacgattggg ataacttcgg agatatcacc gaagatatct tggtgttttt catcgttgcc   1380
acctacggtg agggtgaacc taccgacaat gccgacgagt tccacacctg gttgactgaa   1440
```

-continued

```
gaagctgaca ctttgagtac tttgagatat accgtgttcg ggttgggtaa ctccacctac   1500
gagttcttca atgctattgg tagaaagttt gacagattgt tgagtgagaa aggtggtgac   1560
agatttgctg aatatgctga aggtgacgac ggcactggca ccttggacga agatttcatg   1620
gcctggaagg ataatgtctt tgacgccttg aagaatgact tgaactttga agaaaaggaa   1680
ttgaagtacg aaccaaacgt gaaattgact gagagagatg acttgtctgc tgccgactcc   1740
caagtttcct tgggtgagcc aaacaagaag tacatcaact ccgagggcat cgacttgacc   1800
aagggtccat tcgaccacac ccacccatac ttggccagga tcaccgagac cagagagttg   1860
ttcagctcca aggaaagaca ctgtattcac gttgaatttg acatttctga atcgaacttg   1920
aaatacacca ccggtgacca tctagccatc tggccatcca actccgacga aaacatcaag   1980
caatttgcca agtgtttcgg attggaagat aaactcgaca ctgttattga attgaaggca   2040
ttggactcca cttacaccat tccattccca actccaatta cttacggtgc tgtcattaga   2100
caccatttag aaatctccgg tccagtctcg agacaattct tttgtcgat tgctgggttt   2160
gctcctgatg aagaaacaaa gaagactttc accagacttg gtggtgacaa acaagaattc   2220
gccaccaagg ttacccgcag aaagttcaac attgccgatg ccttgttata ttcctccaac   2280
aacactccat ggtccgatgt tccttttgag ttccttattg aaaacatcca acacttgact   2340
ccacgttact actccatttc ttcttcgtcg ttgagtgaaa aacaactcat caatgttact   2400
gcagtcgttg aggccgaaga agaagccgat ggcagaccag tcactggtgt tgttaccaac   2460
ttgttgaaga acattgaaat tgcgcaaaac aagactggcg aaaagccact tgttcactac   2520
gatttgagcg gcccaagagg caagttcaac aagttcaagt tgccagtgca cgtgagaaga   2580
tccaacttta agttgccaaa gaactccacc accccagtta tcttgattgg tccaggtact   2640
ggtgttgccc cattgagagg tttcgttaga gaaagagttc aacaagtcaa gaatggtgtc   2700
aatgttggca agactttgtt gttttatggt tgcagaaact ccaacgagga ctttttgtac   2760
aagcaagaat gggccgagta cgcttctgtt ttgggtgaaa actttgagat gttcaatgcc   2820
ttctctagac aagacccatc caagaaggtt tacgtccagg ataagatttt agaaaacagc   2880
caacttgtgc acgaattgtt gaccgaaggt gccattatct acgtctgtgg tgacgccagt   2940
agaatggcca gagacgtcca gaccacgatc tccaagattg ttgccaaaag cagagaaatc   3000
agtgaagaca aggccgctga attggtcaag tcctggaaag tccaaaatag ataccaagaa   3060
gatgtttggt agactcaaac gaatctctct ttctcccaac gcatttatga atattctcat   3120
tgaagtttta catatgttct atatttcatt ttttttttat tatattacga aacataggtc   3180
aactatatat acttgattaa atgttataga aacaataatt attatctact cgtctacttc   3240
tttggcattg gcattggcat tggcattggc attgccgttg ccgttggtaa tgccgggata   3300
tttagtacag tatctccaat ccggatttga gctattgtaa atcagctgca agtcattctc   3360
caccttcaac cagtacttat acttcatctt tgacttcaag tccaagtcat aaatattaca   3420
agttagcaag aacttctggc catccacaat atagacgtta ttcacgttat tatgcgacgt   3480
atggatatgg ttatccttat tgaacttctc aaacttcaaa aacaacccca cgtcccgcaa   3540
cgtcattatc aacgacaagt tctgactcac gtcgtcggag ctcgtcaagt tctcaattag   3600
atcgttcttg ttattgatct tctggtactt tctcaactgc tggaacacat tgtcctcgtt   3660
gttcaaatag atcttgaaca acttcttcaa gggaatcaac ttttcgatct gggccaagat   3720
ttccgccggg atcttcagaa acaagtcctg caacccctgg tcgatggtct cggggtacaa   3780
caagtctaag ggcagaagt gtctaggcac gtgtttcaac tggttcaagg aacatgttcg   3840
```

-continued

```
acagtagttc gagttatagt tatcgtacaa ccactttggc ttgatttcga aaatgacgga   3900

gctgatccca tcattctcct ggttcctttc atagtacaac tggcatttct tcgagagact   3960

caactcctcg tagttcccgt ccaagatatt cggcaacaag agcccgtagc gctcacggag   4020

catcaagtcg tggccctggt tgttcaactt gttgatgaag tccgatgtca agacaatcaa   4080

ctggatgtcg atgatctggt gcggaaacaa gttcttgcac tttagctcga tgaagtcgta   4140

caact                                                                4145


<210> SEQ ID NO 83
<211> LENGTH: 679
<212> TYPE: PRT
<213> ORGANISM: CANDIDATROPICALIS

<400> SEQUENCE: 83

Met Ala Leu Asp Lys Leu Asp Leu Tyr Val Ile Ile Thr Leu Val Val
1               5                   10                  15

Ala Val Ala Ala Tyr Phe Ala Lys Asn Gln Phe Leu Asp Gln Pro Gln
            20                  25                  30

Asp Thr Gly Phe Leu Asn Thr Asp Ser Gly Ser Asn Ser Arg Asp Val
        35                  40                  45

Leu Leu Thr Leu Lys Lys Asn Asn Lys Asn Thr Leu Leu Leu Phe Gly
    50                  55                  60

Ser Gln Thr Gly Thr Ala Glu Asp Tyr Ala Asn Lys Leu Ser Arg Glu
65                  70                  75                  80

Leu His Ser Arg Phe Gly Leu Lys Thr Met Val Ala Asp Phe Ala Asp
                85                  90                  95

Tyr Asp Trp Asp Asn Phe Gly Asp Ile Thr Glu Asp Ile Leu Val Phe
            100                 105                 110

Phe Ile Val Ala Thr Tyr Gly Glu Gly Glu Pro Thr Asp Asn Ala Asp
        115                 120                 125

Glu Phe His Thr Trp Leu Thr Glu Glu Ala Asp Thr Leu Ser Thr Leu
    130                 135                 140

Lys Tyr Thr Val Phe Gly Leu Gly Asn Ser Thr Tyr Glu Phe Phe Asn
145                 150                 155                 160

Ala Ile Gly Arg Lys Phe Asp Arg Leu Leu Ser Glu Lys Gly Gly Asp
                165                 170                 175

Arg Phe Ala Glu Tyr Ala Glu Gly Asp Asp Gly Thr Gly Thr Leu Asp
            180                 185                 190

Glu Asp Phe Met Ala Trp Lys Asp Asn Val Phe Asp Ala Leu Lys Asn
        195                 200                 205

Asp Leu Asn Phe Glu Glu Lys Glu Leu Lys Tyr Glu Pro Asn Val Lys
    210                 215                 220

Leu Thr Glu Arg Asp Asp Leu Ser Ala Ala Asp Ser Gln Val Ser Leu
225                 230                 235                 240

Gly Glu Pro Asn Lys Lys Tyr Ile Asn Ser Glu Gly Ile Asp Leu Thr
                245                 250                 255

Lys Gly Pro Phe Asp His Thr His Pro Tyr Leu Ala Arg Ile Thr Glu
            260                 265                 270

Thr Arg Glu Leu Phe Ser Ser Lys Asp Arg His Cys Ile His Val Glu
        275                 280                 285

Phe Asp Ile Ser Glu Ser Asn Leu Lys Tyr Thr Thr Gly Asp His Leu
    290                 295                 300
```

-continued

```
Ala Ile Trp Pro Ser Asn Ser Asp Glu Asn Ile Lys Gln Phe Ala Lys
305                 310                 315                 320

Cys Phe Gly Leu Glu Asp Lys Leu Asp Thr Val Ile Glu Leu Lys Ala
                325                 330                 335

Leu Asp Ser Thr Tyr Thr Ile Pro Phe Pro Thr Pro Ile Thr Tyr Gly
            340                 345                 350

Ala Val Ile Arg His His Leu Glu Ile Ser Gly Pro Val Ser Arg Gln
        355                 360                 365

Phe Phe Leu Ser Ile Ala Gly Phe Ala Pro Asp Glu Glu Thr Lys Lys
    370                 375                 380

Ala Phe Thr Arg Leu Gly Gly Asp Lys Gln Glu Phe Ala Ala Lys Val
385                 390                 395                 400

Thr Arg Arg Lys Phe Asn Ile Ala Asp Ala Leu Leu Tyr Ser Ser Asn
                405                 410                 415

Asn Ala Pro Trp Ser Asp Val Pro Phe Glu Phe Leu Ile Glu Asn Val
            420                 425                 430

Pro His Leu Thr Pro Arg Tyr Tyr Ser Ile Ser Ser Ser Ser Leu Ser
        435                 440                 445

Glu Lys Gln Leu Ile Asn Val Thr Ala Val Val Glu Ala Glu Glu Glu
    450                 455                 460

Ala Asp Gly Arg Pro Val Thr Gly Val Val Thr Asn Leu Leu Lys Asn
465                 470                 475                 480

Val Glu Ile Val Gln Asn Lys Thr Gly Glu Lys Pro Leu Val His Tyr
                485                 490                 495

Asp Leu Ser Gly Pro Arg Gly Lys Phe Asn Lys Phe Lys Leu Pro Val
            500                 505                 510

His Val Arg Arg Ser Asn Phe Lys Leu Pro Lys Asn Ser Thr Thr Pro
        515                 520                 525

Val Ile Leu Ile Gly Pro Gly Thr Gly Val Ala Pro Leu Arg Gly Phe
    530                 535                 540

Val Arg Glu Arg Val Gln Gln Val Lys Asn Gly Val Asn Val Gly Lys
545                 550                 555                 560

Thr Leu Leu Phe Tyr Gly Cys Arg Asn Ser Asn Glu Asp Phe Leu Tyr
                565                 570                 575

Lys Gln Glu Trp Ala Glu Tyr Ala Ser Val Leu Gly Glu Asn Phe Glu
            580                 585                 590

Met Phe Asn Ala Phe Ser Arg Gln Asp Pro Ser Lys Lys Val Tyr Val
        595                 600                 605

Gln Asp Lys Ile Leu Glu Asn Ser Gln Leu Val His Glu Leu Leu Thr
    610                 615                 620

Glu Gly Ala Ile Ile Tyr Val Cys Gly Asp Ala Ser Arg Met Ala Arg
625                 630                 635                 640

Asp Val Gln Thr Thr Ile Ser Lys Ile Val Ala Lys Ser Arg Glu Ile
                645                 650                 655

Ser Glu Asp Lys Ala Ala Glu Leu Val Lys Ser Trp Lys Val Gln Asn
            660                 665                 670

Arg Tyr Gln Glu Asp Val Trp
        675
```

<210> SEQ ID NO 84
<211> LENGTH: 679
<212> TYPE: PRT
<213> ORGANISM: CANDIDATROPICALIS

-continued

<400> SEQUENCE: 84

```
Met Ala Leu Asp Lys Leu Asp Leu Tyr Val Ile Ile Thr Leu Val Val
1               5                   10                  15

Ala Val Ala Ala Tyr Phe Ala Lys Asn Gln Phe Leu Asp Gln Pro Gln
            20                  25                  30

Asp Thr Gly Phe Leu Asn Thr Asp Ser Gly Ser Asn Ser Arg Asp Val
        35                  40                  45

Leu Leu Thr Leu Lys Lys Asn Asn Lys Asn Thr Leu Leu Leu Phe Gly
    50                  55                  60

Ser Gln Thr Gly Thr Ala Glu Asp Tyr Ala Asn Lys Leu Ser Arg Glu
65                  70                  75                  80

Leu His Ser Arg Phe Gly Leu Lys Thr Met Val Ala Asp Phe Ala Asp
                85                  90                  95

Tyr Asp Trp Asp Asn Phe Gly Asp Ile Thr Glu Asp Ile Leu Val Phe
            100                 105                 110

Phe Ile Val Ala Thr Tyr Gly Glu Gly Glu Pro Thr Asp Asn Ala Asp
        115                 120                 125

Glu Phe His Thr Trp Leu Thr Glu Glu Ala Asp Thr Leu Ser Thr Leu
    130                 135                 140

Arg Tyr Thr Val Phe Gly Leu Gly Asn Ser Thr Tyr Glu Phe Phe Asn
145                 150                 155                 160

Ala Ile Gly Arg Lys Phe Asp Arg Leu Leu Ser Glu Lys Gly Gly Asp
                165                 170                 175

Arg Phe Ala Glu Tyr Ala Glu Gly Asp Asp Gly Thr Gly Thr Leu Asp
            180                 185                 190

Glu Asp Phe Met Ala Trp Lys Asp Asn Val Phe Asp Ala Leu Lys Asn
        195                 200                 205

Asp Leu Asn Phe Glu Glu Lys Glu Leu Lys Tyr Glu Pro Asn Val Lys
    210                 215                 220

Leu Thr Glu Arg Asp Asp Leu Ser Ala Ala Asp Ser Gln Val Ser Leu
225                 230                 235                 240

Gly Glu Pro Asn Lys Lys Tyr Ile Asn Ser Glu Gly Ile Asp Leu Thr
                245                 250                 255

Lys Gly Pro Phe Asp His Thr His Pro Tyr Leu Ala Arg Ile Thr Glu
            260                 265                 270

Thr Arg Glu Leu Phe Ser Ser Lys Glu Arg His Cys Ile His Val Glu
        275                 280                 285

Phe Asp Ile Ser Glu Ser Asn Leu Lys Tyr Thr Thr Gly Asp His Leu
    290                 295                 300

Ala Ile Trp Pro Ser Asn Ser Asp Glu Asn Ile Lys Gln Phe Ala Lys
305                 310                 315                 320

Cys Phe Gly Leu Glu Asp Lys Leu Asp Thr Val Ile Glu Leu Lys Ala
                325                 330                 335

Leu Asp Ser Thr Tyr Thr Ile Pro Phe Pro Thr Pro Ile Thr Tyr Gly
            340                 345                 350

Ala Val Ile Arg His His Leu Glu Ile Ser Gly Pro Val Ser Arg Gln
        355                 360                 365

Phe Phe Leu Ser Ile Ala Gly Phe Ala Pro Asp Glu Glu Thr Lys Lys
    370                 375                 380

Thr Phe Thr Arg Leu Gly Gly Asp Lys Gln Glu Phe Ala Thr Lys Val
385                 390                 395                 400

Thr Arg Arg Lys Phe Asn Ile Ala Asp Ala Leu Leu Tyr Ser Ser Asn
                405                 410                 415
```

-continued

```
Asn Thr Pro Trp Ser Asp Val Pro Phe Glu Phe Leu Ile Glu Asn Ile
            420                 425                 430

Gln His Leu Thr Pro Arg Tyr Tyr Ser Ile Ser Ser Ser Ser Leu Ser
        435                 440                 445

Glu Lys Gln Leu Ile Asn Val Thr Ala Val Val Glu Ala Glu Glu Glu
    450                 455                 460

Ala Asp Gly Arg Pro Val Thr Gly Val Val Thr Asn Leu Leu Lys Asn
465                 470                 475                 480

Ile Glu Ile Ala Gln Asn Lys Thr Gly Glu Lys Pro Leu Val His Tyr
                485                 490                 495

Asp Leu Ser Gly Pro Arg Gly Lys Phe Asn Lys Phe Lys Leu Pro Val
            500                 505                 510

His Val Arg Arg Ser Asn Phe Lys Leu Pro Lys Asn Ser Thr Thr Pro
        515                 520                 525

Val Ile Leu Ile Gly Pro Gly Thr Gly Val Ala Pro Leu Arg Gly Phe
    530                 535                 540

Val Arg Glu Arg Val Gln Gln Val Lys Asn Gly Val Asn Val Gly Lys
545                 550                 555                 560

Thr Leu Leu Phe Tyr Gly Cys Arg Asn Ser Asn Glu Asp Phe Leu Tyr
                565                 570                 575

Lys Gln Glu Trp Ala Glu Tyr Ala Ser Val Leu Gly Glu Asn Phe Glu
            580                 585                 590

Met Phe Asn Ala Phe Ser Arg Gln Asp Pro Ser Lys Lys Val Tyr Val
        595                 600                 605

Gln Asp Lys Ile Leu Glu Asn Ser Gln Leu Val His Glu Leu Leu Thr
    610                 615                 620

Glu Gly Ala Ile Ile Tyr Val Cys Gly Asp Ala Ser Arg Met Ala Arg
625                 630                 635                 640

Asp Val Gln Thr Thr Ile Ser Lys Ile Val Ala Lys Ser Arg Glu Ile
                645                 650                 655

Ser Glu Asp Lys Ala Ala Glu Leu Val Lys Ser Trp Lys Val Gln Asn
            660                 665                 670

Arg Tyr Gln Glu Asp Val Trp
        675
```

<210> SEQ ID NO 85
<211> LENGTH: 4115
<212> TYPE: DNA
<213> ORGANISM: Candida tropicalis

<400> SEQUENCE: 85

```
catatgcgct aatcttcttt ttctttttat cacaggagaa actatcccac ccccacttcg      60

aaacacaatg acaactcctg cgtaacttgc aaattcttgt ctgactaatt gaaaactccg     120

gacgagtcag acctccagtc aaacggacag acagacaaac acttggtgcg atgttcatac     180

ctacagacat gtcaacgggt gttagacgac ggtttcttgc aaagacaggt gttggcatct     240

cgtacgatgg caactgcagg aggtgtcgac ttctccttta ggcaatagaa aaagactaag     300

agaacagcgt ttttacaggt tgcattggtt aatgtagtat ttttttagtc ccagcattct     360

gtgggttgct ctgggtttct agaataggaa atcacaggag aatgcaaatt cagatggaag     420

aacaaagaga taaaaaaacaa aaaaaaactg agttttgcac caatagaatg tttgatgata     480

tcatccactc gctaaacgaa tcatgtgggt gatcttctct ttagttttgg tctatcataa     540

aacacatgaa agtgaaatcc aaatacacta cactccgggt attgtccttc gttttacaga     600
```

-continued

```
tgtctcattg tcttactttt gaggtcatag gagttgcctg tgagagatca cagagattat    660
cacactcaca tttatcgtag tttcctatct catgctgtgt gtctctggtt ggttcatgag    720
tttggattgt tgtacattaa aggaatcgct ggaaagcaaa gctaactaaa ttttctttgt    780
cacaggtaca ctaacctgta aaacttcact gccacgccag tctttcctga ttgggcaagt    840
gcacaaacta caacctgcaa aacagcactc cgcttgtcac aggttgtctc ctctcaacca    900
acaaaaaaat aagattaaac tttctttgct catgcatcaa tcggagttat ctctgaaaga    960
gttgcctttg tgtaatgtgt gccaaactca aactgcaaaa ctaaccacag aatgatttcc   1020
ctcacaatta tataaactca cccacatttc cacagaccgt aatttcatgt ctcactttct   1080
cttttgctct tcttttactt agtcaggttt gataacttcc ttttttatta ccctatctta   1140
tttatttatt tattcattta taccaaccaa ccaaccatgg ccacacaaga aatcatcgat   1200
tctgtacttc cgtacttgac caaatggtac actgtgatta ctgcagcagt attagtcttc   1260
cttatctcca caaacatcaa gaactacgtc aaggcaaaga aattgaaatg tgtcgatcca   1320
ccatacttga aggatgccgg tctcactggt attctgtctt tgatcgccgc catcaaggcc   1380
aagaacgacg gtagattggc taactttgcc gatgaagttt tcgacgagta cccaaaccac   1440
accttctact tgtctgttgc cggtgctttg aagattgtca tgactgttga cccagaaaac   1500
atcaaggctg tcttggccac ccaattcact gacttctcct tgggtaccag acacgcccac   1560
tttgctcctt tgttgggtga cggtatcttc accttggacg gagaaggttg gaagcactcc   1620
agagctatgt tgagaccaca gtttgctaga gaccagattg gacacgttaa agccttggaa   1680
ccacacatcc aaatcatggc taagcagatc aagttgaacc agggaaagac tttcgatatc   1740
caagaattgt tctttagatt taccgtcgac accgctactg agttcttgtt tggtgaatcc   1800
gttcactcct tgtacgatga aaaattgggc atcccaactc caaacgaaat cccaggaaga   1860
gaaaactttg ccgctgcttt caacgtttcc caacactact tggccaccag aagttactcc   1920
cagacttttt actttttgac caaccctaag gaattcagag actgtaacgc caaggtccac   1980
cacttggcca agtactttgt caacaaggcc ttgaacttta ctcctgaaga actcgaagag   2040
aaatccaagt ccggttacgt tttcttgtac gaattggtta agcaaaccag agatccaaag   2100
gtcttgcaag atcaattgtt gaacattatg gttgccggaa gagacaccac tgccggtttg   2160
ttgtcctttg ctttgtttga attggctaga cacccagaga tgtggtccaa gttgagagaa   2220
gaaatcgaag ttaactttgg tgttggtgaa gactcccgcg ttgaagaaat taccttcgaa   2280
gccttgaaga gatgtgaata cttgaaggct atccttaacg aaaccttgcg tatgtaccca   2340
tctgttcctg tcaactttag aaccgccacc agagacacca ctttgccaag aggtggtggt   2400
gctaacggta ccgacccaat ctacattcct aaaggctcca ctgttgctta cgttgtctac   2460
aagacccacc gtttggaaga atactacggt aaggacgcta acgacttcag accagaaaga   2520
tggtttgaac catctactaa gaagttgggc tgggcttatg ttccattcaa cggtggtcca   2580
agagtctgct tgggtcaaca attcgccttg actgaagctt cttatgtgat cactagattg   2640
gcccagatgt ttgaaactgt ctcatctgat ccaggtctcg aataccctcc accaaagtgt   2700
attcacttga ccatgagtca caacgatggt gtctttgtca agatgtaaag tagtcgatgc   2760
tgggtattcg attacatgtg tataggaaga ttttggtttt ttattcgttc ttttttttaa   2820
tttttgttaa attagtttag agatttcatt aatacataga tgggtgctat ttccgaaact   2880
ttacttctat cccctgtatc ccttattatc cctctcagtc acatgattgc tgtaattgtc   2940
```

-continued

```
gtgcaggaca caaactccct aacggactta aaccataaac aagctcagaa ccataagccg   3000

acatcactcc ttcttctctc ttctccaacc aatagcatgg acagacccac cctcctatcc   3060

gaatcgaaga cccttattga ctccataccc acctggaagc cctcaagcc acacacgtca   3120

tccagcccac ccatcaccac atccctctac tcgacaacgt ccaaagacgg cgagttctgg   3180

tgtgcccgga aatcagccat cccggccaca tacaagcagc cgttgattgc gtgcatactc   3240

ggcgagccca caatgggagc cacgcattcg gaccatgaag caaagtacat tcacgagatc   3300

acgggtgttt cagtgtcgca gattgagaag ttcgacgatg gatggaagta cgatctcgtt   3360

gcggattacg acttcggtgg gttgttatct aaacgaagat tctatgagac gcagcatgtg   3420

tttcggttcg aggattgtgc gtacgtcatg agtgtgcctt ttgatggacc caaggaggaa   3480

ggttacgtgg ttgggacgta cagatccatt gaaaggttga gctggggtaa agacggggac   3540

gtggagtgga ccatggcgac gacgtcggat cctggtgggt ttatcccgca atggataact   3600

cgattgagca tccctggagc aatcgcaaaa gatgtgccta gtgtattaaa ctacatacag   3660

aaataaaaac gtgtcttgat tcattggttt ggttcttgtt gggttccgag ccaatatttc   3720

acatcatctc ctaaattctc caagaatccc aacgtagcgt agtccagcac gccctctgag   3780

atcttattta atatcgactt ctcaaccacc ggtggaatcc cgttcagacc attgttacct   3840

gtagtgtgtt tgctcttgtt cttgatgaca atgatgtatt tgtcacgata cctgaaataa   3900

taaaacatcc agtcattgag cttattactc gtgaacttat gaaagaactc attcaagccg   3960

ttcccaaaaa acccagaatt gaagatcttg ctcaactggt catgcaagta gtagatcgcc   4020

atgatctgat actttaccaa gctatcctct ccaagttctc ccacgtacgg caagtacggc   4080

aacgagctct ggaagctttg ttgtttgggg tcata                              4115
```

<210> SEQ ID NO 86
<211> LENGTH: 3948
<212> TYPE: DNA
<213> ORGANISM: Candida tropicalis

<400> SEQUENCE: 86

```
gacctgtgac gcttccggtg tcttgccacc agtctccaag ttgaccgacg cccaagtcat     60

gtaccacttt atttccggtt acacttccaa gatggctggt actgaagaag gtgtcacgga    120

accacaagct actttctccg cttgtttcgg tcaaccattc ttggtgttgc acccaatgaa    180

gtacgctcaa caattgtctg acaagatctc gcaacacaag gctaacgcct ggttgttgaa    240

caccggttgg gttggttctt ctgctgctag aggtggtaag agatgctcat tgaagtacac    300

cagagccatt ttggacgcta tccactctgg tgaattgtcc aaggttgaat acgaaacttt    360

cccagtcttc aacttgaatg tcccaacctc ctgtccaggt gtcccaagtg aaatcttgaa    420

cccaaccaag gcctggaccg gaaggtgttg actccttcaa caaggaaatc aagtctttgg    480

ctggtaagtt tgctgaaaac ttcaagacct atgctgacca agctaccgct gaagtgagag    540

ctgcaggtcc agaagcttaa agatatttat tcattattta gtttgcctat ttatttctca    600

ttacccatca tcattcaaca ctatatataa agttacttcg gatatcattg taatcgtgcg    660

tgtcgcaatt ggatgatttg gaactgcgct tgaaacggat tcatgcacga agcggagata    720

aaagattacg taatttatct cctgagacaa ttttagccgt gttcacacgc ccttctttgt    780

tctgagcgaa ggataaataa ttagacttcc acagctcatt ctaatttccg tcacgcgaat    840

attgaagggg ggtacatgtg gccgctgaat gtgggggcag taaacgcagt ctctcctctc    900

ccaggaatag tgcaacggag gaaggataac ggatagaaag cggaatgcga ggaaaatttt    960
```

-continued

```
gaacgcgcaa gaaaagcaat atccgggcta ccaggttttg agccagggaa cacactccta   1020
tttctgctca atgactgaac atagaaaaaa caccaagacg caatgaaacg cacatggaca   1080
tttagacctc cccacatgtg atagtttgtc ttaacagaaa agtataataa gaacccatgc   1140
cgtccctttt ctttcgccgc ttcaactttt ttttttttat cttacacaca tcacgaccat   1200
gactgtacac gatattatcg ccacatactt caccaaatgg tacgtgatag taccactcgc   1260
tttgattgct tatagagtcc tcgactactt ctatggcaga tacttgatgt acaagcttgg   1320
tgctaaacca tttttccaga aacagacaga cggctgtttc ggattcaaag ctccgcttga   1380
attgttgaag aagaagagcg acggtaccct catagacttc acactccagc gtatccacga   1440
tctcgatcgt cccgatatcc caactttcac attcccggtc ttttccatca accttgtcaa   1500
tacccttgag ccggagaaca tcaaggccat cttggccact cagttcaacg atttctcctt   1560
gggtaccaga cactcgcact ttgctccttt gttgggtgat ggtatcttta cgttggatgg   1620
cgccggctgg aagcacagca gatctatgtt gagaccacag tttgccagag aacagatttc   1680
ccacgtcaag ttgttggagc cacacgttca ggtgttcttc aaacacgtca gaaaggcaca   1740
gggcaagact tttgacatcc aggaattgtt tttcagattg accgtcgact ccgccaccga   1800
gtttttgttt ggtgaatccg ttgagtcctt gagagatgaa tctatcggca tgtccatcaa   1860
tgcgcttgac tttgacggca aggctggctt tgctgatgct tttaactatt cgcagaatta   1920
tttggcttcg agagcggtta tgcaacaatt gtactgggtg ttgaacggga aaaagtttaa   1980
ggagtgcaac gctaaagtgc acaagtttgc tgactactac gtcaacaagg ctttggactt   2040
gacgcctgaa caattggaaa agcaggatgg ttatgtgttt ttgtacgaat tggtcaagca   2100
aaccagagac aagcaagtgt tgagagacca attgttgaac atcatggttg ctggtagaga   2160
caccaccgcc ggtttgttgt cgtttgtttt ctttgaattg gccagaaacc cagaagttac   2220
caacaagttg agagaagaaa ttgaggacaa gtttggactc ggtgagaatg ctagtgttga   2280
agacatttcc tttgagtcgt tgaagtcctg tgaatacttg aaggctgttc tcaacgaaac   2340
cttgagattg tacccatccg tgccacagaa tttcagagtt gccaccaaga acactaccct   2400
cccaagaggt ggtggtaagg acgggttgtc tcctgttttg gtgagaaagg gtcagaccgt   2460
tatttacggt gtctacgcag cccacagaaa cccagctgtt tacggtaagg acgctcttga   2520
gtttagacca gagagatggt ttgagccaga gacaaagaag cttggctggg ccttcctccc   2580
attcaacggt ggtccaagaa tctgtttggg acagcagttt gccttgacag aagcttcgta   2640
tgtcactgtc aggttgctcc aggagtttgc acacttgtct atggacccag acaccgaata   2700
tccacctaag aaaatgtcgc atttgaccat gtcgcttttc gacggtgcca atattgagat   2760
gtattagagg gtcatgtgtt attttgattg tttagtttgt aattactgat taggttaatt   2820
catggattgt tatttattga taggggtttg cgcgtgttgc attcacttgg gatcgttcca   2880
ggttgatgtt tccttccatc ctgtcgagtc aaaaggagtt ttgttttgta actccggacg   2940
atgttttaaa tagaaggtcg atctccatgt gattgttttg actgttactg tgattatgta   3000
atctgcggac gttatacaag catgtgattg tggttttgca gccttttgca cgacaaatga   3060
tcgtcagacg attacgtaat ctttgttaga ggggtaaaaa aaaacaaaat ggcagccaga   3120
atttcaaaca ttctgcaaac aatgcaaaaa atgggaaact ccaacagaca aaaaaaaaaa   3180
ctccgcagca ctccgaaccc acagaacaat ggggcgccag aattattgac tattgtgact   3240
tttttacgct aacgctcatt gcagtgtagt gcgtcttaca cggggtattg ctttctacaa   3300
```

-continued

```
tgcaagggca cagttgaagg tttgcaccta acgttgcccc gtgtcaactc aatttgacga   3360

gtaacttcct aagctcgaat tatgcagctc gtgcgtcaac ctatgtgcag gaaagaaaaa   3420

atccaaaaaa atcgaaaatg cgactttcga ttttgaataa accaaaaaga aaaatgtcgc   3480

acttttttct cgctctcgct ctctcgaccc aaatcacaac aaatcctcgc gcgcagtatt   3540

tcgacgaaac cacaacaaat aaaaaaaaca aattctacac cacttctttt tcttcaccag   3600

tcaacaaaaa acaacaaatt atacaccatt tcaacgattt ttgctcttat aaatgctata   3660

taatggttta attcaactca ggtatgttta ttttactgtt ttcagctcaa gtatgttcaa   3720

atactaacta cttttgatgt ttgtcgcttt tctagaatca aaacaacgcc cacaacacgc   3780

cgagcttgtc gaatagacgg tttgtttact cattagatgg tcccagatta cttttcaagc   3840

caaagtctct cgagttttgt ttgctgtttc cccaattcct aactatgaag ggtttttata   3900

aggtccaaag accccaaggc atagtttttt tggttccttc ttgtcgtg               3948
```

<210> SEQ ID NO 87
<211> LENGTH: 3755
<212> TYPE: DNA
<213> ORGANISM: Candida tropicalis

<400> SEQUENCE: 87

```
gctcaacaat tgtctgacaa gatctcgcaa cacaaggcta acgcctggtt gttgaacact     60

ggttgggttg gttcttctgc tgctagaggt ggtaagagat gttcattgaa gtacaccaga    120

gccattttgg acgctatcca ctctggtgaa ttgtccaagg ttgaatacga gactttccca    180

gtcttcaact tgaatgtccc aacctcctgc ccaggtgtcc caagtgaaat cttgaaccca    240

accaaggcct ggaccgaagg tgttgactcc ttcaacaagg aaatcaagtc tttggctggt    300

aagtttgctg aaaacttcaa gacctatgct gaccaagcta ccgctgaagt tagagctgca    360

ggtccagaag cttaaagata tttattcact atttagtttg cctatttatt tctcatcacc    420

catcatcatt caacaatata tataaagtta tttcggaact catatatcat tgtaatcgtg    480

cgtgttgcaa ttgggtaatt tgaaactgta gttggaacgg attcatgcac gatgcggaga    540

taacacgaga ttatctccta agacaatttt ggcctcattc acacgccctt cttctgagct    600

aaggataaat aattagactt cacaagttca ttaaaatatc cgtcacgcga aaactgcaac    660

aataaggaag gggggggtag acgtagccga tgaatgtggg gtgccagtaa acgcagtctc    720

tctctccccc cccccccccc ccccctcagg aatagtacaa cgggggaagg ataacggata    780

gcaagtggaa tgcgaggaaa attttgaatg cgcaaggaaa gcaatatccg ggctatcagg    840

ttttgagcca ggggacacac tcctcttctg cacaaaaact taacgtagac aaaaaaaaaa    900

aactccacca agacacaatg aatcgcacat ggacatttag acctccccac atgtgaaagc    960

ttctctggcg aaagcaaaaa aagtataata aggacccatg ccttccctct tcctgggccg   1020

tttcaacttt ttctttttct ttgtctatca acacacacac acctcacgac catgactgca   1080

caggatatta tcgccacata catcaccaaa tggtacgtga tagtaccact cgctttgatt   1140

gcttataggg tcctcgacta cttttacggc agatacttga tgtacaagct tggtgctaaa   1200

ccgtttttcc agaaacaaac agacggttat ttcggattca aagctccact tgaattgtta   1260

aaaaagaaga gtgacggtac cctcatagac ttcactctcg agcgtatcca agcgctcaat   1320

cgtccagata tcccaacttt tacattccca atcttttcca tcaaccttat cagcacccctt   1380

gagccggaga acatcaaggc tatcttggcc acccagttca acgatttctc cttgggcacc   1440

agacactcgc actttgctcc tttgttgggc gatggtatct ttaccttgga cggtgccggc   1500
```

-continued

```
tggaagcaca gcagatctat gttgagacca cagtttgcca gagaacagat ttcccacgtc   1560
aagttgttgg agccacacat gcaggtgttc ttcaagcacg tcagaaaggc acagggcaag   1620
acttttgaca tccaagaatt gtttttcaga ttgaccgtcg actccgccac tgagtttttg   1680
tttggtgaat ccgttgagtc cttgagagat gaatctattg ggatgtccat caatgcactt   1740
gactttgacg gcaaggctgg ctttgctgat gcttttaact actcgcagaa ctatttggct   1800
tcgagagcgg ttatgcaaca attgtactgg gtgttgaacg ggaaaaagtt taaggagtgc   1860
aacgctaaag tgcacaagtt tgctgactat tacgtcagca aggctttgga cttgacacct   1920
gaacaattgg aaaagcagga tggttatgtg ttcttgtacg agttggtcaa gcaaaccaga   1980
gacaggcaag tgttgagaga ccagttgttg aacatcatgg ttgccggtag agacaccacc   2040
gccggtttgt tgtcgtttgt tttctttgaa ttggccagaa acccagaggt gaccaacaag   2100
ttgagagaag aaatcgagga caagtttggt cttggtgaga atgctcgtgt tgaagacatt   2160
tcctttgagt cgttgaagtc atgtgaatac ttgaaggctg ttctcaacga aactttgaga   2220
ttgtacccat ccgtgccaca gaatttcaga gttgccacca aaaacactac ccttccaagg   2280
ggaggtggta aggacgggtt atctcctgtt ttggtcagaa agggtcaaac cgttatgtac   2340
ggtgtctacg ctgcccacag aaacccagct gtctacggta aggacgccct tgagtttaga   2400
ccagagaggt ggtttgagcc agagacaaag aagcttggct gggccttcct tccattcaac   2460
ggtggtccaa gaatttgctt gggacagcag tttgccttga cagaagcttc gtatgtcact   2520
gtcagattgc tccaagagtt tggacacttg tctatggacc ccaacaccga atatccacct   2580
aggaaaatgt cgcatttgac catgtccctt ttcgacggtg ccaacattga gatgtattag   2640
aggatcatgt gttatttttg attggtttag tctgtttgta gctattgatt aggttaattc   2700
acggattgtt atttattgat agggggtgcg tgtgtgtgtg tgtgttgcat tcacatggga   2760
tcgttccagg ttgttgtttc cttccatcct gttgagtcaa aaggagtttt gttttgtaac   2820
tccggacgat gtcttagata gaaggtcgat ctccatgtga ttgtttgact gctactctga   2880
ttatgtaatc tgtaaagcct agacgttatg caagcatgtg attgtggttt ttgcaacctg   2940
tttgcacgac aaatgatcga cagtcgatta cgtaatccat attatttaga ggggtaataa   3000
aaaataaatg gcagccagaa tttcaaacat tttgcaaaca atgcaaaaga tgagaaactc   3060
caacagaaaa aataaaaaaa ctccgcagca ctccgaacca acaaaacaat ggggggcgcc   3120
agaattattg actattgtga cttttttttta tttttccgt taactttcat tgcagtgaag   3180
tgtgttacac ggggtggtga tggtgttggt ttctacaatg caagggcaca gttgaaggtt   3240
tccacataac gttgcaccat atcaactcaa tttatcctca ttcatgtgat aaaagaagag   3300
ccaaaaggta attggcagac cccccaaggg gaacacggag tagaaagcaa tggaaacacg   3360
cccatgacag tgccatttag cccacaacac atctagtatt cttttttttt tttgtgcgca   3420
ggtgcacacc tggactttag ttattgcccc ataaagttaa caatctcacc tttggctctc   3480
ccagtgtctc cgcctccaga tgctcgtttt acaccctcga gctaacgaca acacaacacc   3540
catgagggga atgggcaaag ttaaacactt ttggtttcaa tgattcctat ttgctactct   3600
cttgttttgt gttttgattt gcaccatgtg aaataaacga caattatata taccttttcg   3660
tctgtcctcc aatgtctctt tttgctgcca ttttgctttt tgctttttgc ttttgcactc   3720
tctcccactc ccacaatcag tgcagcaaca cacaa                              3755
```

-continued

<210> SEQ ID NO 88
<211> LENGTH: 3900
<212> TYPE: DNA
<213> ORGANISM: Candida tropicalis

<400> SEQUENCE: 88
gacatcataa tgacccggtt atttcgccct caggttgctt atttgagccg taaagtgcag 60
tagaaacttt gccttgggtt caaactctag tataatggtg ataactggtt gcactcttgc 120
cataggcatg aaaataggcc gttatagtac tatatttaat aagcgtagga gtataggatg 180
catatgaccg gtttttctat atttttaaga taatctctag taaattttgt attctcagta 240
ggatttcatc aaatttcgca accaattctg gcgaaaaaat gattctttta cgtcaaaagc 300
tgaatagtgc agtttaaagc acctaaaatc acatatacag cctctagata cgacagagaa 360
gctctttatg atctgaagaa gcattagaat agctactatg agccactatt ggtgtatata 420
ttagggattg gtgcaattaa gtacgtacta ataaacagaa gaaaatactt aaccaatttc 480
tggtgtatac ttagtggtga gggacctttt ctgaacattc gggtcaaact tttttttgga 540
gtgcgacatc gatttttcgt ttgtgtaata atagtgaacc tttgtgtaat aaatcttcat 600
gcaagacttg cataattcga gcttgggagt tcacgccaat ttgacctcgt tcatgtgata 660
aaagaaaagc caaaaggtaa ttagcagacg caatgggaac atggagtgga aagcaatgga 720
agcacgccca ggacggagta atttagtcca cactacatct ggggggtttt tttttgtgcg 780
caagtacaca cctggacttt agtttttgcc ccataaagtt aacaatctaa cctttggctc 840
tccaactctc tccgccccca aatattcgtt tttacaccct caagctagcg acagcacaac 900
acccattaga ggaatggggc aaagttaaac acttttggct tcaatgattc ctattcgcta 960
ctacattctt ctcttgtttt gtgctttgaa ttgcaccatg tgaaataaac gacaattata 1020 tataccttttt catccctcct cctatatctc tttttgctac attttgtttt ttacgtttct 1080
tgcttttgca ctctcccact cccacaaaga aaaaaaaact acactatgtc gtcttctcca 1140
tcgtttgccc aagaggttct cgctaccact agtccttaca tcgagtactt tcttgacaac 1200
tacaccagat ggtactactt catacctttg gtgcttcttt cgttgaactt tataagtttg 1260
ctccacacaa ggtacttgga acgcaggttc cacgccaagc cactcggtaa ctttgtcagg 1320
gaccctacgt ttggtatcgc tactccgttg cttttgatct acttgaagtc gaaaggtacg 1380
gtcatgaagt ttgcttgggg cctctggaac aacaagtaca tcgtcagaga cccaaagtac 1440
aagacaactg ggctcaggat tgttggcctc ccattgattg aaaccatgga cccagagaac 1500
atcaaggctg ttttggctac tcagttcaat gatttctctt tgggaaccag acacgatttc 1560
ttgtactcct tgttgggtga cggtattttc accttggacg gtgctggctg gaaacatagt 1620
agaactatgt tgagaccaca gtttgctaga gaacaggttt ctcacgtcaa gttgttggag 1680
ccacacgttc aggtgttctt caagcacgtt agaaagcacc gcggtcaaac gttcgacatc 1740
caagaattgt tcttcaggtt gaccgtcgac tccgccaccg agttcttgtt tggtgagtct 1800
gctgaatcct tgagggacga atctattgga ttgaccccaa ccaccaagga tttcgatggc 1860
agaagagatt tcgctgacgc tttcaactat tcgcagactt accaggccta cagatttttg 1920
ttgcaacaaa tgtactggat cttgaatggc tcggaattca gaaagtcgat tgctgtcgtg 1980
cacaagtttg ctgaccacta tgtgcaaaag gctttggagt tgaccgacga tgacttgcag 2040
aaacaagacg gctatgtgtt cttgtacgag ttggctaagc aaaccagaga cccaaaggtc 2100

-continued

```
ttgagagacc agttattgaa cattttggtt gccggtagag acacgaccgc cggtttgttg   2160
tcatttgttt tctacgagtt gtcaagaaac cctgaggtgt ttgctaagtt gagagaggag   2220
gtggaaaaca gatttggact cggtgaagaa gctcgtgttg aagagatctc gtttgagtcc   2280
ttgaagtctt gtgagtactt gaaggctgtc atcaatgaaa ccttgagatt gtacccatcg   2340
gttccacaca actttagagt tgctaccaga aacactaccc tcccaagagg tggtggtgaa   2400
gatggatact cgccaattgt cgtcaagaag ggtcaagttg tcatgtacac tgttattgct   2460
acccacagag acccaagtat ctacggtgcc gacgctgacg tcttcagacc agaaagatgg   2520
tttgaaccag aaactagaaa gttgggctgg gcatacgttc cattcaatgg tggtccaaga   2580
atctgtttgg gtcaacagtt tgccttgacc gaagcttcat acgtcactgt cagattgctc   2640
caggagtttg cacacttgtc tatggaccca gacaccgaat atccaccaaa attgcagaac   2700
accttgacct tgtcgctctt tgatggtgct gatgttagaa tgtactaagg ttgcttttcc   2760
ttgctaattt tcttctgtat agcttgtgta tttaaattga atcggcaatt gatttttctg   2820
ataccaataa ccgtagtgcg atttgaccaa aaccgttcaa actttttgtt ctctcgttga   2880
cgtgctcgct catcagcact gtttgaagac gaaagagaaa atttttttgta aacaacactg   2940
tccaaattta cccaacgtga accattatgc aaatgagcgg ccctttcaac tggtcgctgg   3000
aagcattcgg ggatatctac aacgccctta agtttgaaac agacattgat ttagacacca   3060
tagatttcag cggcatcaag aatgaccttg cccacatttt gacgacccca acaccactgg   3120
aagaatcacg ccagaaacta ggcgatggat ccaagcctgt gaccttgccc aatggagacg   3180
aagtggagtt gaaccaagcg ttcctagaag ttaccacatt attgtcgaat gagtttgact   3240
tggaccaatt gaacgcggca gagttgttat actacgctgg cgacatatcc tacaagaagg   3300
gcacatcaat cgcagacagt gccagattgt cttattattt gagagcaaac tacatcttga   3360
acatacttgg gtatttgatt tcgaagcagc gattggattt gatagtcacg gacaacgacg   3420
cgttgtttga tagtattttg aaaagttttg aaaagatcta caagttgata agcgtgttga   3480
acgatatgat tgacaagcaa aaggtgacaa gcgacatcaa cagtctagca ttcatcaatt   3540
gcatcaacta ctcgagaggt caactattct ccgcacacga acttttggga ctggttttgt   3600
ttggattggt cgacatctat ttcaaccagt ttggcacatt agacaactac aagaaggtat   3660
tggcattgat actgaagaac atcagcgatg aagacatctt gatcatacac ttcctcccat   3720
cgacactaca attgtttaag ctggtgttgg acaagaaaga cgacgctgca gttgaacagt   3780
tctacaagta catcacttca acagtgtcac gagactacaa ctccaacatc ggctccacag   3840
ccaaagatga tatcgatttg tccaaaacca aactcagtgg ctttgaggtg ttgacgagtt   3900
```

<210> SEQ ID NO 89
<211> LENGTH: 3668
<212> TYPE: DNA
<213> ORGANISM: Candida tropicalis

<400> SEQUENCE: 89

```
cctgcagaat tcgcggccgc gtcgacagag tagcagttat gcaagcatgt gattgtggtt     60
tttgcaacct gtttgcacga caaatgatcg acagtcgatt acgtaatcca tattatttag    120
aggggtaata aaaaataaat ggcagccaga atttcaaaca ttttgcaaac aatgcaaaag    180
atgagaaact ccaacagaaa aaataaaaaa actccgcagc actccgaacc aacaaaacaa    240
tggggggcgc cagaattatt gactattgtg actttttttt attttttccg ttaactttca    300
ttgcagtgaa gtgtgttaca cggggtggtg atggtgttgg tttctacaat gcaagggcac    360
```

-continued

```
agttgaaggt ttccacataa cgttgcacca tatcaactca atttatcctc attcatgtga    420
taaaagaaga gccaaaaggt aattggcaga ccccccaagg ggaacacgga gtagaaagca    480
atggaaacac gcccatgaca gtgccattta gcccacaaca catctagtat tctttttttt    540
ttttgtgcgc aggtgcacac ctggacttta gttattgccc cataaagtta acaatctcac    600
ctttggctct cccagtgtct ccgcctccag atgctcgttt tacaccctcg agctaacgac    660
aacacaacac ccatgagggg aatgggcaaa gttaaacact tttggtttca atgattccta    720
tttgctactc tcttgttttg tgttttgatt tgcaccatgt gaaataaacg acaattatat    780
ataccttttc gtctgtcctc caatgtctct ttttgctgcc attttgcttt ttgctttttg    840
cttttgcact ctctcccact cccacaatca gtgcagcaac acacaaagaa gaaaaataaa    900
aaaacctaca ctatgtcgtc ttctccatcg tttgctcagg aggttctcgc taccactagt    960
ccttacatcg agtactttct tgacaactac accagatggt actacttcat ccctttggtg   1020
cttctttcgt tgaacttcat cagcttgctc cacacaaagt acttggaacg caggttccac   1080
gccaagccgc tcggtaacgt cgtgttggat cctacgtttg gtatcgctac tccgttgatc   1140
ttgatctact taaagtcgaa aggtacagtc atgaagtttg cctggagctt ctggaacaac   1200
aagtacattg tcaaagaccc aaagtacaag accactggcc ttagaattgt cggcctccca   1260
ttgattgaaa ccatagaccc agagaacatc aaagctgtgt tggctactca gttcaacgat   1320
ttctccttgg gaactagaca cgatttcttg tactccttgt tgggcgatgg tatttttacc   1380
ttggacggtg ctggctggaa acacagtaga actatgttga gaccacagtt tgctagagaa   1440
caggtttccc acgtcaagtt gttggaacca cacgttcagg tgttcttcaa gcacgttaga   1500
aaacaccgcg gtcagacttt tgacatccaa gaattgttct tcagattgac cgtcgactcc   1560
gccaccgagt tcttgtttgg tgagtctgct gaatccttga gagacgactc tgttggtttg   1620
accccaacca ccaaggattt cgaaggcaga ggagatttcg ctgacgcttt caactactcg   1680
cagacttacc aggcctacag atttttgttg caacaaatgt actggatttt gaatggcgcg   1740
gaattcagaa agtcgattgc catcgtgcac aagtttgctg accactatgt gcaaaaggct   1800
ttggagttga ccgacgatga cttgcagaaa caagacggct atgtgttctt gtacgagttg   1860
gctaagcaaa ctagagaccc aaaggtcttg agagaccagt tgttgaacat tttggttgcc   1920
ggtagagaca cgaccgccgg tttgttgtcg tttgtgttct acgagttgtc gagaaaccct   1980
gaagtgtttg ccaagttgag agaggaggtg gaaaacagat ttggactcgg cgaagaggct   2040
cgtgttgaag agatctcttt tgagtccttg aagtcctgtg agtacttgaa ggctgtcatc   2100
aatgaagcct tgagattgta cccatctgtt ccacacaact tcagagttgc caccagaaac   2160
actacccttc caagaggcgg tggtaaagac ggatgctcgc caattgttgt caagaagggt   2220
caagttgtca tgtacactgt cattggtacc cacagagacc caagtatcta cggtgccgac   2280
gccgacgtct tcagaccaga aagatggttc gagccagaaa ctagaaagtt gggctgggca   2340
tatgttccat tcaatggtgg tccaagaatc tgtttgggtc agcagtttgc cttgactgaa   2400
gcttcatacg tcactgtcag attgctccaa gagtttggaa acttgtccct ggatccaaac   2460
gctgagtacc caccaaaatt gcagaacacc ttgaccttgt cactctttga tggtgctgac   2520
gttagaatgt tctaaggttg cttatccttg ctagtgttat ttatagtttg tgtatttaaa   2580
ttgaatcggc gattgatttt tctggtacta ataactgtag tgggttttga ccaaaaccgt   2640
tcaaactttt tttttttttt tcttcccct accttcgttg ctcgctcatc agcactgttt   2700
```

-continued

```
gaaaacgaaa aaagaaaatt ttttgtaaac aacattgccc aaacttaccc aacgtgaacc   2760

attataacca aatgagcggc gctttcaact ggtcactgga ggcattcggg gatatctaca   2820

acacccttaa gtttgaggaa gacattgatt tagacaccat agatttcagc ggcatcaaga   2880

atgaccttgt ccacattttg acaaccccaa caccactgga agaatcgcgc cagaaactag   2940

gcgatggatc caagcctgtg gccttgccca atggagacga agtggagttg aaccaagcgt   3000

tcctagaagt taccacatta ttgtcgaacg agtttgactt ggaccaattg aacgcggccg   3060

agttgttata ctacgccggc gacatatcct acaagaaggg cacatcaatt gccgacagtg   3120

ccagattgtc ttactatttg agagcaaact acatcttgaa catacttggg tactttattt   3180

cgaagcagcg attggatgtg atagtcaccg acaacaacgc gttgtttgat aatattttga   3240

aaagttttga aaagatctac aagttgataa gcgcgttgaa cgatatgatt gacaagcaaa   3300

aggtgacaag cgacatcaac agtctagcat ttatcaactg catcaactac tcgaggggtc   3360

aactattctc cgcacacgaa cttttgggac tggttttgtt tggattggtt gacaactatt   3420

tcaaccagtt tggctcatta gacaactaca agaaagtatt ggcattgata ctgaagaaca   3480

tcagtgatga agatatcttg atcgtacgct tcctcccatc gacactacaa ttgtttaagc   3540

tggtgttgga taagaaagac gacgccactg ttgaccagtt ctacaagtac atcacctcaa   3600

cagtgtcgca agactacaac tccaacatcg gagccacagc caaagatgat atcgatttgt   3660

ccaaagcc                                                            3668
```

<210> SEQ ID NO 90
<211> LENGTH: 3826
<212> TYPE: DNA
<213> ORGANISM: Candida tropicalis

<400> SEQUENCE: 90

```
tggagtcgcc agacttgctc acttttgact cccttcgaaa ctcaaagtac gttcaggcgg     60

tgctcaacga aacgctccgt atctacccgg gggtaccacg aaacatgaag acagctacgt    120

gcaacacgac gttgccacgc ggaggaggca aagacggcaa ggaacctatc ttggtgcaga    180

agggacagtc cgttgggttg attactattg ccacgcagac ggacccagag tattttgggg    240

ccgacgctgg tgagtttaag ccggagagat ggtttgattc aagcatgaag aacttggggt    300

gtaaatactt gccgttcaat gctgggccac ggacttgctt ggggcagcag tacactttga    360

ttgaagcgag ctacttgcta gtccggttgg cccagaccta ccgggcaata gatttgcagc    420

caggatcggc gtacccacca agaaagaagt cgttgatcaa catgagtgct gccgacgggg    480

tgtttgtaaa gctttataag gatgtaacgg tagatggata gttgtgtagg aggagcggag    540

ataaattaga tttgattttg tgtaaggttt tggatgtcaa cctactccgc acttcatgca    600

gtgtgtgtga cacaagggtg tactacgtgt gcgtgtgcgc caagagacag cccaaggggg    660

tggtagtgtg tgttggcgga agtgcatgtg acacaacgcg tgggttctgg ccaatggtgg    720

actaagtgca ggtaagcagc gacctgaaac attcctcaac gcttaagaca ctggtggtag    780

agatgcggac caggctattc ttgtcgtgct acccggcgca tggaaaatca actgcgggaa    840

gaataaattt atccgtagaa tccacagagc ggataaattt gcccacctcc atcatcaacc    900

acgccgccac taactacatc actcccctat tttctctctc tctctttgtc ttactccgct    960

cccgtttcct tagccacaga tacacaccca ctgcaaacag cagcaacaat tataaagata   1020

cgccaggccc accttctttc tttttcttca cttttttgac tgcaactttc tacaatccac   1080

cacagccacc accacagccg ctatgattga acaactccta gaatattggt atgtcgttgt   1140
```

-continued

```
gccagtgttg tacatcatca aacaactcct tgcatacaca aagactcgcg tcttgatgaa   1200
aaagttgggt gctgctccag tcacaaacaa gttgtacgac aacgctttcg gtatcgtcaa   1260
tggatggaag gctctccagt tcaagaaaga gggcagggct caagagtaca acgattacaa   1320
gtttgaccac tccaagaacc caagcgtggg cacctacgtc agtattcttt tcggcaccag   1380
gatcgtcgtg accaaagatc cagagaatat caaagctatt ttggcaaccc agtttggtga   1440
tttttctttg ggcaagaggc acactctttt taagcctttg ttaggtgatg ggatcttcac   1500
attggacggc gaaggctgga agcacagcag agccatgttg agaccacagt ttgccagaga   1560
acaagttgct catgtgacgt cgttggaacc acacttccag ttgttgaaga agcatattct   1620
taagcacaag ggtgaatact ttgatatcca ggaattgttc tttagattta ccgttgattc   1680
ggccacggag ttcttatttg gtgagtccgt gcactcctta aaggacgaat ctattggtat   1740
caaccaagac gatatagatt ttgctggtag aaaggacttt gctgagtcgt tcaacaaagc   1800
ccaggaatac ttggctatta gaaccttggt gcagacgttc tactggttgg tcaacaacaa   1860
ggagtttaga gactgtacca agctggtgca caagttcacc aactactatg ttcagaaagc   1920
tttggatgct agcccagaag agcttgaaaa gcaaagtggg tatgtgttct tgtacgagct   1980
tgtcaagcag acaagagacc ccaatgtgtt gcgtgaccag tctttgaaca tcttgttggc   2040
cggaagagac accactgctg ggttgttgtc gtttgctgtc tttgagttgg ccagacaccc   2100
agagatctgg gccaagttga gagaggaaat tgaacaacag tttggtcttg gagaagactc   2160
tcgtgttgaa gagattacct ttgagagctt gaagagatgt gagtacttga aagcgttcct   2220
taatgaaacc ttgcgtattt acccaagtgt cccaagaaac ttcagaatcg ccaccaagaa   2280
cacgacattg ccaaggggcg gtggttcaga cggtacctcg ccaatcttga tccaaaaggg   2340
agaagctgtg tcgtatggta tcaactctac tcatttggac cctgtctatt acggccctga   2400
tgctgctgag ttcagaccag agagatggtt tgagccatca accaaaaagc tcggctgggc   2460
ttacttgcca ttcaacggtg gtccaagaat ctgtttgggt cagcagtttg ccttgacgga   2520
agctggctat gtgttggtta gattggtgca agagttctcc cacgttaggc tggacccaga   2580
cgaggtgtac ccgccaaaga ggttgaccaa cttgaccatg tgtttgcagg atggtgctat   2640
tgtcaagttt gactagcggc gtggtgaatg cgtttgattt tgtagtttct gtttgcagta   2700
atgagataac tattcagata aggcgagtgg atgtacgttt tgtaagagtt tccttacaac   2760
cttggtgggg tgtgtgaggt tgaggttgca tcttggggag attacacctt ttgcagctct   2820
ccgtatacac ttgtactctt tgtaacctct atcaatcatg tggggggggg ggttcattgt   2880
ttggccatgg tggtgcatgt taaatccgcc aactacccaa tctcacatga aactcaagca   2940
cactaaaaaa aaaaaagatg ttgggggaaa actttggttt cccttcttag taattaaaca   3000
ctctcactct cactctcact ctctccactc agacaaacca accacctggg ctgcagacaa   3060
ccagaaaaaa aaagaacaaa atccagatag aaaaacaaag ggctggacaa ccataaataa   3120
acaatctagg gtctactcca tcttccactg tttcttcttc ttcagactta gctaacaaac   3180
aactcacttc accatggatt acgcaggcat cacgcgtggc tccatcagag gcgaggcctt   3240
gaagaaactc gcagaattga ccatccagaa ccagccatcc agcttgaaag aaatcaacac   3300
cggcatccag aaggacgact ttgccaagtt gttgtctgcc accccgaaaa tccccaccaa   3360
gcacaagttg aacggcaacc acgaattgtc tgaggtcgcc attgccaaaa aggagtacga   3420
ggtgttgatt gccttgagcg acgccacaaa agacccaatc aaagtgacct cccagatcaa   3480
```

-continued

```
gatcttgatt gacaagttca aggtgtactt gtttgagttg cctgaccaga agttctccta   3540

ctccatcgtg tccaactccg tcaacatcgc cccctggacc ttgctcgggg agaagttgac   3600

cacgggcttg atcaacttgg ccttccagaa caacaagcag cacttggacg aggtcattga   3660

catcttcaac gagttcatcg acaagttctt tggcaacacg gagccgcaat tgaccaactt   3720

cttgaccttg tgcggtgtgt tggacgggtt gattgaccat gccaacttct tgagcgtgtc   3780

ctcgcggacc ttcaagatct tcttgaactt ggactcgtat gtggac                  3826
```

<210> SEQ ID NO 91
<211> LENGTH: 3910
<212> TYPE: DNA
<213> ORGANISM: Candida tropicalis

<400> SEQUENCE: 91

```
ttacaatcat ggagctcgct aggaacccag atgtctggga gaagctccgc gaagaggtca     60

acacgaactt tggcatggag tcgccagact tgctcacttt tgactctctt agaagctcaa    120

agtacgttca ggcggtgctc aacgaaacgc ttcgtatcta cccgggggtg ccacgaaaca    180

tgaagacagc tacgtgcaac acgacgttgc cgcgtggagg aggcaaagac ggtaaggaac    240

ctattttggt gcagaagggc cagtccgttg ggttgattac tattgccacg cagacggacc    300

cagagtattt tggggcagat gctggtgagt tcaaaccgga gagatggttt gattcaagca    360

tgaagaactt ggggtgtaag tacttgccgt tcaatgctgg gccccggact tgtttggggc    420

agcagtacac tttgattgaa gcgagctatt tgctagtcag gttggcgcag acctaccggg    480

taatcgattt gctgccaggg tcggcgtacc caccaagaaa gaagtcgttg atcaatatga    540

gtgctgccga tggggtggtt gtaaagtttc acaaggatct agatggatat gtaaggtgtg    600

taggaggagc ggagataaat tagatttgat tttgtgtaag gtttagcacg tcaagctact    660

ccgcactttg tgtgtaggga gcacatactc cgtctgcgcc tgtgccaaga gacggcccag    720

gggtagtgtg tggtggtgga agtgcatgtg acacaatacc ctggttctgg ccaattgggg    780

atttagtgta ggtaagctgc gacctgaaac actcctcaac gcttgagaca ctggtgggta    840

gagatgcggg ccaggaggct attcttgtcg tgctacccgt gcacggaaaa tcgattgagg    900

gaagaacaaa tttatccgtg aaatccacag agcggataaa tttgtcacat tgctgcgttg    960

cccacccaca gcattctctt ttctctctct ttgtcttact ccgctcctgt ttccttatcc   1020

agaaatacac accaactcat ataaagatac gctagcccag ctgtctttct ttttcttcac   1080

tttttttggt gtgttgcttt tttggctgct actttctaca accaccacca ccaccaccac   1140

catgattgaa caaatcctag aatattggta tattgttgtg cctgtgttgt acatcatcaa   1200

acaactcatt gcctacagca agactcgcgt cttgatgaaa cagttgggtg ctgctccaat   1260

cacaaaccag ttgtacgaca acgttttcgg tatcgtcaac ggatggaagg ctctccagtt   1320

caagaaagag ggcagagctc aagagtacaa cgatcacaag tttgacagct ccaagaaccc   1380

aagcgtcggc acctatgtca gtattctttt tggcaccaag attgtcgtga ccaaggatcc   1440

agagaatatc aaagctattt tggcaaccca gtttggcgat ttttctttgg gcaagagaca   1500

cgctcttttt aaacctttgt taggtgatgg gatcttcacc ttggacggcg aaggctggaa   1560

gcatagcaga tccatgttaa gaccacagtt tgccagagaa caagttgctc atgtgacgtc   1620

gttggaacca cacttccagt tgttgaagaa gcatatcctt aaacacaagg gtgagtactt   1680

tgatatccag gaattgttct ttagatttac tgtcgactcg gccacggagt tcttatttgg   1740

tgagtccgtg cactccttaa aggacgaaac tatcggtatc aaccaagacg atatagattt   1800
```

-continued

```
tgctggtaga aaggactttg ctgagtcgtt caacaaagcc caggagtatt tgtctattag   1860
aattttggtg cagaccttct actggttgat caacaacaag gagtttagag actgtaccaa   1920
gctggtgcac aagtttacca actactatgt tcagaaagct ttggatgcta ccccagagga   1980
acttgaaaag caaggcgggt atgtgttctt gtatgagctt gtcaagcaga cgagagaccc   2040
caaggtgttg cgtgaccagt ctttgaacat cttgttggca ggaagagaca ccactgctgg   2100
gttgttgtcc tttgctgtgt ttgagttggc cagaaaccca cacatctggg ccaagttgag   2160
agaggaaatt gaacagcagt ttggtcttgg agaagactct cgtgttgaag agattacctt   2220
tgagagcttg aagagatgtg agtacttgaa agcgttcctt aacgaaacct tgcgtgttta   2280
cccaagtgtc ccaagaaact tcagaatcgc caccaagaat acaacattgc caaggggtgg   2340
tggtccagac ggtacccagc caatcttgat ccaaaaggga gaaggtgtgt cgtatggtat   2400
caactctacc cacttagatc ctgtctatta tggccctgat gctgctgagt tcagaccaga   2460
gagatggttt gagccatcaa ccagaaagct cggctgggct tacttgccat tcaacggtgg   2520
gccacgaatc tgtttgggtc agcagtttgc cttgaccgaa gctggttacg ttttggtcag   2580
attggtgcaa gagttctccc acattaggct ggacccagat gaagtgtatc caccaaagag   2640
gttgaccaac ttgaccatgt gtttgcagga tggtgctatt gtcaagtttg actagtacgt   2700
atgagtgcgt ttgattttgt agtttctgtt tgcagtaatg agataactat tcagataagg   2760
cgggtggatg tacgttttgt aagagtttcc ttacaaccct ggtgggtgtg tgaggttgca   2820
tcttagggag agatagcacc ttttgcagct ctccgtatac agttttactc tttgtaacct   2880
atgccaatca tgtggggatt cattgtttgc ccatggtggt gcatgcaaaa tccccccaac   2940
tacccaatct cacatgaaac tcaagcacac tagaaaaaaa agatgttgcg tgggttcttt   3000
tgatgttggg gaaaactttc gtttcctttc tcagtaatta aacgttctca ctcagacaaa   3060
ccacctgggc tgcagacaac cagaaaaaac aaaatccaga tagaagaaga aagggctgga   3120
caaccataaa taaacaacct agggtccact ccatctttca cttcttcttc ttcagactta   3180
tctaacaaac gactcacttc accatggatt acgcaggtat cacgcgtggg tccatcagag   3240
gcgaagcctt gaagaaactc gccgagttga ccatccagaa ccagccatcc agcttgaaag   3300
aaatcaacac cggcatccag aaggacgact ttgccaagtt gttgtcttcc accccgaaaa   3360
tccacaccaa gcacaagttg aatggcaacc acgaattgtc cgaagtcgcc attgccaaaa   3420
aggagtacga ggtgttgatt gccttgagcg acgccacgaa agaaccaatc aaagtcacct   3480
cccagatcaa gatcttgatt gacaagttca aggtgtactt gtttgagttg cccgaccaga   3540
agttctccta ctccatcgtg tccaactccg ttaacattgc cccctggacc ttgctcggtg   3600
agaagttgac cacgggcttg atcaacttgg cgttccagaa caacaagcag cacttggacg   3660
aagtcatcga catcttcaac gagttcatcg acaagttctt tggcaacaca gagccgcaat   3720
tgaccaactt cttgaccttg tccggtgtgt tggacgggtt gattgaccat gccaacttct   3780
tgagcgtgtc ctccaggacc ttcaagatct tcttgaactt ggactcgttt gtggacaact   3840
cggacttctt gaacgacgtg gagaactact ccgacttttt gtacgacgag ccgaacgagt   3900
accagaactt                                                          3910
```

<210> SEQ ID NO 92
<211> LENGTH: 3150
<212> TYPE: DNA
<213> ORGANISM: Candida tropicalis

<400> SEQUENCE: 92
gaattctttg gatctaattc cagctgatct tgctaatcct tatcaacgta gttgtgatca 60
ttgtttgtct gaattataca caccagtgga agaatatggt ctaatttgca cgtcccactg 120
gcattgtgtg tttgtggggg gggggggtg cacacatttt tagtgccatt ctttgttgat 180 taccccctccc ccctatcatt cattcccaca ggattagttt tttcctcact ggaattcgct 240
gtccacctgt caaccccccc cccccccccc cccactgccc taccctgccc tgccctgcac 300
gtcctgtgtt ttgtgctgtg tctttcccac gctataaaag ccctggcgtc cggccaaggt 360
ttttccaccc agccaaaaaa acagtctaaa aaatttggtt gatccttttt ggttgcaagg 420
ttttccacca ccacttccac cacctcaact attcgaacaa aagatgctcg atcagatctt 480
acattactgg tacattgtct tgccattgtt ggccattatc aaccagatcg tggctcatgt 540
caggaccaat tatttgatga agaaattggg tgctaagcca ttcacacacg tccaacgtga 600
cgggtggttg ggcttcaaat tcggccgtga attcctcaaa gcaaaaagtg ctgggagact 660
ggttgattta atcatctccc gtttccacga taatgaggac actttctcca gctatgcttt 720
tggcaaccat gtggtgttca ccagggaccc cgagaatatc aaggcgcttt tggcaaccca 780
gtttggtgat tttcattgg gcagcagggt caagttcttc aaaccattat tggggtacgg 840
tatcttcaca ttggacgccg aaggctggaa gcacagcaga gccatgttga gaccacagtt 900
tgccagagaa caagttgctc atgtgacgtc gttggaacca cacttccagt tgttgaagaa 960
gcatatcctt aaacacaagg gtgagtactt tgatatccag gaattgttct ttagatttac 1020
tgtcgactcg gccacggagt tcttatttgg tgagtccgtg cactccttaa aggacgagga 1080
aattggctac gacacgaaag acatgtctga agaaagacgc agatttgccg acgcgttcaa 1140
caagtcgcaa gtctacgtgg ccaccagagt tgctttacag aacttgtact ggttggtcaa 1200
caacaaagag ttcaaggagt gcaatgacat tgtccacaag tttaccaact actatgttca 1260
gaaagccttg gatgctaccc cagaggaact tgaaaagcaa ggcgggtatg tgttcttgta 1320
tgagcttgtc aagcagacga gagaccccaa ggtgttgcgt gaccagtctt tgaacatctt 1380
gttggcagga agagacacca ctgctgggtt gttgtccttt gctgtgtttg agttggccag 1440
aaacccacac atctgggcca agttgagaga ggaaattgaa cagcagtttg gtcttggaga 1500
agactctcgt gttgaagaga ttacctttga gagcttgaag agatgtgagt acttgaaggc 1560
cgtgttgaac gaaactttga gattacaccc aagtgtccca agaaacgcaa gatttgcgat 1620
taaagacacg actttaccaa gaggcggtgg ccccaacggc aaggatccta tcttgatcag 1680
gaaggatgag gtggtgcagt actccatctc ggcaactcag acaaatcctg cttattatgg 1740
cgccgatgct gctgatttta gaccggaaag atggtttgaa ccatcaacta gaaacttggg 1800
atgggctttc ttgccattca acggtggtcc aagaatctgt ttgggacaac agtttgcttt 1860
gactgaagcc ggttacgttt tggttagact tgttcaggag tttccaaact tgtcacaaga 1920
ccccgaaacc aagtacccac cacctagatt ggcacacttg acgatgtgct tgtttgacgg 1980
tgcacacgtc aagatgtcat aggtttcccc atacaagtag ttcagtaatt atacactgtt 2040
tttactttct cttcatacca aatggacaaa agttttaagc atgcctaaca acgtgaccgg 2100

-continued

```
acaattgtgt cgcactagta tgtaacaatt gtaaaaatag tgtacactaa tttgtggtgg   2160

ccggagataa attacagttt ggttttgtgt aaactcgcgg atatctctgg cagtttctct   2220

tctccgcagc agctttgcca cgggtttgct ctggggccaa caaattcaaa agggggagaa   2280

acttaacacc ccttatctct ccactctagg ttgtagctct tgtggggatg caattgtcgt   2340

acgtttttta tgttttgtct agactttgat gattacgttg gatttcttat gtctgaggcg   2400

tgcttgaaag aagtgtcaaa atgtgacagg cgacgctatt cgacatgaac gcgaaagggt   2460

tatttgcatc aatacgaggg gctgactcta gtctaggatg gcagtcctag gttgcaaaca   2520

tgttgcacca tatccctcct ggagttggtc gacctcgcct acgccaccct cagcgatcgg   2580

cactttccgt tgttcaatat ttctccttcc cattgttcca ggggttatca acaacgttgc   2640

cggcctcctc cccaaattac aagaaaaata aattgtcgca cggcaccgat ctgtcaaaga   2700

tacagataaa ccttaaatct gcaaaaacaa gacccctccc catagcctag aagcaccagc   2760

aagatgatgg agcaactcct ccagtactgg tacatcgcac tctctgtatg gttcatcctt   2820

cgctacttgg cttcccacgc acgagccgtc tacttgcgcc acaagctcgg cgcggcgcca   2880

ttcacgcaca cccagtacga cggctggtat gggttcaagt ttgggcggga gtttctcaag   2940

gcgaagaaga tcgggcggca gacggacttg gtgcatgcgc ggttccgtgg cggcatggac   3000

accttctcga gctacacttt cggcatccat atcatcctta cccgggaccc ggagaacatc   3060

aaggcggtct tggcgacgca gttcgatgac ttctcgctcg gtggcaggat caggttcttg   3120

aagccgttgt tggggtatgg gatattcacg                                    3150
```

<210> SEQ ID NO 93
<211> LENGTH: 3579
<212> TYPE: DNA
<213> ORGANISM: Candida tropicalis

<400> SEQUENCE: 93

```
aaaaccgata caagaagaag acagtcaaca agaacgttaa tgtcaaccag gcgccaagaa     60

gacggtttgg cggacttgga agaatgtggc atttgcccat gatgtttatg ttctggagag    120

gtttttcaag gaatcgtcat cctccgccac cacaagaacc accagttaac gagatccata    180

ttcacaaccc accgcaaggt gacaatgctc aacaacaaca gcaacaacaa caaccccccac    240

aagaacagtg gaataatgcc agtcaacaaa gagtggtgac agacgaggga gaaaacgcaa    300

gcaacagtgg ttctgatgca agatcagcta caccgcttca tcaggaaaag caggagctcc    360

caccaccata tgcccatcac gagcaacacc agcaggttag tgtatagtag tctgtagtta    420

agtcaatgca atgtaccaat aagactatcc cttcttacaa ccaagttttc tgccgcgcct    480

gtctggcaac agatgctggc cgacacactt tcaactgagt ttggtctaga attcttgcac    540

atgcacgaca aggaaactct tacaaagaca acacttgtgc tctgatgcca cttgatcttg    600

ctaagcctta tcaacgtaat tgagatcatt gtttgtctga attatacaca ccagtggaag    660

aatctggtct aatctgcacg cctcatgggc attgtgtgtt ttggggggggg gggggggggt    720

gcacacattt ttagtgcgaa tgtttgtttg ctggttcccc ctcccccctc ccccctatca    780

tgcccacagg attagttttt tcctcactgg aattcgctgt ccacctgtca accccctcac    840

tgccctgccc tgccctgcac gccctgtgtt ttgtgctgtg gcactcccac gctataaaag    900

ccctggcgta cggccaaggt ttttcctcac agccaaaaaa aaatttggct gatccttttg    960

ggctgcaagg tttttcacca ccaccaccac caccacctca actattcaaa caaaggatgc   1020

tcgaccagat cttccattac tggtacattg tcttgccatt gttggtcatt atcaagcaga   1080
```

-continued

```
tcgtggctca tgccaggacc aattatttga tgaagaagtt gggcgctaag ccattcacac   1140
atgtccaact agacgggtgg tttggcttca aatttggccg tgaattcctc aaagctaaaa   1200
gtgctgggag gcaggttgat ttaatcatct cccgtttcca cgataatgag gacactttct   1260
ccagctatgc ttttggcaac catgtggtgt tcaccaggga ccccgagaat atcaaggcgc   1320
ttttggcaac ccagtttggt gatttttcat tgggaagcag ggtcaaattc ttcaaaccat   1380
tgttggggta cggtatcttc accttggacg gcgaaggctg gaagcacagc agagccatgt   1440
tgagaccaca gtttgccaga gagcaagttg ctcatgtgac gtcgttggaa ccacatttcc   1500
agttgttgaa gaagcatatt cttaagcaca agggtgaata ctttgatatc caggaattgt   1560
tctttagatt taccgttgat tcagcgacgg agttcttatt tggtgagtcc gtgcactcct   1620
taagggacga ggaaattggc tacgatacga aggacatggc tgaagaaaga cgcaaatttg   1680
ccgacgcgtt caacaagtcg caagtctatt tgtccaccag agttgcttta cagacattgt   1740
actggttggt caacaacaaa gagttcaagg agtgcaacga cattgtccac aagttcacca   1800
actactatgt tcagaaagcc ttggatgcta ccccagagga acttgaaaaa caaggcgggt   1860
atgtgttctt gtacgagctt gccaagcaga cgaaagaccc caatgtgttg cgtgaccagt   1920
ctttgaacat cttgttggct ggaagggaca ccactgctgg gttgttgtcc tttgctgtgt   1980
ttgagttggc caggaaccca cacatctggg ccaagttgag agaggaaatt gaatcacact   2040
ttgggctggg tgaggactct cgtgttgaag agattacctt tgagagcttg aagagatgtg   2100
agtacttgaa agccgtgttg aacgaaacgt tgagattaca cccaagtgtc ccaagaaacg   2160
caagatttgc gattaaagac acgactttac caagaggcgg tggccccaac ggcaaggatc   2220
ctatcttgat cagaaagaat gaggtggtgc aatactccat ctcggcaact cagacaaatc   2280
ctgcttatta tggcgccgat gctgctgatt ttagaccgga aagatggttt gagccatcaa   2340
ctagaaactt gggatgggct tacttgccat tcaacggtgg tccaagaatc tgcttgggac   2400
aacagtttgc tttgaccgaa gccggttacg ttttggttag acttgttcag gaattcccta   2460
gcttgtcaca ggaccccgaa actgagtacc caccacctag attggcacac ttgacgatgt   2520
gcttgtttga cggggcatac gtcaagatgc aataggtttt ggtttgactt tgtttccata   2580
tgcaagtagt tcagtaatta cacactaatt tgtggtggcc ggcgataaat taccgtttgg   2640
ttttgtgtaa aaattcggac atctctggtg gtttcccttc tccgcagcag ctttgccacg   2700
ggtttgctct gcggccaaca aattcgaaag gggggggggg gggggagaaa gttaacaccc   2760
cctgttccca ccgtaggctg tagctcttgt ggggggatgt aattgtcgta cgttttcatg   2820
tttggcccag actttgatga ttacgtaggc tttcttatgt ctaaggcgtg cttgacacaa   2880
gtgtcaaaag gtgacaggcg acgttattcg acatgaacgc aaaagggtaa tttgcatcga   2940
tacgaggggt tgcctctggt ctaagaagga ccccccaggt tgcaaacatg ttgcactgca   3000
tcccactcag agttggtcga ccacgcctac gcttaccctc agcgatcggc actttccgtt   3060
gctcaatatt tctctccccc ctgcttcccc ccattgttcc agggattatc aacaacgttg   3120
ccggtctcct ctcccccccc tccccccagt tatgtacaag aaaattaaat tgtcgcacgg   3180
caccgatacg tcaaagatac agagaaacct taatccctcc catagcctag aagcatcaaa   3240
aagatgattg agcaactcct ccagtactgg tacattgcac tccctgtatg gttcattctc   3300
cgctacgtgg cttcccacgc acgaaccatc tacttgcgcc acaagctcgg cgcggcgccg   3360
ttcacgcaca cccagtacga cggatggtat gggttcaagt ttgggcggga gtttctcaag   3420
```

-continued

```
gcgaagaaga ttggaaggca gacggacttg gtgcatgcgc ggttccgtgg agggggcatg   3480

gatactttct cgagctatac tttcggcatc catatcattc ttactcggga cccggagaac   3540

atcaaggcgg tcttggcgac gcagttcgat gacttttcg                          3579
```

<210> SEQ ID NO 94
<211> LENGTH: 3348
<212> TYPE: DNA
<213> ORGANISM: Candida tropicalis

<400> SEQUENCE: 94

```
gatgtggtgc ttgatttctc gagacacatc cttgtgaggt gccatgaatc tgtacctgtc     60

tgtaagcaca gggaactgct tcaacacctt attgcatatt ctgtctattg caagcgtgtg    120

ctgcaacgat atctgccaag gtatatagca gaacgtgctg atggttcctc cggtcatatt    180

ctgttggtag ttctgcaggt aaatttggat gtcaggtagt ggagggaggt ttgtatcggt    240

tgtgttttct tcttcctctc tctctgattc aacctccacg tctccttcgg gttctgtgtc    300

tgtgtctgag tcgtactgtt ggattaagtc catcgcatgt gtgaaaaaaa gtagcgctta    360

tttagacaac cagttcgttg ggcgggtatc agaaatagtc tgttgtgcac gaccatgagt    420

atgcaacttg acgagacgtc gttaggaatc cacagaatga tagcaggaag cttactacgt    480

gagagattct gcttagagga tgttctcttc ttgttgattc cattaggtgg gtatcatctc    540

cggtggtgac aacttgacac aagcagttcc gagaaccacc cacaacaatc accattccag    600

ctatcacttc tacatgtcaa cctacgatgt atctcatcac catctagttt cttggcaatc    660

gtttatttgt tatgggtcaa catccaatac aactccacca atgaagaaga aaaacggaaa    720

gcagaatacc agaatgacag tgtgagttcc tgaccattgc taatctatgg ctatatctag    780

tttgctatcg tgggatgtga tctgtgtcgt cttcatttgc gtttgtgttt atttcgggta    840

tgaatattgt tatactaaat acttgatgca caaacatggc gctcgagaaa tcgagaatgt    900

gatcaacgat gggttctttg ggttccgctt acctttgcta ctcatgcgag ccagcaatga    960

gggccgactt atcgagttca gtgtcaagag attcgagtcg gcgccacatc cacagaacaa   1020

gacattggtc aaccgggcat tgagcgttcc tgtgatactc accaaggacc cagtgaatat   1080

caaagcgatg ctatcgaccc agtttgatga cttttccctt gggttgagac tacaccagtt   1140

tgcgccgttg ttggggaaag gcatctttac tttggacggc ccagagtgga agcagagccg   1200

atctatgttg cgtccgcaat ttgccaaaga tcgggtttct catatcctgg atctagaacc   1260

gcattttgtg ttgcttcgga agcacattga tggccacaat ggagactact tcgacatcca   1320

ggagctctac ttccggttct cgatggatgt ggcgacgggg tttttgtttg gcgagtctgt   1380

ggggtcgttg aaagacgaag atgcgaggtt cctggaagca ttcaatgagt cgcagaagta   1440

tttggcaact agggcaacgt tgcacgagtt gtactttctt tgtgacgggt ttaggtttcg   1500

ccagtacaac aaggttgtgc gaaagttctg cagccagtgt gtccacaagg cgttagatgt   1560

tgcaccggaa gacaccagcg agtacgtgtt tctccgcgag ttggtcaaac acactcgaga   1620

tcccgttgtt ttacaagacc aagcgttgaa cgtcttgctt gctggacgcg acaccaccgc   1680

gtcgttatta tcgtttgcaa catttgagct agcccggaat gaccacatgt ggaggaagct   1740

acgagaggag gttatcctga cgatgggacc gtccagtgat gaaataaccg tggccgggtt   1800

gaagagttgc cgttacctca aagcaatcct aaacgaaact cttcgactat acccaagtgt   1860

gcctaggaac gcgagatttg ctacgaggaa tacgacgctt cctcgtggcg gaggtccaga   1920

tggatcgttt ccgattttga taagaaaggg ccagccagtg ggtatttca tttgtgctac    1980
```

-continued

```
acacttgaat gagaaggtat atgggaatga tagccatgtg tttcgaccgg agagatgggc   2040
tgcgttagag ggcaagagtt tggctggtc gtatcttcca ttcaacggcg gcccgagaag   2100
ctgccttggt cagcagtttg caatccttga agcttcgtat gttttggctc gattgacaca   2160
gtgctacacg acgatacagc ttagaactac cgagtaccca ccaaagaaac tcgttcatct   2220
cacgatgagt cttctcaacg gggtgtacat ccgaactaga acttgattat gtgtttatgg   2280
ttaatcgggg caaagcactg caagtcattg atgtttgtgg aagcccagca ttggtgttcc   2340
ggagcatcaa taaccaatgt cttgaagggt ttgattttct tgaccttctt cttcctgagc   2400
ttctttccgt caaacttgta cagaatggcc atcatttcag gaacaaccac gtacgacggc   2460
cggtaccgca tctggagtat ctcgccgtcg ttcaagtagc acgaaaacag caacgacgtc   2520
accatctgct tcccaatctt gacacccaca gataccctg cggcttcatg gatcaaaaac   2580
gtcggcaacc ccgcgtatat gtccatgtaa ttctccatgg ccacctccat caacacactg   2640
atggagcgac tgacggtgcc accactgccc tcggttgagt caaggcagta tgatgccggg   2700
atccagtact ccaatgggaa cctctgcacg gtgtcgctgc agtttttgag gcgtatttcg   2760
atccatgatc gttctttggt gctgtagtat aacgagctct tggtgtcctt gaaatggaac   2820
aggttggatg tgttgttgag tttgtctgcg tgcttggttt gcaagtcttc gatcgagcgt   2880
agtgagtaga cagttggcgg gggtggtggc tcgggcttta ttctgtgttt gtgtttcctt   2940
cttagtcttg gaatgacgct gttatcgacg gttcgtagta taagtagcgc caatatgaga   3000
atgtatatcc gcatcaccca agactcttca gcctgttaca acgactgagg ctgttggccg   3060
tgtgaccaat tggtttcttt ggtgacctag attggtcccg cagggaaagc aagggctgct   3120
agggggcat accaaacaag gtcgtgtaat cagtatctat ggtgctacca tgtgtgtggt   3180
tgggggaaa ttcccgcatt tttgtgtaac gaaagttcta gaaagttctc gtgggttctg   3240
agaatctgct ggaaccatcc acccgcattt ccgttgccaa agtgggaaga gcaatcaacc   3300
caccctgctt tgcccaatca gccattcccc tgggaatata aattcaac                 3348
```

```
<210> SEQ ID NO 95
<211> LENGTH: 523
<212> TYPE: PRT
<213> ORGANISM: CANDIDATROPICALIS

<400> SEQUENCE: 95

Met Ala Thr Gln Glu Ile Ile Asp Ser Val Leu Pro Tyr Leu Thr Lys
1               5                   10                  15

Trp Tyr Thr Val Ile Thr Ala Ala Val Leu Val Phe Leu Ile Ser Thr
            20                  25                  30

Asn Ile Lys Asn Tyr Val Lys Ala Lys Lys Leu Lys Cys Val Asp Pro
        35                  40                  45

Pro Tyr Leu Lys Asp Ala Gly Leu Thr Gly Ile Leu Ser Leu Ile Ala
    50                  55                  60

Ala Ile Lys Ala Lys Asn Asp Gly Arg Leu Ala Asn Phe Ala Asp Glu
65                  70                  75                  80

Val Phe Asp Glu Tyr Pro Asn His Thr Phe Tyr Leu Ser Val Ala Gly
                85                  90                  95

Ala Leu Lys Ile Val Met Thr Val Asp Pro Glu Asn Ile Lys Ala Val
            100                 105                 110

Leu Ala Thr Gln Phe Thr Asp Phe Ser Leu Gly Thr Arg His Ala His
        115                 120                 125
```

-continued

```
Phe Ala Pro Leu Leu Gly Asp Gly Ile Phe Thr Leu Asp Gly Glu Gly
    130                 135                 140

Trp Lys His Ser Arg Ala Met Leu Arg Pro Gln Phe Ala Arg Asp Gln
145                 150                 155                 160

Ile Gly His Val Lys Ala Leu Glu Pro His Ile Gln Ile Met Ala Lys
                165                 170                 175

Gln Ile Lys Leu Asn Gln Gly Lys Thr Phe Asp Ile Gln Glu Leu Phe
            180                 185                 190

Phe Arg Phe Thr Val Asp Thr Ala Thr Glu Phe Leu Phe Gly Glu Ser
        195                 200                 205

Val His Ser Leu Tyr Asp Glu Lys Leu Gly Ile Pro Thr Pro Asn Glu
    210                 215                 220

Ile Pro Gly Arg Glu Asn Phe Ala Ala Ala Phe Asn Val Ser Gln His
225                 230                 235                 240

Tyr Leu Ala Thr Arg Ser Tyr Ser Gln Thr Phe Tyr Phe Leu Thr Asn
                245                 250                 255

Pro Lys Glu Phe Arg Asp Cys Asn Ala Lys Val His His Leu Ala Lys
            260                 265                 270

Tyr Phe Val Asn Lys Ala Leu Asn Phe Thr Pro Glu Glu Leu Glu Glu
        275                 280                 285

Lys Ser Lys Ser Gly Tyr Val Phe Leu Tyr Glu Leu Val Lys Gln Thr
    290                 295                 300

Arg Asp Pro Lys Val Leu Gln Asp Gln Leu Leu Asn Ile Met Val Ala
305                 310                 315                 320

Gly Arg Asp Thr Thr Ala Gly Leu Leu Ser Phe Ala Leu Phe Glu Leu
                325                 330                 335

Ala Arg His Pro Glu Met Trp Ser Lys Leu Arg Glu Glu Ile Glu Val
            340                 345                 350

Asn Phe Gly Val Gly Glu Asp Ser Arg Val Glu Glu Ile Thr Phe Glu
        355                 360                 365

Ala Leu Lys Arg Cys Glu Tyr Leu Lys Ala Ile Leu Asn Glu Thr Leu
    370                 375                 380

Arg Met Tyr Pro Ser Val Pro Val Asn Phe Arg Thr Ala Thr Arg Asp
385                 390                 395                 400

Thr Thr Leu Pro Arg Gly Gly Gly Ala Asn Gly Thr Asp Pro Ile Tyr
                405                 410                 415

Ile Pro Lys Gly Ser Thr Val Ala Tyr Val Val Tyr Lys Thr His Arg
            420                 425                 430

Leu Glu Glu Tyr Tyr Gly Lys Asp Ala Asn Asp Phe Arg Pro Glu Arg
        435                 440                 445

Trp Phe Glu Pro Ser Thr Lys Lys Leu Gly Trp Ala Tyr Val Pro Phe
    450                 455                 460

Asn Gly Gly Pro Arg Val Cys Leu Gly Gln Gln Phe Ala Leu Thr Glu
465                 470                 475                 480

Ala Ser Tyr Val Ile Thr Arg Leu Ala Gln Met Phe Glu Thr Val Ser
                485                 490                 495

Ser Asp Pro Gly Leu Glu Tyr Pro Pro Pro Lys Cys Ile His Leu Thr
            500                 505                 510

Met Ser His Asn Asp Gly Val Phe Val Lys Met
        515                 520
```

<210> SEQ ID NO 96
<211> LENGTH: 522
<212> TYPE: PRT

-continued

```
<213> ORGANISM: CANDIDATROPICALIS

<400> SEQUENCE: 96

Met Thr Val His Asp Ile Ile Ala Thr Tyr Phe Thr Lys Trp Tyr Val
1               5                   10                  15

Ile Val Pro Leu Ala Leu Ile Ala Tyr Arg Val Leu Asp Tyr Phe Tyr
            20                  25                  30

Gly Arg Tyr Leu Met Tyr Lys Leu Gly Ala Lys Pro Phe Phe Gln Lys
        35                  40                  45

Gln Thr Asp Gly Cys Phe Gly Phe Lys Ala Pro Leu Glu Leu Leu Lys
    50                  55                  60

Lys Lys Ser Asp Gly Thr Leu Ile Asp Phe Thr Leu Gln Arg Ile His
65                  70                  75                  80

Asp Leu Asp Arg Pro Asp Ile Pro Thr Phe Thr Phe Pro Val Phe Ser
                85                  90                  95

Ile Asn Leu Val Asn Thr Leu Glu Pro Glu Asn Ile Lys Ala Ile Leu
            100                 105                 110

Ala Thr Gln Phe Asn Asp Phe Ser Leu Gly Thr Arg His Ser His Phe
        115                 120                 125

Ala Pro Leu Leu Gly Asp Gly Ile Phe Thr Leu Asp Gly Ala Gly Trp
    130                 135                 140

Lys His Ser Arg Ser Met Leu Arg Pro Gln Phe Ala Arg Glu Gln Ile
145                 150                 155                 160

Ser His Val Lys Leu Leu Glu Pro His Val Gln Val Phe Phe Lys His
                165                 170                 175

Val Arg Lys Ala Gln Gly Lys Thr Phe Asp Ile Gln Glu Leu Phe Phe
            180                 185                 190

Arg Leu Thr Val Asp Ser Ala Thr Glu Phe Leu Phe Gly Glu Ser Val
        195                 200                 205

Glu Ser Leu Arg Asp Glu Ser Ile Gly Met Ser Ile Asn Ala Leu Asp
    210                 215                 220

Phe Asp Gly Lys Ala Gly Phe Ala Asp Ala Phe Asn Tyr Ser Gln Asn
225                 230                 235                 240

Tyr Leu Ala Ser Arg Ala Val Met Gln Gln Leu Tyr Trp Val Leu Asn
                245                 250                 255

Gly Lys Lys Phe Lys Glu Cys Asn Ala Lys Val His Lys Phe Ala Asp
            260                 265                 270

Tyr Tyr Val Asn Lys Ala Leu Asp Leu Thr Pro Glu Gln Leu Glu Lys
        275                 280                 285

Gln Asp Gly Tyr Val Phe Leu Tyr Glu Leu Val Lys Gln Thr Arg Asp
    290                 295                 300

Lys Gln Val Leu Arg Asp Gln Leu Leu Asn Ile Met Val Ala Gly Arg
305                 310                 315                 320

Asp Thr Thr Ala Gly Leu Leu Ser Phe Val Phe Phe Glu Leu Ala Arg
                325                 330                 335

Asn Pro Glu Val Thr Asn Lys Leu Arg Glu Glu Ile Glu Asp Lys Phe
            340                 345                 350

Gly Leu Gly Glu Asn Ala Ser Val Glu Asp Ile Ser Phe Glu Ser Leu
        355                 360                 365

Lys Ser Cys Glu Tyr Leu Lys Ala Val Leu Asn Glu Thr Leu Arg Leu
    370                 375                 380

Tyr Pro Ser Val Pro Gln Asn Phe Arg Val Ala Thr Lys Asn Thr Thr
385                 390                 395                 400
```

-continued

```
Leu Pro Arg Gly Gly Gly Lys Asp Gly Leu Ser Pro Val Leu Val Arg
                405                 410                 415

Lys Gly Gln Thr Val Ile Tyr Gly Val Tyr Ala Ala His Arg Asn Pro
            420                 425                 430

Ala Val Tyr Gly Lys Asp Ala Leu Glu Phe Arg Pro Glu Arg Trp Phe
        435                 440                 445

Glu Pro Glu Thr Lys Lys Leu Gly Trp Ala Phe Leu Pro Phe Asn Gly
    450                 455                 460

Gly Pro Arg Ile Cys Leu Gly Gln Gln Phe Ala Leu Thr Glu Ala Ser
465                 470                 475                 480

Tyr Val Thr Val Arg Leu Leu Gln Glu Phe Ala His Leu Ser Met Asp
                485                 490                 495

Pro Asp Thr Glu Tyr Pro Pro Lys Lys Met Ser His Leu Thr Met Ser
            500                 505                 510

Leu Phe Asp Gly Ala Asn Ile Glu Met Tyr
        515                 520


<210> SEQ ID NO 97
<211> LENGTH: 522
<212> TYPE: PRT
<213> ORGANISM: CANDIDATROPICALIS

<400> SEQUENCE: 97

Met Thr Ala Gln Asp Ile Ile Ala Thr Tyr Ile Thr Lys Trp Tyr Val
1               5                   10                  15

Ile Val Pro Leu Ala Leu Ile Ala Tyr Arg Val Leu Asp Tyr Phe Tyr
            20                  25                  30

Gly Arg Tyr Leu Met Tyr Lys Leu Gly Ala Lys Pro Phe Phe Gln Lys
        35                  40                  45

Gln Thr Asp Gly Tyr Phe Gly Phe Lys Ala Pro Leu Glu Leu Leu Lys
    50                  55                  60

Lys Lys Ser Asp Gly Thr Leu Ile Asp Phe Thr Leu Glu Arg Ile Gln
65                  70                  75                  80

Ala Leu Asn Arg Pro Asp Ile Pro Thr Phe Thr Phe Pro Ile Phe Ser
                85                  90                  95

Ile Asn Leu Ile Ser Thr Leu Glu Pro Glu Asn Ile Lys Ala Ile Leu
            100                 105                 110

Ala Thr Gln Phe Asn Asp Phe Ser Leu Gly Thr Arg His Ser His Phe
        115                 120                 125

Ala Pro Leu Leu Gly Asp Gly Ile Phe Thr Leu Asp Gly Ala Gly Trp
    130                 135                 140

Lys His Ser Arg Ser Met Leu Arg Pro Gln Phe Ala Arg Glu Gln Ile
145                 150                 155                 160

Ser His Val Lys Leu Leu Glu Pro His Met Gln Val Phe Phe Lys His
                165                 170                 175

Val Arg Lys Ala Gln Gly Lys Thr Phe Asp Ile Gln Glu Leu Phe Phe
            180                 185                 190

Arg Leu Thr Val Asp Ser Ala Thr Glu Phe Leu Phe Gly Glu Ser Val
        195                 200                 205

Glu Ser Leu Arg Asp Glu Ser Ile Gly Met Ser Ile Asn Ala Leu Asp
    210                 215                 220

Phe Asp Gly Lys Ala Gly Phe Ala Asp Ala Phe Asn Tyr Ser Gln Asn
225                 230                 235                 240

Tyr Leu Ala Ser Arg Ala Val Met Gln Gln Leu Tyr Trp Val Leu Asn
                245                 250                 255
```

-continued

```
Gly Lys Lys Phe Lys Glu Cys Asn Ala Lys Val His Lys Phe Ala Asp
            260                 265                 270

Tyr Tyr Val Ser Lys Ala Leu Asp Leu Thr Pro Glu Gln Leu Glu Lys
        275                 280                 285

Gln Asp Gly Tyr Val Phe Leu Tyr Glu Leu Val Lys Gln Thr Arg Asp
    290                 295                 300

Arg Gln Val Leu Arg Asp Gln Leu Leu Asn Ile Met Val Ala Gly Arg
305                 310                 315                 320

Asp Thr Thr Ala Gly Leu Leu Ser Phe Val Phe Phe Glu Leu Ala Arg
                325                 330                 335

Asn Pro Glu Val Thr Asn Lys Leu Arg Glu Glu Ile Glu Asp Lys Phe
            340                 345                 350

Gly Leu Gly Glu Asn Ala Arg Val Glu Asp Ile Ser Phe Glu Ser Leu
        355                 360                 365

Lys Ser Cys Glu Tyr Leu Lys Ala Val Leu Asn Glu Thr Leu Arg Leu
    370                 375                 380

Tyr Pro Ser Val Pro Gln Asn Phe Arg Val Ala Thr Lys Asn Thr Thr
385                 390                 395                 400

Leu Pro Arg Gly Gly Gly Lys Asp Gly Leu Ser Pro Val Leu Val Arg
                405                 410                 415

Lys Gly Gln Thr Val Met Tyr Gly Val Tyr Ala Ala His Arg Asn Pro
            420                 425                 430

Ala Val Tyr Gly Lys Asp Ala Leu Glu Phe Arg Pro Glu Arg Trp Phe
        435                 440                 445

Glu Pro Glu Thr Lys Lys Leu Gly Trp Ala Phe Leu Pro Phe Asn Gly
    450                 455                 460

Gly Pro Arg Ile Cys Leu Gly Gln Gln Phe Ala Leu Thr Glu Ala Ser
465                 470                 475                 480

Tyr Val Thr Val Arg Leu Leu Gln Glu Phe Gly His Leu Ser Met Asp
                485                 490                 495

Pro Asn Thr Glu Tyr Pro Pro Arg Lys Met Ser His Leu Thr Met Ser
            500                 505                 510

Leu Phe Asp Gly Ala Asn Ile Glu Met Tyr
        515                 520


<210> SEQ ID NO 98
<211> LENGTH: 540
<212> TYPE: PRT
<213> ORGANISM: CANDIDATROPICALIS

<400> SEQUENCE: 98

Met Ser Ser Ser Pro Ser Phe Ala Gln Glu Val Leu Ala Thr Thr Ser
1               5                   10                  15

Pro Tyr Ile Glu Tyr Phe Leu Asp Asn Tyr Thr Arg Trp Tyr Tyr Phe
            20                  25                  30

Ile Pro Leu Val Leu Leu Ser Leu Asn Phe Ile Ser Leu Leu His Thr
        35                  40                  45

Arg Tyr Leu Glu Arg Arg Phe His Ala Lys Pro Leu Gly Asn Phe Val
    50                  55                  60

Arg Asp Pro Thr Phe Gly Ile Ala Thr Pro Leu Leu Leu Ile Tyr Leu
65                  70                  75                  80

Lys Ser Lys Gly Thr Val Met Lys Phe Ala Trp Gly Leu Trp Asn Asn
                85                  90                  95
```

-continued

```
Lys Tyr Ile Val Arg Asp Pro Lys Tyr Lys Thr Thr Gly Leu Arg Ile
            100                 105                 110

Val Gly Leu Pro Leu Ile Glu Thr Met Asp Pro Glu Asn Ile Lys Ala
        115                 120                 125

Val Leu Ala Thr Gln Phe Asn Asp Phe Ser Leu Gly Thr Arg His Asp
    130                 135                 140

Phe Leu Tyr Ser Leu Leu Gly Asp Gly Ile Phe Thr Leu Asp Gly Ala
145                 150                 155                 160

Gly Trp Lys His Ser Arg Thr Met Leu Arg Pro Gln Phe Ala Arg Glu
                165                 170                 175

Gln Val Ser His Val Lys Leu Leu Glu Pro His Val Gln Val Phe Phe
            180                 185                 190

Lys His Val Arg Lys His Arg Gly Gln Thr Phe Asp Ile Gln Glu Leu
        195                 200                 205

Phe Phe Arg Leu Thr Val Asp Ser Ala Thr Glu Phe Leu Phe Gly Glu
    210                 215                 220

Ser Ala Glu Ser Leu Arg Asp Glu Ser Ile Gly Leu Thr Pro Thr Thr
225                 230                 235                 240

Lys Asp Phe Asp Gly Arg Arg Asp Phe Ala Asp Ala Phe Asn Tyr Ser
                245                 250                 255

Gln Thr Tyr Gln Ala Tyr Arg Phe Leu Leu Gln Gln Met Tyr Trp Ile
            260                 265                 270

Leu Asn Gly Ser Glu Phe Arg Lys Ser Ile Ala Val Val His Lys Phe
        275                 280                 285

Ala Asp His Tyr Val Gln Lys Ala Leu Glu Leu Thr Asp Asp Asp Leu
    290                 295                 300

Gln Lys Gln Asp Gly Tyr Val Phe Leu Tyr Glu Leu Ala Lys Gln Thr
305                 310                 315                 320

Arg Asp Pro Lys Val Leu Arg Asp Gln Leu Leu Asn Ile Leu Val Ala
                325                 330                 335

Gly Arg Asp Thr Thr Ala Gly Leu Leu Ser Phe Val Phe Tyr Glu Leu
            340                 345                 350

Ser Arg Asn Pro Glu Val Phe Ala Lys Leu Arg Glu Glu Val Glu Asn
        355                 360                 365

Arg Phe Gly Leu Gly Glu Glu Ala Arg Val Glu Glu Ile Ser Phe Glu
    370                 375                 380

Ser Leu Lys Ser Cys Glu Tyr Leu Lys Ala Val Ile Asn Glu Thr Leu
385                 390                 395                 400

Arg Leu Tyr Pro Ser Val Pro His Asn Phe Arg Val Ala Thr Arg Asn
                405                 410                 415

Thr Thr Leu Pro Arg Gly Gly Gly Glu Asp Gly Tyr Ser Pro Ile Val
            420                 425                 430

Val Lys Lys Gly Gln Val Val Met Tyr Thr Val Ile Ala Thr His Arg
        435                 440                 445

Asp Pro Ser Ile Tyr Gly Ala Asp Ala Asp Val Phe Arg Pro Glu Arg
    450                 455                 460

Trp Phe Glu Pro Glu Thr Arg Lys Leu Gly Trp Ala Tyr Val Pro Phe
465                 470                 475                 480

Asn Gly Gly Pro Arg Ile Cys Leu Gly Gln Gln Phe Ala Leu Thr Glu
                485                 490                 495

Ala Ser Tyr Val Thr Val Arg Leu Leu Gln Glu Phe Ala His Leu Ser
            500                 505                 510
```

-continued

```
Met Asp Pro Asp Thr Glu Tyr Pro Pro Lys Leu Gln Asn Thr Leu Thr
        515                 520                 525

Leu Ser Leu Phe Asp Gly Ala Asp Val Arg Met Tyr
    530                 535                 540


<210> SEQ ID NO 99
<211> LENGTH: 540
<212> TYPE: PRT
<213> ORGANISM: CANDIDATROPICALIS

<400> SEQUENCE: 99

Met Ser Ser Ser Pro Ser Phe Ala Gln Glu Val Leu Ala Thr Thr Ser
1               5                   10                  15

Pro Tyr Ile Glu Tyr Phe Leu Asp Asn Tyr Thr Arg Trp Tyr Tyr Phe
            20                  25                  30

Ile Pro Leu Val Leu Leu Ser Leu Asn Phe Ile Ser Leu Leu His Thr
        35                  40                  45

Lys Tyr Leu Glu Arg Arg Phe His Ala Lys Pro Leu Gly Asn Val Val
    50                  55                  60

Leu Asp Pro Thr Phe Gly Ile Ala Thr Pro Leu Ile Leu Ile Tyr Leu
65                  70                  75                  80

Lys Ser Lys Gly Thr Val Met Lys Phe Ala Trp Ser Phe Trp Asn Asn
                85                  90                  95

Lys Tyr Ile Val Lys Asp Pro Lys Tyr Lys Thr Thr Gly Leu Arg Ile
            100                 105                 110

Val Gly Leu Pro Leu Ile Glu Thr Ile Asp Pro Glu Asn Ile Lys Ala
        115                 120                 125

Val Leu Ala Thr Gln Phe Asn Asp Phe Ser Leu Gly Thr Arg His Asp
    130                 135                 140

Phe Leu Tyr Ser Leu Leu Gly Asp Gly Ile Phe Thr Leu Asp Gly Ala
145                 150                 155                 160

Gly Trp Lys His Ser Arg Thr Met Leu Arg Pro Gln Phe Ala Arg Glu
                165                 170                 175

Gln Val Ser His Val Lys Leu Leu Glu Pro His Val Gln Val Phe Phe
            180                 185                 190

Lys His Val Arg Lys His Arg Gly Gln Thr Phe Asp Ile Gln Glu Leu
        195                 200                 205

Phe Phe Arg Leu Thr Val Asp Ser Ala Thr Glu Phe Leu Phe Gly Glu
    210                 215                 220

Ser Ala Glu Ser Leu Arg Asp Asp Ser Val Gly Leu Thr Pro Thr Thr
225                 230                 235                 240

Lys Asp Phe Glu Gly Arg Gly Asp Phe Ala Asp Ala Phe Asn Tyr Ser
                245                 250                 255

Gln Thr Tyr Gln Ala Tyr Arg Phe Leu Leu Gln Gln Met Tyr Trp Ile
            260                 265                 270

Leu Asn Gly Ala Glu Phe Arg Lys Ser Ile Ala Ile Val His Lys Phe
        275                 280                 285

Ala Asp His Tyr Val Gln Lys Ala Leu Glu Leu Thr Asp Asp Asp Leu
    290                 295                 300

Gln Lys Gln Asp Gly Tyr Val Phe Leu Tyr Glu Leu Ala Lys Gln Thr
305                 310                 315                 320

Arg Asp Pro Lys Val Leu Arg Asp Gln Leu Leu Asn Ile Leu Val Ala
                325                 330                 335

Gly Arg Asp Thr Thr Ala Gly Leu Leu Ser Phe Val Phe Tyr Glu Leu
            340                 345                 350
```

-continued

```
Ser Arg Asn Pro Glu Val Phe Ala Lys Leu Arg Glu Glu Val Glu Asn
        355                 360                 365

Arg Phe Gly Leu Gly Glu Glu Ala Arg Val Glu Glu Ile Ser Phe Glu
    370                 375                 380

Ser Leu Lys Ser Cys Glu Tyr Leu Lys Ala Val Ile Asn Glu Ala Leu
385                 390                 395                 400

Arg Leu Tyr Pro Ser Val Pro His Asn Phe Arg Val Ala Thr Arg Asn
                405                 410                 415

Thr Thr Leu Pro Arg Gly Gly Gly Lys Asp Gly Cys Ser Pro Ile Val
            420                 425                 430

Val Lys Lys Gly Gln Val Val Met Tyr Thr Val Ile Gly Thr His Arg
        435                 440                 445

Asp Pro Ser Ile Tyr Gly Ala Asp Ala Asp Val Phe Arg Pro Glu Arg
    450                 455                 460

Trp Phe Glu Pro Glu Thr Arg Lys Leu Gly Trp Ala Tyr Val Pro Phe
465                 470                 475                 480

Asn Gly Gly Pro Arg Ile Cys Leu Gly Gln Gln Phe Ala Leu Thr Glu
                485                 490                 495

Ala Ser Tyr Val Thr Val Arg Leu Leu Gln Glu Phe Gly Asn Leu Ser
            500                 505                 510

Leu Asp Pro Asn Ala Glu Tyr Pro Pro Lys Leu Gln Asn Thr Leu Thr
        515                 520                 525

Leu Ser Leu Phe Asp Gly Ala Asp Val Arg Met Phe
    530                 535                 540


<210> SEQ ID NO 100
<211> LENGTH: 517
<212> TYPE: PRT
<213> ORGANISM: CANDIDATROPICALIS

<400> SEQUENCE: 100

Met Ile Glu Gln Leu Leu Glu Tyr Trp Tyr Val Val Val Pro Val Leu
1               5                   10                  15

Tyr Ile Ile Lys Gln Leu Leu Ala Tyr Thr Lys Thr Arg Val Leu Met
            20                  25                  30

Lys Lys Leu Gly Ala Ala Pro Val Thr Asn Lys Leu Tyr Asp Asn Ala
        35                  40                  45

Phe Gly Ile Val Asn Gly Trp Lys Ala Leu Gln Phe Lys Lys Glu Gly
    50                  55                  60

Arg Ala Gln Glu Tyr Asn Asp Tyr Lys Phe Asp His Ser Lys Asn Pro
65                  70                  75                  80

Ser Val Gly Thr Tyr Val Ser Ile Leu Phe Gly Thr Arg Ile Val Val
                85                  90                  95

Thr Lys Asp Pro Glu Asn Ile Lys Ala Ile Leu Ala Thr Gln Phe Gly
            100                 105                 110

Asp Phe Ser Leu Gly Lys Arg His Thr Leu Phe Lys Pro Leu Leu Gly
        115                 120                 125

Asp Gly Ile Phe Thr Leu Asp Gly Glu Gly Trp Lys His Ser Arg Ala
    130                 135                 140

Met Leu Arg Pro Gln Phe Ala Arg Glu Gln Val Ala His Val Thr Ser
145                 150                 155                 160

Leu Glu Pro His Phe Gln Leu Leu Lys Lys His Ile Leu Lys His Lys
                165                 170                 175
```

-continued

```
Gly Glu Tyr Phe Asp Ile Gln Glu Leu Phe Phe Arg Phe Thr Val Asp
            180                 185                 190

Ser Ala Thr Glu Phe Leu Phe Gly Glu Ser Val His Ser Leu Lys Asp
        195                 200                 205

Glu Ser Ile Gly Ile Asn Gln Asp Asp Ile Asp Phe Ala Gly Arg Lys
    210                 215                 220

Asp Phe Ala Glu Ser Phe Asn Lys Ala Gln Glu Tyr Leu Ala Ile Arg
225                 230                 235                 240

Thr Leu Val Gln Thr Phe Tyr Trp Leu Val Asn Asn Lys Glu Phe Arg
                245                 250                 255

Asp Cys Thr Lys Leu Val His Lys Phe Thr Asn Tyr Tyr Val Gln Lys
            260                 265                 270

Ala Leu Asp Ala Ser Pro Glu Glu Leu Glu Lys Gln Ser Gly Tyr Val
        275                 280                 285

Phe Leu Tyr Glu Leu Val Lys Gln Thr Arg Asp Pro Asn Val Leu Arg
    290                 295                 300

Asp Gln Ser Leu Asn Ile Leu Leu Ala Gly Arg Asp Thr Thr Ala Gly
305                 310                 315                 320

Leu Leu Ser Phe Ala Val Phe Glu Leu Ala Arg His Pro Glu Ile Trp
                325                 330                 335

Ala Lys Leu Arg Glu Glu Ile Glu Gln Gln Phe Gly Leu Gly Glu Asp
            340                 345                 350

Ser Arg Val Glu Glu Ile Thr Phe Glu Ser Leu Lys Arg Cys Glu Tyr
        355                 360                 365

Leu Lys Ala Phe Leu Asn Glu Thr Leu Arg Ile Tyr Pro Ser Val Pro
    370                 375                 380

Arg Asn Phe Arg Ile Ala Thr Lys Asn Thr Thr Leu Pro Arg Gly Gly
385                 390                 395                 400

Gly Ser Asp Gly Thr Ser Pro Ile Leu Ile Gln Lys Gly Glu Ala Val
                405                 410                 415

Ser Tyr Gly Ile Asn Ser Thr His Leu Asp Pro Val Tyr Tyr Gly Pro
            420                 425                 430

Asp Ala Ala Glu Phe Arg Pro Glu Arg Trp Phe Glu Pro Ser Thr Lys
        435                 440                 445

Lys Leu Gly Trp Ala Tyr Leu Pro Phe Asn Gly Gly Pro Arg Ile Cys
    450                 455                 460

Leu Gly Gln Gln Phe Ala Leu Thr Glu Ala Gly Tyr Val Leu Val Arg
465                 470                 475                 480

Leu Val Gln Glu Phe Ser His Val Arg Leu Asp Pro Asp Glu Val Tyr
                485                 490                 495

Pro Pro Lys Arg Leu Thr Asn Leu Thr Met Cys Leu Gln Asp Gly Ala
            500                 505                 510

Ile Val Lys Phe Asp
        515


<210> SEQ ID NO 101
<211> LENGTH: 517
<212> TYPE: PRT
<213> ORGANISM: CANDIDATROPICALIS

<400> SEQUENCE: 101

Met Ile Glu Gln Ile Leu Glu Tyr Trp Tyr Ile Val Val Pro Val Leu
1               5                   10                  15
```

-continued

```
Tyr Ile Ile Lys Gln Leu Ile Ala Tyr Ser Lys Thr Arg Val Leu Met
            20                  25                  30

Lys Gln Leu Gly Ala Ala Pro Ile Thr Asn Gln Leu Tyr Asp Asn Val
        35                  40                  45

Phe Gly Ile Val Asn Gly Trp Lys Ala Leu Gln Phe Lys Lys Glu Gly
    50                  55                  60

Arg Ala Gln Glu Tyr Asn Asp His Lys Phe Asp Ser Ser Lys Asn Pro
65                  70                  75                  80

Ser Val Gly Thr Tyr Val Ser Ile Leu Phe Gly Thr Lys Ile Val Val
                85                  90                  95

Thr Lys Asp Pro Glu Asn Ile Lys Ala Ile Leu Ala Thr Gln Phe Gly
            100                 105                 110

Asp Phe Ser Leu Gly Lys Arg His Ala Leu Phe Lys Pro Leu Leu Gly
        115                 120                 125

Asp Gly Ile Phe Thr Leu Asp Gly Glu Gly Trp Lys His Ser Arg Ser
    130                 135                 140

Met Leu Arg Pro Gln Phe Ala Arg Glu Gln Val Ala His Val Thr Ser
145                 150                 155                 160

Leu Glu Pro His Phe Gln Leu Leu Lys Lys His Ile Leu Lys His Lys
                165                 170                 175

Gly Glu Tyr Phe Asp Ile Gln Glu Leu Phe Phe Arg Phe Thr Val Asp
            180                 185                 190

Ser Ala Thr Glu Phe Leu Phe Gly Glu Ser Val His Ser Leu Lys Asp
        195                 200                 205

Glu Thr Ile Gly Ile Asn Gln Asp Asp Ile Asp Phe Ala Gly Arg Lys
    210                 215                 220

Asp Phe Ala Glu Ser Phe Asn Lys Ala Gln Glu Tyr Leu Ser Ile Arg
225                 230                 235                 240

Ile Leu Val Gln Thr Phe Tyr Trp Leu Ile Asn Asn Lys Glu Phe Arg
                245                 250                 255

Asp Cys Thr Lys Leu Val His Lys Phe Thr Asn Tyr Tyr Val Gln Lys
            260                 265                 270

Ala Leu Asp Ala Thr Pro Glu Glu Leu Glu Lys Gln Gly Gly Tyr Val
        275                 280                 285

Phe Leu Tyr Glu Leu Val Lys Gln Thr Arg Asp Pro Lys Val Leu Arg
    290                 295                 300

Asp Gln Ser Leu Asn Ile Leu Leu Ala Gly Arg Asp Thr Thr Ala Gly
305                 310                 315                 320

Leu Leu Ser Phe Ala Val Phe Glu Leu Ala Arg Asn Pro His Ile Trp
                325                 330                 335

Ala Lys Leu Arg Glu Glu Ile Glu Gln Gln Phe Gly Leu Gly Glu Asp
            340                 345                 350

Ser Arg Val Glu Glu Ile Thr Phe Glu Ser Leu Lys Arg Cys Glu Tyr
        355                 360                 365

Leu Lys Ala Phe Leu Asn Glu Thr Leu Arg Val Tyr Pro Ser Val Pro
    370                 375                 380

Arg Asn Phe Arg Ile Ala Thr Lys Asn Thr Thr Leu Pro Arg Gly Gly
385                 390                 395                 400

Gly Pro Asp Gly Thr Gln Pro Ile Leu Ile Gln Lys Gly Glu Gly Val
                405                 410                 415

Ser Tyr Gly Ile Asn Ser Thr His Leu Asp Pro Val Tyr Tyr Gly Pro
            420                 425                 430
```

-continued

```
Asp Ala Ala Glu Phe Arg Pro Glu Arg Trp Phe Glu Pro Ser Thr Arg
        435                 440                 445

Lys Leu Gly Trp Ala Tyr Leu Pro Phe Asn Gly Gly Pro Arg Ile Cys
    450                 455                 460

Leu Gly Gln Gln Phe Ala Leu Thr Glu Ala Gly Tyr Val Leu Val Arg
465                 470                 475                 480

Leu Val Gln Glu Phe Ser His Ile Arg Leu Asp Pro Asp Glu Val Tyr
                485                 490                 495

Pro Pro Lys Arg Leu Thr Asn Leu Thr Met Cys Leu Gln Asp Gly Ala
            500                 505                 510

Ile Val Lys Phe Asp
        515


<210> SEQ ID NO 102
<211> LENGTH: 512
<212> TYPE: PRT
<213> ORGANISM: CANDIDATROPICALIS

<400> SEQUENCE: 102

Met Leu Asp Gln Ile Leu His Tyr Trp Tyr Ile Val Leu Pro Leu Leu
1               5                   10                  15

Ala Ile Ile Asn Gln Ile Val Ala His Val Arg Thr Asn Tyr Leu Met
            20                  25                  30

Lys Lys Leu Gly Ala Lys Pro Phe Thr His Val Gln Arg Asp Gly Trp
        35                  40                  45

Leu Gly Phe Lys Phe Gly Arg Glu Phe Leu Lys Ala Lys Ser Ala Gly
    50                  55                  60

Arg Leu Val Asp Leu Ile Ile Ser Arg Phe His Asp Asn Glu Asp Thr
65                  70                  75                  80

Phe Ser Ser Tyr Ala Phe Gly Asn His Val Val Phe Thr Arg Asp Pro
                85                  90                  95

Glu Asn Ile Lys Ala Leu Leu Ala Thr Gln Phe Gly Asp Phe Ser Leu
            100                 105                 110

Gly Ser Arg Val Lys Phe Phe Lys Pro Leu Leu Gly Tyr Gly Ile Phe
        115                 120                 125

Thr Leu Asp Ala Glu Gly Trp Lys His Ser Arg Ala Met Leu Arg Pro
    130                 135                 140

Gln Phe Ala Arg Glu Gln Val Ala His Val Thr Ser Leu Glu Pro His
145                 150                 155                 160

Phe Gln Leu Leu Lys Lys His Ile Leu Lys His Lys Gly Glu Tyr Phe
                165                 170                 175

Asp Ile Gln Glu Leu Phe Phe Arg Phe Thr Val Asp Ser Ala Thr Glu
            180                 185                 190

Phe Leu Phe Gly Glu Ser Val His Ser Leu Lys Asp Glu Glu Ile Gly
        195                 200                 205

Tyr Asp Thr Lys Asp Met Ser Glu Glu Arg Arg Arg Phe Ala Asp Ala
    210                 215                 220

Phe Asn Lys Ser Gln Val Tyr Val Ala Thr Arg Val Ala Leu Gln Asn
225                 230                 235                 240

Leu Tyr Trp Leu Val Asn Asn Lys Glu Phe Lys Glu Cys Asn Asp Ile
                245                 250                 255

Val His Lys Phe Thr Asn Tyr Tyr Val Gln Lys Ala Leu Asp Ala Thr
            260                 265                 270

Pro Glu Glu Leu Glu Lys Gln Gly Gly Tyr Val Phe Leu Tyr Glu Leu
        275                 280                 285
```

-continued

Val Lys Gln Thr Arg Asp Pro Lys Val Leu Arg Asp Gln Ser Leu Asn
290 295 300

Ile Leu Leu Ala Gly Arg Asp Thr Thr Ala Gly Leu Leu Ser Phe Ala
305 310 315 320

Val Phe Glu Leu Ala Arg Asn Pro His Ile Trp Ala Lys Leu Arg Glu
325 330 335

Glu Ile Glu Gln Gln Phe Gly Leu Gly Glu Asp Ser Arg Val Glu Glu
340 345 350

Ile Thr Phe Glu Ser Leu Lys Arg Cys Glu Tyr Leu Lys Ala Val Leu
355 360 365

Asn Glu Thr Leu Arg Leu His Pro Ser Val Pro Arg Asn Ala Arg Phe
370 375 380

Ala Ile Lys Asp Thr Thr Leu Pro Arg Gly Gly Gly Pro Asn Gly Lys
385 390 395 400

Asp Pro Ile Leu Ile Arg Lys Asp Glu Val Val Gln Tyr Ser Ile Ser
405 410 415

Ala Thr Gln Thr Asn Pro Ala Tyr Tyr Gly Ala Asp Ala Ala Asp Phe
420 425 430

Arg Pro Glu Arg Trp Phe Glu Pro Ser Thr Arg Asn Leu Gly Trp Ala
435 440 445

Phe Leu Pro Phe Asn Gly Gly Pro Arg Ile Cys Leu Gly Gln Gln Phe
450 455 460

Ala Leu Thr Glu Ala Gly Tyr Val Leu Val Arg Leu Val Gln Glu Phe
465 470 475 480

Pro Asn Leu Ser Gln Asp Pro Glu Thr Lys Tyr Pro Pro Pro Arg Leu
485 490 495

Ala His Leu Thr Met Cys Leu Phe Asp Gly Ala His Val Lys Met Ser
500 505 510

<210> SEQ ID NO 103
<211> LENGTH: 512
<212> TYPE: PRT
<213> ORGANISM: CANDIDATROPICALIS

<400> SEQUENCE: 103

Met Leu Asp Gln Ile Phe His Tyr Trp Tyr Ile Val Leu Pro Leu Leu
1 5 10 15

Val Ile Ile Lys Gln Ile Val Ala His Ala Arg Thr Asn Tyr Leu Met
20 25 30

Lys Lys Leu Gly Ala Lys Pro Phe Thr His Val Gln Leu Asp Gly Trp
35 40 45

Phe Gly Phe Lys Phe Gly Arg Glu Phe Leu Lys Ala Lys Ser Ala Gly
50 55 60

Arg Gln Val Asp Leu Ile Ile Ser Arg Phe His Asp Asn Glu Asp Thr
65 70 75 80

Phe Ser Ser Tyr Ala Phe Gly Asn His Val Val Phe Thr Arg Asp Pro
85 90 95

Glu Asn Ile Lys Ala Leu Leu Ala Thr Gln Phe Gly Asp Phe Ser Leu
100 105 110

Gly Ser Arg Val Lys Phe Phe Lys Pro Leu Leu Gly Tyr Gly Ile Phe
115 120 125

Thr Leu Asp Gly Glu Gly Trp Lys His Ser Arg Ala Met Leu Arg Pro
130 135 140

-continued

Gln Phe Ala Arg Glu Gln Val Ala His Val Thr Ser Leu Glu Pro His
145 150 155 160

Phe Gln Leu Leu Lys Lys His Ile Leu Lys His Lys Gly Glu Tyr Phe
165 170 175

Asp Ile Gln Glu Leu Phe Phe Arg Phe Thr Val Asp Ser Ala Thr Glu
180 185 190

Phe Leu Phe Gly Glu Ser Val His Ser Leu Arg Asp Glu Glu Ile Gly
195 200 205

Tyr Asp Thr Lys Asp Met Ala Glu Glu Arg Arg Lys Phe Ala Asp Ala
210 215 220

Phe Asn Lys Ser Gln Val Tyr Leu Ser Thr Arg Val Ala Leu Gln Thr
225 230 235 240

Leu Tyr Trp Leu Val Asn Asn Lys Glu Phe Lys Glu Cys Asn Asp Ile
245 250 255

Val His Lys Phe Thr Asn Tyr Tyr Val Gln Lys Ala Leu Asp Ala Thr
260 265 270

Pro Glu Glu Leu Glu Lys Gln Gly Gly Tyr Val Phe Leu Tyr Glu Leu
275 280 285

Ala Lys Gln Thr Lys Asp Pro Asn Val Leu Arg Asp Gln Ser Leu Asn
290 295 300

Ile Leu Leu Ala Gly Arg Asp Thr Thr Ala Gly Leu Leu Ser Phe Ala
305 310 315 320

Val Phe Glu Leu Ala Arg Asn Pro His Ile Trp Ala Lys Leu Arg Glu
325 330 335

Glu Ile Glu Ser His Phe Gly Leu Gly Glu Asp Ser Arg Val Glu Glu
340 345 350

Ile Thr Phe Glu Ser Leu Lys Arg Cys Glu Tyr Leu Lys Ala Val Leu
355 360 365

Asn Glu Thr Leu Arg Leu His Pro Ser Val Pro Arg Asn Ala Arg Phe
370 375 380

Ala Ile Lys Asp Thr Thr Leu Pro Arg Gly Gly Gly Pro Asn Gly Lys
385 390 395 400

Asp Pro Ile Leu Ile Arg Lys Asn Glu Val Val Gln Tyr Ser Ile Ser
405 410 415

Ala Thr Gln Thr Asn Pro Ala Tyr Tyr Gly Ala Asp Ala Ala Asp Phe
420 425 430

Arg Pro Glu Arg Trp Phe Glu Pro Ser Thr Arg Asn Leu Gly Trp Ala
435 440 445

Tyr Leu Pro Phe Asn Gly Gly Pro Arg Ile Cys Leu Gly Gln Gln Phe
450 455 460

Ala Leu Thr Glu Ala Gly Tyr Val Leu Val Arg Leu Val Gln Glu Phe
465 470 475 480

Pro Ser Leu Ser Gln Asp Pro Glu Thr Glu Tyr Pro Pro Pro Arg Leu
485 490 495

Ala His Leu Thr Met Cys Leu Phe Asp Gly Ala Tyr Val Lys Met Gln
500 505 510

<210> SEQ ID NO 104
<211> LENGTH: 499
<212> TYPE: PRT
<213> ORGANISM: CANDIDATROPICALIS

<400> SEQUENCE: 104

-continued

```
Met Ala Ile Ser Ser Leu Leu Ser Trp Asp Val Ile Cys Val Val Phe
1               5                   10                  15

Ile Cys Val Cys Val Tyr Phe Gly Tyr Glu Tyr Cys Tyr Thr Lys Tyr
            20                  25                  30

Leu Met His Lys His Gly Ala Arg Glu Ile Glu Asn Val Ile Asn Asp
        35                  40                  45

Gly Phe Phe Gly Phe Arg Leu Pro Leu Leu Leu Met Arg Ala Ser Asn
    50                  55                  60

Glu Gly Arg Leu Ile Glu Phe Ser Val Lys Arg Phe Glu Ser Ala Pro
65                  70                  75                  80

His Pro Gln Asn Lys Thr Leu Val Asn Arg Ala Leu Ser Val Pro Val
                85                  90                  95

Ile Leu Thr Lys Asp Pro Val Asn Ile Lys Ala Met Leu Ser Thr Gln
            100                 105                 110

Phe Asp Asp Phe Ser Leu Gly Leu Arg Leu His Gln Phe Ala Pro Leu
        115                 120                 125

Leu Gly Lys Gly Ile Phe Thr Leu Asp Gly Pro Glu Trp Lys Gln Ser
    130                 135                 140

Arg Ser Met Leu Arg Pro Gln Phe Ala Lys Asp Arg Val Ser His Ile
145                 150                 155                 160

Leu Asp Leu Glu Pro His Phe Val Leu Leu Arg Lys His Ile Asp Gly
                165                 170                 175

His Asn Gly Asp Tyr Phe Asp Ile Gln Glu Leu Tyr Phe Arg Phe Ser
            180                 185                 190

Met Asp Val Ala Thr Gly Phe Leu Phe Gly Glu Ser Val Gly Ser Leu
        195                 200                 205

Lys Asp Glu Asp Ala Arg Phe Leu Glu Ala Phe Asn Glu Ser Gln Lys
    210                 215                 220

Tyr Leu Ala Thr Arg Ala Thr Leu His Glu Leu Tyr Phe Leu Cys Asp
225                 230                 235                 240

Gly Phe Arg Phe Arg Gln Tyr Asn Lys Val Val Arg Lys Phe Cys Ser
                245                 250                 255

Gln Cys Val His Lys Ala Leu Asp Val Ala Pro Glu Asp Thr Ser Glu
            260                 265                 270

Tyr Val Phe Leu Arg Glu Leu Val Lys His Thr Arg Asp Pro Val Val
        275                 280                 285

Leu Gln Asp Gln Ala Leu Asn Val Leu Leu Ala Gly Arg Asp Thr Thr
    290                 295                 300

Ala Ser Leu Leu Ser Phe Ala Thr Phe Glu Leu Ala Arg Asn Asp His
305                 310                 315                 320

Met Trp Arg Lys Leu Arg Glu Glu Val Ile Leu Thr Met Gly Pro Ser
                325                 330                 335

Ser Asp Glu Ile Thr Val Ala Gly Leu Lys Ser Cys Arg Tyr Leu Lys
            340                 345                 350

Ala Ile Leu Asn Glu Thr Leu Arg Leu Tyr Pro Ser Val Pro Arg Asn
        355                 360                 365

Ala Arg Phe Ala Thr Arg Asn Thr Thr Leu Pro Arg Gly Gly Gly Pro
    370                 375                 380

Asp Gly Ser Phe Pro Ile Leu Ile Arg Lys Gly Gln Pro Val Gly Tyr
385                 390                 395                 400

Phe Ile Cys Ala Thr His Leu Asn Glu Lys Val Tyr Gly Asn Asp Ser
                405                 410                 415
```

-continued

```
His Val Phe Arg Pro Glu Arg Trp Ala Ala Leu Glu Gly Lys Ser Leu
            420                 425                 430

Gly Trp Ser Tyr Leu Pro Phe Asn Gly Gly Pro Arg Ser Cys Leu Gly
        435                 440                 445

Gln Gln Phe Ala Ile Leu Glu Ala Ser Tyr Val Leu Ala Arg Leu Thr
    450                 455                 460

Gln Cys Tyr Thr Thr Ile Gln Leu Arg Thr Thr Glu Tyr Pro Pro Lys
465                 470                 475                 480

Lys Leu Val His Leu Thr Met Ser Leu Leu Asn Gly Val Tyr Ile Arg
                485                 490                 495

Thr Arg Thr
```

<210> SEQ ID NO 105
<211> LENGTH: 1712
<212> TYPE: DNA
<213> ORGANISM: Candida tropicalis

<400> SEQUENCE: 105

```
ggtaccgagc tcacgagttt tgggattttc gagtttggat tgtttccttt gttgattgaa     60
ttgacgaaac cagaggtttt caagacagat aagattgggt ttatcaaaac gcagtttgaa    120
atattccagt tggtttccaa gatatcttga agaagattga cgatttgaaa tttgaagaag    180
tggagaagat ctggtttgga ttgttggaga atttcaagaa tctcaagatt tactctaacg    240
acgggtacaa cgagaattgt attgaattga tcaagaacat gatcttggtg ttacagaaca    300
tcaagttctt ggaccagact gagaatgcca cagatataca aggcgtcatg tgataaaatg    360
gatgagattt atcccacaat tgaagaaaga gtttatggaa agtggtcaac cagaagctaa    420
acaggaagaa gcaaacgaag aggtgaaaca agaagaagaa ggtaaataag tattttgtat    480
tatataacaa acaaagtaag gaatacagat ttatacaata aattgccata ctagtcacgt    540
gagatatctc atccattccc caactcccaa gaaaaaaaaa aagtgaaaaa aaaaatcaaa    600
cccaaagatc aacctcccca tcatcatcgt catcaaaccc ccagctcaat tcgcaatggt    660
tagcacaaaa acatacacag aaagggcatc agcacacccc tccaaggttg cccaacgttt    720
attccgctta atggagtcca aaaagaccaa cctctgcgcc tcgatcgacg tgaccacaac    780
cgccgagttc ctttcgctca tcgacaagct cggtccccac atctgtctcg tgaagacgca    840
catcgatatc atctcagact tcagctacga gggcacgatt gagccgttgc ttgtgcttgc    900
agagcgccac gggttcttga tattcgagga caggaagttt gctgatatcg gaaacaccgt    960
gatgttgcag tacacctcgg gggtataccg gatcgcggcg tggagtgaca tcacgaacgc   1020
gcacggagtg actgggaagg gcgtcgttga agggttgaaa cgcggtgcgg agggggtaga   1080
aaaggaaagg ggcgtgttga tgttggcgga gttgtcgagt aaaggctcgt tggcgcatgg   1140
tgaatatacc cgtgagacga tcgagattgc gaagagtgat cgggagttcg tgattgggtt   1200
catcgcgcag cgggacatgg ggggtagaga agaagggttt gattggatca tcatgacgcc   1260
tggtgtgggg ttggatgata aaggcgatgc gttgggccag cagtatagga ctgttgatga   1320
ggtggttctg actggtaccg atgtgattat tgtcgggaga gggttgtttg gaaaaggaag   1380
agaccctgag gtggagggaa agagatacag ggatgctgga tggaaggcat acttgaagag   1440
aactggtcag ttagaataaa tattgtaata aataggtcta tatacataca ctaagcttct   1500
aggacgtcat tgtagtcttc gaagttgtct gctagtttag ttctcatgat ttcgaaaacc   1560
aataacgcaa tggatgtagc agggatggtg gttagtgcgt tcctgacaaa cccagagtac   1620
```

-continued

```
gccgcctcaa accacgtcac attcgccctt tgcttcatcc gcatcacttg cttgaaggta   1680

tccacgtacg agttgtaata caccttgaag aa                                 1712


<210> SEQ ID NO 106
<211> LENGTH: 267
<212> TYPE: PRT
<213> ORGANISM: CANDIDATROPICALIS

<400> SEQUENCE: 106

Met Val Ser Thr Lys Thr Tyr Thr Glu Arg Ala Ser Ala His Pro Ser
1               5                   10                  15

Lys Val Ala Gln Arg Leu Phe Arg Leu Met Glu Ser Lys Lys Thr Asn
            20                  25                  30

Leu Cys Ala Ser Ile Asp Val Thr Thr Thr Ala Glu Phe Leu Ser Leu
        35                  40                  45

Ile Asp Lys Leu Gly Pro His Ile Cys Leu Val Lys Thr His Ile Asp
    50                  55                  60

Ile Ile Ser Asp Phe Ser Tyr Glu Gly Thr Ile Glu Pro Leu Leu Val
65                  70                  75                  80

Leu Ala Glu Arg His Gly Phe Leu Ile Phe Glu Asp Arg Lys Phe Ala
                85                  90                  95

Asp Ile Gly Asn Thr Val Met Leu Gln Tyr Thr Ser Gly Val Tyr Arg
            100                 105                 110

Ile Ala Ala Trp Ser Asp Ile Thr Asn Ala His Gly Val Thr Gly Lys
        115                 120                 125

Gly Val Val Glu Gly Leu Lys Arg Gly Ala Glu Gly Val Glu Lys Glu
    130                 135                 140

Arg Gly Val Leu Met Leu Ala Glu Leu Ser Ser Lys Gly Ser Leu Ala
145                 150                 155                 160

His Gly Glu Tyr Thr Arg Glu Thr Ile Glu Ile Ala Lys Ser Asp Arg
                165                 170                 175

Glu Phe Val Ile Gly Phe Ile Ala Gln Arg Asp Met Gly Gly Arg Glu
            180                 185                 190

Glu Gly Phe Asp Trp Ile Ile Met Thr Pro Gly Val Gly Leu Asp Asp
        195                 200                 205

Lys Gly Asp Ala Leu Gly Gln Gln Tyr Arg Thr Val Asp Glu Val Val
    210                 215                 220

Leu Thr Gly Thr Asp Val Ile Ile Val Gly Arg Gly Leu Phe Gly Lys
225                 230                 235                 240

Gly Arg Asp Pro Glu Val Glu Gly Lys Arg Tyr Arg Asp Ala Gly Trp
                245                 250                 255

Lys Ala Tyr Leu Lys Arg Thr Gly Gln Leu Glu
            260                 265


<210> SEQ ID NO 107
<211> LENGTH: 473
<212> TYPE: DNA
<213> ORGANISM: Artificial Sequence
<220> FEATURE:
<223> OTHER INFORMATION: Description of Artificial Sequence: Primer

<400> SEQUENCE: 107

gtcaaagcaa attgttggcc caagcagact cttggaccac cgttgaatgg aacataagcc     60

cagcccaact tcttagtaga tggttcaaac catctttctg gtctgaagtc gttagcgtcc    120

ttaccgtagt attcttccaa acggtgggtc ttgtagacaa cgtaagcaac agtggagcct    180
```

-continued

```
ttaggaatgt agattgggtc ggtaccgtta gcaccaccac ctcttggcaa agtggtgtct    240

ctggtggcgg ttctaaagtt gacaggaaca gatgggtaca tacgcaaggt ttcgttaagg    300

atagccttca agtattcaca tctcttcaag gcttcgaaag taatttcttc aacgcgggag    360

tcttcaccaa caccaaagtt aacttcgatt tcttctctca acttggacca catctctggg    420

tgtctagcca attcaaacaa agcaaaggac aacaaacccg cggtggtgtc tct           473


<210> SEQ ID NO 108
<211> LENGTH: 540
<212> TYPE: DNA
<213> ORGANISM: Candida tropicalis

<400> SEQUENCE: 108

tactaacttg ttgaggatct tataaccata cagcaacacg gtcacaacat gtagtagttt     60

gttgaggaac gtatgtgttt ctgagcgcag aactactttt tcaacccacg acgaggtcag    120

tgtttgttca acatgctgtt gcgaaagcca tagcagttac ctaccttccg agaggtcaag    180

ttctttctcc cgtcccgagt tctcatgttg ctaatgttca aactggtgag gttcttgggt    240

tcgcacccgt ggatgcagtc ataagaaaag ccgtggtcct agcagcactg gtttctaggt    300

ctcttatagt ttcgataaaa ccgttgggtc aaaccactaa aaagaaaccc gttctccgtg    360

tgagaaaaat tcggaaacaa tccactaccc tagaagtgta acctgccgct tccgaccttc    420

gtgtcgtctc ggtacaactc tggtgtcaaa cggtctcttg ttcaacgagt acactgcagc    480

aaccttggtg tgaaggtcaa caacttcttc gtataagaat tcgtgttccc acttatgaaa    540


<210> SEQ ID NO 109
<211> LENGTH: 29
<212> TYPE: DNA
<213> ORGANISM: Bacteriophage T7

<400> SEQUENCE: 109

ggatcctaat acgactcact atagggagg                                       29


<210> SEQ ID NO 110
<211> LENGTH: 523
<212> TYPE: PRT
<213> ORGANISM: CANDIDATROPICALIS

<400> SEQUENCE: 110

Met Ala Thr Gln Glu Ile Ile Asp Ser Val Leu Pro Tyr Leu Thr Lys
1               5                   10                  15

Trp Tyr Thr Val Ile Thr Ala Ala Val Leu Val Phe Leu Ile Ser Thr
            20                  25                  30

Asn Ile Lys Asn Tyr Val Lys Ala Lys Lys Leu Lys Cys Val Asp Pro
        35                  40                  45

Pro Tyr Leu Lys Asp Ala Gly Leu Thr Gly Ile Ser Ser Leu Ile Ala
    50                  55                  60

Ala Ile Lys Ala Lys Asn Asp Gly Arg Leu Ala Asn Phe Ala Asp Glu
65                  70                  75                  80

Val Phe Asp Glu Tyr Pro Asn His Thr Phe Tyr Leu Ser Val Ala Gly
                85                  90                  95

Ala Leu Lys Ile Val Met Thr Val Asp Pro Glu Asn Ile Lys Ala Val
            100                 105                 110

Leu Ala Thr Gln Phe Thr Asp Phe Ser Leu Gly Thr Arg His Ala His
        115                 120                 125
```

-continued

```
Phe Ala Pro Leu Leu Gly Asp Gly Ile Phe Thr Leu Asp Gly Glu Gly
    130                 135                 140

Trp Lys His Ser Arg Ala Met Leu Arg Pro Gln Phe Ala Arg Asp Gln
145                 150                 155                 160

Ile Gly His Val Lys Ala Leu Glu Pro His Ile Gln Ile Met Ala Lys
                165                 170                 175

Gln Ile Lys Leu Asn Gln Gly Lys Thr Phe Asp Ile Gln Glu Leu Phe
            180                 185                 190

Phe Arg Phe Thr Val Asp Thr Ala Thr Glu Phe Leu Phe Gly Glu Ser
        195                 200                 205

Val His Ser Leu Tyr Asp Glu Lys Leu Gly Ile Pro Thr Pro Asn Glu
    210                 215                 220

Ile Pro Gly Arg Glu Asn Phe Ala Ala Ala Phe Asn Val Ser Gln His
225                 230                 235                 240

Tyr Leu Ala Thr Arg Ser Tyr Ser Gln Thr Phe Tyr Phe Leu Thr Asn
                245                 250                 255

Pro Lys Glu Phe Arg Asp Cys Asn Ala Lys Val His His Leu Ala Lys
            260                 265                 270

Tyr Phe Val Asn Lys Ala Leu Asn Phe Thr Pro Glu Glu Leu Glu Glu
        275                 280                 285

Lys Ser Lys Ser Gly Tyr Val Phe Leu Tyr Glu Leu Val Lys Gln Thr
    290                 295                 300

Arg Asp Pro Lys Val Leu Gln Asp Gln Leu Leu Asn Ile Met Val Ala
305                 310                 315                 320

Gly Arg Asp Thr Thr Ala Gly Leu Leu Ser Phe Ala Leu Phe Glu Leu
                325                 330                 335

Ala Arg His Pro Glu Met Trp Ser Lys Leu Arg Glu Glu Ile Glu Val
            340                 345                 350

Asn Phe Gly Val Gly Glu Asp Ser Arg Val Glu Glu Ile Thr Phe Glu
        355                 360                 365

Ala Leu Lys Arg Cys Glu Tyr Leu Lys Ala Ile Leu Asn Glu Thr Leu
    370                 375                 380

Arg Met Tyr Pro Ser Val Pro Val Asn Phe Arg Thr Ala Thr Arg Asp
385                 390                 395                 400

Thr Thr Leu Pro Arg Gly Gly Gly Ala Asn Gly Thr Asp Pro Ile Tyr
                405                 410                 415

Ile Pro Lys Gly Ser Thr Val Ala Tyr Val Val Tyr Lys Thr His Arg
            420                 425                 430

Leu Glu Glu Tyr Tyr Gly Lys Asp Ala Asn Asp Phe Arg Pro Glu Arg
        435                 440                 445

Trp Phe Glu Pro Ser Thr Lys Lys Leu Gly Trp Ala Tyr Val Pro Phe
    450                 455                 460

Asn Gly Gly Pro Arg Val Cys Leu Gly Gln Gln Phe Ala Leu Thr Glu
465                 470                 475                 480

Ala Ser Tyr Val Ile Thr Arg Leu Ala Gln Met Phe Glu Thr Val Ser
                485                 490                 495

Ser Asp Pro Gly Leu Glu Tyr Pro Pro Pro Lys Cys Ile His Leu Thr
            500                 505                 510

Met Ser His Asn Asp Gly Val Phe Val Lys Met
        515                 520
```

<210> SEQ ID NO 111
<211> LENGTH: 540

-continued

<212> TYPE: PRT
<213> ORGANISM: CANDIDATROPICALIS

<400> SEQUENCE: 111

```
Met Ser Ser Ser Pro Ser Phe Ala Gln Glu Val Leu Ala Thr Thr Ser
1               5                   10                  15

Pro Tyr Ile Glu Tyr Phe Leu Asp Asn Tyr Thr Arg Trp Tyr Tyr Phe
            20                  25                  30

Ile Pro Leu Val Leu Leu Ser Leu Asn Phe Ile Ser Leu Leu His Thr
        35                  40                  45

Lys Tyr Leu Glu Arg Arg Phe His Ala Lys Pro Leu Gly Asn Val Val
    50                  55                  60

Leu Asp Pro Thr Phe Gly Ile Ala Thr Pro Leu Ile Leu Ile Tyr Leu
65                  70                  75                  80

Lys Ser Lys Gly Thr Val Met Lys Phe Ala Trp Ser Phe Trp Asn Asn
                85                  90                  95

Lys Tyr Ile Val Lys Asp Pro Lys Tyr Lys Thr Thr Gly Leu Arg Ile
            100                 105                 110

Val Gly Leu Pro Leu Ile Glu Thr Ile Asp Pro Glu Asn Ile Lys Ala
        115                 120                 125

Val Leu Ala Thr Gln Phe Asn Asp Phe Ser Leu Gly Thr Arg His Asp
    130                 135                 140

Phe Leu Tyr Ser Leu Leu Gly Asp Gly Ile Phe Thr Leu Asp Gly Ala
145                 150                 155                 160

Gly Trp Lys His Ser Arg Thr Met Leu Arg Pro Gln Phe Ala Arg Glu
                165                 170                 175

Gln Val Ser His Val Lys Leu Leu Glu Pro His Val Gln Val Phe Phe
            180                 185                 190

Lys His Val Arg Lys His Arg Gly Gln Thr Phe Asp Ile Gln Glu Leu
        195                 200                 205

Phe Phe Arg Leu Thr Val Asp Ser Ala Thr Glu Phe Leu Phe Gly Glu
    210                 215                 220

Ser Ala Glu Ser Leu Arg Asp Asp Ser Val Gly Leu Thr Pro Thr Thr
225                 230                 235                 240

Lys Asp Phe Glu Gly Arg Gly Asp Phe Ala Asp Ala Phe Asn Tyr Ser
                245                 250                 255

Gln Thr Tyr Gln Ala Tyr Arg Phe Leu Leu Gln Gln Met Tyr Trp Ile
            260                 265                 270

Leu Asn Gly Ala Glu Phe Arg Lys Ser Ile Ala Ile Val His Lys Phe
        275                 280                 285

Ala Asp His Tyr Val Gln Lys Ala Leu Glu Leu Thr Asp Asp Asp Leu
    290                 295                 300

Gln Lys Gln Asp Gly Tyr Val Phe Leu Tyr Glu Leu Ala Lys Gln Thr
305                 310                 315                 320

Arg Asp Pro Lys Val Leu Arg Asp Gln Leu Leu Asn Ile Leu Val Ala
                325                 330                 335

Gly Arg Asp Thr Thr Ala Gly Leu Leu Ser Phe Val Phe Tyr Glu Leu
            340                 345                 350

Ser Arg Asn Pro Glu Val Phe Ala Lys Leu Arg Glu Glu Val Glu Asn
        355                 360                 365

Arg Phe Gly Leu Gly Glu Glu Ala Arg Val Glu Glu Ile Ser Phe Glu
    370                 375                 380

Ser Leu Lys Ser Cys Glu Tyr Leu Lys Ala Val Ile Asn Glu Ala Leu
385                 390                 395                 400
```

-continued

```
Arg Leu Tyr Pro Ser Val Pro His Asn Phe Arg Val Ala Thr Arg Asn
                405                 410                 415

Thr Thr Leu Pro Arg Gly Gly Gly Lys Asp Gly Cys Ser Pro Ile Val
            420                 425                 430

Val Lys Lys Gly Gln Val Val Met Tyr Thr Val Ile Gly Thr His Arg
        435                 440                 445

Asp Pro Ser Ile Tyr Gly Ala Asp Ala Asp Val Phe Arg Pro Glu Arg
    450                 455                 460

Trp Phe Glu Pro Glu Thr Arg Lys Leu Gly Trp Ala Tyr Val Pro Phe
465                 470                 475                 480

Asn Gly Gly Pro Arg Ile Cys Leu Gly Gln Gln Phe Ala Leu Thr Glu
                485                 490                 495

Ala Ser Tyr Val Thr Val Arg Leu Leu Gln Glu Phe Gly Asn Leu Ser
            500                 505                 510

Ser Asp Pro Asn Ala Glu Tyr Pro Pro Lys Leu Gln Asn Thr Leu Thr
        515                 520                 525

Leu Ser Leu Phe Asp Gly Ala Asp Val Arg Met Phe
    530                 535                 540


<210> SEQ ID NO 112
<211> LENGTH: 517
<212> TYPE: PRT
<213> ORGANISM: CANDIDATROPICALIS

<400> SEQUENCE: 112

Met Ile Glu Gln Leu Leu Glu Tyr Trp Tyr Val Val Val Pro Val Leu
1               5                   10                  15

Tyr Ile Ile Lys Gln Leu Leu Ala Tyr Thr Lys Thr Arg Val Leu Met
            20                  25                  30

Lys Lys Leu Gly Ala Ala Pro Val Thr Asn Lys Leu Tyr Asp Asn Ala
        35                  40                  45

Phe Gly Ile Val Asn Gly Trp Lys Ala Leu Gln Phe Lys Lys Glu Gly
    50                  55                  60

Arg Ala Gln Glu Tyr Asn Asp Tyr Lys Phe Asp His Ser Lys Asn Pro
65                  70                  75                  80

Ser Val Gly Thr Tyr Val Ser Ile Leu Phe Gly Thr Arg Ile Val Val
                85                  90                  95

Thr Lys Asp Pro Glu Asn Ile Lys Ala Ile Leu Ala Thr Gln Phe Gly
            100                 105                 110

Asp Phe Ser Leu Gly Lys Arg His Thr Leu Phe Lys Pro Leu Leu Gly
        115                 120                 125

Asp Gly Ile Phe Thr Leu Asp Gly Glu Gly Trp Lys His Ser Arg Ala
    130                 135                 140

Met Leu Arg Pro Gln Phe Ala Arg Glu Gln Val Ala His Val Thr Ser
145                 150                 155                 160

Leu Glu Pro His Phe Gln Leu Leu Lys Lys His Ile Leu Lys His Lys
                165                 170                 175

Gly Glu Tyr Phe Asp Ile Gln Glu Leu Phe Phe Arg Phe Thr Val Asp
            180                 185                 190

Ser Ala Thr Glu Phe Leu Phe Gly Glu Ser Val His Ser Leu Lys Asp
        195                 200                 205

Glu Ser Ile Gly Ile Asn Gln Asp Asp Ile Asp Phe Ala Gly Arg Lys
    210                 215                 220
```

-continued

```
Asp Phe Ala Glu Ser Phe Asn Lys Ala Gln Glu Tyr Leu Ala Ile Arg
225                 230                 235                 240

Thr Leu Val Gln Thr Phe Tyr Trp Leu Val Asn Asn Lys Glu Phe Arg
                245                 250                 255

Asp Cys Thr Lys Ser Val His Lys Phe Thr Asn Tyr Tyr Val Gln Lys
            260                 265                 270

Ala Leu Asp Ala Ser Pro Glu Glu Leu Glu Lys Gln Ser Gly Tyr Val
        275                 280                 285

Phe Leu Tyr Glu Leu Val Lys Gln Thr Arg Asp Pro Asn Val Leu Arg
    290                 295                 300

Asp Gln Ser Leu Asn Ile Leu Leu Ala Gly Arg Asp Thr Thr Ala Gly
305                 310                 315                 320

Leu Leu Ser Phe Ala Val Phe Glu Leu Ala Arg His Pro Glu Ile Trp
                325                 330                 335

Ala Lys Leu Arg Glu Glu Ile Glu Gln Gln Phe Gly Leu Gly Glu Asp
            340                 345                 350

Ser Arg Val Glu Glu Ile Thr Phe Glu Ser Leu Lys Arg Cys Glu Tyr
        355                 360                 365

Leu Lys Ala Phe Leu Asn Glu Thr Leu Arg Ile Tyr Pro Ser Val Pro
    370                 375                 380

Arg Asn Phe Arg Ile Ala Thr Lys Asn Thr Thr Leu Pro Arg Gly Gly
385                 390                 395                 400

Gly Ser Asp Gly Thr Ser Pro Ile Leu Ile Gln Lys Gly Glu Ala Val
                405                 410                 415

Ser Tyr Gly Ile Asn Ser Thr His Leu Asp Pro Val Tyr Tyr Gly Pro
            420                 425                 430

Asp Ala Ala Glu Phe Arg Pro Glu Arg Trp Phe Glu Pro Ser Thr Lys
        435                 440                 445

Lys Leu Gly Trp Ala Tyr Leu Pro Phe Asn Gly Gly Pro Arg Ile Cys
    450                 455                 460

Leu Gly Gln Gln Phe Ala Leu Thr Glu Ala Gly Tyr Val Leu Val Arg
465                 470                 475                 480

Leu Val Gln Glu Phe Ser His Val Arg Ser Asp Pro Asp Glu Val Tyr
                485                 490                 495

Pro Pro Lys Arg Leu Thr Asn Leu Thr Met Cys Leu Gln Asp Gly Ala
            500                 505                 510

Ile Val Lys Phe Asp
        515


<210> SEQ ID NO 113
<211> LENGTH: 517
<212> TYPE: PRT
<213> ORGANISM: CANDIDATROPICALIS

<400> SEQUENCE: 113

Met Ile Glu Gln Ile Leu Glu Tyr Trp Tyr Ile Val Val Pro Val Leu
1               5                   10                  15

Tyr Ile Ile Lys Gln Leu Ile Ala Tyr Ser Lys Thr Arg Val Leu Met
            20                  25                  30

Lys Gln Leu Gly Ala Ala Pro Ile Thr Asn Gln Leu Tyr Asp Asn Val
        35                  40                  45

Phe Gly Ile Val Asn Gly Trp Lys Ala Leu Gln Phe Lys Lys Glu Gly
    50                  55                  60
```

-continued

```
Arg Ala Gln Glu Tyr Asn Asp His Lys Phe Asp Ser Ser Lys Asn Pro
65                  70                  75                  80

Ser Val Gly Thr Tyr Val Ser Ile Leu Phe Gly Thr Lys Ile Val Val
                85                  90                  95

Thr Lys Asp Pro Glu Asn Ile Lys Ala Ile Leu Ala Thr Gln Phe Gly
            100                 105                 110

Asp Phe Ser Leu Gly Lys Arg His Ala Leu Phe Lys Pro Leu Leu Gly
        115                 120                 125

Asp Gly Ile Phe Thr Leu Asp Gly Glu Gly Trp Lys His Ser Arg Ser
    130                 135                 140

Met Leu Arg Pro Gln Phe Ala Arg Glu Gln Val Ala His Val Thr Ser
145                 150                 155                 160

Leu Glu Pro His Phe Gln Leu Leu Lys Lys His Ile Leu Lys His Lys
                165                 170                 175

Gly Glu Tyr Phe Asp Ile Gln Glu Leu Phe Phe Arg Phe Thr Val Asp
            180                 185                 190

Ser Ala Thr Glu Phe Leu Phe Gly Glu Ser Val His Ser Leu Lys Asp
        195                 200                 205

Glu Thr Ile Gly Ile Asn Gln Asp Asp Ile Asp Phe Ala Gly Arg Lys
    210                 215                 220

Asp Phe Ala Glu Ser Phe Asn Lys Ala Gln Glu Tyr Leu Ser Ile Arg
225                 230                 235                 240

Ile Leu Val Gln Thr Phe Tyr Trp Leu Ile Asn Asn Lys Glu Phe Arg
                245                 250                 255

Asp Cys Thr Lys Ser Val His Lys Phe Thr Asn Tyr Tyr Val Gln Lys
            260                 265                 270

Ala Leu Asp Ala Thr Pro Glu Glu Leu Glu Lys Gln Gly Gly Tyr Val
        275                 280                 285

Phe Leu Tyr Glu Leu Val Lys Gln Thr Arg Asp Pro Lys Val Leu Arg
    290                 295                 300

Asp Gln Ser Leu Asn Ile Leu Leu Ala Gly Arg Asp Thr Thr Ala Gly
305                 310                 315                 320

Leu Leu Ser Phe Ala Val Phe Glu Leu Ala Arg Asn Pro His Ile Trp
                325                 330                 335

Ala Lys Leu Arg Glu Glu Ile Glu Gln Gln Phe Gly Leu Gly Glu Asp
            340                 345                 350

Ser Arg Val Glu Glu Ile Thr Phe Glu Ser Leu Lys Arg Cys Glu Tyr
        355                 360                 365

Leu Lys Ala Phe Leu Asn Glu Thr Leu Arg Val Tyr Pro Ser Val Pro
    370                 375                 380

Arg Asn Phe Arg Ile Ala Thr Lys Asn Thr Thr Leu Pro Arg Gly Gly
385                 390                 395                 400

Gly Pro Asp Gly Thr Gln Pro Ile Leu Ile Gln Lys Gly Glu Gly Val
                405                 410                 415

Ser Tyr Gly Ile Asn Ser Thr His Leu Asp Pro Val Tyr Tyr Gly Pro
            420                 425                 430

Asp Ala Ala Glu Phe Arg Pro Glu Arg Trp Phe Glu Pro Ser Thr Arg
        435                 440                 445

Lys Leu Gly Trp Ala Tyr Leu Pro Phe Asn Gly Gly Pro Arg Ile Cys
    450                 455                 460

Leu Gly Gln Gln Phe Ala Leu Thr Glu Ala Gly Tyr Val Leu Val Arg
465                 470                 475                 480
```

-continued

```
Leu Val Gln Glu Phe Ser His Ile Arg Ser Asp Pro Asp Glu Val Tyr
                485                 490                 495

Pro Pro Lys Arg Leu Thr Asn Leu Thr Met Cys Leu Gln Asp Gly Ala
            500                 505                 510

Ile Val Lys Phe Asp
        515


<210> SEQ ID NO 114
<211> LENGTH: 512
<212> TYPE: PRT
<213> ORGANISM: CANDIDATROPICALIS

<400> SEQUENCE: 114

Met Leu Asp Gln Ile Leu His Tyr Trp Tyr Ile Val Leu Pro Leu Leu
1               5                   10                  15

Ala Ile Ile Asn Gln Ile Val Ala His Val Arg Thr Asn Tyr Leu Met
            20                  25                  30

Lys Lys Leu Gly Ala Lys Pro Phe Thr His Val Gln Arg Asp Gly Trp
        35                  40                  45

Leu Gly Phe Lys Phe Gly Arg Glu Phe Leu Lys Ala Lys Ser Ala Gly
    50                  55                  60

Arg Ser Val Asp Leu Ile Ile Ser Arg Phe His Asp Asn Glu Asp Thr
65                  70                  75                  80

Phe Ser Ser Tyr Ala Phe Gly Asn His Val Val Phe Thr Arg Asp Pro
                85                  90                  95

Glu Asn Ile Lys Ala Leu Leu Ala Thr Gln Phe Gly Asp Phe Ser Leu
            100                 105                 110

Gly Ser Arg Val Lys Phe Phe Lys Pro Leu Leu Gly Tyr Gly Ile Phe
        115                 120                 125

Thr Leu Asp Ala Glu Gly Trp Lys His Ser Arg Ala Met Leu Arg Pro
    130                 135                 140

Gln Phe Ala Arg Glu Gln Val Ala His Val Thr Ser Leu Glu Pro His
145                 150                 155                 160

Phe Gln Leu Leu Lys Lys His Ile Leu Lys His Lys Gly Glu Tyr Phe
                165                 170                 175

Asp Ile Gln Glu Leu Phe Phe Arg Phe Thr Val Asp Ser Ala Thr Glu
            180                 185                 190

Phe Leu Phe Gly Glu Ser Val His Ser Leu Lys Asp Glu Glu Ile Gly
        195                 200                 205

Tyr Asp Thr Lys Asp Met Ser Glu Glu Arg Arg Arg Phe Ala Asp Ala
    210                 215                 220

Phe Asn Lys Ser Gln Val Tyr Val Ala Thr Arg Val Ala Leu Gln Asn
225                 230                 235                 240

Leu Tyr Trp Leu Val Asn Asn Lys Glu Phe Lys Glu Cys Asn Asp Ile
                245                 250                 255

Val His Lys Phe Thr Asn Tyr Tyr Val Gln Lys Ala Leu Asp Ala Thr
            260                 265                 270

Pro Glu Glu Leu Glu Lys Gln Gly Gly Tyr Val Phe Leu Tyr Glu Leu
        275                 280                 285

Val Lys Gln Thr Arg Asp Pro Lys Val Leu Arg Asp Gln Ser Leu Asn
    290                 295                 300

Ile Leu Leu Ala Gly Arg Asp Thr Thr Ala Gly Leu Leu Ser Phe Ala
305                 310                 315                 320

Val Phe Glu Leu Ala Arg Asn Pro His Ile Trp Ala Lys Leu Arg Glu
                325                 330                 335
```

-continued

```
Glu Ile Glu Gln Gln Phe Gly Leu Gly Glu Asp Ser Arg Val Glu Glu
            340                 345                 350

Ile Thr Phe Glu Ser Leu Lys Arg Cys Glu Tyr Leu Lys Ala Val Leu
        355                 360                 365

Asn Glu Thr Leu Arg Leu His Pro Ser Val Pro Arg Asn Ala Arg Phe
    370                 375                 380

Ala Ile Lys Asp Thr Thr Leu Pro Arg Gly Gly Gly Pro Asn Gly Lys
385                 390                 395                 400

Asp Pro Ile Leu Ile Arg Lys Asp Glu Val Val Gln Tyr Ser Ile Ser
                405                 410                 415

Ala Thr Gln Thr Asn Pro Ala Tyr Tyr Gly Ala Asp Ala Ala Asp Phe
            420                 425                 430

Arg Pro Glu Arg Trp Phe Glu Pro Ser Thr Arg Asn Leu Gly Trp Ala
        435                 440                 445

Phe Leu Pro Phe Asn Gly Gly Pro Arg Ile Cys Leu Gly Gln Gln Phe
    450                 455                 460

Ala Leu Thr Glu Ala Gly Tyr Val Leu Val Arg Leu Val Gln Glu Phe
465                 470                 475                 480

Pro Asn Leu Ser Gln Asp Pro Glu Thr Lys Tyr Pro Pro Pro Arg Leu
                485                 490                 495

Ala His Leu Thr Met Cys Leu Phe Asp Gly Ala His Val Lys Met Ser
            500                 505                 510


<210> SEQ ID NO 115
<211> LENGTH: 512
<212> TYPE: PRT
<213> ORGANISM: CANDIDATROPICALIS

<400> SEQUENCE: 115

Met Leu Asp Gln Ile Phe His Tyr Trp Tyr Ile Val Leu Pro Leu Leu
1               5                   10                  15

Val Ile Ile Lys Gln Ile Val Ala His Ala Arg Thr Asn Tyr Leu Met
            20                  25                  30

Lys Lys Leu Gly Ala Lys Pro Phe Thr His Val Gln Leu Asp Gly Trp
        35                  40                  45

Phe Gly Phe Lys Phe Gly Arg Glu Phe Leu Lys Ala Lys Ser Ala Gly
    50                  55                  60

Arg Gln Val Asp Leu Ile Ile Ser Arg Phe His Asp Asn Glu Asp Thr
65                  70                  75                  80

Phe Ser Ser Tyr Ala Phe Gly Asn His Val Val Phe Thr Arg Asp Pro
                85                  90                  95

Glu Asn Ile Lys Ala Leu Leu Ala Thr Gln Phe Gly Asp Phe Ser Leu
            100                 105                 110

Gly Ser Arg Val Lys Phe Phe Lys Pro Leu Leu Gly Tyr Gly Ile Phe
        115                 120                 125

Thr Leu Asp Gly Glu Gly Trp Lys His Ser Arg Ala Met Leu Arg Pro
    130                 135                 140

Gln Phe Ala Arg Glu Gln Val Ala His Val Thr Ser Leu Glu Pro His
145                 150                 155                 160

Phe Gln Leu Leu Lys Lys His Ile Leu Lys His Lys Gly Glu Tyr Phe
                165                 170                 175

Asp Ile Gln Glu Leu Phe Phe Arg Phe Thr Val Asp Ser Ala Thr Glu
            180                 185                 190
```

-continued

Phe Leu Phe Gly Glu Ser Val His Ser Leu Arg Asp Glu Glu Ile Gly
195 200 205

Tyr Asp Thr Lys Asp Met Ala Glu Glu Arg Arg Lys Phe Ala Asp Ala
210 215 220

Phe Asn Lys Ser Gln Val Tyr Leu Ser Thr Arg Val Ala Leu Gln Thr
225 230 235 240

Leu Tyr Trp Leu Val Asn Asn Lys Glu Phe Lys Glu Cys Asn Asp Ile
245 250 255

Val His Lys Phe Thr Asn Tyr Tyr Val Gln Lys Ala Leu Asp Ala Thr
260 265 270

Pro Glu Glu Leu Glu Lys Gln Gly Gly Tyr Val Phe Leu Tyr Glu Leu
275 280 285

Ala Lys Gln Thr Lys Asp Pro Asn Val Leu Arg Asp Gln Ser Leu Asn
290 295 300

Ile Leu Leu Ala Gly Arg Asp Thr Thr Ala Gly Leu Leu Ser Phe Ala
305 310 315 320

Val Phe Glu Leu Ala Arg Asn Pro His Ile Trp Ala Lys Leu Arg Glu
325 330 335

Glu Ile Glu Ser His Phe Gly Ser Gly Glu Asp Ser Arg Val Glu Glu
340 345 350

Ile Thr Phe Glu Ser Leu Lys Arg Cys Glu Tyr Leu Lys Ala Val Leu
355 360 365

Asn Glu Thr Leu Arg Leu His Pro Ser Val Pro Arg Asn Ala Arg Phe
370 375 380

Ala Ile Lys Asp Thr Thr Leu Pro Arg Gly Gly Gly Pro Asn Gly Lys
385 390 395 400

Asp Pro Ile Leu Ile Arg Lys Asn Glu Val Val Gln Tyr Ser Ile Ser
405 410 415

Ala Thr Gln Thr Asn Pro Ala Tyr Tyr Gly Ala Asp Ala Ala Asp Phe
420 425 430

Arg Pro Glu Arg Trp Phe Glu Pro Ser Thr Arg Asn Leu Gly Trp Ala
435 440 445

Tyr Leu Pro Phe Asn Gly Gly Pro Arg Ile Cys Leu Gly Gln Gln Phe
450 455 460

Ala Leu Thr Glu Ala Gly Tyr Val Leu Val Arg Leu Val Gln Glu Phe
465 470 475 480

Pro Ser Leu Ser Gln Asp Pro Glu Thr Glu Tyr Pro Pro Pro Arg Leu
485 490 495

Ala His Leu Thr Met Cys Leu Phe Asp Gly Ala Tyr Val Lys Met Gln
500 505 510

<210> SEQ ID NO 116
<211> LENGTH: 499
<212> TYPE: PRT
<213> ORGANISM: CANDIDATROPICALIS

<400> SEQUENCE: 116

Met Ala Ile Ser Ser Leu Leu Ser Trp Asp Val Ile Cys Val Val Phe
1 5 10 15

Ile Cys Val Cys Val Tyr Phe Gly Tyr Glu Tyr Cys Tyr Thr Lys Tyr
20 25 30

Leu Met His Lys His Gly Ala Arg Glu Ile Glu Asn Val Ile Asn Asp
35 40 45

-continued

```
Gly Phe Phe Gly Phe Arg Leu Pro Leu Leu Leu Met Arg Ala Ser Asn
    50                  55                  60

Glu Gly Arg Leu Ile Glu Phe Ser Val Lys Arg Phe Glu Ser Ala Pro
65                  70                  75                  80

His Pro Gln Asn Lys Thr Leu Val Asn Arg Ala Leu Ser Val Pro Val
                85                  90                  95

Ile Leu Thr Lys Asp Pro Val Asn Ile Lys Ala Met Leu Ser Thr Gln
            100                 105                 110

Phe Asp Asp Phe Ser Leu Gly Leu Arg Leu His Gln Phe Ala Pro Leu
        115                 120                 125

Leu Gly Lys Gly Ile Phe Thr Leu Asp Gly Pro Glu Trp Lys Gln Ser
    130                 135                 140

Arg Ser Met Leu Arg Pro Gln Phe Ala Lys Asp Arg Val Ser His Ile
145                 150                 155                 160

Ser Asp Leu Glu Pro His Phe Val Leu Leu Arg Lys His Ile Asp Gly
                165                 170                 175

His Asn Gly Asp Tyr Phe Asp Ile Gln Glu Leu Tyr Phe Arg Phe Ser
            180                 185                 190

Met Asp Val Ala Thr Gly Phe Leu Phe Gly Glu Ser Val Gly Ser Leu
        195                 200                 205

Lys Asp Glu Asp Ala Arg Phe Ser Glu Ala Phe Asn Glu Ser Gln Lys
    210                 215                 220

Tyr Leu Ala Thr Arg Ala Thr Leu His Glu Leu Tyr Phe Leu Cys Asp
225                 230                 235                 240

Gly Phe Arg Phe Arg Gln Tyr Asn Lys Val Val Arg Lys Phe Cys Ser
                245                 250                 255

Gln Cys Val His Lys Ala Leu Asp Val Ala Pro Glu Asp Thr Ser Glu
            260                 265                 270

Tyr Val Phe Leu Arg Glu Leu Val Lys His Thr Arg Asp Pro Val Val
        275                 280                 285

Leu Gln Asp Gln Ala Leu Asn Val Leu Leu Ala Gly Arg Asp Thr Thr
    290                 295                 300

Ala Ser Leu Leu Ser Phe Ala Thr Phe Glu Leu Ala Arg Asn Asp His
305                 310                 315                 320

Met Trp Arg Lys Leu Arg Glu Glu Val Ile Ser Thr Met Gly Pro Ser
                325                 330                 335

Ser Asp Glu Ile Thr Val Ala Gly Leu Lys Ser Cys Arg Tyr Leu Lys
            340                 345                 350

Ala Ile Leu Asn Glu Thr Leu Arg Leu Tyr Pro Ser Val Pro Arg Asn
        355                 360                 365

Ala Arg Phe Ala Thr Arg Asn Thr Thr Leu Pro Arg Gly Gly Gly Pro
    370                 375                 380

Asp Gly Ser Phe Pro Ile Leu Ile Arg Lys Gly Gln Pro Val Gly Tyr
385                 390                 395                 400

Phe Ile Cys Ala Thr His Leu Asn Glu Lys Val Tyr Gly Asn Asp Ser
                405                 410                 415

His Val Phe Arg Pro Glu Arg Trp Ala Ala Leu Glu Gly Lys Ser Leu
            420                 425                 430

Gly Trp Ser Tyr Leu Pro Phe Asn Gly Gly Pro Arg Ser Cys Leu Gly
        435                 440                 445

Gln Gln Phe Ala Ile Leu Glu Ala Ser Tyr Val Leu Ala Arg Leu Thr
    450                 455                 460
```

-continued

Gln Cys Tyr Thr Thr Ile Gln Leu Arg Thr Thr Glu Tyr Pro Pro Lys
465                 470                 475                 480

Lys Leu Val His Leu Thr Met Ser Leu Leu Asn Gly Val Tyr Ile Arg
                485                 490                 495

Thr Arg Thr

<210> SEQ ID NO 117
<211> LENGTH: 679
<212> TYPE: PRT
<213> ORGANISM: CANDIDATROPICALIS

<400> SEQUENCE: 117

Met Ala Leu Asp Lys Leu Asp Leu Tyr Val Ile Ile Thr Leu Val Val
1               5                   10                  15

Ala Val Ala Ala Tyr Phe Ala Lys Asn Gln Phe Leu Asp Gln Pro Gln
            20                  25                  30

Asp Thr Gly Phe Leu Asn Thr Asp Ser Gly Ser Asn Ser Arg Asp Val
        35                  40                  45

Leu Ser Thr Leu Lys Lys Asn Asn Lys Asn Thr Leu Leu Leu Phe Gly
    50                  55                  60

Ser Gln Thr Gly Thr Ala Glu Asp Tyr Ala Asn Lys Leu Ser Arg Glu
65                  70                  75                  80

Leu His Ser Arg Phe Gly Leu Lys Thr Met Val Ala Asp Phe Ala Asp
                85                  90                  95

Tyr Asp Trp Asp Asn Phe Gly Asp Ile Thr Glu Asp Ile Leu Val Phe
            100                 105                 110

Phe Ile Val Ala Thr Tyr Gly Glu Gly Glu Pro Thr Asp Asn Ala Asp
        115                 120                 125

Glu Phe His Thr Trp Leu Thr Glu Glu Ala Asp Thr Leu Ser Thr Leu
    130                 135                 140

Lys Tyr Thr Val Phe Gly Leu Gly Asn Ser Thr Tyr Glu Phe Phe Asn
145                 150                 155                 160

Ala Ile Gly Arg Lys Phe Asp Arg Leu Leu Ser Glu Lys Gly Gly Asp
                165                 170                 175

Arg Phe Ala Glu Tyr Ala Glu Gly Asp Asp Gly Thr Gly Thr Leu Asp
            180                 185                 190

Glu Asp Phe Met Ala Trp Lys Asp Asn Val Phe Asp Ala Leu Lys Asn
        195                 200                 205

Asp Leu Asn Phe Glu Glu Lys Glu Leu Lys Tyr Glu Pro Asn Val Lys
    210                 215                 220

Leu Thr Glu Arg Asp Asp Leu Ser Ala Ala Asp Ser Gln Val Ser Leu
225                 230                 235                 240

Gly Glu Pro Asn Lys Lys Tyr Ile Asn Ser Glu Gly Ile Asp Leu Thr
                245                 250                 255

Lys Gly Pro Phe Asp His Thr His Pro Tyr Leu Ala Arg Ile Thr Glu
            260                 265                 270

Thr Arg Glu Leu Phe Ser Ser Lys Asp Arg His Cys Ile His Val Glu
        275                 280                 285

Phe Asp Ile Ser Glu Ser Asn Leu Lys Tyr Thr Thr Gly Asp His Leu
    290                 295                 300

Ala Ile Trp Pro Ser Asn Ser Asp Glu Asn Ile Lys Gln Phe Ala Lys
305                 310                 315                 320

Cys Phe Gly Leu Glu Asp Lys Leu Asp Thr Val Ile Glu Leu Lys Ala
                325                 330                 335

-continued

```
Leu Asp Ser Thr Tyr Thr Ile Pro Phe Pro Thr Pro Ile Thr Tyr Gly
            340                 345                 350

Ala Val Ile Arg His His Leu Glu Ile Ser Gly Pro Val Ser Arg Gln
        355                 360                 365

Phe Phe Leu Ser Ile Ala Gly Phe Ala Pro Asp Glu Glu Thr Lys Lys
    370                 375                 380

Ala Phe Thr Arg Leu Gly Gly Asp Lys Gln Glu Phe Ala Ala Lys Val
385                 390                 395                 400

Thr Arg Arg Lys Phe Asn Ile Ala Asp Ala Leu Leu Tyr Ser Ser Asn
                405                 410                 415

Asn Ala Pro Trp Ser Asp Val Pro Phe Glu Phe Leu Ile Glu Asn Val
            420                 425                 430

Pro His Leu Thr Pro Arg Tyr Tyr Ser Ile Ser Ser Ser Ser Leu Ser
        435                 440                 445

Glu Lys Gln Leu Ile Asn Val Thr Ala Val Val Glu Ala Glu Glu Glu
    450                 455                 460

Ala Asp Gly Arg Pro Val Thr Gly Val Val Thr Asn Leu Leu Lys Asn
465                 470                 475                 480

Val Glu Ile Val Gln Asn Lys Thr Gly Glu Lys Pro Leu Val His Tyr
                485                 490                 495

Asp Leu Ser Gly Pro Arg Gly Lys Phe Asn Lys Phe Lys Leu Pro Val
            500                 505                 510

His Val Arg Arg Ser Asn Phe Lys Leu Pro Lys Asn Ser Thr Thr Pro
        515                 520                 525

Val Ile Leu Ile Gly Pro Gly Thr Gly Val Ala Pro Leu Arg Gly Phe
    530                 535                 540

Val Arg Glu Arg Val Gln Gln Val Lys Asn Gly Val Asn Val Gly Lys
545                 550                 555                 560

Thr Leu Leu Phe Tyr Gly Cys Arg Asn Ser Asn Glu Asp Phe Leu Tyr
                565                 570                 575

Lys Gln Glu Trp Ala Glu Tyr Ala Ser Val Leu Gly Glu Asn Phe Glu
            580                 585                 590

Met Phe Asn Ala Phe Ser Arg Gln Asp Pro Ser Lys Lys Val Tyr Val
        595                 600                 605

Gln Asp Lys Ile Leu Glu Asn Ser Gln Leu Val His Glu Leu Leu Thr
    610                 615                 620

Glu Gly Ala Ile Ile Tyr Val Cys Gly Asp Ala Ser Arg Met Ala Arg
625                 630                 635                 640

Asp Val Gln Thr Thr Ile Ser Lys Ile Val Ala Lys Ser Arg Glu Ile
                645                 650                 655

Ser Glu Asp Lys Ala Ala Glu Leu Val Lys Ser Trp Lys Val Gln Asn
            660                 665                 670

Arg Tyr Gln Glu Asp Val Trp
        675


<210> SEQ ID NO 118
<211> LENGTH: 679
<212> TYPE: PRT
<213> ORGANISM: CANDIDATROPICALIS

<400> SEQUENCE: 118

Met Ala Leu Asp Lys Leu Asp Leu Tyr Val Ile Ile Thr Leu Val Val
1               5                   10                  15

Ala Val Ala Ala Tyr Phe Ala Lys Asn Gln Phe Leu Asp Gln Pro Gln
            20                  25                  30
```

-continued

```
Asp Thr Gly Phe Leu Asn Thr Asp Ser Gly Ser Asn Ser Arg Asp Val
        35                  40                  45

Leu Ser Thr Leu Lys Lys Asn Asn Lys Asn Thr Leu Leu Leu Phe Gly
    50                  55                  60

Ser Gln Thr Gly Thr Ala Glu Asp Tyr Ala Asn Lys Leu Ser Arg Glu
65                  70                  75                  80

Leu His Ser Arg Phe Gly Leu Lys Thr Met Val Ala Asp Phe Ala Asp
                85                  90                  95

Tyr Asp Trp Asp Asn Phe Gly Asp Ile Thr Glu Asp Ile Leu Val Phe
            100                 105                 110

Phe Ile Val Ala Thr Tyr Gly Glu Gly Glu Pro Thr Asp Asn Ala Asp
        115                 120                 125

Glu Phe His Thr Trp Leu Thr Glu Glu Ala Asp Thr Leu Ser Thr Leu
    130                 135                 140

Arg Tyr Thr Val Phe Gly Leu Gly Asn Ser Thr Tyr Glu Phe Phe Asn
145                 150                 155                 160

Ala Ile Gly Arg Lys Phe Asp Arg Leu Leu Ser Glu Lys Gly Gly Asp
                165                 170                 175

Arg Phe Ala Glu Tyr Ala Glu Gly Asp Asp Gly Thr Gly Thr Leu Asp
            180                 185                 190

Glu Asp Phe Met Ala Trp Lys Asp Asn Val Phe Asp Ala Leu Lys Asn
        195                 200                 205

Asp Leu Asn Phe Glu Glu Lys Glu Leu Lys Tyr Glu Pro Asn Val Lys
    210                 215                 220

Leu Thr Glu Arg Asp Asp Leu Ser Ala Ala Asp Ser Gln Val Ser Leu
225                 230                 235                 240

Gly Glu Pro Asn Lys Lys Tyr Ile Asn Ser Glu Gly Ile Asp Leu Thr
                245                 250                 255

Lys Gly Pro Phe Asp His Thr His Pro Tyr Leu Ala Arg Ile Thr Glu
            260                 265                 270

Thr Arg Glu Leu Phe Ser Ser Lys Glu Arg His Cys Ile His Val Glu
        275                 280                 285

Phe Asp Ile Ser Glu Ser Asn Leu Lys Tyr Thr Thr Gly Asp His Leu
    290                 295                 300

Ala Ile Trp Pro Ser Asn Ser Asp Glu Asn Ile Lys Gln Phe Ala Lys
305                 310                 315                 320

Cys Phe Gly Leu Glu Asp Lys Leu Asp Thr Val Ile Glu Leu Lys Ala
                325                 330                 335

Leu Asp Ser Thr Tyr Thr Ile Pro Phe Pro Thr Pro Ile Thr Tyr Gly
            340                 345                 350

Ala Val Ile Arg His His Leu Glu Ile Ser Gly Pro Val Ser Arg Gln
        355                 360                 365

Phe Phe Leu Ser Ile Ala Gly Phe Ala Pro Asp Glu Glu Thr Lys Lys
    370                 375                 380

Thr Phe Thr Arg Leu Gly Gly Asp Lys Gln Glu Phe Ala Thr Lys Val
385                 390                 395                 400

Thr Arg Arg Lys Phe Asn Ile Ala Asp Ala Leu Leu Tyr Ser Ser Asn
                405                 410                 415

Asn Thr Pro Trp Ser Asp Val Pro Phe Glu Phe Leu Ile Glu Asn Ile
            420                 425                 430

Gln His Leu Thr Pro Arg Tyr Tyr Ser Ile Ser Ser Ser Ser Leu Ser
        435                 440                 445
```

-continued

```
Glu Lys Gln Leu Ile Asn Val Thr Ala Val Val Glu Ala Glu Glu Glu
    450                 455                 460

Ala Asp Gly Arg Pro Val Thr Gly Val Val Thr Asn Leu Leu Lys Asn
465                 470                 475                 480

Ile Glu Ile Ala Gln Asn Lys Thr Gly Glu Lys Pro Leu Val His Tyr
                485                 490                 495

Asp Leu Ser Gly Pro Arg Gly Lys Phe Asn Lys Phe Lys Leu Pro Val
            500                 505                 510

His Val Arg Arg Ser Asn Phe Lys Leu Pro Lys Asn Ser Thr Thr Pro
        515                 520                 525

Val Ile Leu Ile Gly Pro Gly Thr Gly Val Ala Pro Leu Arg Gly Phe
    530                 535                 540

Val Arg Glu Arg Val Gln Gln Val Lys Asn Gly Val Asn Val Gly Lys
545                 550                 555                 560

Thr Leu Leu Phe Tyr Gly Cys Arg Asn Ser Asn Glu Asp Phe Leu Tyr
                565                 570                 575

Lys Gln Glu Trp Ala Glu Tyr Ala Ser Val Leu Gly Glu Asn Phe Glu
            580                 585                 590

Met Phe Asn Ala Phe Ser Arg Gln Asp Pro Ser Lys Lys Val Tyr Val
        595                 600                 605

Gln Asp Lys Ile Leu Glu Asn Ser Gln Leu Val His Glu Leu Leu Thr
    610                 615                 620

Glu Gly Ala Ile Ile Tyr Val Cys Gly Asp Ala Ser Arg Met Ala Arg
625                 630                 635                 640

Asp Val Gln Thr Thr Ile Ser Lys Ile Val Ala Lys Ser Arg Glu Ile
                645                 650                 655

Ser Glu Asp Lys Ala Ala Glu Leu Val Lys Ser Trp Lys Val Gln Asn
            660                 665                 670

Arg Tyr Gln Glu Asp Val Trp
        675
```